(12) United States Patent
Macielag et al.

(10) Patent No.: US 11,732,019 B2
(45) Date of Patent: *Aug. 22, 2023

(54) CYCLIC PEPTIDE TYROSINE TYROSINE COMPOUNDS AS MODULATORS OF NEUROPEPTIDE Y RECEPTORS

(71) Applicant: Janssen Pharmaceutica NV, Beerse (BE)

(72) Inventors: Mark Macielag, Lower Gwynedd, PA (US); Raymond J. Patch, Yardley, PA (US); Rui Zhang, Belle Mead, NJ (US); Martin A. Case, San Diego, CA (US); Mark J. Wall, Lansdale, PA (US); Yue-Mei Zhang, Wellesley, MA (US)

(73) Assignee: Janssen Pharmaceutica NV, Beerse (BE)

( * ) Notice: Subject to any disclaimer, the term of this patent is extended or adjusted under 35 U.S.C. 154(b) by 130 days.

This patent is subject to a terminal disclaimer.

(21) Appl. No.: 17/168,325

(22) Filed: Feb. 5, 2021

(65) Prior Publication Data

US 2021/0206822 A1 Jul. 8, 2021

Related U.S. Application Data

(63) Continuation of application No. 16/344,141, filed as application No. PCT/US2017/058451 on Oct. 26, 2017, now Pat. No. 10,961,293.

(Continued)

(51) Int. Cl.
*C07K 14/575* (2006.01)
*A61K 47/68* (2017.01)
(Continued)

(52) U.S. Cl.
CPC .......... *C07K 14/575* (2013.01); *A61K 9/0019* (2013.01); *A61K 38/17* (2013.01); *A61K 38/1709* (2013.01); *A61K 38/22* (2013.01); *A61K 38/26* (2013.01); *A61K 45/06* (2013.01); *A61K 47/60* (2017.08); *A61K 47/64* (2017.08); *A61K 47/68* (2017.08); *A61K 47/6811* (2017.08); *A61K 47/6845* (2017.08); *A61K 47/6883* (2017.08); *A61K 49/0032* (2013.01); *A61K 49/0052* (2013.01); *A61K 49/0056* (2013.01); *A61P 3/00* (2018.01); *A61P 3/04* (2018.01); *A61P 3/06* (2018.01); *A61P 3/08* (2018.01); *A61P 3/10* (2018.01); *C07K 1/061* (2013.01); *C07K 1/1072* (2013.01); *C07K 1/12* (2013.01); *C07K 1/18* (2013.01); *C07K 5/0205* (2013.01); *C07K 14/57545* (2013.01); *C07K 16/00* (2013.01); *C07K 16/24* (2013.01); *A61K 38/00* (2013.01); *A61K 2039/505* (2013.01); *C07K 2317/14* (2013.01);

(Continued)

(58) Field of Classification Search
None
See application file for complete search history.

(56) References Cited

U.S. PATENT DOCUMENTS 4,248,890 A 2/1981 Maffrand
5,627,044 A 5/1997 Brown
(Continued)

FOREIGN PATENT DOCUMENTS

WO 2005077094 A2 8/2005
WO 2005080424 A2 9/2005
(Continued)

OTHER PUBLICATIONS

Altschul et al., "Gapped BLAST and PSI-BLAST: A New Generation of Protein Database Search Programs," Nucleic Acids Research, vol. 25, No. 17, pp. 3389-3402 (1997).

(Continued)

*Primary Examiner* — Adam Weidner
(74) *Attorney, Agent, or Firm* — Seed IP Law Group LLP

(57) ABSTRACT

The present invention comprises compounds of Formula I.

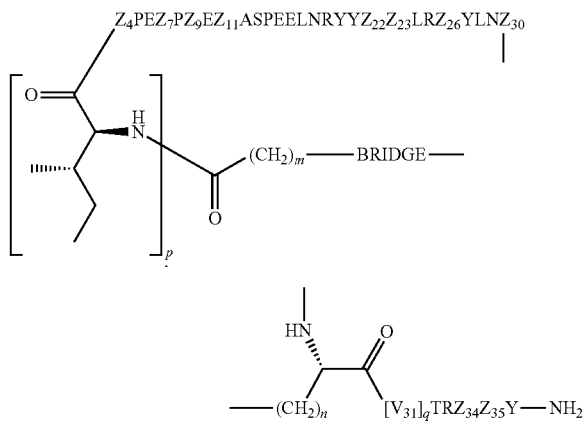

Formula I wherein:
$Z_4$, $Z_7$, $Z_9$, $Z_{11}$, $Z_{22}$, $Z_{23}$, $Z_{26}$, $Z_{30}$, $Z_{34}$, $Z_{35}$, p, m, n, q, and BRIDGE are defined in the specification. The invention also relates to pharmaceutical compositions and methods for use thereof. The novel compounds are useful for preventing, treating or ameliorating diseases and disorders, such as obesity, type 2 diabetes, the metabolic syndrome, insulin resistance, and dyslipidemia, among others.

15 Claims, No Drawings
Specification includes a Sequence Listing.

Related U.S. Application Data

(60) Provisional application No. 62/413,586, filed on Oct. 27, 2016, provisional application No. 62/413,613, filed on Oct. 27, 2016.

(51) Int. Cl.

| | |
|---|---|
| *C07K 16/24* | (2006.01) |
| *A61K 9/00* | (2006.01) |
| *A61K 38/17* | (2006.01) |
| *A61K 38/26* | (2006.01) |
| *C07K 1/06* | (2006.01) |
| *C07K 1/107* | (2006.01) |
| *A61K 47/64* | (2017.01) |
| *A61P 3/10* | (2006.01) |
| *A61K 49/00* | (2006.01) |
| *C07K 1/12* | (2006.01) |
| *C07K 1/18* | (2006.01) |
| *C07K 5/02* | (2006.01) |
| *A61K 47/60* | (2017.01) |
| *A61P 3/08* | (2006.01) |
| *A61P 3/00* | (2006.01) |
| *A61P 3/04* | (2006.01) |
| *A61P 3/06* | (2006.01) |
| *A61K 38/22* | (2006.01) |
| *A61K 45/06* | (2006.01) |
| *C07K 16/00* | (2006.01) |
| *A61K 38/00* | (2006.01) |
| *A61K 39/00* | (2006.01) |

(52) U.S. Cl.
CPC ...... *C07K 2317/21* (2013.01); *C07K 2317/24* (2013.01); *C07K 2317/33* (2013.01); *C07K 2317/52* (2013.01); *C07K 2317/55* (2013.01); *C07K 2317/56* (2013.01); *C07K 2317/565* (2013.01); *C07K 2317/567* (2013.01); *C07K 2317/71* (2013.01); *C07K 2317/92* (2013.01); *C07K 2317/94* (2013.01); *C07K 2319/30* (2013.01)

(56) References Cited

U.S. PATENT DOCUMENTS

| | | | |
|---|---|---|---|
| 7,166,575 | B2 | 1/2007 | Quay |
| 8,759,295 | B2 | 6/2014 | Ghosh |
| 2006/0094653 | A1 | 5/2006 | Levy |
| 2007/0244041 | A1 | 10/2007 | Larsen |
| 2010/0292172 | A1 | 11/2010 | Ghosh |
| 2013/0040877 | A1 | 2/2013 | Kofoed |
| 2015/0258209 | A1 | 9/2015 | Benz |
| 2016/0108098 | A1 | 4/2016 | Dock |

FOREIGN PATENT DOCUMENTS

| | | |
|---|---|---|
| WO | 2005089789 A2 | 9/2005 |
| WO | 2011006497 A1 | 1/2011 |
| WO | 2014102299 A2 | 7/2014 |

OTHER PUBLICATIONS

Altschul et al. "Basic Local Alignment Search Tool" J. Mol. Biol., vol. 215, pp. 403-410, 1990.

Andrushchenko et al., "Optimization of the hydrochloric acid concentration used for trifluoroacetate removal from Synthetic peptides" Journal of Peptide Science, vol. 13, pp. 37-43, 2007.

Batterham et al., "Gut hormone PYY3-36 physiologically inhibits food intake.", Nature, Aug. 8, 2002, pp. 650-654, vol. 418.

Batterham et al., "Inhibition of Food Intake in Obese Subjects by Peptide YY 3-36", The New England Journal of Medicine, vol. 349, No. 10, pp. 941-948, Sep. 2003.

Challis et al., "Acute effects on PYY3-36 on food intake and hypothalamic neuropeptide expression in the mouse," Biochem Biophys Res Commun 311, vol. No. 4, pp. 915-919, Oct. 2003.

Franssen et al., "Obesity and Dyslipidemia," Med. Clin. N. Am., vol. 95, pp. 893-902 (2011).

Germain et al., "Analogs of pancreatic polypeptide and peptide YY with a locked PP-fold structure are biologically active," Peptides vol. 39, pp. 6-10, 2013.

Int'l Search Report and Written Opinion dated Feb. 21, 2018 in Int'l Application No. PCT/US2017/058451 (13 pages).

Int'l Search Report and Written Opinion dated Mar. 13, 2018 in Int'l Application No. PCT/US2017/058455 (11 pages).

Kai Holland-Nell et al., "Maintaining Biological Activity by Using Triazoles as Disufide Bond Mimetics", Angewandte Chemie, International Edition, DE, (May 23, 2011), vol. 50, No. 22, doi:10.1002/anie.201005846, ISSN 1433-7851, pp. 5204-5206, XP055454226.

Kaiser et al., "Color Test for Detection of Free Terminal Amino Groups in the Solid-Phase Synthesis of Peptides,", Anal. Biochem., 1970, pp. 595-598, vol. 34.

Klop et al., "Dyslipidemia in Obesity: Mechanisms and Potential Targets," Nutrients, vol. 5, pp. 1218-1240 (2013).

Le Roux et al., "Gut Hormone Profiles Following Bariatric Surgery Favor an Anorectic State, Facilitate Weight Loss, and Improve Metabolic Parameters.", Annals of Surgery, Jan. 2006, pp. 108-114, vol. 243(1).

Lecklin et al., "Agonists for neuropeptide Y receptors Y1 and Y5 stimulate different phases of feeding in guinea pigs," Br. J. Pharmacol. 139(8):1433-40 (2003).

Maria "The expansion of the therapeutic applications of peptides: drivers and challenges" oligos and peptides, chimica oggo 33(2) (Year: 2015) pp. 5-15.

Mayo "Metabolic Syndrome" accessed from mayoclinic.org on Feb. 24, 2020 (Year: 2020) (5 pages).

Moll "dyslipidemia causes and treatment" accessed from verywellhealth.com on Feb. 24, 2020 (Year: 2020) (6 pages).

Nichols "Diabetes: the difference between types 1 and 2" accessed from medicalnewstoday.com on Feb. 24, 2020 (Year: 2019) (19 pages).

Palasek et al., "Limiting racemization and aspartimide formation in microwave-enhanced Fmoc solid phase peptide synthesis," Journal of Peptide Science, vol. 13, No. 3, pp. 143-148, 2007.

Pittner et al., "Effects of PYY[3-36] in rodent models of diabetes and obesity.", International Journal of Obesity, 2004, pp. 963-971, vol. 28.

Torang et al., "In vivo and in vitro degradation of peptide YY3-36 to inactive peptide YY3-34 in humans," Am. J. Physiol. Regul. Integr. Comp. Physiol., vol. 310, pp. R866-R874, 2016.

Vrang et al., "PYY (3-36) reduces food intake and body weight and improves insulin sensitivity in rodent models of diet-induced obesity", Am J Physiol Regul Integr Comp Physiol, 291, pages R367-R375, 2006.

Wang et al., "New insights into the mechanism of low high-density lipoprotein cholesterol in obesity," Lipids in Health and Disease, vol. 10, No. 176, 10 pages (2011).

Yu et al., "Enhanced Coupling Efficiency in Solid-Phase Peptide Synthesis by Microwave Irradiation.", Journal of Organic Chemistry, Aug. 28, 1992, pp. 4781-4784, vol. 57(18).

CYCLIC PEPTIDE TYROSINE TYROSINE COMPOUNDS AS MODULATORS OF NEUROPEPTIDE Y RECEPTORS

CROSS-REFERENCE TO RELATED APPLICATIONS

This application is a continuation of U.S. patent application Ser. No. 16/344,141, filed on Apr. 23, 2019, that is a Section 371 of International Application No. PCT/US2017/058451, filed on Oct. 26, 2017, which was published in the English language on May 3, 2018 under International Publication No. WO 2018/081367 A1, which claims priority to U.S. Provisional Patent Application No. 62/413,613, filed on Oct. 27, 2016, and U.S. Provisional Patent Application No. 62/413,586 filed on Oct. 27, 2016. Each disclosure is incorporated herein by reference in its entirety.

FIELD OF THE INVENTION

The present invention is directed generally to novel cyclic peptide tyrosine tyrosine (PYY) compounds, which are modulators of the neuropeptide Y2 receptor. The invention also relates to pharmaceutical compositions and methods for use thereof. The novel compounds are useful for preventing, treating or ameliorating diseases and disorders, such as obesity, type 2 diabetes, the metabolic syndrome, insulin resistance, and dyslipidemia, among others.

REFERENCE TO SEQUENCE LISTING SUBMITTED ELECTRONICALLY

This application contains a sequence listing, which is submitted electronically via EFS-Web as an ASCII formatted sequence listing with a file name "64US3_Sequence_Listing" and a creation date of Feb. 4, 2021 and having a size of 93 kb. The sequence listing submitted via EFS-Web is part of the specification and is herein incorporated by reference in its entirety. In the event of any inconsistency with regard to the structures for SEQ ID NOs: 1-111 between the information described herein and the Sequence Listing submitted electronically via EFS-Web with a file name "64US3_Sequence_Listing," the information herein will prevail.

BACKGROUND OF THE INVENTION

Neuropeptide Y (NPY) receptors are activated by a closely related group of peptide agonists termed "NPY family" which have differing affinities for each receptor sub-type. NPY, peptide tyrosine-tyrosine (PYY) and pancreatic polypeptide (PP), all 36 amino acids in length, are agonists for the NPY family of receptors. NPY is a neurotransmitter, synthesized, co-stored and released with norepinephrine and epinephrine. NPY is one of the most abundant and widely distributed peptides in the central nervous system (CNS) of humans and rodents and is expressed in areas of the brain related to feeding and stress. In the peripheral nervous system, NPY-containing neurons are predominantly sympathetic. PYY is predominantly synthesized and released by intestinal endocrine cells. Cleavage of NPY and PYY by the endothelial serine-protease, di-peptidyl peptidase IV (DPP-IV), generates $NPY_{3-36}$ and $PYY_{3-36}$ which are selective ligands for Y2 and Y5 sub-types of the NPY receptor family. PP is mainly found in pancreatic islet cells distinct from those storing insulin, glucagon or somatostatin.

Five distinct NPY receptors have been identified to date, four of which are understood as relevant to human physiology. The receptors Y1, Y2 and Y5 preferentially bind NPY and PYY, whereas the Y4 receptor preferentially binds PP. The Y2 and Y5 receptors are also potently activated by NPY3-36 and PYY3-36. In general, the NPY family of ligands possesses variable selectivity for each of the NPY receptor isoforms, with PYY3-36 previously reported to have modest-to-robust selectivity for the Y2 isoform. Each of these receptors is coupled to inhibition of adenylate cyclase via pertussis-toxin sensitive Gαi.

PYY is secreted from endocrine L-cells in response to food, and in particular following fat ingestion. $PYY_{1-36}$ predominates in the fasting state, with $PYY_{3-36}$ being the major form found post-prandially in humans, with plasma concentrations negatively correlated with the number of calories consumed. $PYY_{3-36}$ has been demonstrated to reduce food intake in humans, monkeys, rats, rabbits, and mice (Batterham R L et al. *Nature* 2002 Aug. 8; 418(6898): 650-4; Batterham R L et al. *N Engl J Med* 2003 Sep. 4; 349(10):941-8; Challis B G et al., *Biochem Biophys Res Commun* 2003 Nov. 28; 311(4):915-9). The anorexigenic effects of $PYY_{3-36}$ are believed to be Y2-mediated, based on preferential binding at this receptor and loss of feeding efficacy in Y2-deficient mice (Batterham R L, et al. *Nature* 2002 Aug. 8; 418(6898):650-4). Intra-arcuate injection of PYY3-36 reduces food intake in rats and mice (Batterham et al. *Nature* 2002 Aug. 8; 418(6898):650-4), suggesting that engagement of hypothalamic Y2 receptors may mediate these effects. Acute effects on feeding have also been shown to translate to dose-dependent effects on bodyweight in ob/ob mice, DIO mice and Zucker fa/fa mice (Pittner R A et al. *Int J Obes relat Metab Disord* 2004 August; 28(8):963-71). In addition, $PYY_{3-36}$ has also been shown to improve insulin-mediated glucose disposal and insulin sensitivity in DIO rodents (Vrang N et al., *Am J Physiol Regul Integr Comp Physiol* August; 291(2):R367-75). Bariatric surgery results in increased circulating PYY-immunoreactivity (le Roux C W et al., *Ann Surg* 2006 January; 243(1); 108-14), which appears to play a role in postoperative weight loss.

Given its role in controlling appetite and food intake as well as its anti-secretory and pro-absorptive effects in the gastrointestinal tract in mammals, $PYY_{3-36}$ may be effective in treating obesity and associated conditions as well as in a number of gastrointestinal disorders. However, the therapeutic utility of $PYY_{3-36}$ itself as a treatment agent is limited by its rapid metabolism and resultant short circulating half-life (Torang et al., Am. J. Physiol. Regul. Integr. Comp. Physiol. 310:R866-R874 (2016)).

Thus, it is desirable to obtain a PYY analogue or derivative thereof with an improved metabolic stability and pharmacokinetic profile relative to PYY3-36. Such derivatives, with a protracted half-life in vivo, would provide Y2 receptor modulation with greater duration of action, making them suitable as therapeutic agents for subjects in need of such modulation.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

One general aspect of the invention relates to a compound of Formula I:

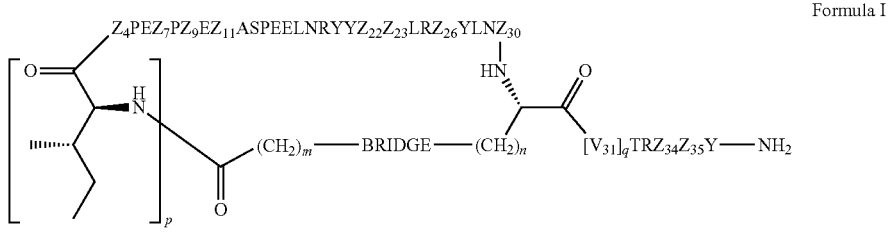

Formula I wherein p is 0 or 1;

m is 0, 1, 2, 3, 4, or 5;

n is 1, 2, 3, or 4;

q is 0 or 1; provided that q is 1 only when $Z_{30}$ is absent;

BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;

$Z_4$ is K, A, E, S, or R;

$Z_7$ is A or K;

$Z_9$ is G or K;

$Z_{11}$ is D or K;

$Z_{22}$ is A or K;

$Z_{23}$ is S or K;

$Z_{26}$ is A or H;

$Z_{30}$ is L, W, absent, or K;

provided that $Z_{30}$ is absent only when q is 1;

$Z_{34}$ is

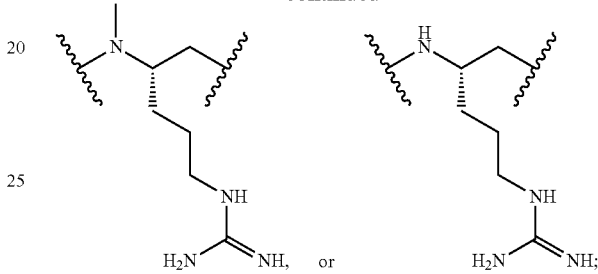

$Z_{35}$ is

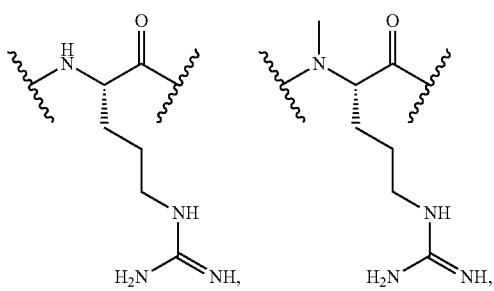

or a derivative thereof; wherein the derivative is the compound of Formula I that is modified by one or more processes comprising amidation, glycosylation, carbamylation, sulfation, phosphorylation, cyclization, lipidation, or pegylation; or a pharmaceutically acceptable salt thereof.

The present invention also provides methods of preventing, treating, delaying the onset of, or ameliorating a syndrome, disorder or disease, or any one or more symptoms of said syndrome, disorder, or disease, wherein said syndrome, disorder or disease is selected from the group consisting of obesity, type 2 diabetes, metabolic syndrome (i.e., Syndrome X), insulin resistance, impaired glucose tolerance (e.g., glucose intolerance), hyperglycemia, hyperinsulinemia, hypertriglyceridemia, dyslipidemia, atherosclerosis, diabetic nephropathy, and other cardiovascular risk factors such as hypertension and cardiovascular risk factors related to unmanaged cholesterol and/or lipid levels, osteoporosis, inflammation, and eczema, comprising administering to a subject in need thereof an effective amount of a compound of Formula I, a derivative or pharmaceutically acceptable salt thereof, or a form, composition or medicament thereof, or any of the combinations described herein.

The present invention also contemplates preventing, treating, delaying the onset of, or ameliorating any of the diseases, disorders, syndromes, or symptoms described herein with a combination therapy that comprises administering to a subject in need thereof an effective amount of a compound of Formula I, a derivative or pharmaceutically acceptable salt thereof, or a form, composition or medicament thereof, in combination with any one or more of the following additional compounds: a dipeptidyl peptidase-4 (DPP-4) inhibitor (e.g., sitagliptin, saxagliptin, linagliptin, alogliptin, etc.); a GLP-1 receptor agonist (e.g., short-acting GLP-1 receptor agonists such as exenatide and lixisenatide; intermediate-acting GLP-1 receptor agonists such as liraglutide; long-acting GLP-1 receptor agonists such as exenatide extended-release, albiglutide, dulaglutide); a sodium-glucose co-transporter-2 (SGLT-2) inhibitors (e.g., canaglifozin, dapaglifozin, empaglifozin, etc.); bile acid sequestrants (e.g., colesevelam, etc.); and dopamine receptor agonists (e.g., bromocriptine quick-release). In some embodiments, the dose of the additional compound is reduced when given in combination with a compound of Formula I, a derivative or pharmaceutically acceptable salt thereof. In some embodiments, when used in combination with a compound of Formula I, the additional compounds may be used in lower doses than when each is used singly.

The present invention contemplates preventing, treating, delaying the onset of, or ameliorating any of the diseases, disorders, syndromes, or symptoms described herein with a combination therapy that comprises administering to a subject in need thereof an effective amount of a compound of Formula I, a derivative or pharmaceutically acceptable salt thereof, or a form, composition or medicament thereof, in combination with any one or more of the following additional compounds: biguanides (e.g., metformin, etc.); insulin; oxyntomodulin; sulfonylureas (e.g., chlorpropamide, glimepiride, glipizide, glyburide, glibenclamide, glibornuride, glisoxepide, glyclopyramide, tolazamide, tolbutamide, acetohexamide, carbutamide, etc.); and thiazolidinediones (e.g; pioglitazone, rosiglitazone, lobeglitazone, ciglitazone, darglitazone, englitazone, netoglitazone, rivoglitazone, troglitazone, etc.). In some embodiments, when used in combination with a compound of Formula I, a derivative or pharmaceutically acceptable salt thereof, the additional compounds may be used in lower doses than when each is used singly.

In yet other embodiments, the present invention contemplates preventing, treating, delaying the onset of, or ameliorating any of the diseases, disorders, syndromes, or symptoms described herein, with a combination therapy that comprises administering to a subject in need thereof an effective amount of a compound of Formula I, a derivative or pharmaceutically acceptable salt thereof, or a form, composition or medicament thereof, in combination with a surgical therapy, such as bariatric surgery (e.g., gastric bypass surgery, such as Roux-en-Y gastric bypass surgery; sleeve gastrectomy; adjustable gastric band surgery; biliopancreatic diversion with duodenal switch; intragastric balloon; gastric plication; and combinations thereof).

Further aspects, features and advantages of the present invention will be better appreciated upon a reading of the following detailed description of the invention and claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or openended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., cyclic PYY3-36 polypeptide sequences), refer to two or more sequences or subsequences that are the same or have a specified percentage of amino acid residues or nucleotides that are the same, when compared and aligned for maximum correspondence, as measured using one of the following sequence comparison algorithms or by visual inspection using methods known in the art in view of the present disclosure.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel))

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The term "administering" with respect to the methods of the invention, means a method for therapeutically or prophylactically preventing, treating or ameliorating a syndrome, disorder or disease as described herein by using a compound of the invention or a pharmaceutically acceptable salt thereof, optionally conjugated to a half-life extension moiety, or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating a syndrome, disorder, or disease being treated, or the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

Compounds

In one general aspect, the present invention comprises a compound of Formula I:

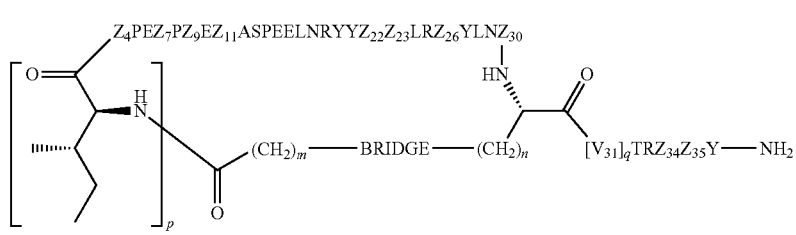

Formula I wherein p is 0 or 1;

m is 0, 1, 2, 3, 4, or 5;

n is 1, 2, 3, or 4;

q is 0 or 1; provided that q is 1 only when $Z_{30}$ is absent;

BRIDGE is -Ph-$CH_2$—S—, -triazolyl-, —NHC(O)$CH_2$S—, —S$CH_2$C(O)NH—, (O$CH_2CH_2$)$_2$NHC(O)$CH_2$S, —NHC(O)—, or —$CH_2$S—;

$Z_4$ is K, A, E, S, or R;

$Z_7$ is A or K;

$Z_9$ is G or K;

$Z_{11}$ is D or K;

$Z_{22}$ is A or K;

$Z_{23}$ is S or K;

$Z_{26}$ is A or H;

$Z_{30}$ is L, W, absent, or K;

provided that $Z_{30}$ is absent only when q is 1;

$Z_{34}$ is

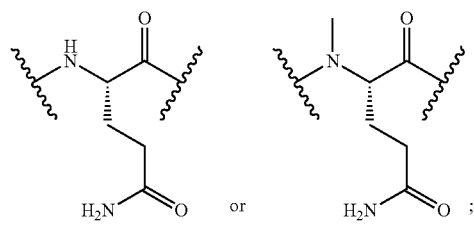 [SMILES: *N[C@@H](CCC(N)=O)C(*)=O ; *C(=O)[C@H](CCC(N)=O)N(*)C]

$Z_{35}$ is

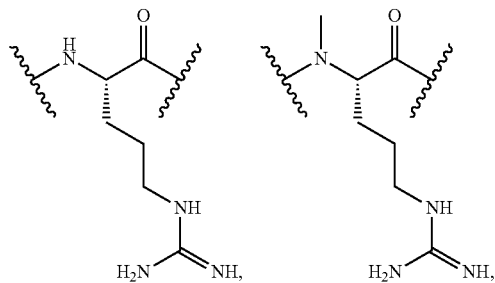

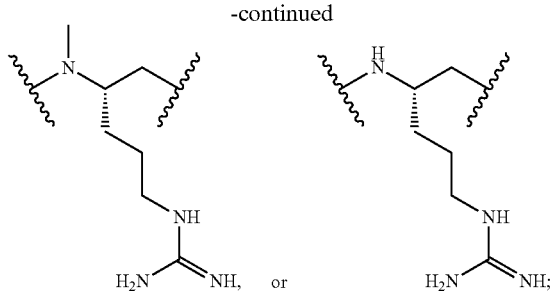

or a derivative thereof; wherein the derivative is the compound of Formula I that is modified by one or more processes comprising amidation, glycosylation, carbamylation, sulfation, phosphorylation, cyclization, lipidation, or pegylation; or a pharmaceutically acceptable salt thereof.

In one embodiment, the invention comprises the compound of claim 1 or a derivative thereof, wherein the derivative is the compound of Formula I that is modified by one or more processes comprising amidation, lipidation, or pegylation; or a pharmaceutically acceptable salt thereof.

In another embodiment, the invention comprises the compound of Formula I or a derivative thereof, wherein:

p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-CH$_2$—S—, -triazolyl-, —NHC(O)CH$_2$S—, —SCH2C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K, wherein the amino side chain of said K is optionally substituted with

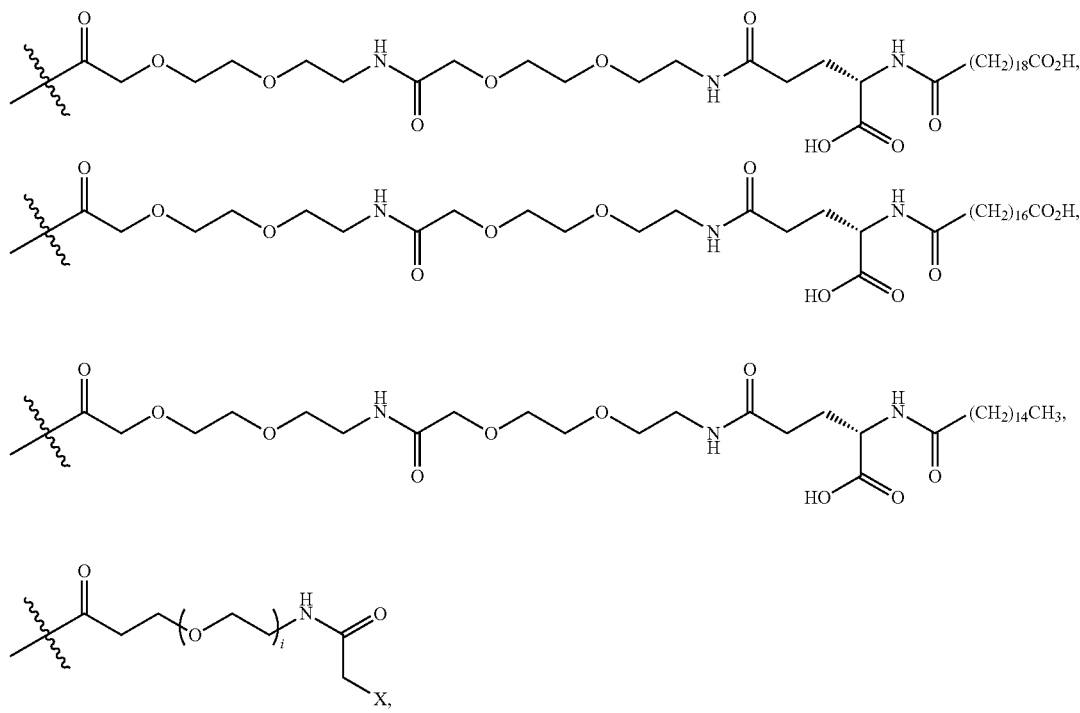

wherein i is an integer of 0 to 24, and X=Br, I or Cl, —C(O)CH$_2$Br, —C(O)CH$_2$I, or —C(O)CH$_2$Cl;

$Z_9$ is G or K, wherein the amino side chain of said K is optionally substituted with

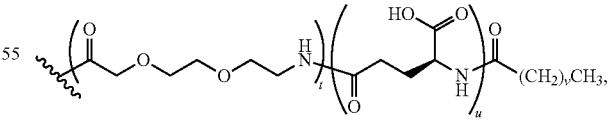

wherein t is 0, 1, or 2;
u is 0 or 1; and
v is 14, 16, or 18;

11
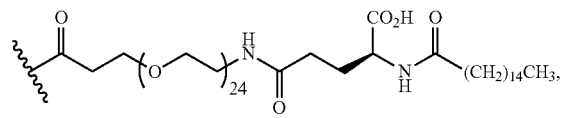
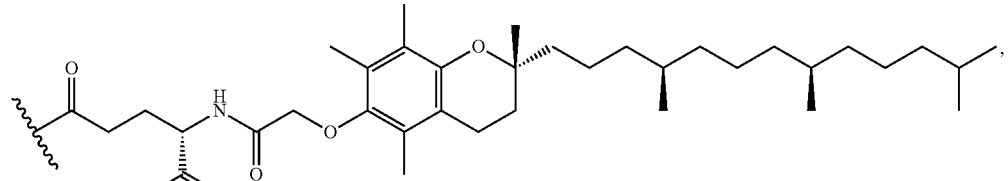
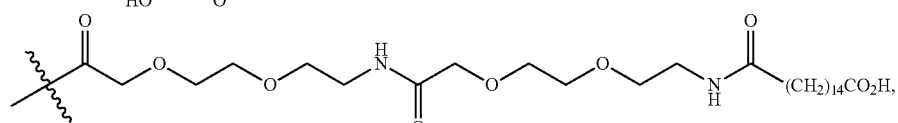
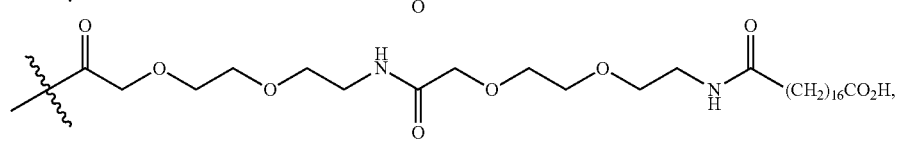
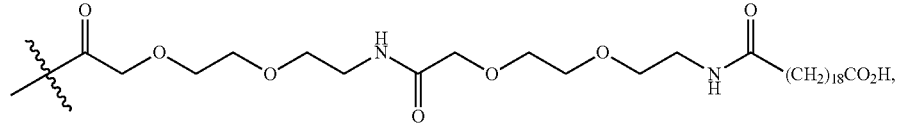
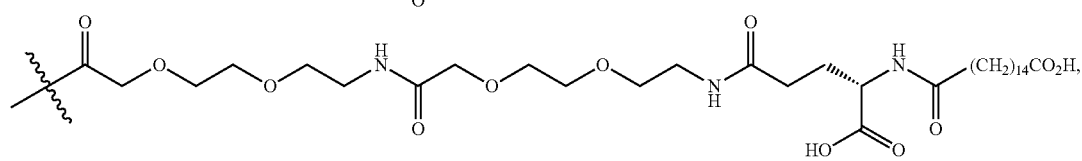
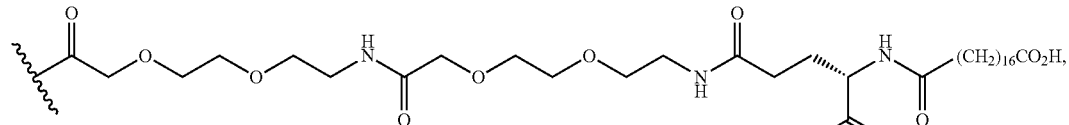
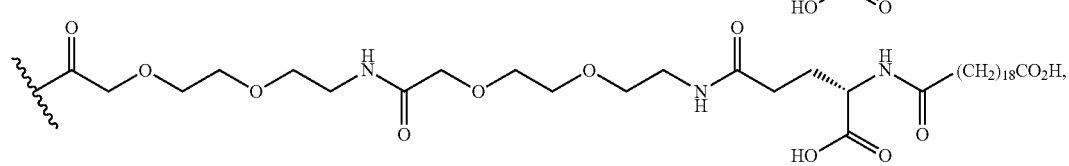
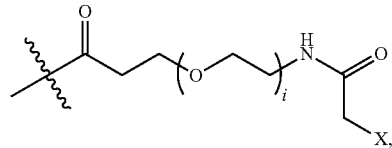
wherein i is an integer of 0 to 24, and X=Br, I or Cl, —C(O)CH$_2$Br, —C(O)CH$_2$I, or —C(O)CH$_2$Cl;
Z$_{11}$ is D or K, wherein the amino side chain of said K is optionally substituted with
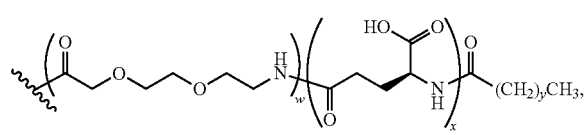
wherein w is 0, 1, 2, or 4;
x is 0 or 1; and
y is 14, 16, or 18;
12
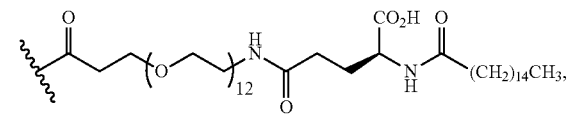
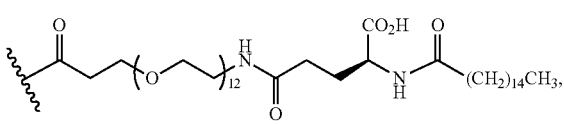
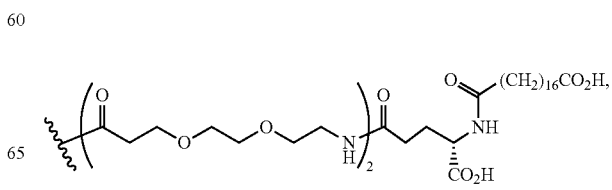

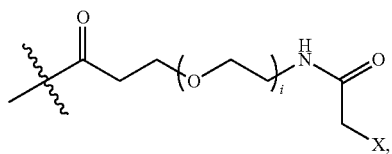
wherein i is an integer of 0 to 24, and X=Br, I or Cl
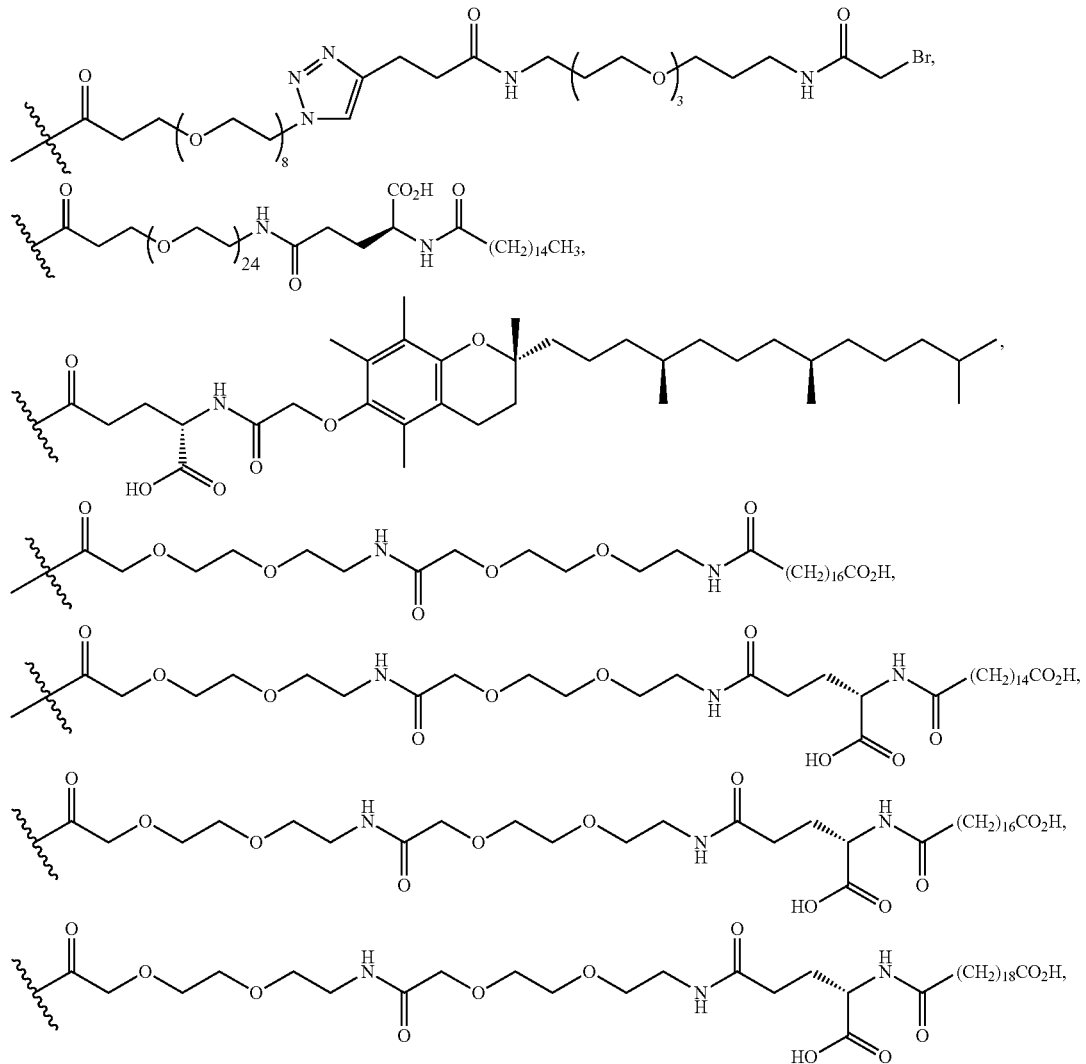
—C(O)CH$_2$Br, —C(O)CH$_2$I, or —C(O)CH$_2$Cl;
Z$_{22}$ is A or K, wherein the amino side chain of said K is optionally substituted with
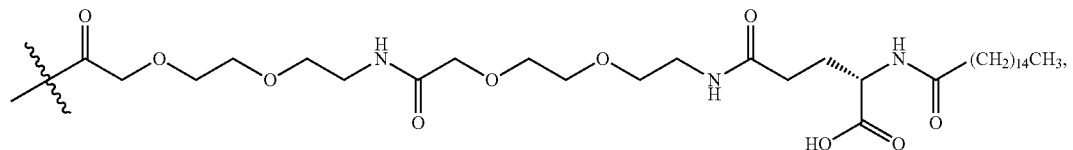

-continued
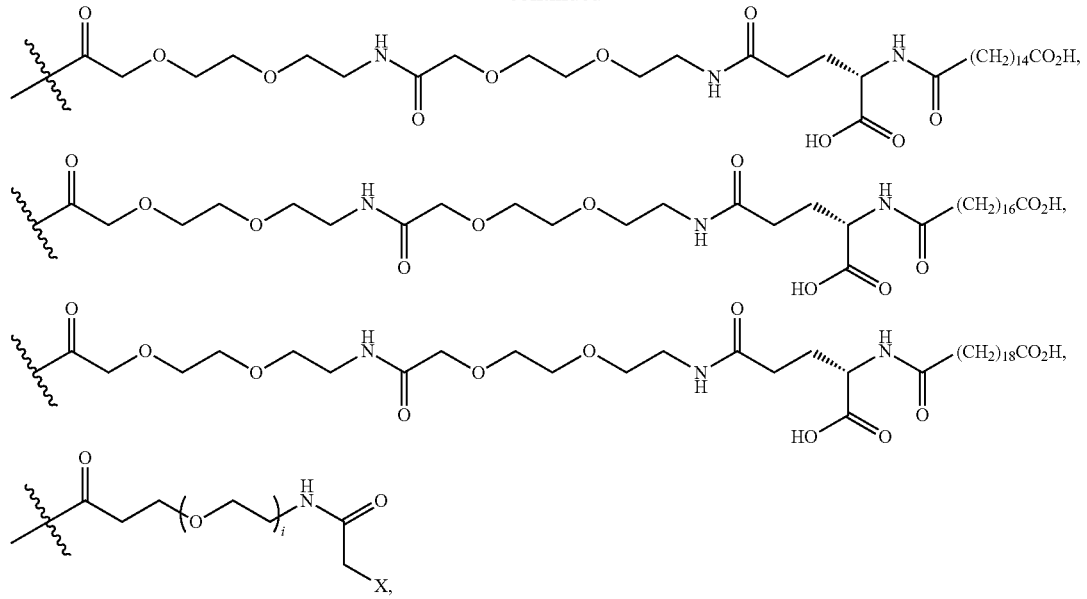
wherein i is an integer of 0 to 24, and X=Br, I or Cl, —C(O)CH$_2$Br, —C(O)CH$_2$I, or —C(O)CH$_2$Cl;
$Z_{23}$ is S or K, wherein the amino side chain of said K is optionally substituted with
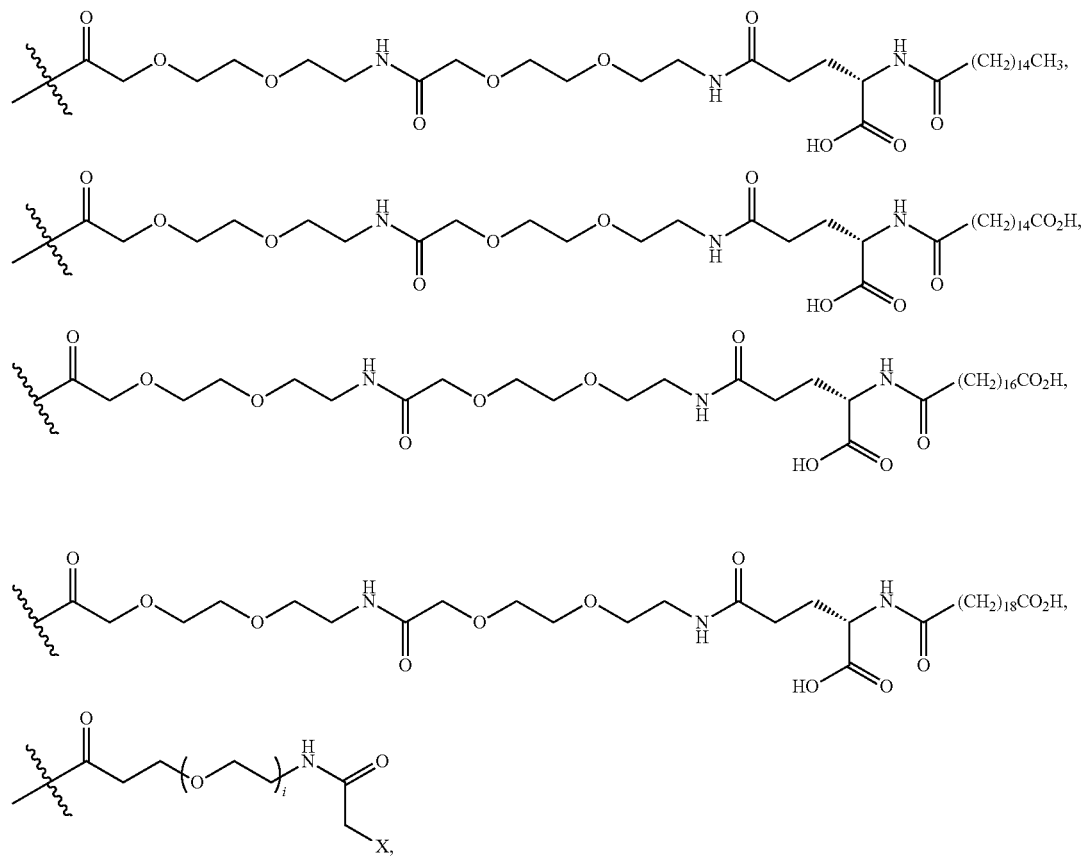

wherein i is an integer of 0 to 24, and X=Br, I or Cl, C(O)CH$_2$Br, —C(O)CH$_2$I, or —C(O)CH$_2$Cl
Z$_{26}$ is A or H;
Z$_{30}$ is L, W, absent, or K, provided that Z$_{30}$ is absent only when q is 1, wherein the amino side chain of said K is optionally substituted with
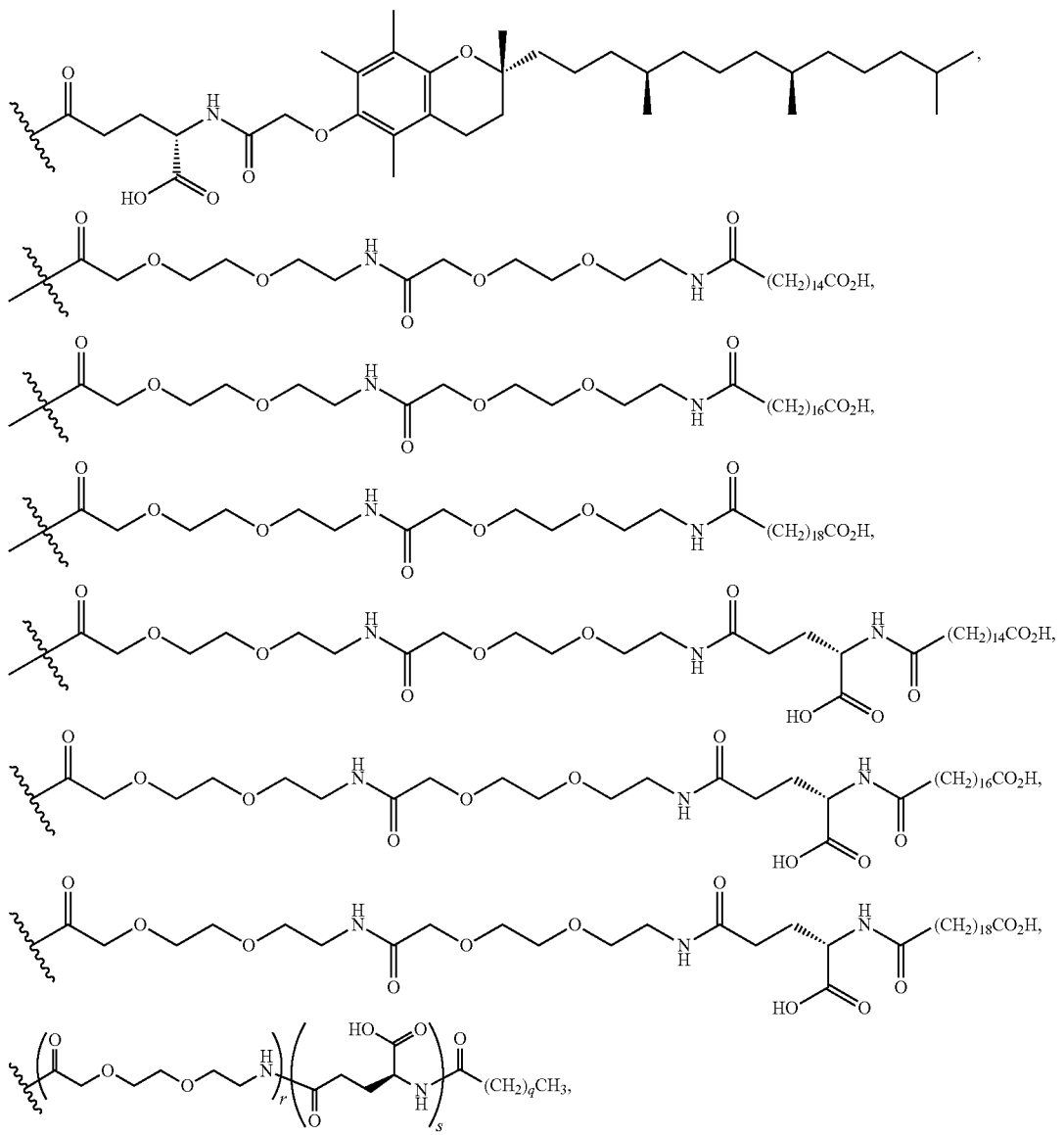
wherein r is 0, 1, or 2;
s is 0 or 1; and
q is 14, 16, or 18; or
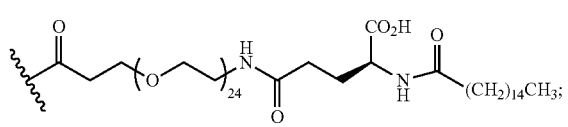
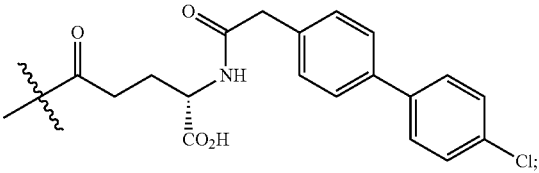

-continued
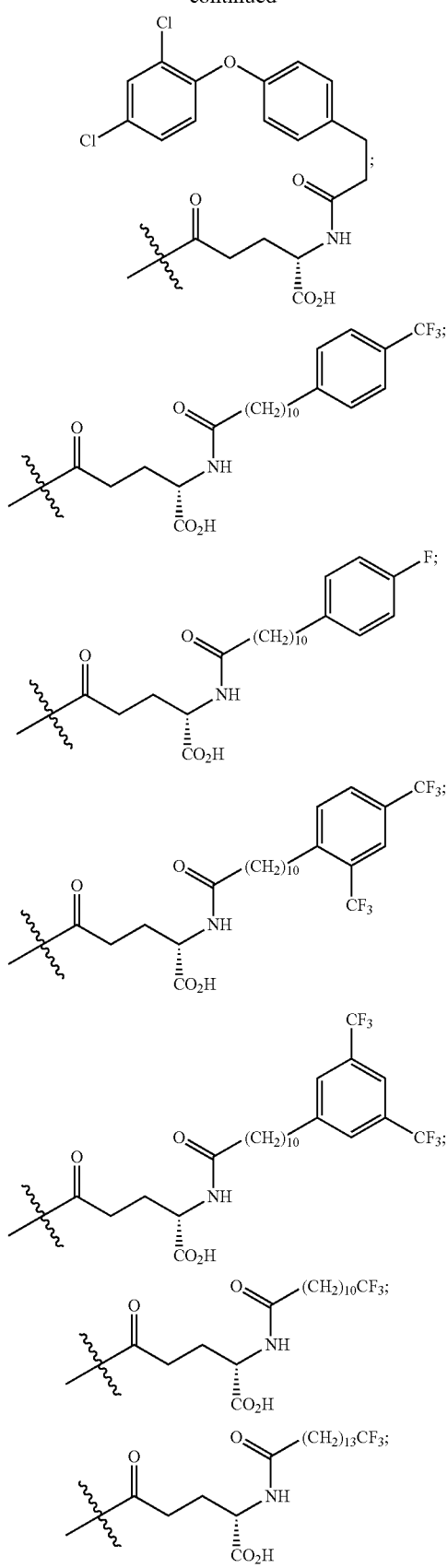
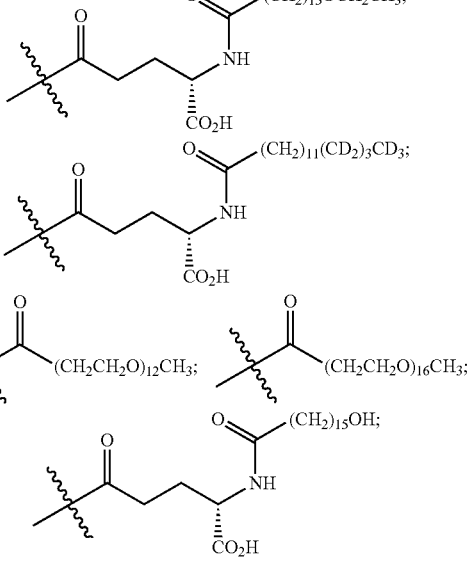
$Z_{34}$
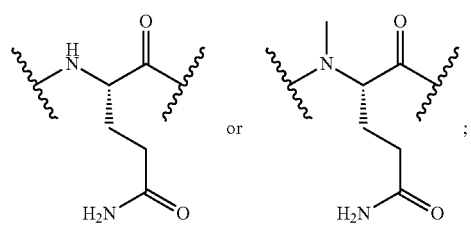 [SMILES: *N[C@@H](CCC(N)=O)C(*)=O ; *C(=O)[C@H](CCC(N)=O)N(*)C]
$Z_{35}$ is
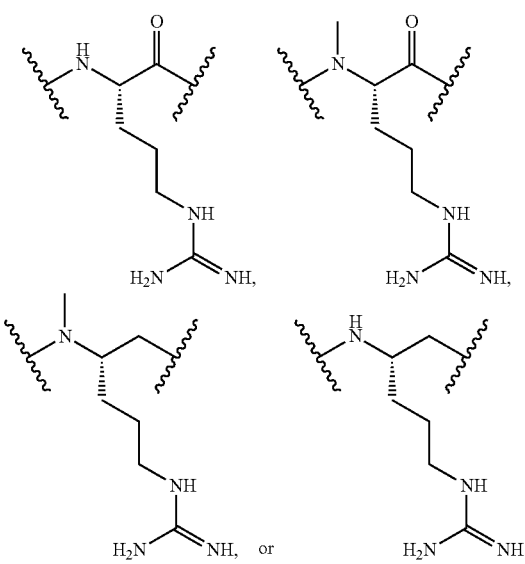
or a pharmaceutically acceptable salt thereof.
In another embodiment, the invention comprises the compound of Formula I or a derivative thereof, wherein:
p is 0 or 1;
m is 0, 1, 2, 3, or 5;

n is 1, 2, or 4;
q is 0 or 1; provided that q is 1 only when $Z_{30}$ is absent;
BRIDGE is -Ph-CH$_2$—S—, -triazolyl-, —NHC(O)CH$_2$S—, —(OCH$_2$CH$_2$)$_2$NHC(O)CH$_2$S—, —NHC(O)—, or —CH$_2$S—;
$Z_4$ is K, A, E, S, or R;
$Z_7$ is A or K, wherein the amino side chain of said K is substituted with

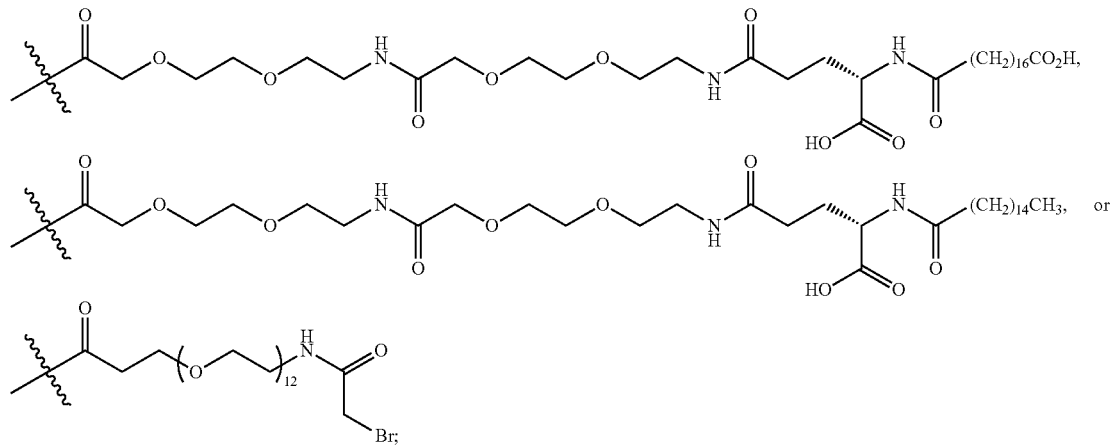

$Z_9$ is G or K, wherein the amino side chain of said K is substituted with

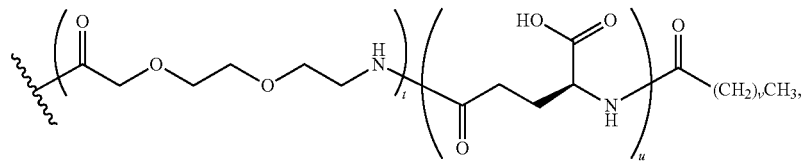

wherein t is 0;
u is 1; and
v is 14;
$Z_{11}$ is D or K, wherein the amino side chain of said K is optionally substituted with

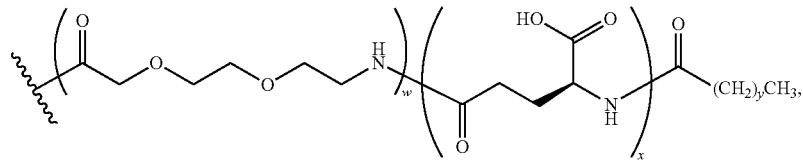

wherein w is 0, or 4;
x is 1; and
y is 14;

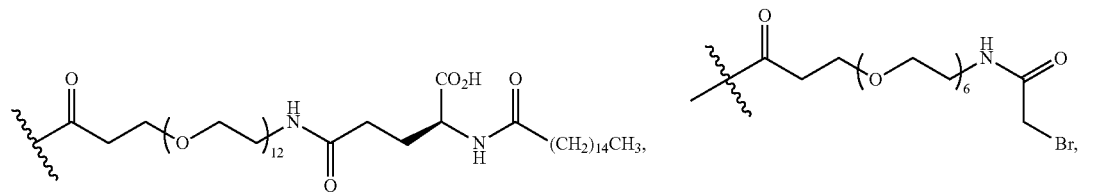

-continued
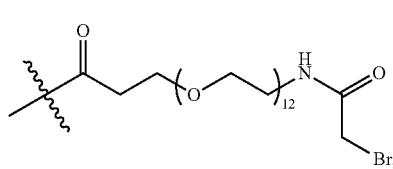 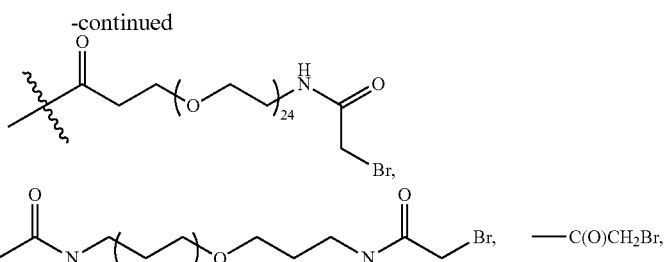
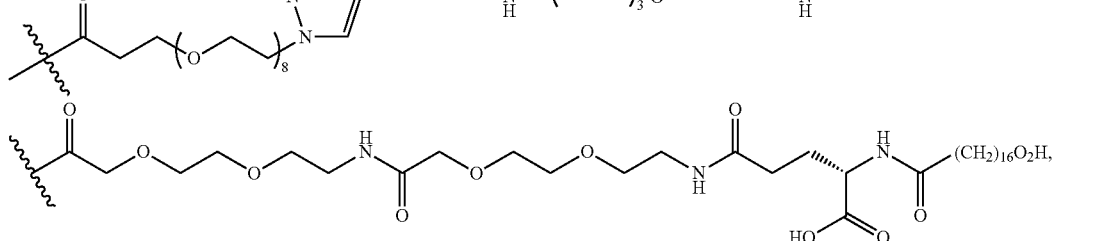
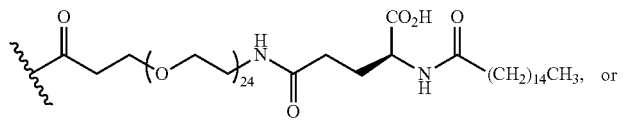
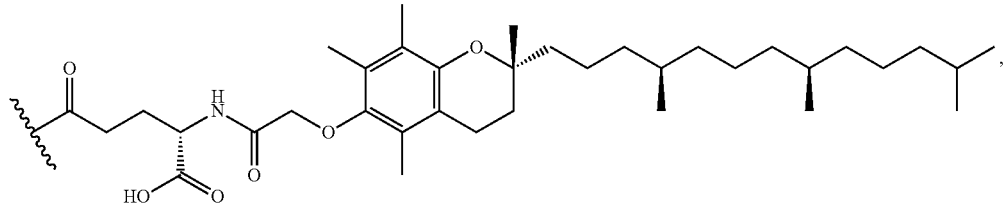
$Z_{22}$ is A or K, wherein the amino side chain of said K is substituted with
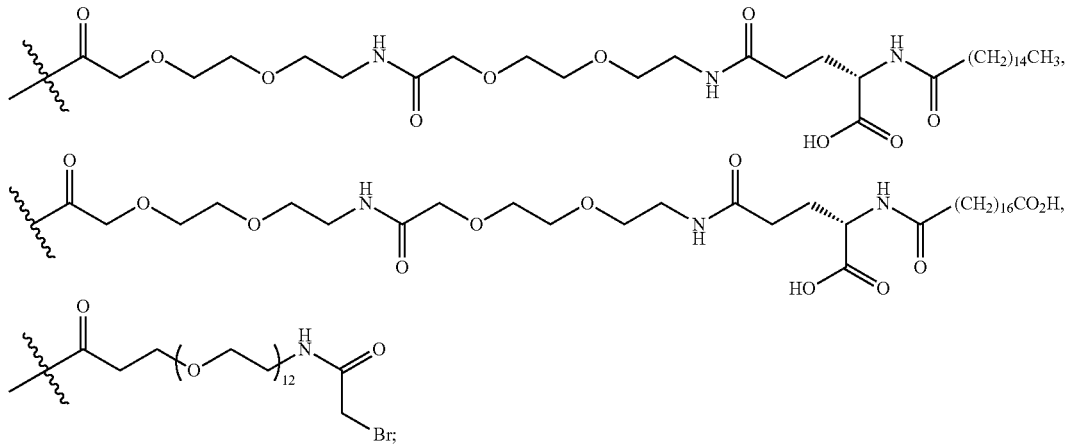
$Z_{23}$ is S or K, wherein the amino side chain of said K is substituted with
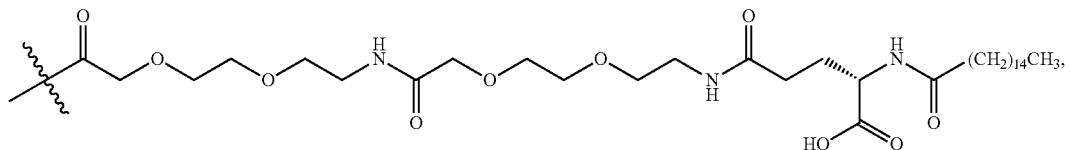

-continued
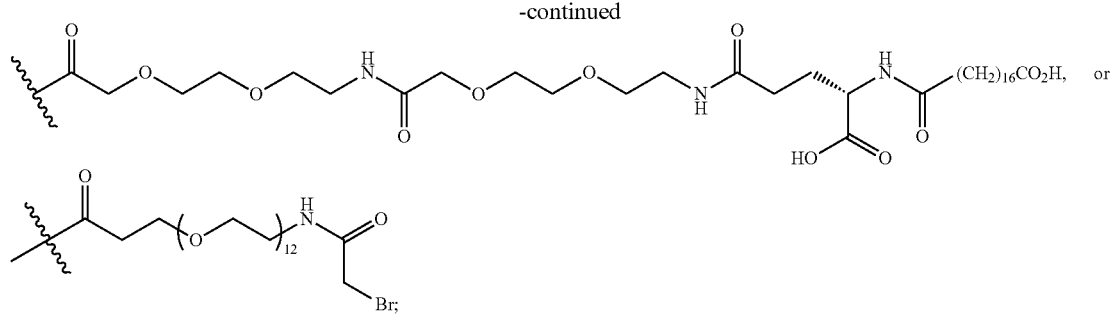
$Z_{26}$ is A or H;
$Z_{30}$ is L, W, absent, or K, provided that $Z_{30}$ is absent only when q is 1, wherein the amino side chain of said K is substituted with
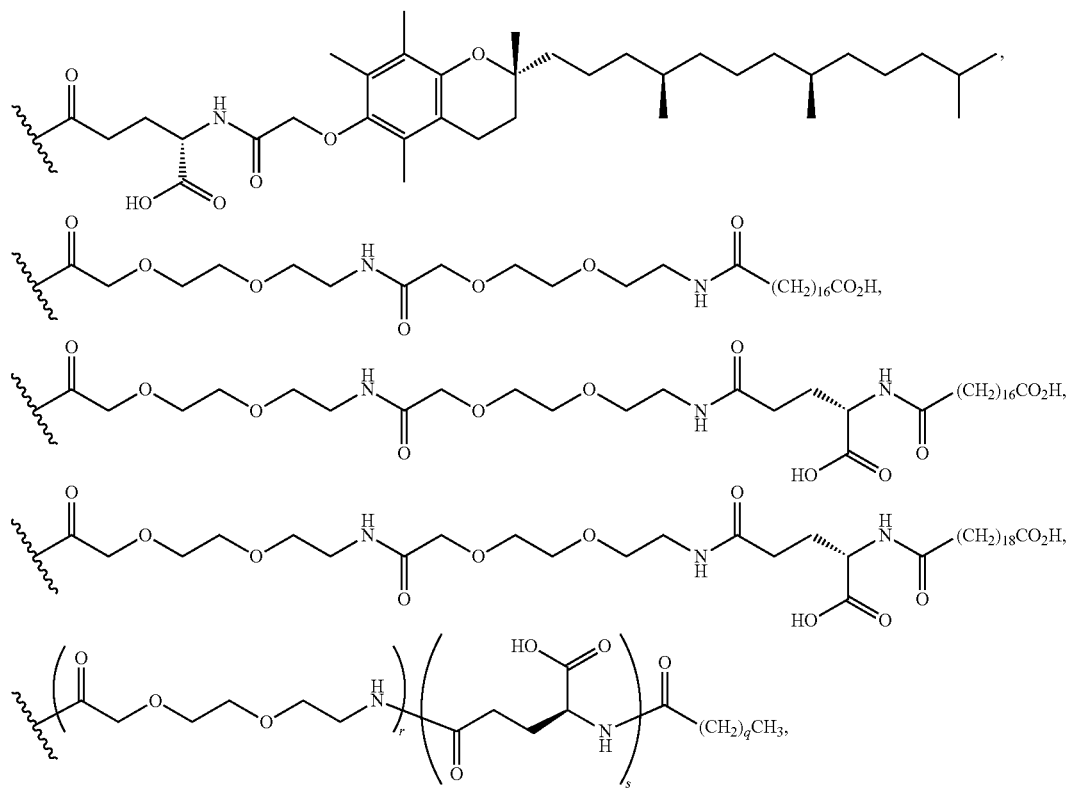
wherein r is 0, or 2;
s is 1; and
q is 14, 16, or 18; or
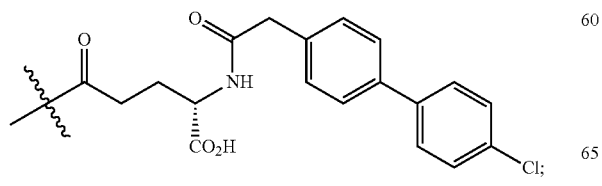
-continued
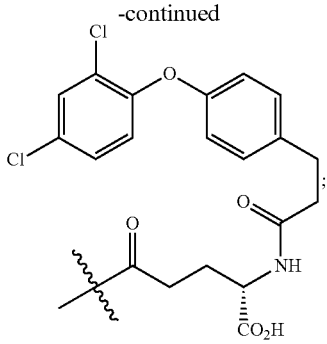

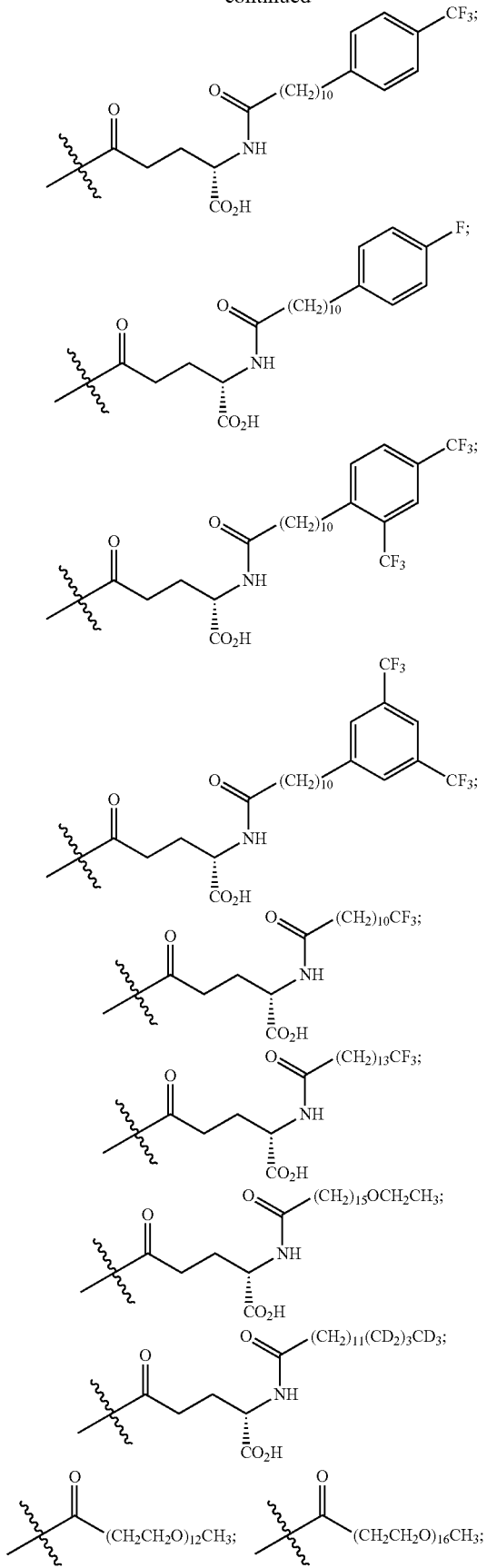

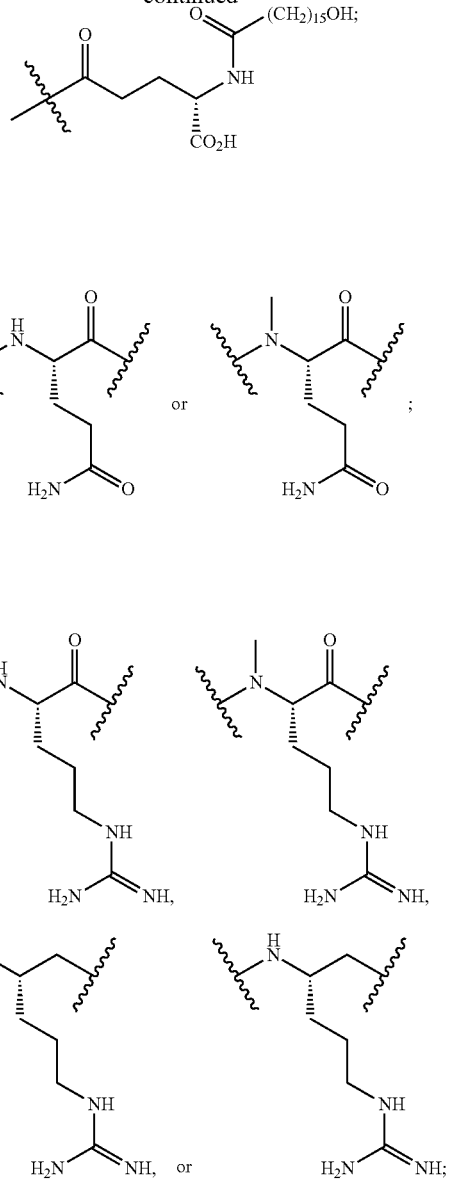

or a pharmaceutically acceptable salt thereof.

In another embodiment, the invention comprises the compound of Formula I or a derivative thereof, wherein:

p is 0 or 1;

m is 0, 1, 2, 3, or 5;

n is 1, 2, or 4;

q is 0 or 1; provided that q is 1 only when $Z_{30}$ is absent;

BRIDGE is -Ph-CH$_2$—S—, -triazolyl-, —NHC(O)CH$_2$S—, —(OCH$_2$CH$_2$)$_2$NHC(O)CH$_2$S, —NHC(O)—, or —CH$_2$S—;

$Z_4$ is K, A, E, S, or R;

$Z_7$ is A or K, wherein the amino side chain of said K is substituted with

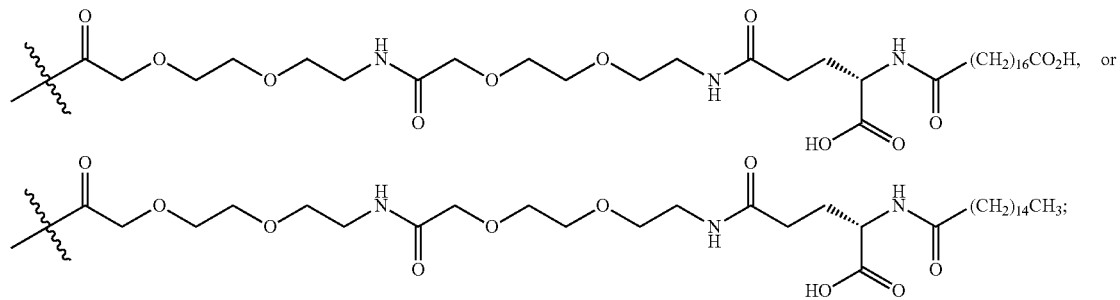
$Z_9$ is G or K, wherein the amino side chain of said K is substituted with
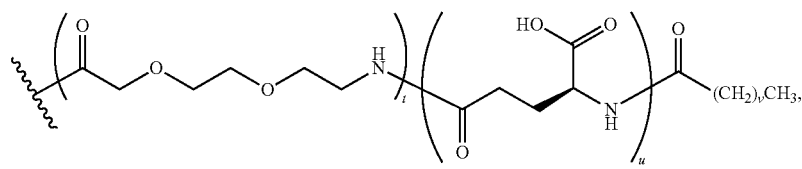
wherein t is 0;
u is 1; and
v is 14;
$Z_{11}$ is D or K, wherein the amino side chain of said K is optionally substituted with
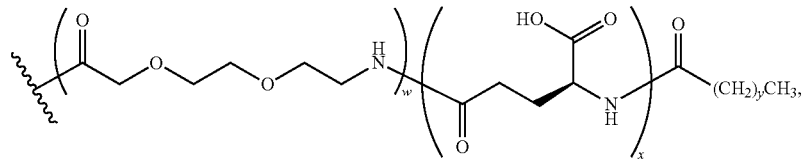
wherein w is 0, or 4;
x is 1; and
y is 14;
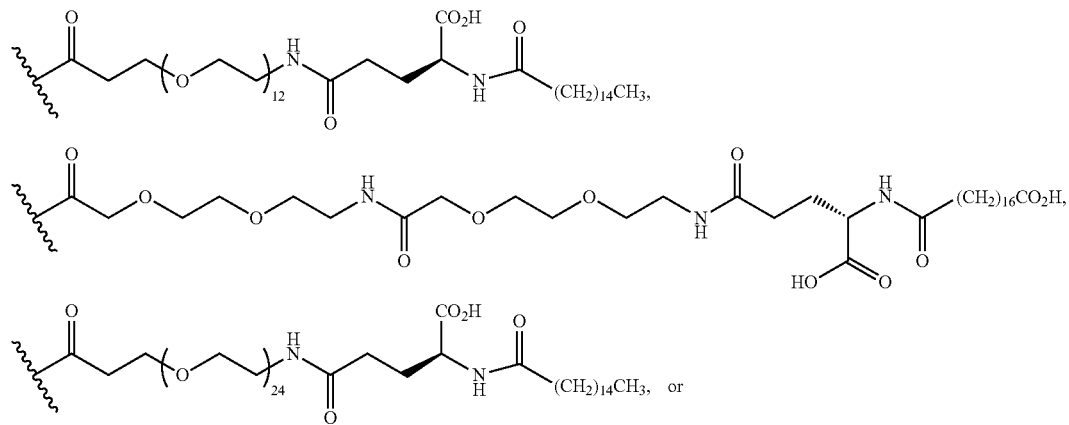

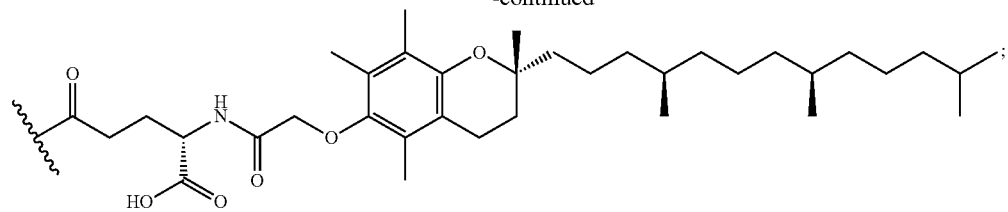
$Z_{22}$ is A or K, wherein the amino side chain of said K is substituted with
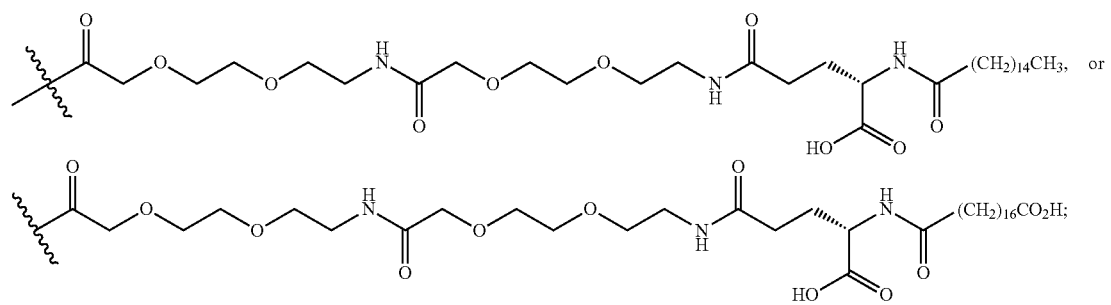
$Z_{23}$ is S or K, wherein the amino side chain of said K is substituted with
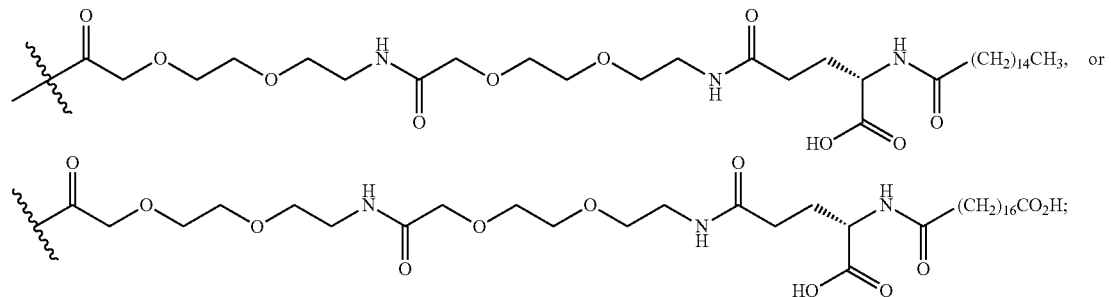
$Z_{26}$ is A or H;
$Z_{30}$ is L, W, absent, or K, provided that $Z_{30}$ is absent only when q is 1, wherein the amino side chain of said K is substituted with
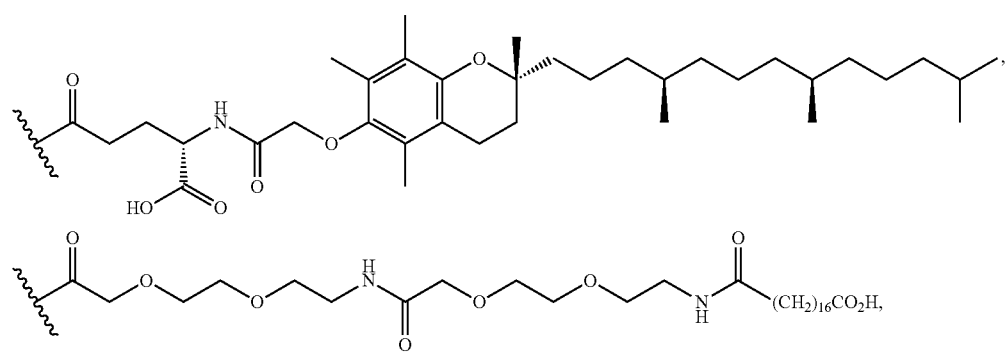

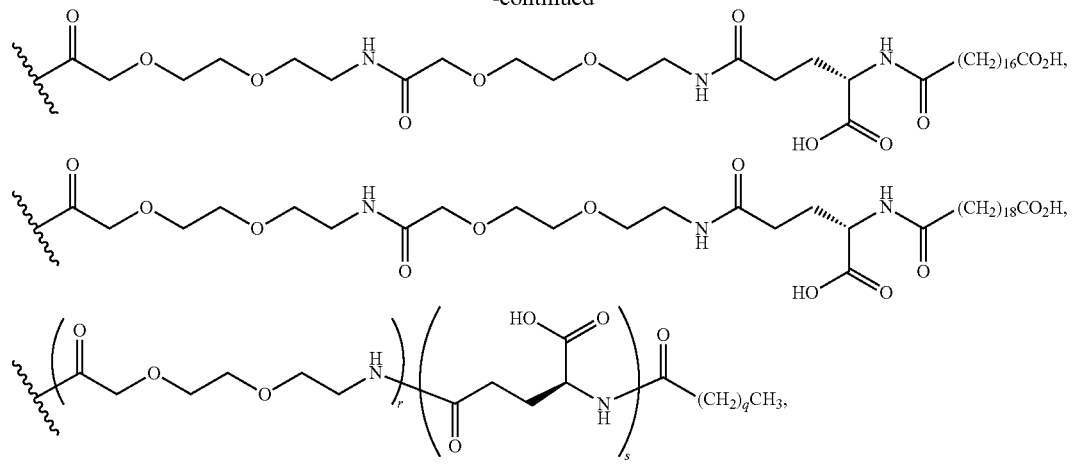
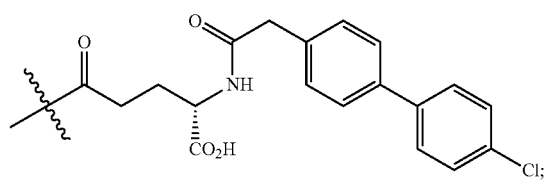
wherein r is 0, or 2;
s is 1; and
q is 14, 16, or 18; or
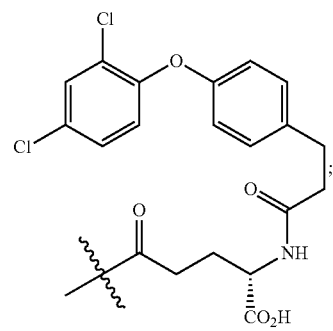
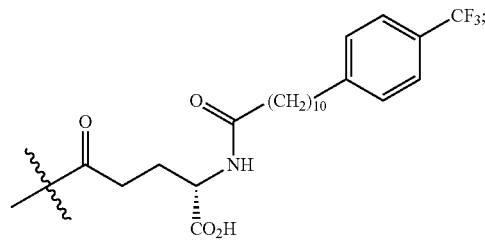
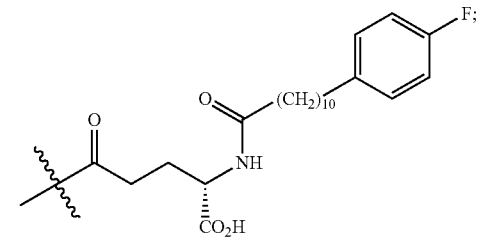
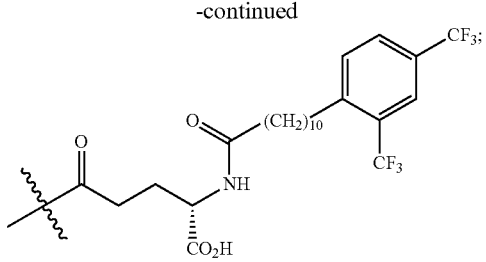
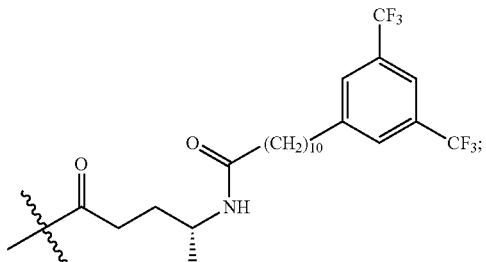
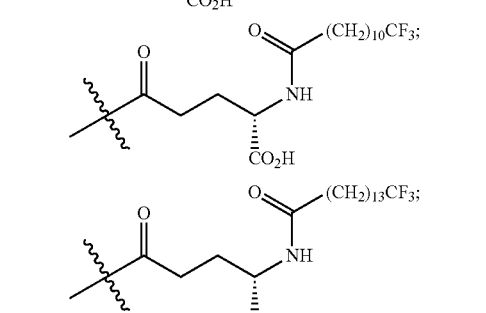
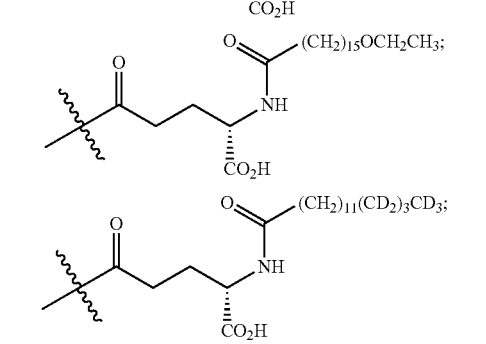
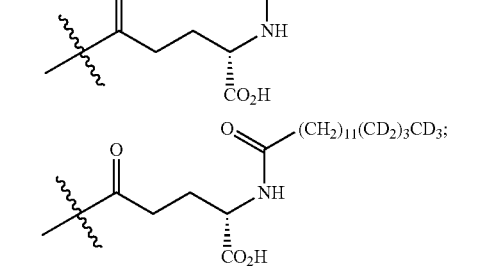

$Z_{34}$ is

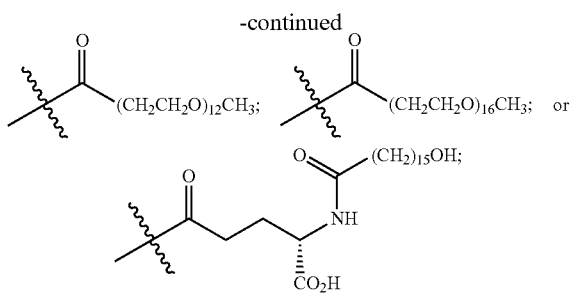

$Z_{35}$ is

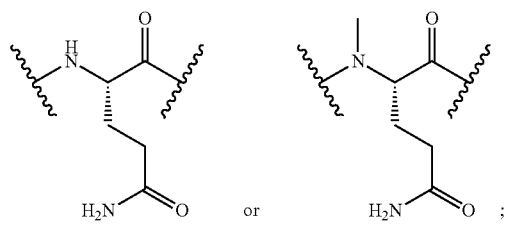 [SMILES: *N[C@@H](CCC(N)=O)C(*)=O ; *C(=O)[C@H](CCC(N)=O)N(*)C]

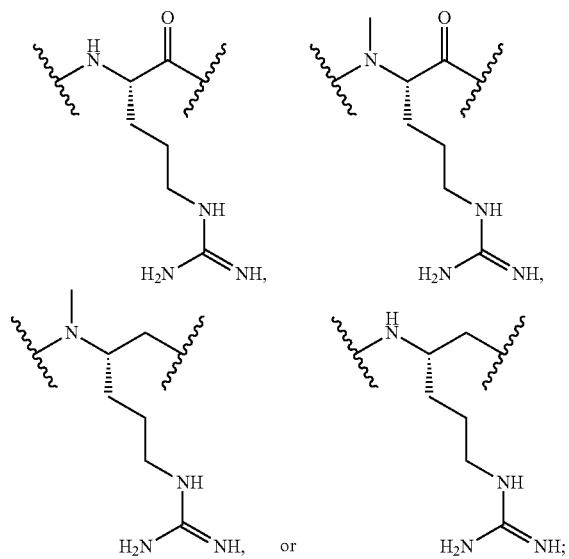

or a pharmaceutically acceptable salt thereof.

Another embodiment of the invention is a compound of Formula I or a derivative thereof, selected from the group consisting of SEQ ID NO: 1 to SEQ ID NO: 110, or a pharmaceutically acceptable salt thereof.

Another embodiment of the invention is a compound of Formula I or a derivative thereof, selected from the group consisting of SEQ ID NO: 2 to SEQ ID NO: 72, or a pharmaceutically acceptable salt thereof.

Another general aspect of the invention relates to a conjugate comprising a compound of Formula I, a derivative or a pharmaceutically acceptable salt thereof and a half-life extension moiety conjugated thereto. As used herein, the term "conjugated" refers to a compound of the invention covalently linked to or covalently connected to a half-life extension moiety, directly or via a linker. In the present disclosure, with respect to a compound of Formula I, a derivative or a pharmaceutically acceptable salt thereof, the phrase "a conjugate comprising a compound and a half-life extension moiety conjugated thereto" is used interchangeably with the phrase "a compound conjugated to a half-life extension moiety."

As used herein, the term "linker" refers to a chemical module comprising a covalent or atomic chain that covalently connects a compound of the invention to a half-life extension moiety. The linker can, for example, include, but is not limited to, a peptide linker, a hydrocarbon linker, a polyethylene glycol (PEG) linker, a polypropylene glycol (PPG) linker, a polysaccharide linker, a polyester linker, a hybrid linker consisting of PEG and an embedded heterocycle, and a hydrocarbon chain. The linker can, for example, be first covalently connected to a compound of the invention, then covalently connected to a half-life extension moiety.

As used herein, a "half-life extension moiety" is used interchangeably with the term "half-life extending moiety." Exemplary half-life extension moieties include, but are not limited to, monoclonal antibodies or fragments thereof, albumin, albumin variants, albumin-binding proteins and/or domains, transferrin and fragments and analogues thereof. Additional half-life extension moieties that can be incorporated into the conjugates of the invention include, for example, polyethylene glycol (PEG) molecules, such as PEG5000 or PEG20,000, α-tocopherolyl, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties.

The compounds of the invention can be covalently linked to one or more of half-life extension moieties using methods known in the art in view of the present disclosure. For example, as illustrated by the Examples below, a half-life extension moiety, such as a PEG moiety or a lipophilic moiety, can be added to a peptide molecule of the invention, e.g., by incorporating a cysteine or lysine residue to the molecule and attaching the half-life extension moiety to the cysteine or lysine using well known methods. Examples of compounds of the invention conjugated to a monoclonal antibody as the half-life extension moiety are also described in U.S. Provisional Patent Application No. 62/413,586, filed on Oct. 27, 2016, and U.S. patent application Ser. No. 15/794,171 entitled "Antibody-coupled cyclic peptide tyrosine tyrosine compounds as modulators of neuropeptide receptors," the contents of both applications are hereby incorporated by reference in their entireties.

According to embodiments of the invention, an electrophile is introduced onto a sidechain of a cyclic PYY of the invention, such as bromoacetamide or maleimide, that reacts site specifically with the sulfhydryl group of the Cys residue engineered into a half-life extension moiety, such as a monoclonal antibody or fragment thereof, thereby creating a covalent linkage between the cyclic PYY peptide and the half-life extension moiety. A compound of the invention can be covalently linked to one or more of half-life extension moieties directly, or through a linker. Linkers useful for the invention include, but are not limited to, a peptide linker, a hydrocarbon linker, a polyethylene glycol (PEG) linker, a polypropylene glycol (PPG) linker, a polysaccharide linker, a polyester linker, or a hybrid linker consisting of PEG and an embedded heterocycle. In certain embodiments, the half-life extension moiety with a linker, can be conjugated to a compound of the invention at one or more amino acid positions of the cyclic PYY, such as amino acid residue 4, 7, 9, 10, 11, 13, 14, 15, 16, 17, 18, 19, 20, 21, 22, 23, 24, 26, 30, or 31 of the PYY using methods known in the art. In certain embodiments, the half-life extension moiety without a linker, can be conjugated to a compound of the invention at one or more amino acid positions of the cyclic PYY, such as amino acid residue 4, 7, 9, 10, 11, 13, 14, 15, 16, 17, 18, 19, 20, 21, 22, 23, 24, 26, 30, or 31 of the PYY using methods known in the art. The amino acid residue numbering follows that of hPYY3-36. Any of the compounds of the present invention, including but not limited to SEQ ID NO: 1 to SEQ ID NO: 110 can be conjugated to a half-life extension moiety, directly or indirectly through a linker. According to embodiments of the invention, a compound selected from the group consisting of SEQ ID NO: 74, 95, 98, 99, 100, 101, 102, 103, 104, 105, 106, 107, 108, 109 and 110, or a pharmaceutical acceptable salt thereof, can be covalently linked to a half-life extension moiety, such as a monoclonal antibody or a fragment thereof, via a linker.

A peptide molecule of the invention, or a conjugate comprising the peptide molecule covalently linked to one or more half-life extension moieties can be assayed for functionality by known assays in view of the present disclosure. For example, the biological or pharmacokinetic activities of a peptide molecule of the invention, alone or in a conjugate according to the invention, can be assayed using known in vitro or in vivo assays and compared.

In one embodiment, the present invention comprises a compound of Formula II

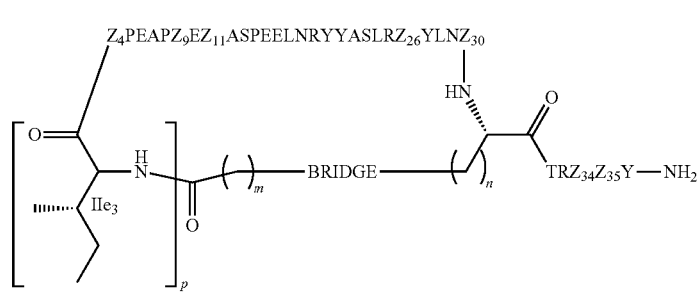

Formula II wherein
p is 0 or 1;
m is 0, 1, 2, 3, 4, or 5;
n is 1, 2, 3, or 4;
BRIDGE is -Ph-CH$_2$—S—, -triazolyl-, or —NHC(O)CH$_2$S—;
Z$_4$ is K, A, E, or S;
Z$_9$ is G or K, wherein the amino side chain of said K is substituted with

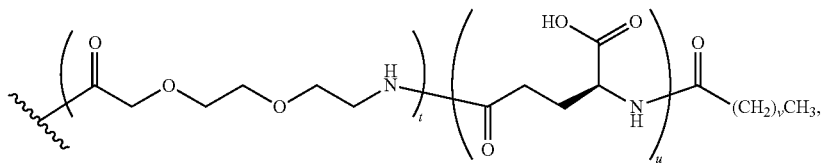

wherein t is 0, 1, or 2;
u is 0 or 1; and
v is 14, 16, or 18;

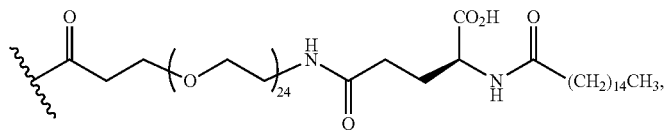

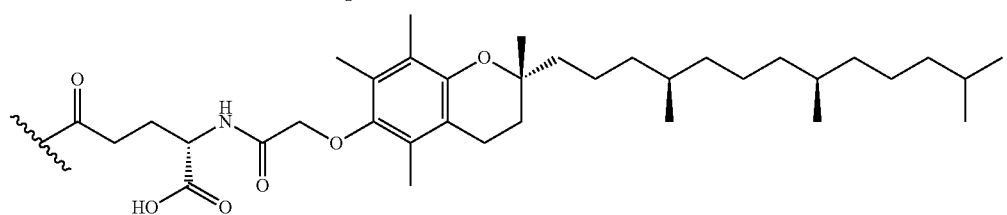

,

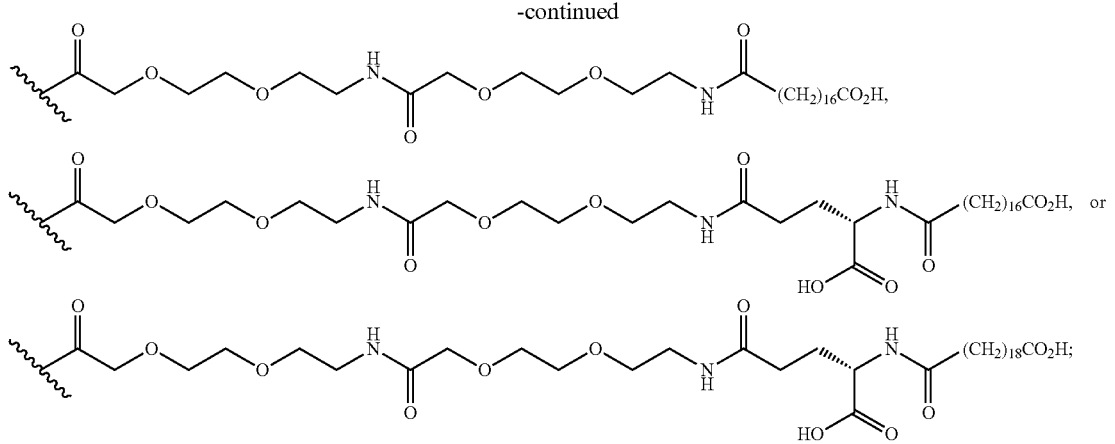
$Z_{11}$ is D or K, wherein the amino side chain of said K is substituted with
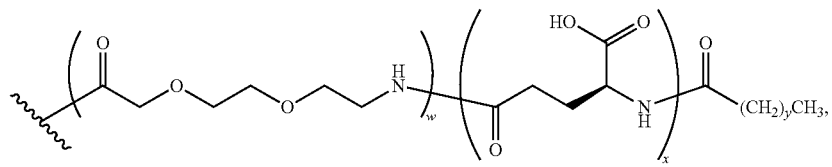
wherein w is 0, 1, or 2;
x is 0 or 1; and
y is 14, 16, or 18;
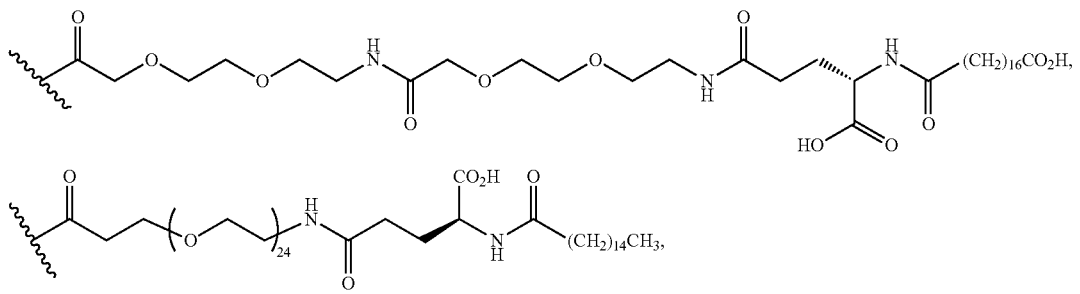
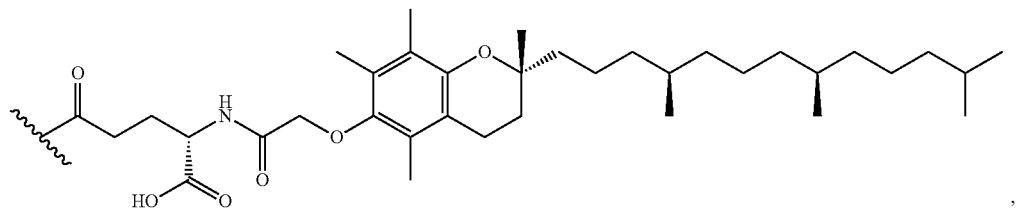
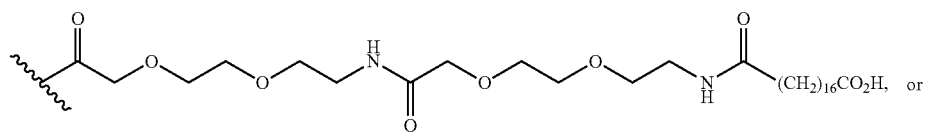

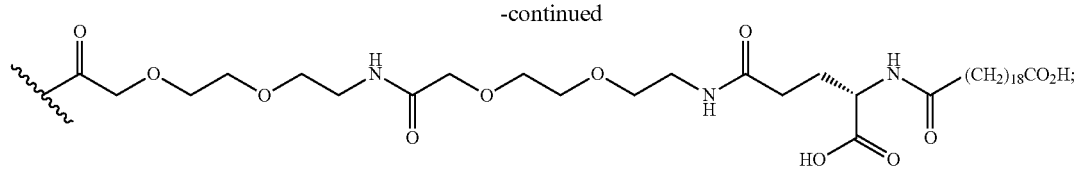
$Z_{26}$ is A or H;
$Z_{30}$ is L or K, wherein the amino side chain of said K is substituted with
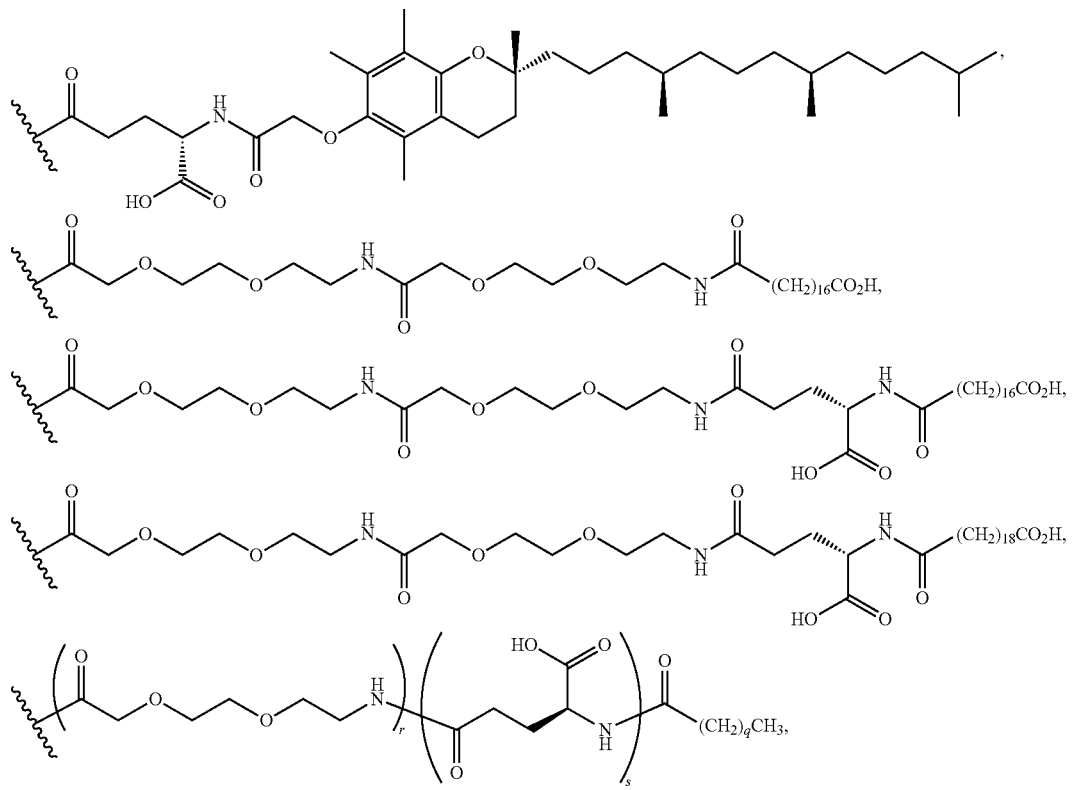
wherein $r$ is 0, 1, or 2;
$s$ is 0 or 1; and
$q$ is 14, 16, or 18; or
$Z_{34}$ is
$Z_{35}$ is
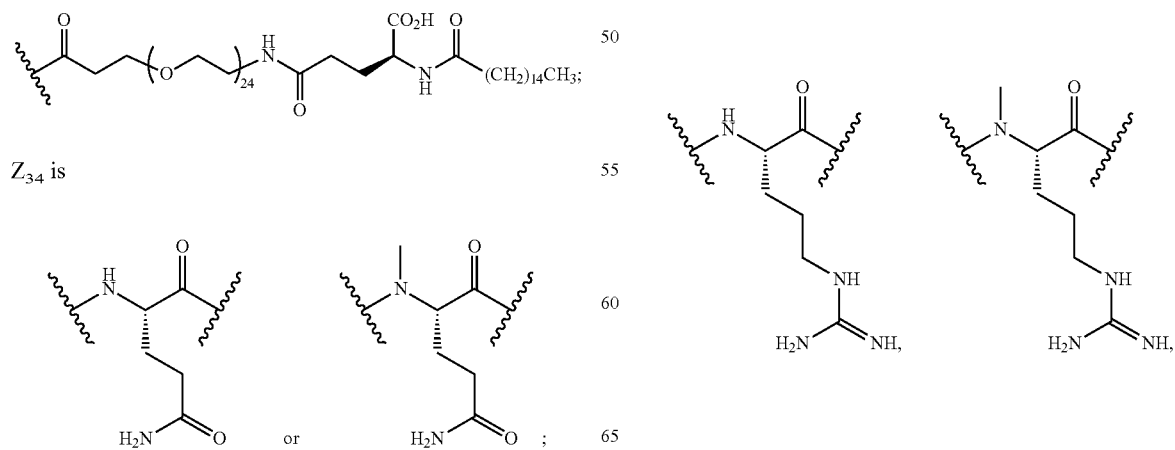

-continued

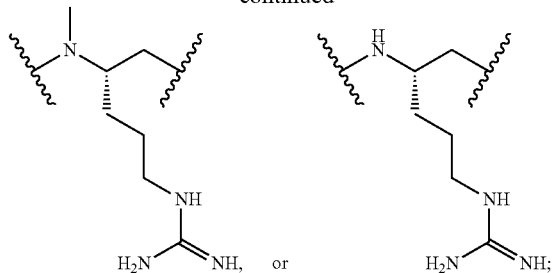

or a pharmaceutically acceptable salt thereof.

In another embodiment, the present invention comprises a compound of Formula II, wherein:
p is 0 or 1;
m is 0, 2, 3, or 5;
n is 1, 2, or 4;
BRIDGE is -Ph-CH$_2$—S—, -triazolyl-, or —NHC(O)CH$_2$S—;
$Z_4$ is K, A, E, or S;
$Z_9$ is G or K, wherein the amino side chain of said K is substituted with

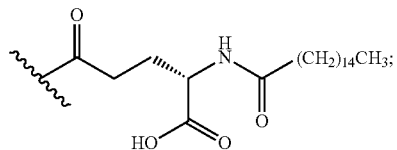

$Z_{11}$ is D or K, wherein the amino side chain of said K is substituted with

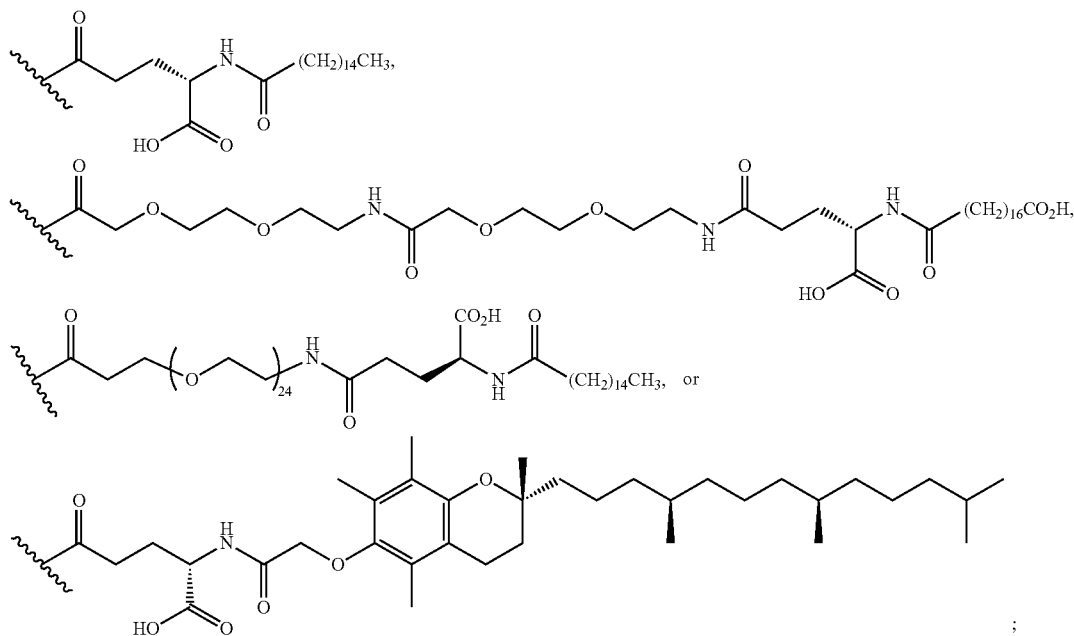

$Z_{26}$ is A or H;
$Z_{30}$ is L or K, wherein the amino side chain of said K is substituted with

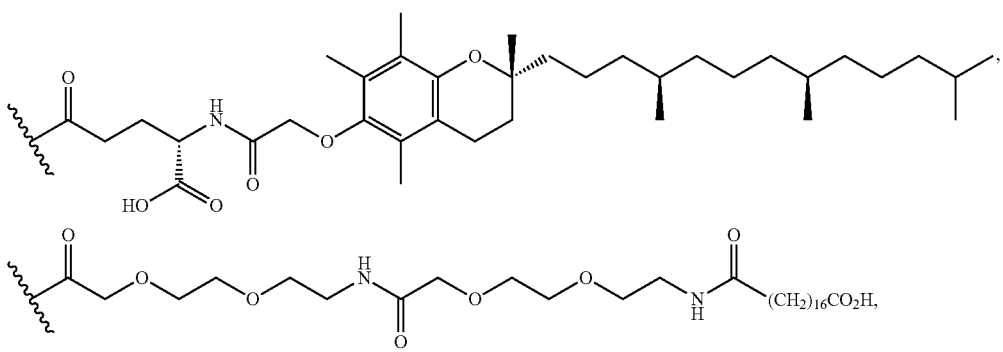

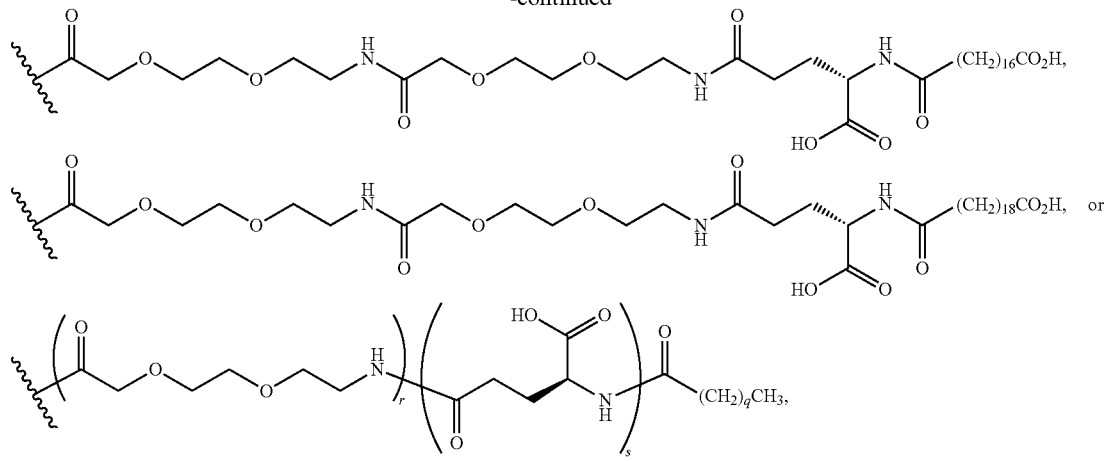

wherein r is 0, or 2;
s is 0 or 1; and
q is 14, 16, or 18;
$Z_{34}$ is

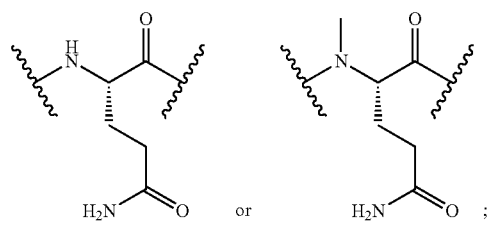 [SMILES: *N[C@@H](CCC(N)=O)C(*)=O ; *C(=O)[C@H](CCC(N)=O)N(*)C]

$Z_{35}$ is

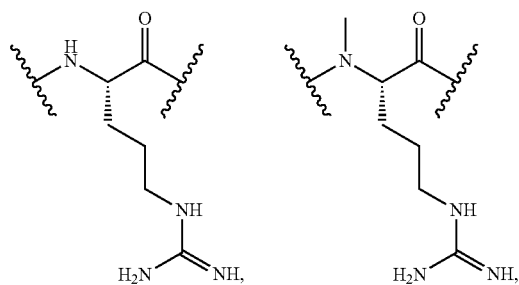

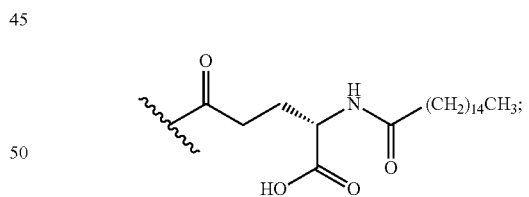

or a pharmaceutically acceptable salt thereof.

In another embodiment, the present invention comprises a compound of Formula II, wherein
p is 0 or 1;
m is 0, 2, 3, or 5;
n is 1, 2, or 4;
BRIDGE is -Ph-CH$_2$—S—, -triazolyl-, or —NHC(O)CH$_2$S—;
$Z_4$ is K, A, E, or S;
$Z_9$ is G or K, wherein the amino side chain of said K is substituted with

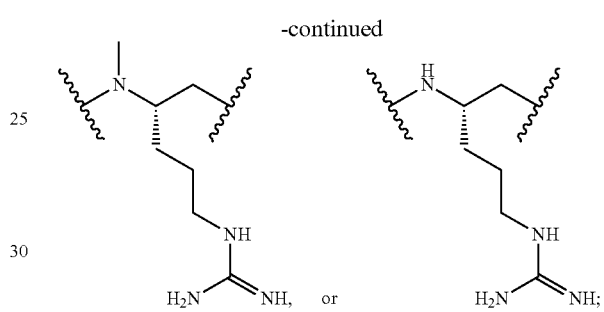

$Z_{11}$ is D or K, wherein the amino side chain of said K is substituted with

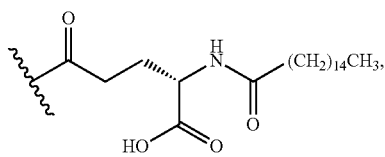

-continued
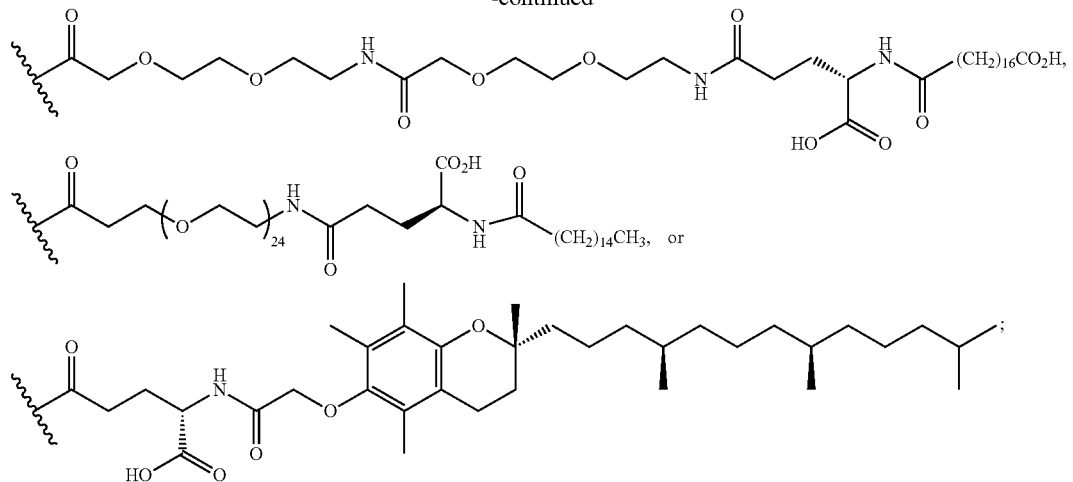
$Z_{26}$ is A or H;
$Z_{30}$ is L or K, wherein the amino side chain of said K is substituted with
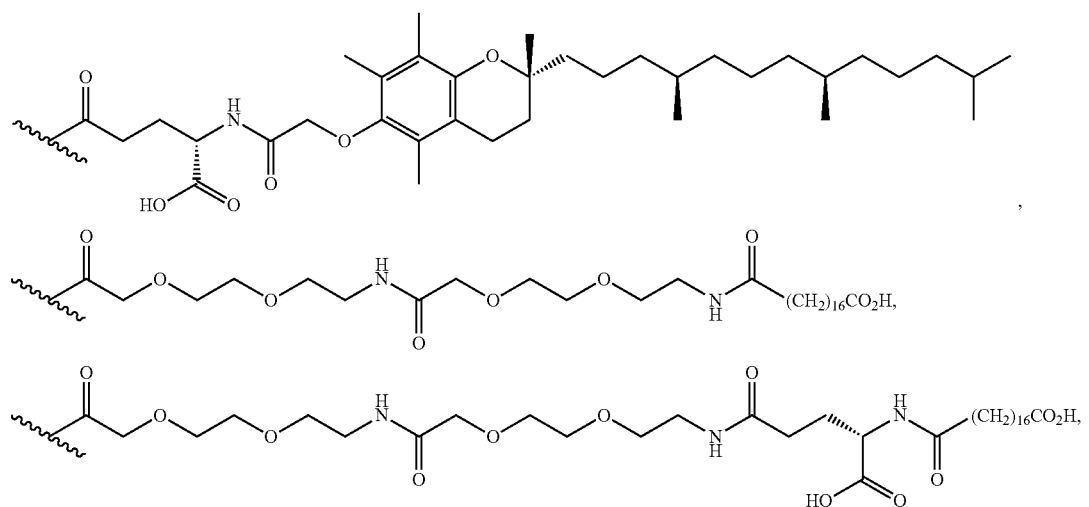
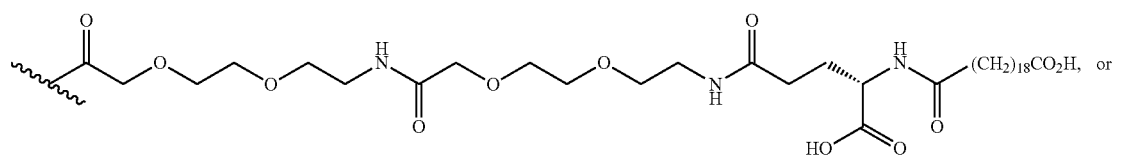
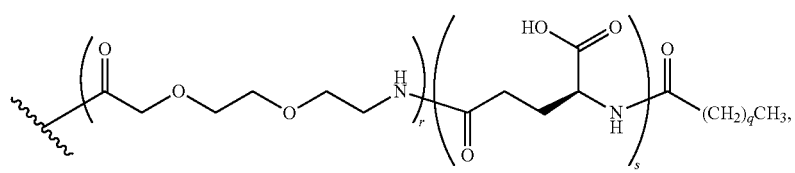

wherein r is 0, or 2;
s is 0 or 1; and
q is 14, 16, or 18;

$Z_{34}$ is

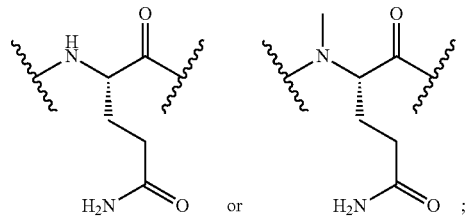

$Z_{35}$ is

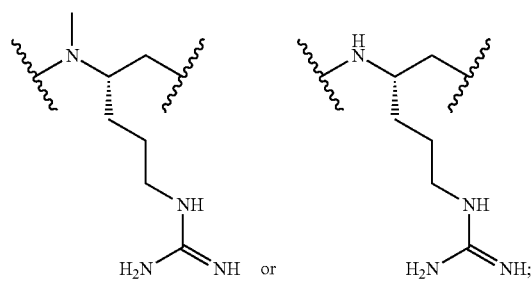 [SMILES: *C[C@H](CCCNC(=N)N)N(*)C ; *C[C@H](CCCNC(=N)N)N*]

or a pharmaceutically acceptable salt thereof.

In another embodiment, the present invention comprises a compound of Formula II, wherein:
p is 0 or 1;
m is 0, 2, 3, or 5;
n is 1, 2, or 4;
BRIDGE is -Ph-CH$_2$—S—, -triazolyl-, or —NHC(O)CH$_2$S—;
$Z_4$ is K, A, E, or S;
$Z_9$ is G or K, wherein the amino side chain of said K is substituted with

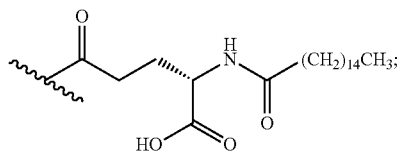

$Z_{11}$ is D or K, wherein the amino side chain of said K is substituted with

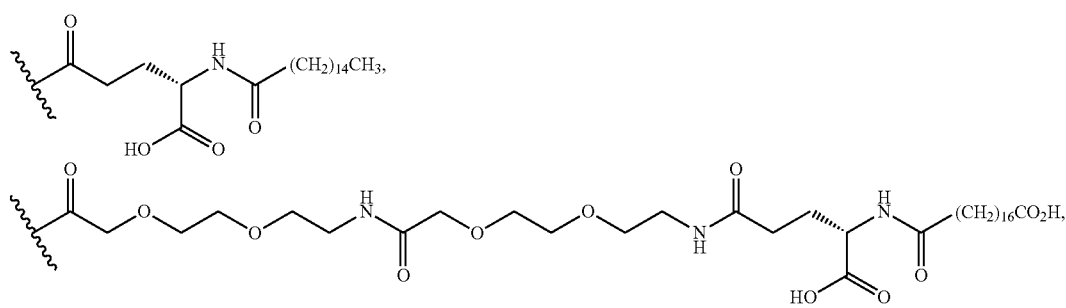

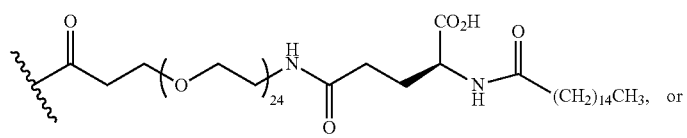

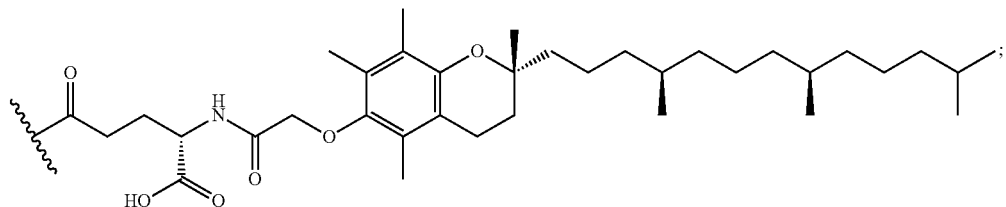

$Z_{26}$ is A or H;
$Z_{30}$ is L or K, wherein the amino side chain of said K is substituted with

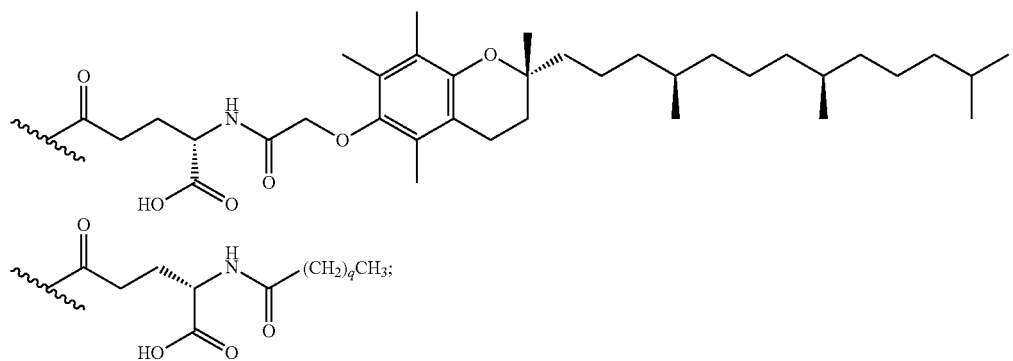

, or wherein q is 14, 16, or 18;
Z$_{34}$ is

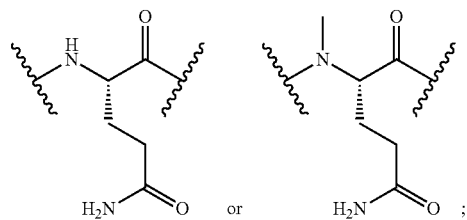 [SMILES: *N[C@@H](CCC(N)=O)C(*)=O ; *C(=O)[C@H](CCC(N)=O)N(*)C]

Z$_{35}$ is

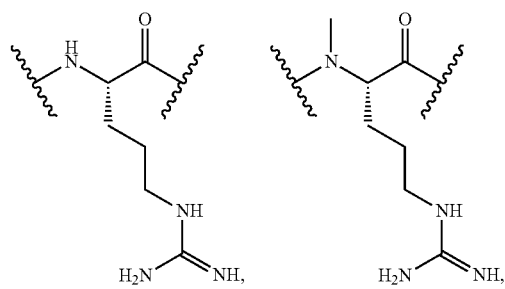

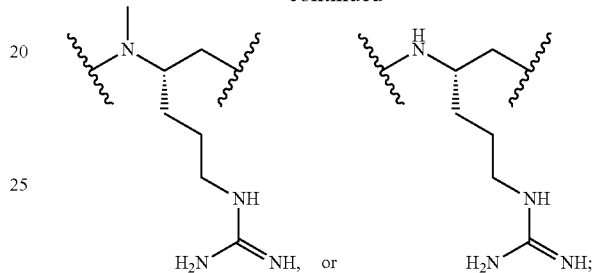

or a pharmaceutically acceptable salt thereof.

In another embodiment, the present invention comprises a compound of Formula II, wherein:
p is 0 or 1;
m is 0, 2, 3, or 5;
n is 1, 2, or 4;
BRIDGE is -Ph-CH$_2$—S—, -triazolyl-, or —NHC(O)CH$_2$S—;
Z$_4$ is K, A, E, or S;
Z$_9$ is G or K, wherein the amino side chain of said K is substituted with

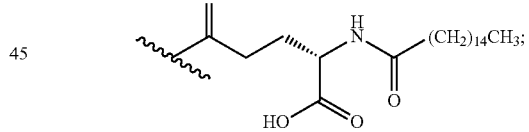

Z$_{11}$ is D or K, wherein the amino side chain of said K is substituted with

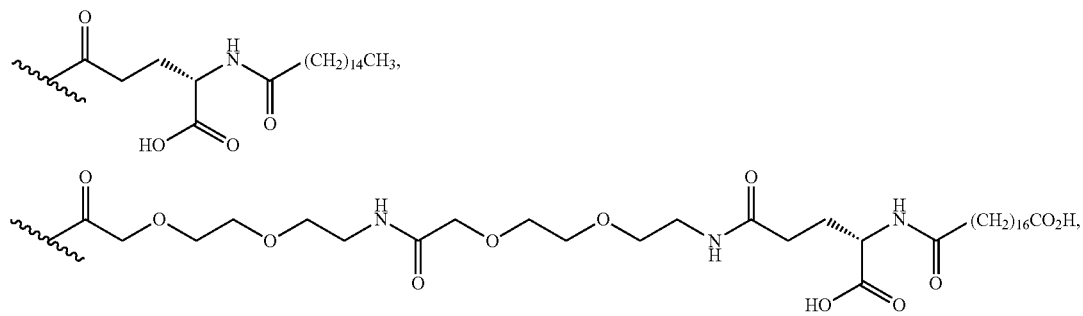

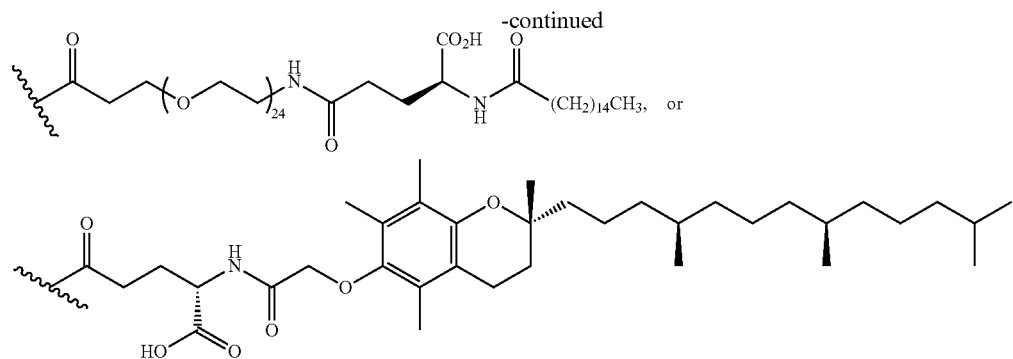

$Z_{26}$ is A or H;
$Z_{30}$ is L or K, wherein the amino side chain of said K is substituted with

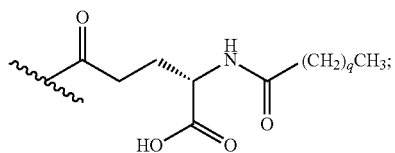

wherein q is 14, 16, or 18;
$Z_{34}$ is

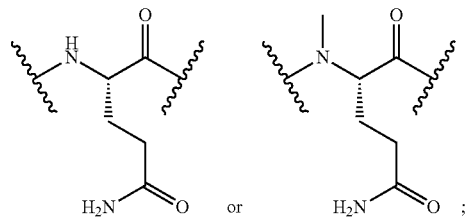

$Z_{35}$ is

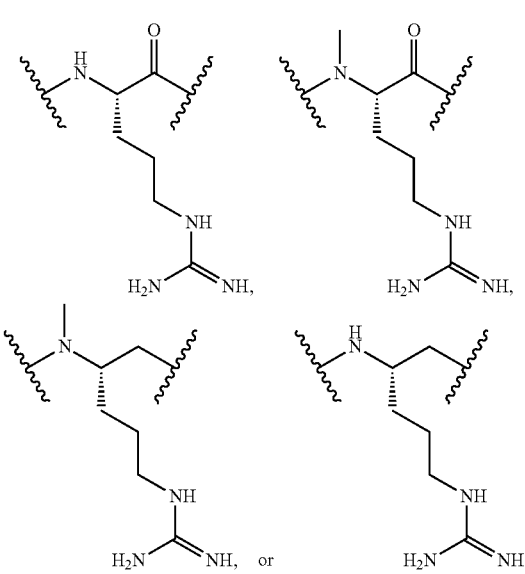

or a pharmaceutically acceptable salt thereof.

In another embodiment, the present invention comprises a compound of Formula II, wherein:
p is 0 or 1;
m is 0, 2, 3, or 5;
n is 1, 2, or 4;
BRIDGE is -Ph-CH$_2$-S-, -triazolyl-, or -NHC(O)CH$_2$S-;
$Z_4$ is K, A, E, or S;
$Z_9$ is G;
$Z_{11}$ is D;
$Z_{26}$ is A or H;
$Z_{30}$ is L or K, wherein the amino side chain of said K is substituted with

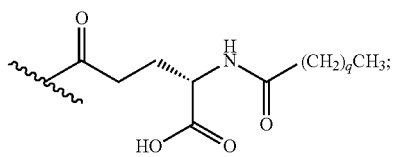

wherein q is 14, 16, or 18;
$Z_{34}$ is

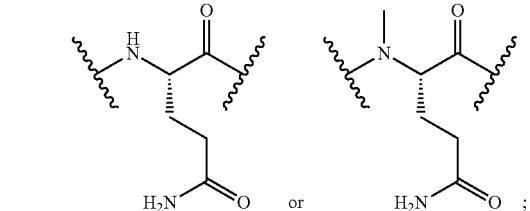

$Z_{35}$ is

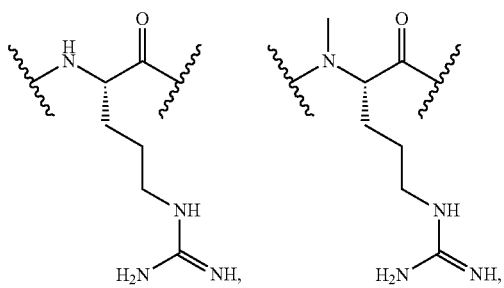

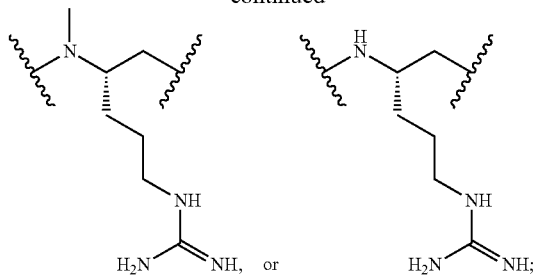

or a pharmaceutically acceptable salt thereof.

In another embodiment, the present invention comprises a compound of Formula II selected from the group consisting of SEQ ID NO: 2 to SEQ ID NO: 46.

Another embodiment of the invention comprises N-terminus to side chain cyclic analogues of PYY exhibiting at least 70%, 75% 80%, 85%, 90%, 95%, or 99% sequence identity to hPYY$_{(3-36)}$. As an example of a method for determination of the sequence identity between two analogues the two peptides food intake as well as its anti-secretory and pro-absorptive effects in the gastrointestinal tract in mammals, PYY3-36 may be effective in treating obesity and associated conditions as well as in a number of gastrointestinal disorders. However, the therapeutic utility of PYY3-36 itself as a treatment agent is limited by its rapid metabolism and short circulating half-life. Thus, the present invention is generally directed to modified PYY3-36 conjugates, which extend the half-life of the PYY3-36 peptide and reduces the metabolism of the peptide in vivo.

In certain embodiments of the invention, the modified PYY3-36 peptides are cyclic PYY peptides. The terms "cyclic PYY peptide," "cyclic PYY3-36 analog," and "cyclic PYY3-36 peptide analog" can be used interchangeably.

As used herein, the term "NTSC-PYY" is intended to describe N-terminus-to-side-chain cyclic analogues of PYY.

The peptide sequences described herein are written according to the usual convention whereby the N-terminal region of the peptide is on the left and the C-terminal region is on the right. Although isomeric forms of the amino acids are known, it is the L-form of the amino acid that is

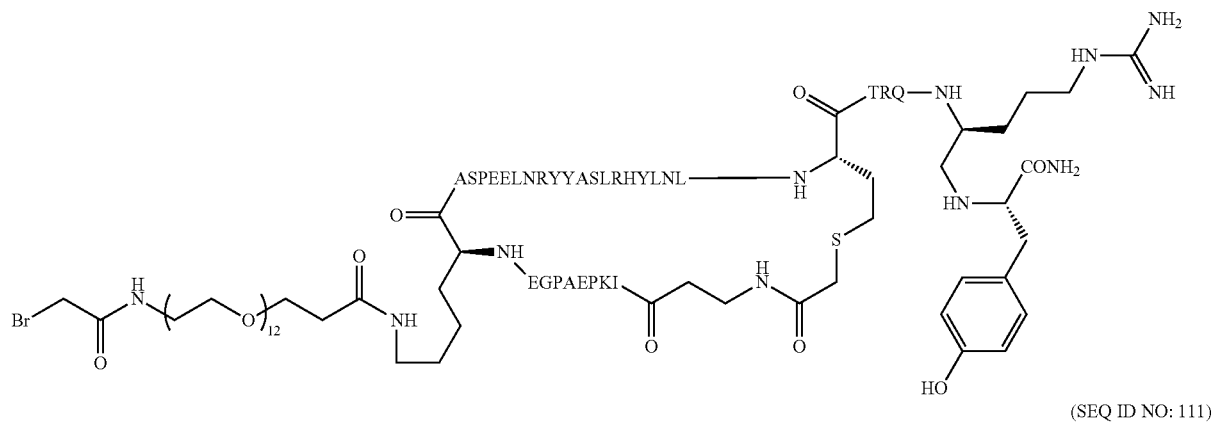

(SEQ ID NO: 1) and hPYY(3-36)

(SEQ ID NO: 111)

are aligned. The sequence identity of the analogue relative to hPYY$_{(3-36)}$ is given by the total number of aligned residues minus the number of different residues (i.e. the number of aligned identical residues) divided by the total number of residues in hPYY$_{3-36}$. In this example the different residues are D11 which has been exchanged for a substituted K11, followed by V31 which has been exchanged for hC31, and finally R35 has been decarbonylated. Accordingly, in said example the sequence identity is (34−3)/34×100.

Cyclic PYY Peptides

PYY3-36 is an endogenous hormone secreted by L cells in the distal gut that acts as an agonist of the Y2 receptor to inhibit food intake. Given its role in controlling appetite and represented unless otherwise expressly indicated. For convenience in describing the molecules of this invention, conventional and non-conventional abbreviations for various amino acids (both single and three-letter codes) and functional moieties are used. These abbreviations are familiar to those skilled in the art, but for clarity are listed as follows: A=Ala=alanine; R=Arg=arginine; N=Asn=asparagine; D=Asp=aspartic acid; ▢A=▢Ala=beta-alanine; C=Cys=cysteine; hC=hCys=homocysteine; E=Glu=glutamic acid; Q=Gln=glutamine; G=Gly=glycine; H=His=histidine; I=Ile=isoleucine; L=Leu=leucine; K=Lys=lysine; Nle=norleucine; F=Phe=phenylalanine; P=Pro=proline;

S=Ser=serine; T=Thr=threonine; W=Trp=tryptophan; Y=Tyr=tyrosine and V=Val=valine.

For convenience, the amino acid residue numbering convention used in naming the NTSC-PYY peptides of the present invention follows that of hPYY3-36. Specific amino acid replacements that have been introduced into the NTSC-PYY peptides, relative to the native residues at the corresponding positions in hPYY3-36, are indicated by the appropriate amino acid code, followed by the position of the substitution. Thus, "S4" in the NTSC-PYY peptide refers to a peptide in which serine has replaced the corresponding native lys4 residue of hPYY3-36. Similarly, "hC31" in the NTSC-PYY peptide refers to a peptide in which homocysteine has replaced the corresponding native val31 residue of hPYY3-36. Additional amino acid replacements occurring within NTSC-PYY peptides are described according to this convention and will be recognized as such by one skilled in the art.

Also, for convenience, the naming convention used for the NTSC-PYY peptides of the present invention incorporates the amino residues involved in the cycle along with the linking group(s) between them in a left-to-right direction, starting from the N-terminal residue involved in the cycle. In all cases, the N-terminal amino acid residue of the cycle links by way of its □-amino functionality to the linking group, which in turn connects to the side chain residue of the amino acid at position 31 of the NTSC-PYY peptide. Thus, "cyclo-(I3-m-COPhCH2-hC31)" is used to describe the cycle of an NTSC-PYY peptide in which the α-amino functionality of Ile3 is acylated with a meta-toluic acid residue, whose methyl group is further linked by way of a thioether bond to the side chain of a hCys31 residue. Similarly, "cyclo-(K4-CO(CH2)2NHCOCH2-hC31)" is used to describe the cycle of an NTSC-PYY peptide, in which the native Ile3 residue has been deleted and whose (now N-terminal) α-amino functionality of lys4 is acylated by a 3-acetamidopropanoyl group, whose acetamido methylene carbon is connected to the side chain of a hCys31 residue by way of a thioether bond.

Lysine residues can be incorporated at various positions of the hPYY$_{3-36}$ sequence to provide a convenient functional handle for further derivatization. The lysine residues can be modified to be coupled to the monoclonal antibody either directly or indirectly. In an indirect coupling to the monoclonal antibody, the lysine residue can be modified to comprise a linker which will allow for the cyclic PYY peptide to be coupled to the monoclonal antibody. One skilled in the art will recognize that related orthologues could also be effectively employed as such and are contemplated herein.

The term, "K(γ-Glu)", appearing in the peptide sequence, represents a lysinyl residue whose side chain ε-amino group has been acylated by the γ-carboxyl group of glutamic acid.

The term, "K(γ-Glu-Pal (palmitoyl))" represents a lysinyl residue whose side chain ε-amino group has been acylated by the γ-carboxyl group of N-hexadecan-1-oylglutamic acid.

The term, "K(γ-Glu-Stear (stearoyl))" represents a lysinyl residue whose side chain ε-amino group has been acylated by the γ-carboxyl group of N-octadecan-1-oylglutamic acid.

The term, "K(γ-Glu-Arach (arachidoyl))" represents a lysinyl residue whose side chain ε-amino group has been acylated by the γ-carboxyl group of N-dodecan-1-oylglutamic acid.

The term, "K(OEG) (8-amino-3,6-dioxaoctanoyl)" represents a lysinyl residue whose side chain ε-amino group has been acylated by 8-amino-3,6-dioxaoctanoic acid.

The term, "(OEG)2" represents two OEG units linked together in succession via an amide linkage (i.e., 17-amino-10-oxo-3,6,12,15-tetraoxa-9-azaheptadecanoic acid).

The term, "K(OEG)2" represents a lysinyl residue whose side chain ε-amino group has been acylated by 17-amino-10-oxo-3,6,12,15-tetraoxa-9-azaheptadecanoic acid.

The term, "K((OEG)2-γ-Glu" represents a lysinyl residue whose side chain ε-amino group has been acylated by (22S)-22-amino-10,19-dioxo-3,6,12,15-tetraoxa-9,18-diazatricosanedioic acid via its 1-carboxylic acid functionality.

The term, "K((OEG)2-γ-Glu-Stear)" represents a lysinyl residue whose side chain ε-amino group has been acylated by (22S)-10,19-dioxo-22-stearamido-3,6,12,15-tetraoxa-9,18-diazatricosanedioic acid via its 1-carboxylic acid functionality.

The term, "K((OEG)2-γ-Glu-COC16CO2H)" represents a lysinyl residue whose side chain ε-amino group has been acylated by (21S)-9,18,23-trioxo-2,5,11,14-tetraoxa-8,17,22-triazanonatriacontane-1,21,39-tricarboxylic acid via its 1-carboxylic acid functionality. Similarly, the term, "K((OEG)2-γ-Glu-COC18CO2H)" represents a lysinyl residue whose side chain ε-amino group has been acylated by (21S)-9,18,23-trioxo-2,5,11,14-tetraoxa-8,17,22-triazahentetracontane-1,21,41-tricarboxylic acid via its 1-carboxylic acid functionality. The term, "K((OEG)2-COC16CO2H)" represents a lysinyl residue whose side chain ε-amino group has been acylated by 10,19-dioxo-3,6,12,15-tetraoxa-9,18-diazahexatriacontanedioic acid via its 1-carboxylic acid functionality.

The term "K(PEG24-AcBr)" represents a lysinyl residue whose side chain ε-amino group has been acylated by N-bromoacetyl-75-amino-4,7,10,13,16,19,22,25,28,31,34,37,40,43,46,49,52,55,58,61,64,67,70,73-tetracosaoxapentaheptacontanoic acid via its 1-carboxylic acid functionality.

The term "K(PEG12-AcBr)" represents a lysinyl residue whose side chain ε-amino group has been acylated by N-bromoacetyl-39-amino-4,7,10,13,16,19,22,25,28,31,34,37-dodecaoxanonatriacontanoic acid via its 1-carboxylic acid functionality.

The term "K(PEG6-AcBr)" represents a lysinyl residue whose side chain ε-amino group has been acylated by N-bromoacetyl-3-[(17-amino-3,6,9,12,15-pentaoxaheptadec-1-yl)oxy]-propanoic acid via its 1-carboxylic acid functionality.

The term "K(PEG8-triazolyl-CH2CH2CO-PEG4-AcBr)" represents a lysinyl residue whose side chain ε-amino group has been acylated by 27-[4-[2-[3-[2-[2-[3-(N-bromoacetylamino)propoxy]ethoxy]ethoxy]propylaminocarbonyl]ethyl]tetrazol-1-yl]-4,7,10,13,16,19,22,25-octaoxaheptacosanoic acid via its 1-carboxylic acid functionality.

The term "K(mPEG16) represents a lysinyl residue whose side chain ε-amino group has been acylated by 4,7,10,13,16,19,22,25,28,31,34,37,40,43,46,49-hexadecaoxapentacontanoic acid via its 1-carboxylic acid functionality.

The term "K(mPEG12)" represents a lysinyl residue whose side chain ε-amino group has been acylated by 4,7,10,13,16,19,22,25,28,31,34,37-dodecaoxaoctatriacontanoic acid via its 1-carboxylic acid functionality.

The term, "VitE" represents an α-tocopheroyl unit in the molecule.

The term, "AcVitE" represents an α-tocopheroyl unit whose phenolic group bears an ether-linked methylenylcarboxy functionality.

The term, "K-γ-Glu-AcVitE" represents a lysinyl residue whose side chain ε-amino group has been acylated by (2-(((2R)-2,5,7,8-tetramethyl-2-((4R,8R)-4,8,12-trimethyltridecyl)chroman-6-yl)oxy)acetyl)-L-glutamic acid via its γ-carboxylic acid functionality.

Many of the compounds of the present invention incorporate a reduced amide bond between the C-terminal residue of the sequence, Y36, and its adjacent residue, R35. This reduced amide linkage is represented by the term, "psi-(R35, Y36)".

Various amino acid residues comprising certain sequences of the present invention contain α-amino groups that have been methylated. Thus, the terms, "N-Me-Q34" or "N-Me-R35" represent α-N-methylated glutamine at position 34 of a sequence, and α-N-methylated arginine at position 35 of a sequence, respectively.

The term, "N-Me-Q34, psi-(R35, Y36)" in a sequence description refers to a sequence containing both an α-methyl glutamine residue at position 34, as well as a reduced amide bond between residues R35 and Y36.

Similarly, the term, "N-Me-R35, psi-(R35, Y36)" in a sequence description refers to a sequence containing both an α-methyl arginine residue at position 35, as well as a reduced amide bond between this residue and Y36.

As used herein, the term "pegylation" refers to covalent conjugates of one or more polyethylene glycol (PEG) molecules and one or more NTSC-PYY peptides. Said conjugates may include, but are not limited to, from 1 to 24 PEG molecules on one NTSC-PYY peptide. Said conjugates may further include suitable linkers between the PEG molecules and the NTSC-PYY molecule, including, but not limited to γ-glutamate, —NHC(O), C(O), and C(1-4)alkyl.

As used herein, the phrase "lipidation" refers to covalent conjugates of an NTSC-PYY peptide and one or more lipophilic groups. Preferred lipophilic groups include long chain hydrocarbon groups. Other lipophilic groups include steroids, terpenes, fat soluble vitamins, phytosterols, terpenoids, phospholipids, glycerols, and natural or synthetic fatty acids. Examples of lipophilic groups include, but are not limited to α-tocopherolyl, stearic acid, palmitic acid, and arachidic acid. Said conjugates may further include suitable linkers between the lipophilic molecules and the NTSC-PYY molecule, including, but not limited to γ-glutamate, —NHC(O), C(O), and C(1-4)alkyl.

The term "PYY3-36" shall refer to the following compound (SEQ ID NO: 111):

positions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methyl sulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, chloroprocaine, choline, cyclohexylamine, diethanolamine, ethylenediamine, lithium, L-ly-

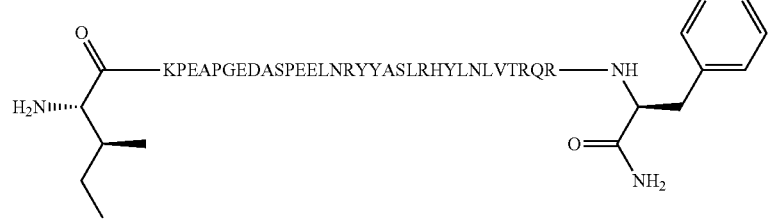

Pharmaceutical Compositions

In another general aspect, the invention relates to a pharmaceutical composition, comprising the conjugates and compounds of the invention and a pharmaceutically acceptable carrier. The term "pharmaceutical composition" as used herein means a product comprising a conjugate of the invention together with a pharmaceutically acceptable carrier. Conjugates and compounds of the invention and comsine, magnesium, meglumine, N-methyl-D-glucamine, piperidine, potassium, procaine, quinine, sodium, triethanolamine, or zinc.

In some embodiments of the invention, pharmaceutical formulations are provided comprising the compounds of the invention in an amount from about 0.001 mg/ml to about 100 mg/ml, from about 0.01 mg/ml to about 50 mg/ml, or from about 0.1 mg/ml to about 25 mg/ml. The pharmaceutical formulation may have a pH from about 3.0 to about 10, for example from about 3 to about 7, or from about 5 to about 9. The formulation may further comprise at least one ingredient selected from the group consisting of a buffer system, preservative(s), tonicity agent(s), chelating agent(s), stabilizer(s) and surfactant(s).

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier may be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation may comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition may be formulated as an injectable which can be injected, for example, via an injection device (e.g., a syringe or an infusion pump). The injection may be delivered subcutaneously, intramuscularly, intraperitoneally, or intravenously, for example.

In another embodiment, the pharmaceutical composition is a solid formulation, e.g., a freeze-dried or spray-dried composition, which may be used as is, or whereto the physician or the patient adds solvents, and/or diluents prior to use. Solid dosage forms may include tablets, such as compressed tablets, and/or coated tablets, and capsules (e.g., hard or soft gelatin capsules). The pharmaceutical composition may also be in the form of sachets, dragees, powders, granules, lozenges, or powders for reconstitution, for example.

The dosage forms may be immediate release, in which case they may comprise a water-soluble or dispersible carrier, or they may be delayed release, sustained release, or modified release, in which case they may comprise water-insoluble polymers that regulate the rate of dissolution of the dosage form in the gastrointestinal tract.

In other embodiments, the pharmaceutical composition may be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer may be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of buffers include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative may be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent may be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent may be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer may be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may, for example, be selected from the group consisting of anionic surfactants, cationic surfactants, nonionic surfactants, and/or zwitterionic surfactants. The surfactant may be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor may be present individually or in the aggregate, in a concentration from about 0.1 mg/ml to about 20 mg/ml. Pharmaceutical compositions comprising each one of these specific protease inhibitors constitute alternative embodiments of the invention.

The pharmaceutical composition of the invention may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present. The amino acid base may be present individually or in the combination with other amino acid bases, in a concentration from about 0.01 mg/ml to about 50 mg/ml, for example from about 0.1 mg/ml to about 20 mg/ml. Pharmaceutical compositions comprising each one of these specific amino acid bases constitute alternative embodiments of the invention.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

For all indications, the compounds of the invention are preferably administered peripherally at a dose of about 1 µg to about 5 mg per day in single or divided doses (e.g., a single dose can be divided into 2, 3, 4, 5, 6, 7, 8, 9, or 10 subdoses), or at about 0.01 µg/kg to about 500 µg/kg per dose, more preferably about 0.05 µg/kg to about 250 µg/kg, most preferably below about 50 µg/kg. Dosages in these ranges will vary with the potency of each agonist, of course, and are readily determined by one of skill in the art. The above dosages are thus exemplary of the average case. There can, of course, be individual instances where higher or lower dosage ranges are merited, and such are within the scope of this invention.

In certain embodiments, the compounds of the invention are administered at a dose of about 1 µg to about 5 mg, or at a dose of about 0.01 µg/kg to about 500 µg/kg, more preferably at a dose of about 0.05 µg/kg to about 250 µg/kg, most preferably at a dose below about 50 µg/kg with a dose of a second therapeutic agent (e.g., liraglutide) at a dose of about 1 µg to about 5 mg, or at a dose of about 0.01 µg/kg to about 500 µg/kg, more preferably at a dose of about 0.05 µg/kg to about 250 µg/kg, most preferably at a dose below about 50 µg/kg.

The pharmaceutically-acceptable salts of the compounds of the invention include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Administration may be by the oral route. Suitable formulations for parenteral administration include aqueous solutions of the active conjugates in water-soluble form, for example, water-soluble salts, acidic solutions, alkaline solutions, dextrose-water solutions, isotonic carbohydrate solutions and cyclodextrin inclusion complexes The present invention also encompasses a method of making a pharmaceutical composition comprising mixing a pharmaceutically acceptable carrier with any of the compounds of the present invention. Additionally, the present invention includes pharmaceutical compositions made by mixing one or more pharmaceutically acceptable carriers with any of the compounds of the present invention.

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the conjugates of the present invention. Thus, in the methods of treatment of the present invention, the term "administering" shall encompass the means for treating, ameliorating or preventing a syndrome, disorder or disease described herein with the conjugates of the present invention or a polymorph or solvate thereof, which would obviously be included within the scope of the invention albeit not specifically disclosed.

In another embodiment, the invention relates to the compounds of the invention for use as a medicament.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to the compounds of the invention, shall comprise all isotopes and isotopic mixtures of said element, either naturally occurring or synthetically produced, either with natural abundance or in an isotopically enriched form. For example, a reference to hydrogen includes within its scope 1H, 2H (D), and 3H (T). Similarly, references to carbon and oxygen include within their scope respectively 12C, 13C and 14C and 16O and 18O. The isotopes may be radioactive or non-radioactive. Radiolabeled compounds of the invention may comprise a radioactive isotope selected from the group of 3H, 11C, 18F, 122I, 123I, 125I, 131I, 75Br, 76Br, 77Br and 82Br. Preferably, the radioactive isotope is selected from the group of 3H, 11C and 18F.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column via high performance liquid chromatography (HPLC) or SFC. In some instances rotamers of compounds may exist which are observable by 1H NMR leading to complex multiplets and peak integration in the 1H NMR spectrum.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, each of which is herein incorporated by reference in its entirety for all purposes. The protecting groups may be removed at a convenient subsequent stage using methods known from the art.

Methods of Use

The present invention is directed to a method for preventing, treating or ameliorating a Y2 receptor mediated syndrome, disorder or disease in a subject in need thereof comprising administering to the subject in need thereof an effective amount of a compound, a derivative or a pharmaceutically acceptable salt thereof, optionally conjugated to a half-life extension moiety, or a pharmaceutical composition of the invention.

The present invention also provides a method for preventing, treating, delaying the onset of, or ameliorating a disorder, disease, or condition or any one or more symptoms of said disorder, disease, or condition in a subject in need thereof, comprising administering to the subject in need thereof an effective amount of a compound, a derivative or a pharmaceutically acceptable salt thereof, optionally conjugated to a half-life extension moiety, or a pharmaceutical composition of the invention.

According to particular embodiments, the disease disorder, or condition is selected from the group consisting of obesity, type I or II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and/or eczema.

According to particular embodiments, a therapeutically effective amount refers to the amount of therapy which is sufficient to achieve one, two, three, four, or more of the following effects: (i) reduce or ameliorate the severity of the disease, disorder, or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

As used herein, the terms "treat," "treating," and "treatment" are all intended to refer to an amelioration or reversal of at least one measurable physical parameter related the disease, disorder, or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

In one embodiment, the invention provides a method for preventing, treating, delaying the onset of, or ameliorating obesity, or any one or more symptoms of obesity in a subject in need thereof, the method comprising administering to the subject in need thereof an effective amount of a compound, a derivative or a pharmaceutically acceptable salt thereof, optionally conjugated to a half-life extension moiety, or a pharmaceutical composition of the invention. In some embodiments, the body weight of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to the body weight of a subject prior to administration of any of the conjugates, compounds, pharmaceutical compositions, forms, or medicaments of the invention described herein, or compared to control subjects not receiving any of the conjugates, compositions, forms, medicaments, or combinations of the invention described herein.

In some embodiments, the reduction in body weight is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of preventing, treating, delaying the onset of, or ameliorating a syndrome, disorder or disease, or any one or more symptoms of said syndrome, disorder, or disease in a subject in need thereof, wherein said syndrome, disorder or disease is selected from the group consisting of obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, comprising administering to the subject in need thereof an effective amount of a compound, a derivative or a pharmaceutically acceptable salt thereof, optionally conjugated to a half-life extension moiety, or a pharmaceutical composition of the invention.

As used herein, metabolic syndrome refers to a subject having any one or more of the following: high blood sugar (e.g., high fasting blood sugar), high blood pressure, abnormal cholesterol levels (e.g., low HDL levels), abnormal triglyceride levels (e.g., high triglycerides), a large waistline (i.e., waist circumference), increased fat in the abdominal area, insulin resistance, glucose intolerance, elevated C-reactive protein levels (i.e., a proinflammatory state), and increased plasma plasminogen activator inhibitor-1 and fibrinogen levels (i.e., a prothrombotic state).

The present invention provides a method of reducing food intake in a subject in need thereof, the method comprising administering to the subject in need thereof an effective amount of a compound, a derivative or a pharmaceutically acceptable salt thereof, optionally conjugated to a half-life extension moiety, or a pharmaceutical composition of the invention. In some embodiments, food intake of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to food intake of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

In some embodiments, the reduction in food intake is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of reducing glycated hemoglobin (A1C) in a subject in need thereof, the method comprising administering to the subject in need thereof an effective amount of a compound, a derivative or a pharmaceutically acceptable salt thereof, optionally conjugated to a half-life extension moiety, or a pharmaceutical composition of the invention. In some embodiments, A1C of a subject is reduced, for example, by between about 0.001% and about 0.01%, between about 0.01% and about 0.1%, between about 0.1% and about 0.2%, between about 0.2% and about 0.3%, between about 0.3% and about 0.4%, between about 0.4% and about 0.5%, between about 0.5% and about 1%, between about 1% and about 1.5%, between about 1.5% and about 2%, between about 2% and about 2.5%, between about 2.5% and about 3%, between about 3% and about 4%, between about 4% and about 5%, between about 5% and about 6%, between about 6% and about 7%, between about 7% and about 8%, between about 8% and about 9%, or between about 9% and about 10% relative to the A1C of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

In other embodiments, methods are provided for reducing fasting blood glucose levels in a subject in need thereof, the methods comprising administering to the subject in need thereof an effective amount of a compound, a derivative or a pharmaceutically acceptable salt thereof, optionally conjugated to a half-life extension moiety, or a pharmaceutical composition of the invention. Fasting blood glucose levels may be reduced to less than about 140 to about 150 mg/dL, less than about 140 to about 130 mg/dL, less than about 130 to about 120 mg/dL, less than about 120 to about 110 mg/dL, less than about 110 to about 100 mg/dL, less than about 100 to about 90 mg/dL, or less than about 90 to about 80 mg/dL, relative to the fasting blood glucose levels of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

The present invention provides a method of modulating Y2 receptor activity in a subject in need thereof, the method comprising administering to the subject in need thereof an effective amount of a compound, a derivative or a pharmaceutically acceptable salt thereof, optionally conjugated to a half-life extension moiety, or a pharmaceutical composition of the invention. As used herein, "modulating" refers to increasing or decreasing receptor activity.

In some embodiments, an effective amount of a compound, a derivative or a pharmaceutically acceptable salt thereof, optionally conjugated to a half-life extension moiety, or a pharmaceutical composition of the invention is administered to a subject in need thereof once daily, twice daily, three times daily, four times daily, five times daily, six times daily, seven times daily, or eight times daily. In other embodiments, an effective amount of a compound, a derivative or a pharmaceutically acceptable salt thereof, optionally conjugated to a half-life extension moiety, or a pharmaceutical composition of the invention is administered to a subject in need thereof once every other day, once per week, twice per week, three times per week, four times per week, five times per week, six times per week, two times per month, three times per month, or four times per month.

Another embodiment of the invention comprises a method of preventing, treating, delaying the onset of, or ameliorating a disease, disorder or syndrome, or one or more symptoms of any of said diseases, disorders, or syndromes in a subject in need thereof, the method comprising administering to the subject in need thereof an effective amount of a compound, a derivative or a pharmaceutically acceptable salt thereof, optionally conjugated to a half-life extension moiety, or a pharmaceutical composition of the invention in a combination therapy. In certain embodiments, the combination therapy is a second therapeutic agent. In certain embodiments, the combination therapy is a surgical therapy.

As used herein, the term "in combination," in the context of the administration of two or more therapies to a subject, refers to the use of more than one therapy.

As used herein, combination therapy refers to administering to a subject in need thereof one or more additional therapeutic agents, or one or more surgical therapies, concurrently with an effective amount of a compound, a derivative or a pharmaceutically acceptable salt thereof, optionally conjugated to a half-life extension moiety, or a pharmaceutical composition of the invention. In some embodiments, the one or more additional therapeutic agents or surgical therapies can be administered on the same day as an effective amount of a compound, a derivative or a pharmaceutically acceptable salt thereof, optionally conjugated to a half-life extension moiety, or a pharmaceutical composition of the invention, and in other embodiments, the one or more additional therapeutic agents or surgical therapies may be administered in the same week or the same month as an effective amount of a compound, a derivative or a pharmaceutically acceptable salt thereof, optionally conjugated to a half-life extension moiety, or a pharmaceutical composition of the invention.

In certain embodiments, wherein the disease or disorder is selected from the group consisting of obesity, type II diabetes, metabolic syndrome, insulin resistance and dyslipidemia, the second therapeutic agent can be an antidiabetic agent. In certain embodiments, the antidiabetic agent can be a glucagon-like peptide-1 (GLP-1) receptor modulator.

The present invention also contemplates preventing, treating, delaying the onset of, or ameliorating any of the diseases, disorders, syndromes, or symptoms described herein in a subject in need thereof with a combination therapy that comprises administering to the subject in need thereof an effective amount of a compound, a derivative or a pharmaceutically acceptable salt thereof, optionally conjugated to a half-life extension moiety, or a pharmaceutical composition of the invention, in combination with any one or more of the following therapeutic agents: a dipeptidyl peptidase-4 (DPP-4) inhibitor (e.g., sitagliptin, saxagliptin, linagliptin, alogliptin, etc.); a GLP-1 receptor agonist (e.g., short-acting GLP-1 receptor agonists such as exenatide and lixisenatide; intermediate-acting GLP-1 receptor agonists such as liraglutide; long-acting GLP-1 receptor agonists such as exenatide extended-release, albiglutide, dulaglutide); a sodium-glucose co-transporter-2 (SGLT-2) inhibitors (e.g., canaglifozin, dapaglifozin, empaglifozin, etc.); bile acid sequestrants (e.g., colesevelam, etc.); dopamine receptor agonists (e.g., bromocriptine quick-release); biguanides (e.g., metformin, etc.); insulin; oxyntomodulin; sulfonylureas (e.g., chlorpropamide, glimepiride, glipizide, glyburide, glibenclamide, glibornuride, glisoxepide, glyclopyramide, tolazamide, tolbutamide, acetohexamide, carbutamide, etc.); and thiazolidinediones (e.g; pioglitazone, rosiglitazone, lobeglitazone, ciglitazone, darglitazone, englitazone, netoglitazone, rivoglitazone, troglitazone, etc.). In some embodiments, the dose of the additional therapeutic agent(s) is reduced when given in combination with a compound, a derivative or a pharmaceutically acceptable salt thereof, optionally conjugated to a half-life extension moiety, or a pharmaceutical composition of the invention. In some embodiments, when used in combination with a conjugate or compound of the invention, the additional therapeutic agent(s) may be used in lower doses than when each is used singly.

In certain embodiments, wherein the disease or disorder is selected from the group consisting of obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, the second therapeutic agent can be liraglutide.

The present invention contemplates preventing, treating, delaying the onset of, or ameliorating any of the diseases, disorders, syndromes, or symptoms described herein in a subject in need thereof, with a combination therapy that comprises administering to the subject in need thereof an effective amount of a compound, a derivative or a pharmaceutically acceptable salt thereof, optionally conjugated to a half-life extension moiety, or a pharmaceutical composition of the invention in combination with a surgical therapy. In certain embodiments, the surgical therapy can be bariatric surgery (e.g., gastric bypass surgery, such as Roux-en-Y gastric bypass surgery; sleeve gastrectomy; adjustable gastric band surgery; biliopancreatic diversion with duodenal switch; intragastric balloon; gastric plication; and combinations thereof).

In embodiments in which the one or more additional therapeutic agents or surgical therapies is administered on the same day as an effective amount of a conjugate or compound of the invention, the conjugate or compound of the invention may be administered prior to, after, or simultaneously with the additional therapeutic agent or surgical therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Abbreviations

Herein and throughout the application, the following abbreviations may be used. Abu: 4-aminobutyric acid; Ac2O: acetic anhydride; aq: aqueous; alloc: allyloxycarbonyl; arach: arachidoyl; Boc: tert-butoxycarbonyl; BSA: bovine serum albumin; CDI: 1,1'-carbonyldiimidazole; DCM: dichloromethane; Dde: 1-(4,4-dimethyl-2,6-dioxocyclohex-1-yliden)ethyl; DIBAL-H: diisobutylaluminum hydride; DIC: diisopropylcarbodiimide; DIEA: diisopropylethylamine; DMA: N, N-dimethylacetamide; DMF: N, N-dimethylformamide; DMSO: methyl sulfoxide; DODT: 2,2'-(ethylenedioxy)diethanethiol; EDC: N-(3-dimethylaminopropyl)-N'-ethylcarbodiimide; EDCI: 1-(3-dimethylaminopropyl)-3-ethylcarbodiimide hydrochloride; Et: ethyl; EtOAc: ethyl acetate; EtOH: ethyl alcohol; FBS: fetal bovine serum; Fmoc: 9-fluorenylmethyloxycarbonyl; g: gram(s); h: hour(s); HATU: 2-(1H-7-azabenztriazol-1-yl)-1,1,3,3-tetramethylaminium hexafluorophosphate; HBSS: Hank's balanced salt solution; HBTU: 2-(1H-Benzotriazol-1-yl)-1,1,3,3-tetramethyluronium hexafluorophosphate); HCTU: 2-(6-chloro-1H-benztriazol-1-yl)-1,1,3,3-tetramethylaminium hexafluorophosphate; HCl: hydrochloric acid; HEPES: 4-(2-hydroxyethyl)-1-piperazineethanesulfonic acid; HOBT: 1-hydroxybenztriazole; HPLC: high performance liquid chromatography; ivDde: 1-(4,4-dimethyl-2,6-dioxocyclohex-1-yliden)-3-methylbutyl; LAH: lithium aluminum hydride; LCMS: high pressure liquid chromatography with mass spectrometer; Me: methyl; MeCN: acetonitrile; MeOH: methyl alcohol; mg: milligram; min: minute(s); Mmt: 4-methoxytrityl; mpm: mL per minute; Mtt: 4-methyltrityl; NHS: N-hydroxysuccinimide; NMP: 1-methyl-2-pyrrolidone; OEG: 8-amino-3,6-dioxaoctanoyl; Oxyma: ethyl cyano(hydroxyimino)acetate; Pal: palmitoyl; Pbf: 2,2,4,6,7-pentamethyldihydrobenzofuran-5-sulfonyl; Pd(PPh3)4: tetrakis(triphenylphosphine)palladium (0); PhSiH3: phenylsilane; psi: reduced amide bond (between adjacent amino acids); PyBroP: bromo-tris-pyrrolidino-phosphonium hexafluorophosphate; Pyoxim: 1-cyano-2-ethoxy-2-oxoethylideneaminooxy-tris-pyrrolidino-phosphonium hexafluorophosphate; rt: room temperature; RT: retention time; satd.: saturated; SPPS: solid phase peptide synthesis; Stear: stearoyl; t-Bu: tert-butyl; TBTU: 2-(1H-benzotriazol-1-yl)-1,1,3,3-tetramethylaminium tetrafluoroborate; TFA: trifluoroacetic acid; THF: tetrahydrofuran; THP: tetrahydropyranyl; TIPS: triisopropylsilane; Tris: tris(hydroxymethyl)aminomethane; Trt: triphenylmethyl Synthesis Compounds of Formula I in the present invention can be synthesized in accordance with the general synthetic methods known to those who are skilled in the art. The following description of the synthesis is for exemplary purposes and is in no way meant to be a limit of the invention.

The NTSC cyclic PYY (NTSC-PYY) analogues or derivatives of this invention may be synthesized by a variety of known, conventional procedures for the formation of successive peptide linkages between amino acids, and are preferentially carried out by solid phase peptide synthesis (SPPS), as generally described by Merrifield (J. Am. Chem. Soc., 1963, 85, 2149-2154), using an automated peptide synthesizer, traditional bench synthesis, or a combination of both approaches. Conventional procedures for peptide synthesis involve the condensation between the free amino group of one amino acid residue, whose other reactive functionalities have been suitably protected, and the free carboxyl group of another amino acid, whose reactive functionalities have also been suitably protected. Examples of condensation agents typically utilized for peptide bond formation include diisopropylcarbodiimide (DIC) with or without 1-hydroxybenztriazole (HOBT) or ethyl cyano(hydroxyimino)acetate (Oxyma Pure), 2-(1H-benzotriazol-1-yl)-1,1,3,3-tetramethylaminium hexafluorophosphate (HBTU), 2-(1H-7-azabenztriazol-1-yl)-1,1,3,3-tetramethylaminium hexafluorophosphate (HATU), 2-(6-chloro-1H-benztriazol-1-yl)-1,1,3,3-tetramethylaminium hexafluorophosphate (HCTU), 1-Cyano-2-ethoxy-2-oxoethylideneaminooxy-tris-pyrrolidino-phosphonium hexafluorophosphate (PyOxim), 2-(1H-benzotriazol-1-yl)-1,1,3,3-tetramethylaminium tetrafluoroborate (TBTU) bromo-tris-pyrrolidino-phosphonium hexafluorophosphate (PyBroP), and the like.

The automated peptide synthetic methodology may be carried out at room temperature, or at elevated temperatures, preferably through the application of microwave heating, as described by Yu (J. Org. Chem., 1992, 57, 4781-4784) and as more recently refined by Palasek (J. Pept. Sci., 2007, 13, 143-148).

Compounds of the present invention (C-terminal amides) can be conveniently prepared using N-α-Fmoc protected amino acid methodology, whereby the carboxy terminus of a suitably protected N-α-Fmoc protected amino acid is coupled onto a conventional solid phase resin using a suitable coupling agent. Suitable conventional, commercially-available solid phase resins include Rink amide MBHA resin, Rink amide AM resin, Tentagel S RAM Resin, Fmoc-PAL-PEG PS resin, SpheriTide Rink amide resin, ChemMatrix Rink resin, Sieber amide resin, TG Sieber resin and the like. The resin-bound Fmoc-amino acid may then be deprotected by exposure to 20% piperidine in either DMF or NMP, treatment of which serves to selectively remove the Fmoc protecting group. Additional Fmoc-protected amino acids are then subsequently coupled and deprotected sequentially, thereby generating the desired resin-bound protected peptide. In certain instances, it may be necessary to utilize an orthogonally reactive protecting group for another amine in the peptide sequence that would withstand the Fmoc deprotection conditions. Protecting groups such 4-methyltrityl (Mtt) or 4-methoxytrityl (Mmt), both removable by 1% TFA/DCM treatments, or preferably allyloxycarbonyl (alloc; removable by Pd(PPh3)4/PhSiH3 treatment), 1-(4,4-dimethyl-2,6-dioxocyclohex-1-yliden)ethyl (Dde; removable by treatment with 2-3% hydrazine/DMF) and 1-(4,4-dimethyl-2,6-dioxocyclohex-1-yliden)-3-methylbutyl (ivDde; removable by treatment with 2-3% hydrazine/DMF) can be used effectively in such instances.

In conventional peptide synthetic methodologies, reactive side chains of alpha amino acids are generally protected throughout the synthesis with suitable protecting groups to render them inert to the coupling and deprotection protocols. While multiple protecting groups for amino acid side chains are known in the art, herein the following protecting groups are most preferred: tert-butyl (t-Bu) for serine, threonine, glutamic acid, aspartic acid and tyrosine; trityl (Trt) for asparagine, glutamine, cysteine, homocysteine and histidine; tert-butyloxycarbonyl (Boc) for tryptophan and the ε-amino group of lysine; and 2,2,4,6,7-pentamethyldihydrobenzofuran-5-sulfonyl (Pbf) for arginine. These protecting groups are removed upon strong acid treatment, such as with high concentrations of trifluoroacetic acid (TFA).

Upon completion of the SPPS, the resin-bound, side chain-protected peptide is deprotected and concomitantly cleaved from the resin using a cleavage cocktail that consists predominantly of (TFA) along with various combinations of carbocation scavengers, such as triisopropylsilane (TIPS), water, phenol and anisole. The crude solid peptide is then isolated by precipitation of the peptide/cocktail filtrate with cold ether. In the special case of Sieber resin-bound protected peptides, cleavage of the protected peptide from the resin may be advantageously effected upon repeated treatment with 1-2% TFA in DCM without causing side chain deprotections. Once isolated, further manipulations of the protected peptide may be carried out in solution phase reactions. Finally, the protected peptide may be globally deprotected using a separate treatment with the cleavage cocktail and precipitated as described above. The crude peptide thus obtained is then dissolved at low concentration (ca., <4 mg/mL) in a largely aqueous solvent system containing an organic co-solvent such as acetonitrile or ethanol. Upon raising the pH of the solution to a >5, the peptide then undergoes an intramolecular cyclization reaction to form the corresponding crude NTSC PYY analogue of the present invention. NTSC PYY analogues thus formed may be purified using purification techniques generally known in the art. A preferable method of peptide purification used herein is reverse phase high pressure liquid chromatography (HPLC). Purified peptides are then characterized by liquid chromatography/mass spectrometry (LC/MS).

General Schemes

A general synthetic procedure for the synthesis of C-terminal amides NTSC-PYY peptides wherein the BRIDGE is -Ph-CH$_2$—S— is shown in Scheme 1.

Scheme 1: Synthesis of Toluoyl Thioether-Linked NTSC-PYY Peptides: C-Terminal Amides.

Fmoc-Rink Resin (PAL-PEG PS resin; ~0.16-0.2 mmol/g)

Fmoc—●

Step A | Automated SPPS
5 eq.
Fmoc—AA(Protected)-OH,
DIC/Oxyma or
HBTU/DIEA

[I]$_p$Z$_4$PEZ$_7$PZ$_9$EZ$_{11}$ASPEELNRYYZ$_{22}$Z$_{23}$LRZ$_{26}$YLNZ$_{30}$Z$_{31}$[V$_{31}$]$_q$TRZ$_{34}$Z$_{35}$Y—NH—●*
|
NH$_2$

Step B | 20 eq. XCH$_2$PhCO$_2$H, 10 eq DIC, μ-wave, 75° C., 15 min

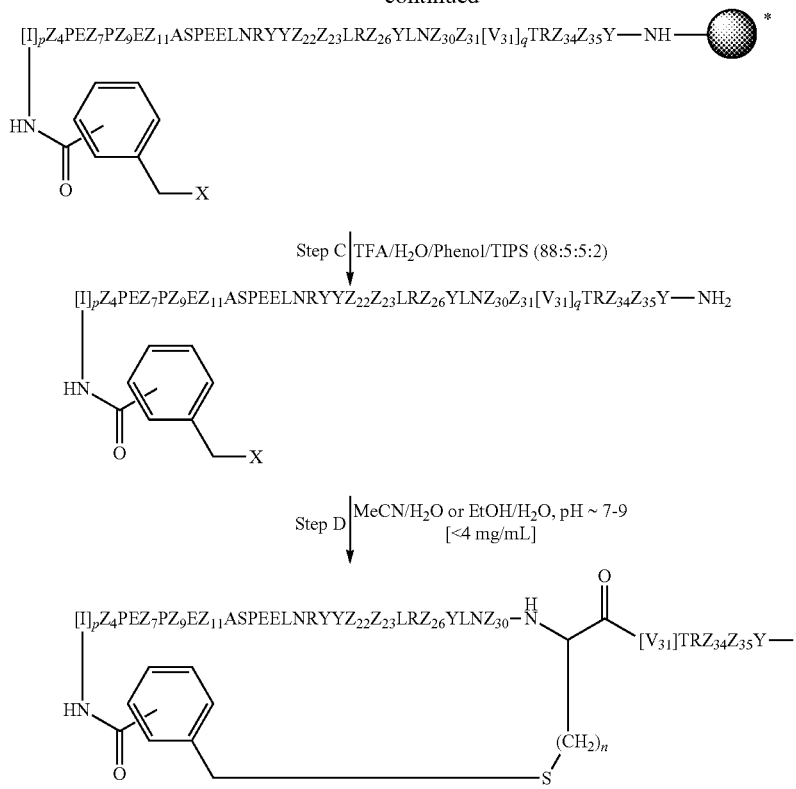

*Amino acids protected, $Z_{31}$ = Cys, homoCys
X is Cl or Br

A) Synthesis of Resin-Bound C-Terminal Amide Peptide

The protected peptidyl resin can be synthesized using Fmoc strategy as described above on a CEM Liberty Blue Microwave peptide synthesizer using low loading Rink amide resins, preferably, Fmoc-PAL-PEGPS resin (ca., 0.16-0.2 meq/g, supplied by Applied Biosystems) on a scale of 0.1 mmol, as depicted in Scheme 1. Standard Fmoc-protected amino acids (supplied by Novabiochem (EMD Millipore), Bachem, Peptides International or Chem-Impex) may be coupled in 5-fold excess relative to resin loading using DIC/Oxyma as the coupling agents and a reaction temperature of ca., 90° C. for 4 min. Fmoc-Arg(Pbf)-OH may be double coupled at 90° C. for 4 min each and Fmoc-His(Trt)-OH may be coupled using a two-stage protocol: 4 min at rt followed by 8 min at 50° C. Single Fmoc deprotections may be carried out using 20% piperidine in DMF (deprotection solution) at 90° C. for 1.5 min.

B) Procedure for Coupling Halomethylbenzoic Acids

The Fmoc-deprotected peptide-resin (0.1 mmol) may be treated with a solution of the desired isomer (meta or para) of either chloro- or bromomethylbenzoic acid (20 eq.) and DIC (10 eq.) in DMF (4 mL) in a microwave reactor at 75° C. for 15 min. Reaction completeness may be determined by the Kaiser ninhydrin test (Kaiser, et al., Anal. Biochem., 1970, 34, 595-598). In cases where the coupling is determined to be incomplete, the coupling may be repeated with fresh reagents.

C) Procedure for Peptide Cleavage from Resin

Upon completion of the SPPS, the resin may be washed extensively with DMF and then with DCM and dried. The resin may then be treated with a cleavage cocktail (10 mL/0.1 mmol scale) consisting of either TFA/water/TIPS (95:2.5:2.5) (Cleavage Cocktail A) or more preferably with TFA/water/phenol/TIPS (88:5:5:2) (Cleavage Cocktail B) and heated in a microwave reactor at 38° C. for 40 min, then filtered. The resin may be washed with TFA and the combined filtrates concentrated under a stream of nitrogen to a volume of ca. 2.5 mL and the peptide may then be precipitated by the addition of cold diethyl ether (40 mL). The peptide/ether suspension may be centrifuged and the ether layer was decanted. The peptide pellet may be re-suspended in ether, centrifuged and decanted, and this process may be repeated a third time. The crude peptide thus obtained may then be dried under a mild nitrogen stream.

D) Procedure for Peptide Cyclization (Thioether Formation)

The crude cysteine- or homocysteine-containing peptide may be dissolved in deoxygenated MeCN/water (50-60% MeCN) or EtOH/water (60% EtOH) at a concentration of <4 mg/mL. The pH of the peptide solution may then be raised to ca. 7-9 through the addition of either solid $NaHCO_3$, sat'd aq. $NaHCO_3$ or 1M aq. Tris buffer (pH 7.5) and the resulting solution may be stirred at rt for 3-16 h. Typically, the cyclizations are complete within 3-4 h, as determined by analytical LC/MS.

E) Procedure for Peptide Purification

The cyclization reaction mixture may be acidified to pH 1.5-3 by the addition of TFA, and the solution concentrated to remove most of the organic co-solvent (MeCN or EtOH) to a point where slight clouding occurs. A minimal amount of the co-solvent may be added back as necessary to render the mixture homogeneous and the resultant solution may then be purified directly by preparative HPLC in multiple injections. Purifications may be performed on either an Agilent PrepStar HPLC system or a Gilson HPLC 2020 Personal Purification System using a reverse phase C18 or C8 column selected from the following: Varian Pursuit XRs C18 (21×250 mm, 100 Å, 5 μm); Varian Pursuit XRs Diphenyl (30×100 mm, 100 Å, 5 μm); Zorbax 300 SB-C8 (21×250 mm, 300 Å, 5 μm); Waters Atlantis T3 C18 (19×250 mm, 100 Å, 5 μm); Agilent Polaris 5 C18-A (30×250 mm, 180 Å, 5 μm). The mobile phase may consist of gradient elutions of buffer A (0.1% TFA in water) and Buffer B (0.1% TFA in MeCN) ranging in initial concentration of 10-20% B to final concentrations of 40-90% B with run times ranging between 36-80 min. UV detection may be monitored at 220 and 254 nm. Product-containing fractions may be analyzed by analytical HPLC on an Agilent 1100 HPLC system using an appropriate column type from above (4.6×250 mm, 5 μm). Pure fractions may be combined, concentrated to remove most of the organic phase, and then lyophilized. TFA/HCl salt exchange may be subsequently carried out by triple lyophilization from 2 mM HCl, according to the procedure described by Andrushchenko, et al., (J. Pept. Sci., 2006, 13, 37-43).

A general synthetic procedure for the synthesis of C-terminal amides NTSC-PYY peptides wherein the BRIDGE is —NHC(O)CH$_2$S— is shown in Scheme 2.

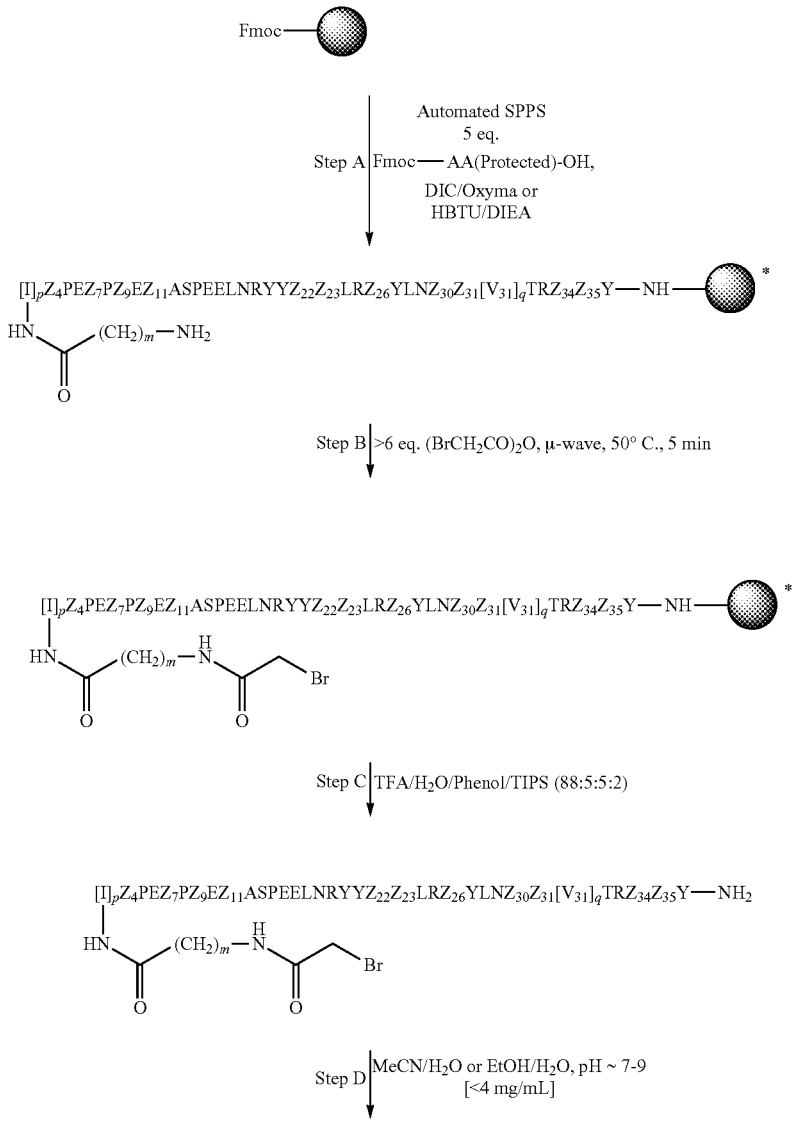

Scheme 2: Synthesis of Acetamidoyl Thioether-linked NTSC-PYY Peptides: C-Terminal Amides
Steps A, C, D, and purification (E) are essentially the same as those described in Scheme 1.

-continued

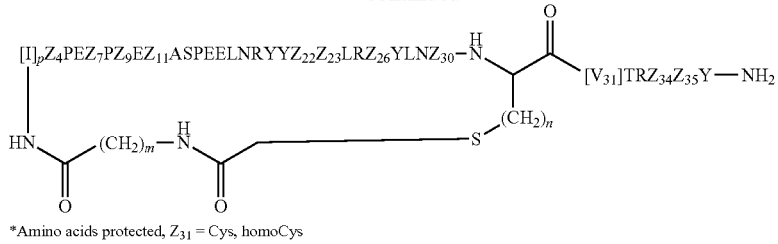

*Amino acids protected, $Z_{31}$ = Cys, homoCys

However, an alternate BRIDGE may be introduced in Step B, as described below.

The Fmoc-deprotected peptide-resin (0.1 mmol) may be treated with a solution of bromoacetic anhydride (6-20 eq.) in DMF (5 mL) in a microwave reactor at 50° C. for 5 min, by which time the reaction may be generally determined to be complete as per a Kaiser ninhydrin test. In cases where the coupling is determined to be incomplete, the coupling may be repeated with fresh reagents.

A general synthetic procedure for the synthesis of C-terminal amide NTSC-PYY peptides wherein $Z_{35}$ is

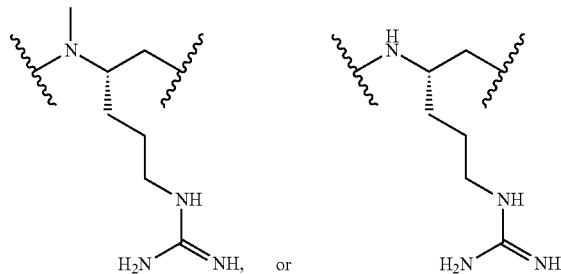 [SMILES: *C[C@H](CCCNC(=N)N)N(*)C ; *C[C@H](CCCNC(=N)N)N* ; "or"]

is shown in Scheme 3.

HATU-Mediated Coupling:

In a fritted microwave reaction vessel (supplied by CEM Corporation), NovaSyn TG Sieber resin (supplied by Novabiochem) (0.1 mmol) may be treated with deprotection solution (5 mL) and heated at 50° C. for 2.5 min. The reaction is drained, washed with DMF and treated again with deprotection solution at 50° C. for 5 min. After draining and washing the resin with DMF, a third deprotection treatment is carried out at 50° C. for 5 min. The resin is drained and washed extensively with DMF and then with DCM. The resin is then treated with a solution of Fmoc-Arg(Pbf)-psi-(N-Boc)Tyr(tBu)-OH from Scheme 14 (3-5 eq.), HATU (2.75-4.5 eq.) and DIEA (6-10 eq.) in DMF (4 mL) and mixed at rt for 24 h. The mixture is drained and the resin was washed extensively with DMF. The resin is then capped by treatment with 20% $Ac_2O$ in DMF (5 mL) under microwave conditions at 50° C. for 5 min. The reaction is drained and the resin is washed extensively with DMF and then with DCM.

A) (Alternative) DIC/Oxyma-Mediated Coupling

In a fritted microwave reaction vessel, NovaSyn TG Sieber resin (0.1 mmol) may be deprotected as described in Scheme 3: Loading of psi-(R35,Y36) Building Block onto Sieber Resin

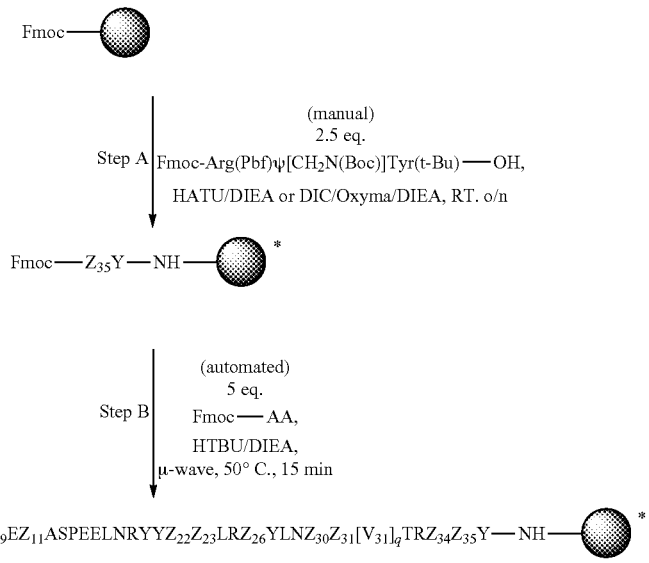

*Amino acids are protected; $Z_{31}$ = Cys, homoCys, Glu, azido-Lys

Step A above, then treated with a solution of moc-Arg(Pbf)-psi-(N-Boc)Tyr(tBu)-OH (2.75 eq.), DIC (2.75 eq.), Oxyma (2.75 eq.) and DIEA (0.275 eq.) in MeCN (4 mL) and mixed at rt for 24 h. The reaction is drained and the resin is washed extensively with DMF and then with DCM and may be used directly without capping.

Elaboration of Reduced Amide (psi-R35,Y36) Peptide on Pre-Loaded Sieber Resin

Further amino acid extensions onto the pre-loaded (psi-R35,Y36)-Sieber resin may be performed on a CEM Liberty Blue Microwave peptide synthesizer. Standard Fmoc-protected amino acids ware coupled in 5-fold excess relative to the initial resin loading using HBTU/DIEA as the coupling agents and a reaction temperature of ca., 50° C. for 15 min. Fmoc-Arg(Pbf)-OH may be double coupled using a two-stage protocol for each coupling: 25 min at rt followed by 15 min at 50° C. and Fmoc-His(Trt)-OH may be double-coupled using a two-stage protocol for each coupling: 4 min at rt followed by 8 min at 50° C. Fmoc deprotections may be carried out in two stages using fresh deprotection solution for each stage: 1) 50° C. for 2.5 min and 2) 50° C. for 5 min. In some cases, double couplings may be used advantageously throughout to improve the quality of the isolated crude peptide.

Installation of the thioether BRIDGE moiety may proceed either by the bromomethylbenzoic acid coupling shown in Scheme 1 step B, with the reaction temperature of 50° C. Alternatively, a thioether BRIDGE moiety may be introduced using the bromoacetylation coupling shown in Scheme 2 Step B.

Upon completion of the SPPS, the resin is washed extensively with DMF and then with DCM and dried. Cleavage of protected peptide from Sieber Resin may be then accomplished with a solution of 1-2% TFA in DCM (10 mL/0.1 mmol scale) and mixed for ca. 10 min, then filtered. This treatment may be repeated 9 additional times using fresh cocktail with each treatment. The combined filtrates are then concentrated to afford the crude protected peptide as a yellow syrup/solid which may be used directly for subsequent global deprotection. The protected peptide obtained above is treated with Cleavage Cocktail B (10 mL) at rt for 2.5 h and is then concentrated under a stream of nitrogen to a volume of ca. 2.5 mL. The crude peptide may be precipitated by the addition of cold diethyl ether (40 mL). The peptide/ether suspension may be centrifuged and the ether layer is decanted. The peptide pellet may be re-suspended in ether, centrifuged and decanted, and this process may be repeated a third time. The crude peptide thus obtained may be dried under a mild nitrogen stream. Cyclization and purification of the reduced amide (psi-R35,Y36) peptides may be accomplished according to the procedures described in Scheme 1 Step D and Step E.

Synthesis of lipidated c-terminal amide NTSC-PYY peptides may be accomplished according to Scheme 4.

Scheme 4: Procedure for Introducing Lipidated Lysine Residues into Peptide Sequences Fmoc-Rink Resin (PAL-PEG PS resin; ~0.16-0.2 mmol/g)

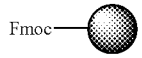

Automated SPPS
5 eq.
Fmoc—AA(Protected)-OH,
DIC/Oxyma, 90° C.,
4 min

ivDde-Fmoc—$Z_{31}[V_{31}]_q TRZ_{34}Z_{35}Y$—NH—*

Step A
1) 5 eq.
FMOC—OEG—$CO_2H$,
DIC/Oxyma, μ-wave, 90° C., 4 min and/or
5 eq.
FMOC-Glu-$CO_2$tBu,
DIC/Oxyma, μ-wave, 90° C., 4 min 2) 5 eq.
Lipophilic acid, DIC/Oxyma, or HBTU/DIEA
μ-wave, 75° C., 15 min

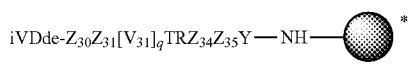

iVDde-$Z_{30}Z_{31}[V_{31}]_q TRZ_{34}Z_{35}Y$—NH—*

Step B
(manual)
[2-3% $H_2NNH_2$ in DMF;
90° C., 3.5 min] × 3

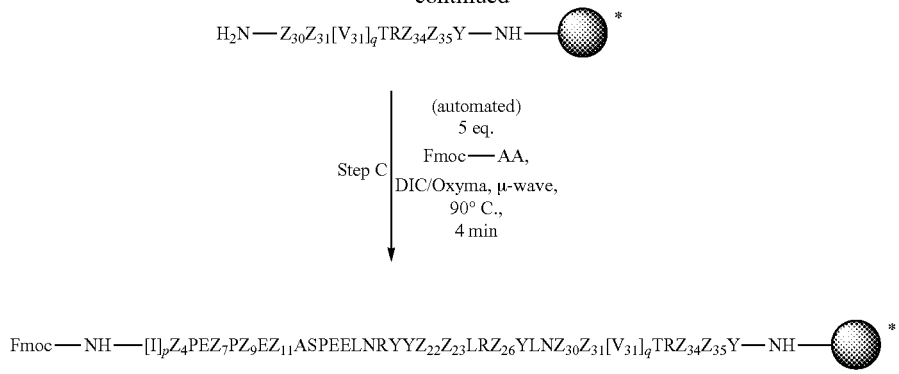

*Amino acids are protected; $Z_{31}$ = Cys, homoCys, Glu, azido-Lys

Synthesized on PAL-PEG PS Rink Amide Resin

A) Procedure for Introducing Derivatized Lysine Residues into Peptide Sequences Built on Standard Rink Amide Resin To a resin-bound C-terminal amide peptide, elaborated to the point preceding the desired point of derivatization and prepared as described in Scheme 1, Step A, may be sequentially coupled either Dde-Lys(Fmoc)-OH or ivDde-Lys(Fmoc)-OH and then Fmoc-Glu-OtBu (all supplied by Novabiochem) under microwave conditions (either manually or on the Liberty Blue Peptide Synthesizer) using DIC/Oxyma coupling methods as described in Scheme 1, Step A. Following Fmoc deprotection, the resin may be treated with a solution of the lipophilic acid [palmitic acid or α-tocopheryloxyacetic acid (AcVitE)] (5-10 eq.), DIC (5-10 eq.) and either HOBT or Oxyma (5-10 eq.) in DMF under microwave conditions at 90° C. for 10 min. The reaction is then drained and the resin is washed with DMF.

B) Procedure for Deprotecting Dde- or ivDde-Protected Lysinyl Peptide

The derivatized lysinyl peptide resin may be treated with a solution of 3% hydrazine in DMF (6 mL/0.1 mmol resin) under microwave conditions at 90° C. for 3.5 min. The reaction is drained and this procedure may be repeated two additional times. The reaction is drained and the resin is washed extensively with DMF and then with DCM.

C) Procedure for Direct Incorporation of Fmoc-Lys(Pal-Glu-OtBu)-OH Residue

In cases where the palmitoylated-γ-Glu-Lysinyl residue is to be incorporated into the sequence, Fmoc-Lys(Pal-Glu-OtBu)-OH (available from Peptides International or Active-Peptide) may be used directly in the procedure described in Scheme 1, Step A.

Compounds of the present invention with Updated lysine residues may be completed by following the procedures of Scheme 1, Steps B, C, D, and E.

Synthesis of lipidated, reduced amide (psi-R35,Y36), c-terminal amide, NTSC-PYY peptides may be accomplished according to Scheme 5.

Scheme 5: Procedure for Introducing Derivatized Lysine Residues into Peptide Sequences

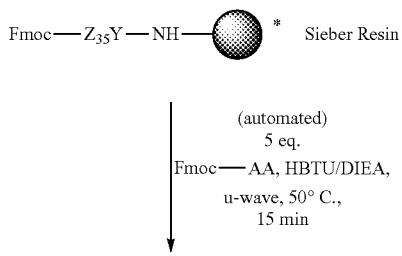

-continued

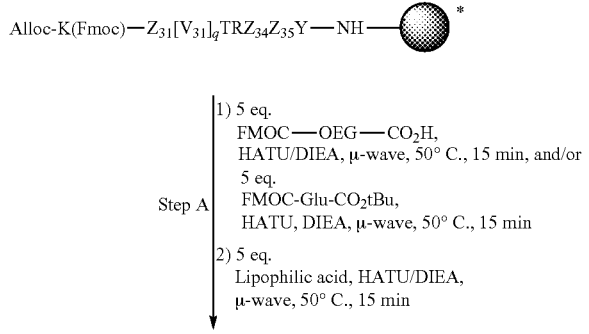

Step A
1) 5 eq.
  FMOC—OEG—CO$_2$H,
  HATU/DIEA, μ-wave, 50° C., 15 min, and/or
  5 eq.
  FMOC-Glu-CO$_2$tBu,
  HATU, DIEA, μ-wave, 50° C., 15 min
2) 5 eq.
  Lipophilic acid, HATU/DIEA,
  μ-wave, 50° C., 15 min

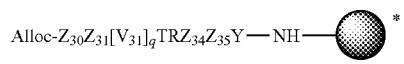

Step B (manual) [Pd(PPh$_3$)$_4$/Ph$_3$SiH, DCM; RT, 30 min] × 2

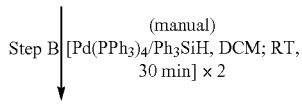

(automated)
5 eq.
Fmoc—AA,
HTBU/DIEA, μ-wave,
50° C.,
15 min

*Amino acids are protected; Z$_{31}$ = Cys, homoCys, azido-Lys

Synthesized on (psi-R35,Y36) Pre-Loaded Sieber Resin

A) Procedure for Introducing Derivatized Lysine Residues into Peptide Sequences Built on (psi-R35,Y36) Pre-Loaded Sieber Resin To a partially elaborated reduced amide (psi-R35,Y36) peptide, prepared as described in Scheme 3, Step A, may be sequentially coupled Alloc-Lys(Fmoc)-OH (available from Chem-Impex or AAPPTec, LLC) followed by Fmoc-Glu-OtBu and then palmitic acid (each at 5 eq., using either HATU/DIEA or HBTU/DIEA coupling methods at 50° C. for 15 min. When the lipophilic acid to be coupled is stearic acid, arachidic acid, octadecanedioic acid, mono-tert-butyl ester (available from AstaTech, Inc.) or 20-(tert-butoxy)-20-oxoicosanoic acid (available from Key Organics, Inc.), NMP may be used as solvent for reasons of improved reagent solubilities, and the coupling reaction may be mediated by HATU/DIEA at 50° C. for 30 min. Alternatively for arachidic acid, the coupling could be carried out using the DIC/Oxyma-mediated procedure described in Scheme 1, Step A, but with reagents at 5 eq. and THF as the reaction solvent.

B) Procedure for Alloc Deprotection

The above resin (0.1 mmol) is washed with deoxygenated DCM and then treated with PhSiH3 (12.5 eq.) in deoxygenated DCM (5 mL). After 2 min, a solution of Pd(PPh3)4 (0.25 eq) in deoxygenated DCM (5 mL) may be added and the reaction is mixed for 0.5 h under a nitrogen atmosphere. The reaction is drained and the resin is washed 1× with deoxygenated DCM. The resin is again treated with PhSiH3 (12.5 eq.) and Pd(PPh3)4 (0.25 eq) as above and reacted for an additional 0.5 h. The reaction is drained and the resin is successively washed extensively with DCM, DMF and DCM.

Further elaboration and completion of the peptide may be performed as described herein above, beginning with Scheme 3, Step B.

Synthesis of C-terminal amide NTSC-PYY analogues wherein BRIDGE is triazolyl is shown in Scheme 6.

Scheme 6: Synthesis of Triazolo-linked NTSC-PYY Analogues: C-terminal Amide Peptides
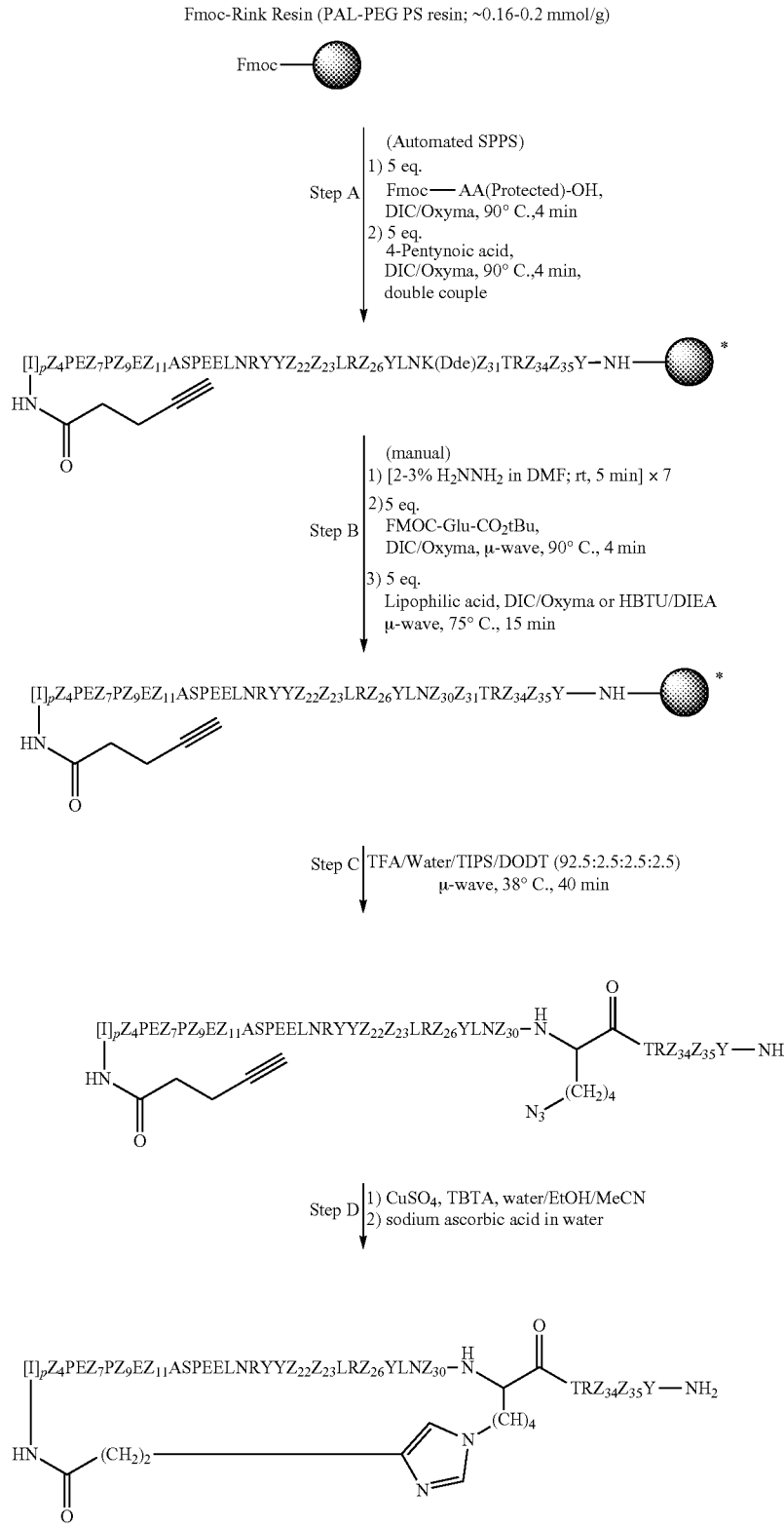
*Amino acids protected, $Z_{31}$ = ε-azido-Nle;

A) Synthesis of Azido- and Akynyl-Containing Resin-Bound C-Terminal Amide Peptides The resin-bound ε-azidonorleucine-containing protected peptide, capped on the N-terminus with 4-pentynoic acid may be prepared according to Scheme 1, Step A. A double-coupling protocol may be used for the incorporation of 4-pentynoic acid.

B) Procedure for Introducing Derivatized Lysine Residues into Azido- and Akynyl-Containing Resin-Bound C-Terminal Amide Peptides Fmoc-Lys(Dde)-OH may be incorporated into the SPPS at the sequence position to be derivatized, following the procedure described in Scheme 1, Step A. Upon completion of the linear sequence (following the incorporation of 4-pentnoic acid), the resin may be treated with 3% hydrazine in DMF (8 mL/0.1 mmol scale) for 5 min at rt and then the mixture is drained. This procedure may be repeated ca. 6×, after which the resin is washed extensively with DMF and then DCM. Fmoc-Glu-OtBu and the lipophilic acid is then sequentially coupled onto the Dde-deprotected resin following the procedure described in Example 6 Å.

C) Procedure for Azido- and Alkynyl-Containing Peptide Cleavage from Resin

Upon completion of the SPPS, the resin may be washed extensively with DMF and then with DCM and dried. The resin is then treated with a cleavage cocktail (10 mL/0.1 mmol scale) consisting of TFA/water/DODT/TIPS (92.5:2.5:2.5:2.5) (Cleavage Cocktail C) and heated in a microwave reactor at 38° C. for 40 min, then filtered. The resin is washed with TFA and the combined filtrates are concentrated under a stream of nitrogen to a volume of ca. 2.5 mL and the peptide may be precipitated by the addition of cold diethyl ether (40 mL). The peptide/ether suspension may be centrifuged and the ether layer is decanted. The peptide pellet may be re-suspended in ether, centrifuged and decanted, and this process may be repeated a third time. The crude peptide thus obtained may be dried under a mild nitrogen stream.

D) Procedure for Peptide Cyclization (Triazole Formation)

The following solutions may be prepared using deoxygenated water:
1) $CuSO_4$ (7 mg in 2 mL of water)
2) 30 mg of TBTA in 5.4 mL of EtOH and 0.6 mL of MeCN
3) Premix solution 1 (943 µL) and solution 2 (4.8 mL)
4) sodium ascorbate acid (30 mg in 3 mL of water)

To a solution of the crude peptide from Step C (0.021 mmol) in either deoxygenated water or HEPES buffer (pH 7.4) (20 mL) may be added solution 3, followed by solution 4 (2.4 mL), and the resultant milky solution is warmed to 35-40° C. until cyclization is complete, as determined by LCMS analysis (ca., 1-5 h). The reaction solution may be diluted to 40 mL with either water (0.1% TFA) or 60% MeCN/water (0.1% TFA), filtered and purified directly by preparative HPLC using multiple injections as described in Scheme 1, Step E.

Synthesis of C-terminal amide NTSC-PYY analogues wherein BRIDGE is a lactam is shown in Scheme 7.

Scheme 7: Synthesis of Lactam-bridged cyclic peptides.

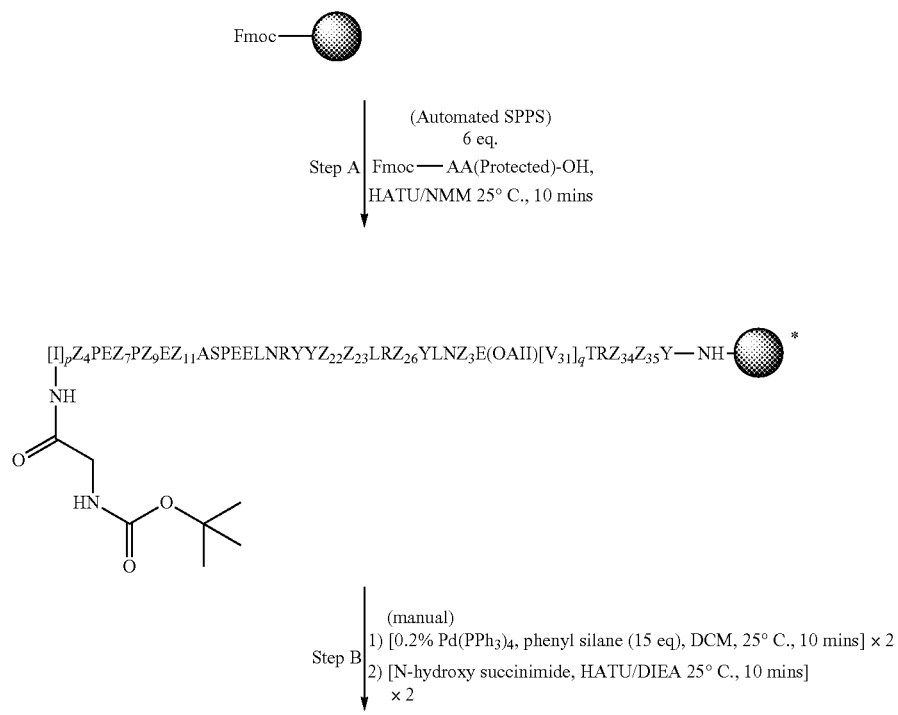

-continued

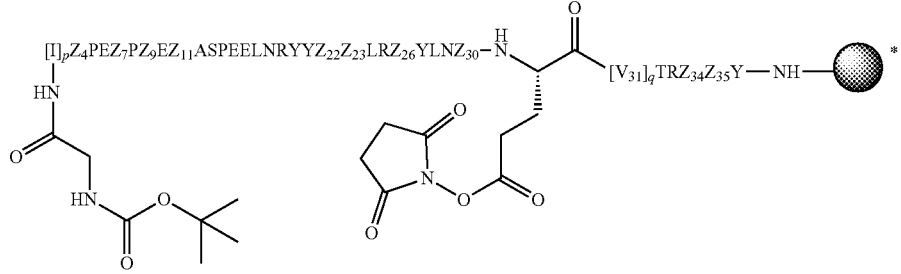

Step C | 1) TFA/TIPS/water (95%/2.5%/2.5%) 2 hrs, 25° C.
2) DMSO, TEA (10 eq), 20 mins, 25° C.
3) 2% hydrazine, DMF, 10 mins, 25° C., × 2

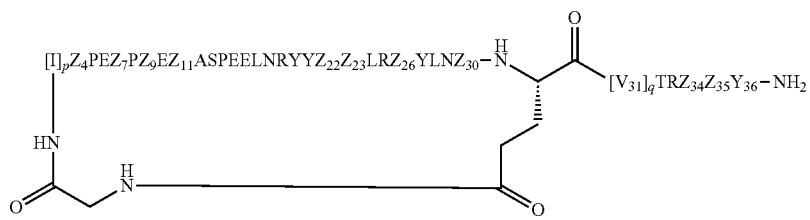

*Amino acids are protected, Lys protected as Dde.

Synthesis of Resin-Bound C-Terminal Amide Peptide

The protected peptidyl resin may be synthesized using an Fmoc strategy on a Symphony X peptide synthesizer from Protein Technologies. Couplings may be performed on either Rink amide resins or Sieber resins using HATU and NMM in DMF for 10 min at rt. Fmoc amino acids may be used in 6-fold excess and double-coupled. For peptides containing psi-(R35,Y36) modification, Fmoc-Arg(Pbf)Ψ[CH$_2$N(Boc)]Tyr(t-Bu)-OH was coupled in 3-fold excess using HATU and NMM in DMF for 1 hr at rt. The α-amino of the terminal residue of the linear sequence may be Boc-protected and the γ-carboxyl group of the glutamic acid residue that forms the lactam bridge may be allyl protected. Lysine(s) in the peptide may be orthogonally Dde protected.

B) Synthesis of γ-Glutamate-N-Hydroxysuccinimide Ester

Following completion of the linear sequence the glutamate side chain allyl protecting group may be removed using Pd(PPh$_3$)$_4$ and PhSiH$_3$ in DCM. The N-hydroxysuccinimide (NHS) ester may be then synthesized by double-coupling NHS using HATU and DIEA for 10 min at RT.

C) Procedure for Lactam Cyclization

The peptide may be cleaved from the resin and globally deprotected by treatment with TFA/TIPS/water (95:2.5:2.5) for 2 h at RT, then precipitated into ether and collected by centrifugation and dried. The crude product may be dissolved in DMSO; TEA (10 eq.) is added and the cyclization allowed to proceed for 1 h at rt. The crude product may be diluted with water and purified by preparative RP-HPLC. Orthogonally dde-protected lysines may be deprotected by dissolving the peptide in 2% hydrazine/DMF (at a concentration of 5 mM) and stirring for 1 h at RT. The reaction mixture may be diluted with water and the pH is adjusted to 2 with the addition of 10% TFA/water and the solution may be directly purified by preparative RP-HPLC as described in Scheme 1, Step E. Solution-phase synthesis of lipidated C-terminal amide NTSC-PYY analogues wherein BRIDGE is a lactam is shown in Scheme 8.

Solution phase synthesis of lipidated C-terminal amide NTSC-PYY analogues wherein BRIDGE is a lactam is shown in Scheme 8.

Scheme 8: Solution-phase lipidation of lactam-bridge C-terminal amide cyclic peptides, shown for $Z_{11}$ lysine.

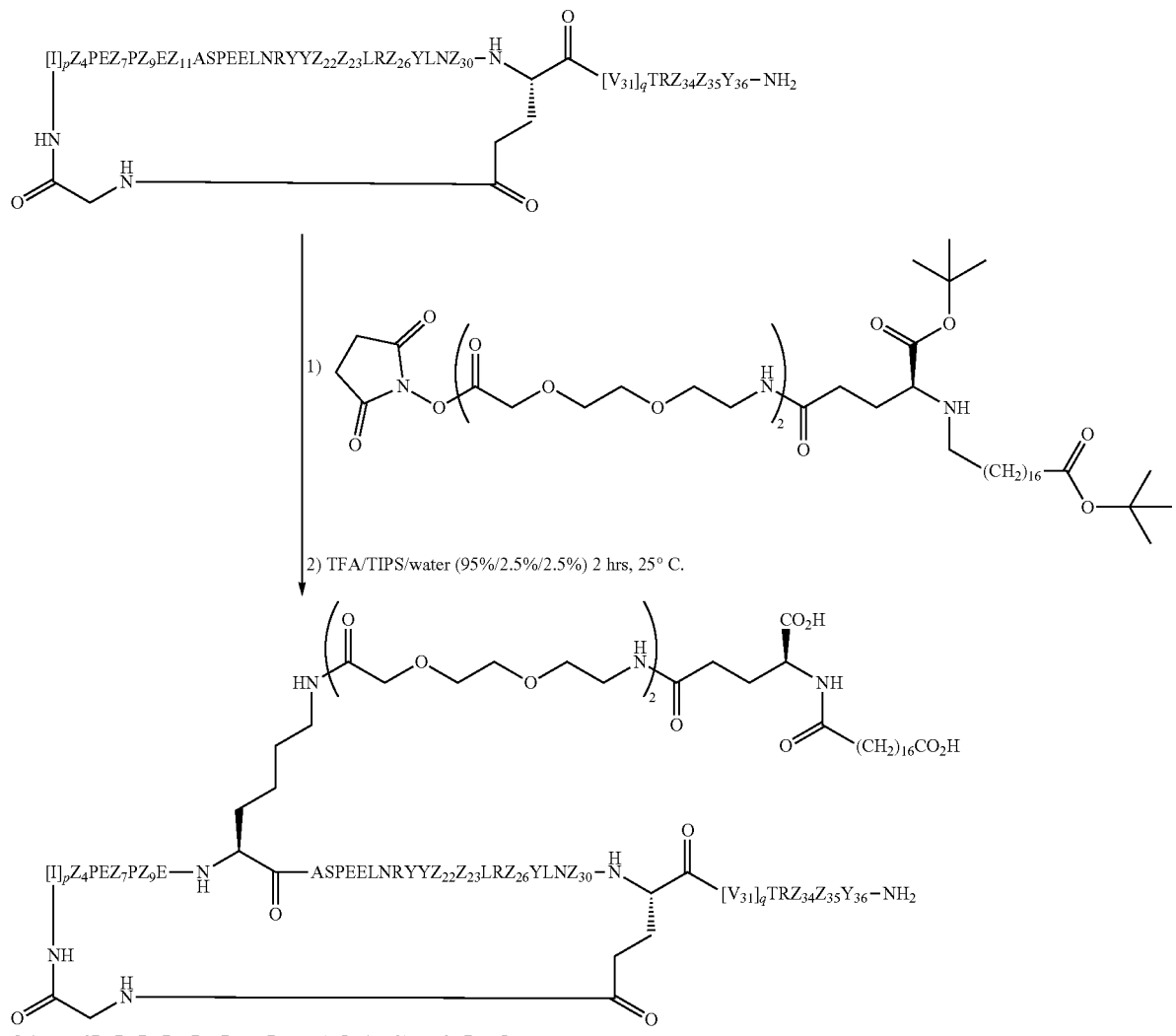

Only one of $Z_4$, $Z_7$, $Z_9$, $Z_{11}$, $Z_{22}$, $Z_{23}$, or $Z_{30}$ may be Lysine; Shown for $Z_{11}$ = Lys The peptide obtained in Scheme 7 above, wherein only one of $Z_4$, $Z_7$, $Z_9$, $Z_{11}$, $Z_{22}$, $Z_{23}$, or $Z_{30}$ may be lysine, is dissolved in DMF (at a concentration of 5 mM), TEA (5 eq.) is added, followed by the N-hydroxy ester of the protected lipid (2 eq). The reaction may be allowed to proceed overnight at rt and then purified by preparative HPLC. The t-butyl esters may be deprotected in TFA/TIPS/water (95: 2.5:2.5) for 30 min at rt and the reaction concentrated and purified by preparative RP-HPLC as described in Scheme 1, Step E.

General Procedures for Synthesis of Bromoacetylated Cyclic-Thioether Peptides

Schemes 9, 10, and 11 all show various routes to bromoacetylated cyclic-thioether peptides of the present invention. In Scheme 9, the thioether bridge is formed by reaction of a thiol-containing amino acid side chain in the peptide sequence with a bromoacetyl group at the amino terminus of the peptide. Scheme 10 illustrates a similar approach as Scheme 9 but with a discrete PEG spacer inserted between the lysine side chain and the bromoacetyl group. Scheme 11 illustrates a strategy for synthesis of another class of bromoacetylated cyclic-thioether peptides in which the bridge is formed by reaction of a thiol nucleophile at the amino terminus of the peptide with a bromoacetyl group covalently attached to a lysine side chain within the peptide sequence.

Synthesis of Resin-Bound C-Terminal Amide Peptide

The protected peptide on resin may be synthesized on Sieber amide or Rink amide resins using FMOC strategy. Standard FMOC-protected amino acids (supplied by Novabiochem (EMD Millipore), Bachem, Peptides International or Chem-Impex) may be coupled in 3-6-fold excess relative to resin loading using DIC/Oxyma, HBTU/DIPEA or HATU/NMM as the coupling agents at room temperature or elevated temperature. Double-coupling might be carried out for superior purity, and especially for the amino acid coupled onto the α-N-alkylated amino acids. For peptides containing psi-(R35,Y36) modification, Fmoc-Arg(Pbf)Ψ[$CH_2$N(Boc)] Tyr(t-Bu)-OH may be coupled in 3-fold excess using HATU and NMM in DMF for 1 hr at rt.

Procedure for Bromoacetylation of Resin-Bound Peptide

The lysine to be bromoacetylated may be orthogonally protected with either an alloc, ivDDE or DDE protecting group. Following completion of the linear sequence on resin the orthogonally protected lysine may be deprotected (for alloc, Pd(Ph$_3$)$_4$ and phenyl silane in DCM; for DDE or ivDDE, 2% hydrazine in DMF) and the amino group may be bromoacetylated under various conditions such as, 1) reacting with a large excess of bromoacetic anhydride in DMF in a microwave reactor at 50° C. for 5 min, by which time the reaction may be generally determined to be complete as per a Kaiser ninhydrin test; 2) reacting with a large excess of bromoacetic anhydride in DMF or DCM in the presence of base such as TEA or DIPEA at room temperature; or 3) coupling with bromoacetic acid using DIC, or DIC/Oxyma.

Procedure for Peptide Cleavage from Resin

Upon completion of the SPPS, the resin may be washed extensively with DMF and then with DCM and dried. With Sieber amide resin-bound peptide, the dried resin may be treated with a solution of 1 to 2% TFA in DCM (10 mL) for 5 to 10 min, then filtered. This treatment may be repeated a few more times using fresh cocktail for each treatment. The filtrates are then combined and concentrated to afford the crude protected peptide as a yellow foam. This foam may be then treated with cleavage cocktail TFA/phenol/H$_2$O/TIPS (88/5/5/2), or TFA/water/TIPS (95:2.5:2.5), or TFA/phenol/H$_2$O/TIPS/DTT (84/10/2.5/2.5/1), and heated in a microwave reactor at 38° C. for 30-45 min, or at room temperature for 2-3.5 h. The crude peptide may be precipitated in cold diethyl ether. The peptide/ether suspension may be centrifuged and the ether layer is decanted. The peptide pellet may be re-suspended in ether, centrifuged and decanted, and this process may be repeated a third time. The crude peptide thus obtained may be dried under a mild nitrogen stream.

Alternatively, the Sieber amide or Rink amide resin-bound peptide may be treated with cleavage cocktail as above without prior treatment with 1-2% TFA in DCM to afford the fully deprotected peptide.

Procedure for Peptide Cyclization (Thioether Formation)

The crude free thiol and bromoacetamide-containing peptide may be dissolved in deoxygenated MeCN/water or EtOH/water at a concentration of 4 to 10 mg/mL with optional addition of EDTA. The pH of the peptide solution may be then raised to ca. 7-9 through the addition of base such as NaHCO$_3$, NaOH, DIPEA, or TEA and the resulting solution is stirred at room temperature for 0.25-2.5 h.

Alternatively, the crude peptide could be purified by HPLC, the peptide fractions combined and basified to about pH 7-9, and stirred at room temperature optionally in the presence of EDTA for 0.25 to 2.5 h. After acidification, the reaction solution may be concentrated at room temperature to remove organic solvent, and then subjected to HPLC purification.

Procedure for Peptide Purification

The cyclization reaction mixture may be acidified with TFA, and the solution is concentrated to remove most of the organic co-solvent (MeCN or EtOH), and the resultant solution may be then purified directly by preparative HPLC on a reversed-phase column. The mobile phase consists of gradient elutions of buffer A (0.1% TFA in water) and Buffer B (0.1% TFA in MeCN) ranging in initial concentration of 0-20% B to final concentrations of 40-90% B with run times ranging between 20-60 min. UV detection may be monitored at 220 and 254 nm. Product-containing fractions may be analyzed by HPLC on an Agilent 1100 HPLC system using a Waters T3 Atlantis C18 column (4.6×250 mm, 5 µm). Pure fractions may be combined, concentrated to remove most of the organic phase, and then lyophilized.

Scheme 9. Synthesis of bromoacetylated cyclic-thioether C-terminal amide peptides, wherein the thioether bridge is formed by reaction of a thiol-containing amino acid side chain in the peptide sequence with a bromoacetyl group at the amino terminus of the peptide. In this scheme, a dde protecting group is employed to protect the lysine side chain and is removed by treatment with 2% hydrazine in DMF.

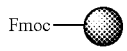

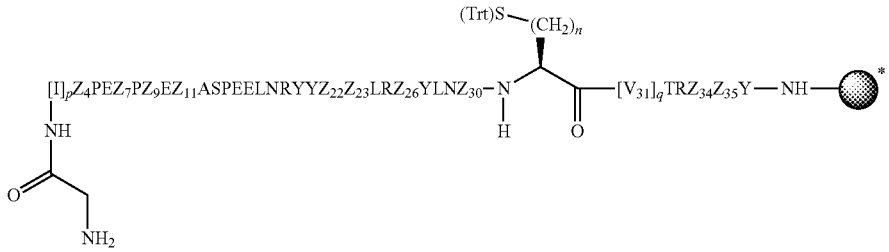

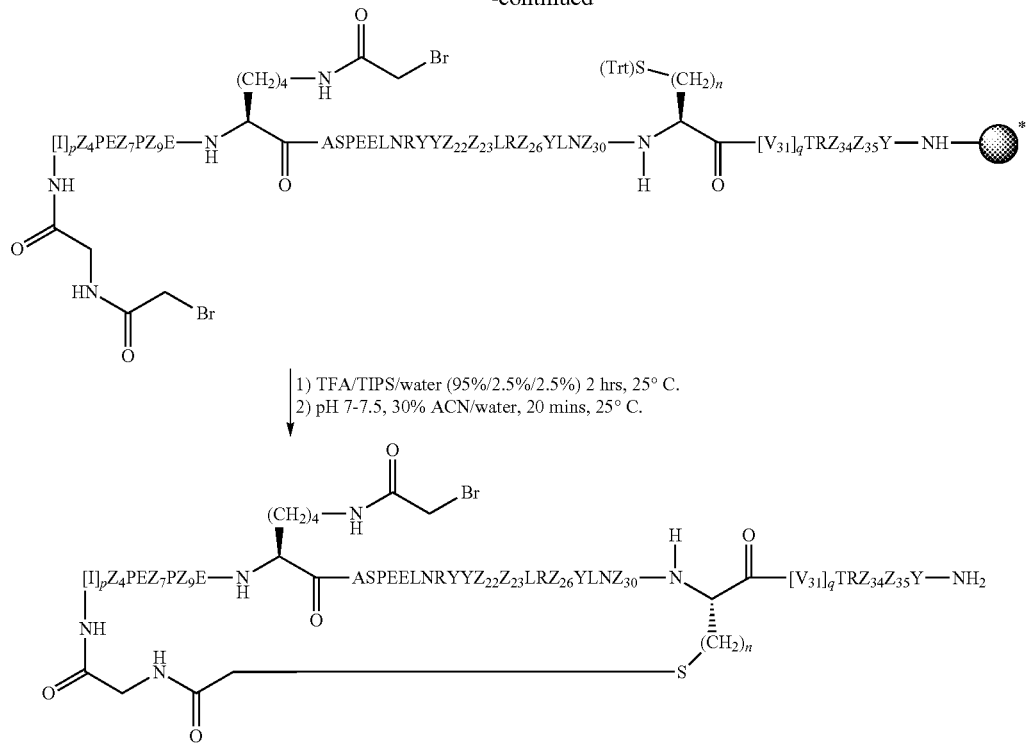

*Amino acids are protected; Z11 = Lys(dde).

Scheme 10. Synthesis of bromoacetylated cyclic-thioether peptides, wherein the thioether bridge is formed by reaction of a thiol-containing amino acid side chain in the peptide sequence with a bromoacetyl group at the amino terminus of the peptide and a discrete PEG spacer is introduced between the group and a lysine side chain. In this scheme, an alloc protecting group is employed to protect the lysine side chain is removed by treatment with Pd(Phh3)4 and phenylsilane.

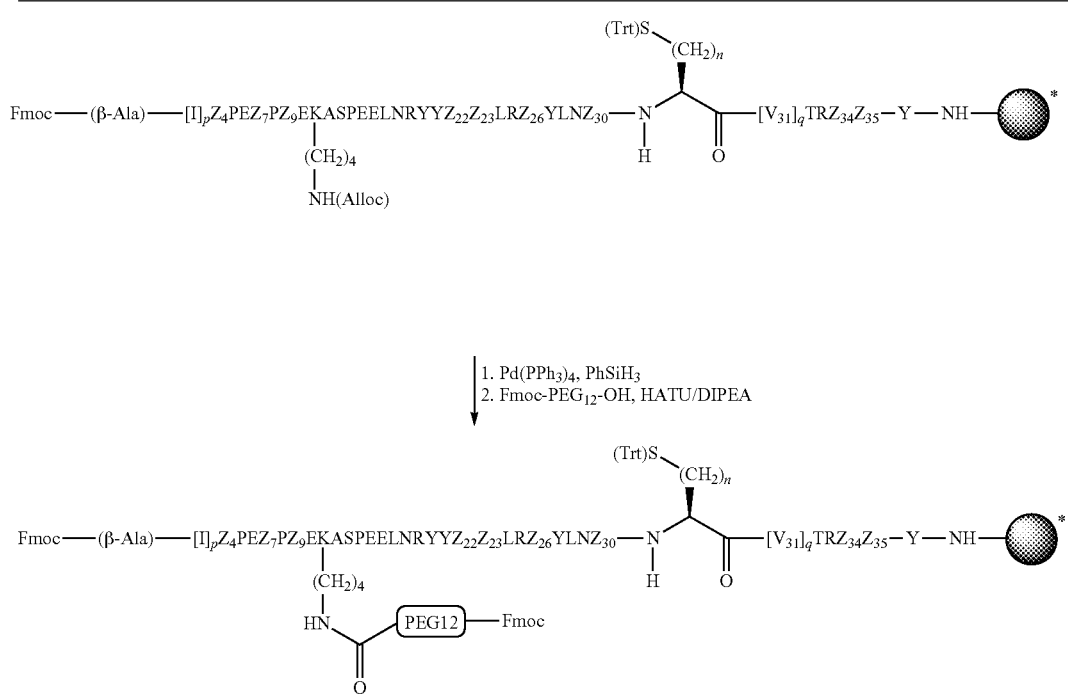

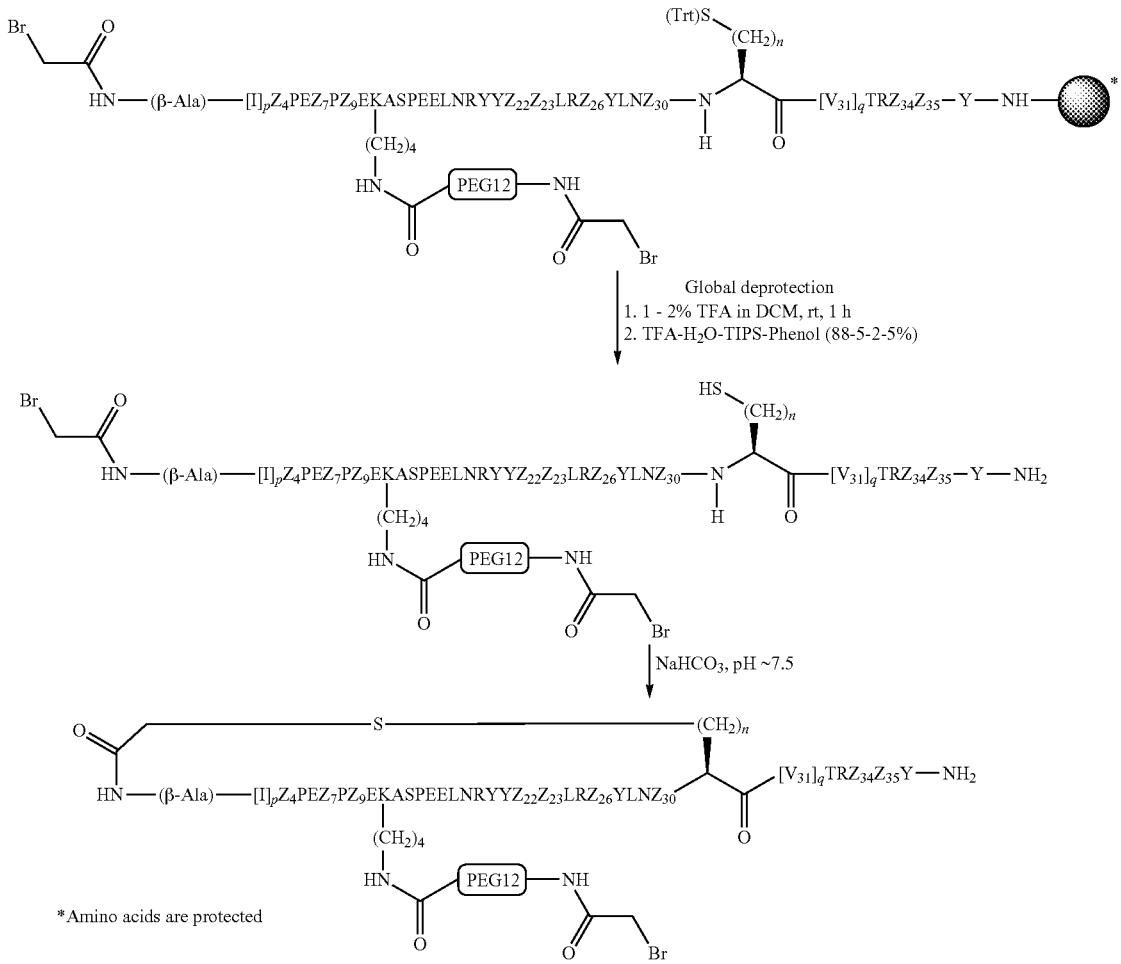
Scheme 11. Synthesis of bromoacetylated cyclic-thioether peptides, wherein the thioether bridge is formed by reaction of a thiol group at the amino terminus of the peptide with a bromoacetylated side chain in the peptide sequence and a discrete PEG spacer is introduced between the bromoacetyl group and another lysine side chain.
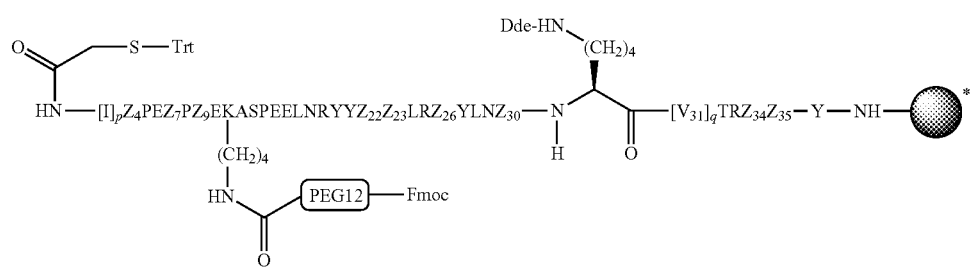

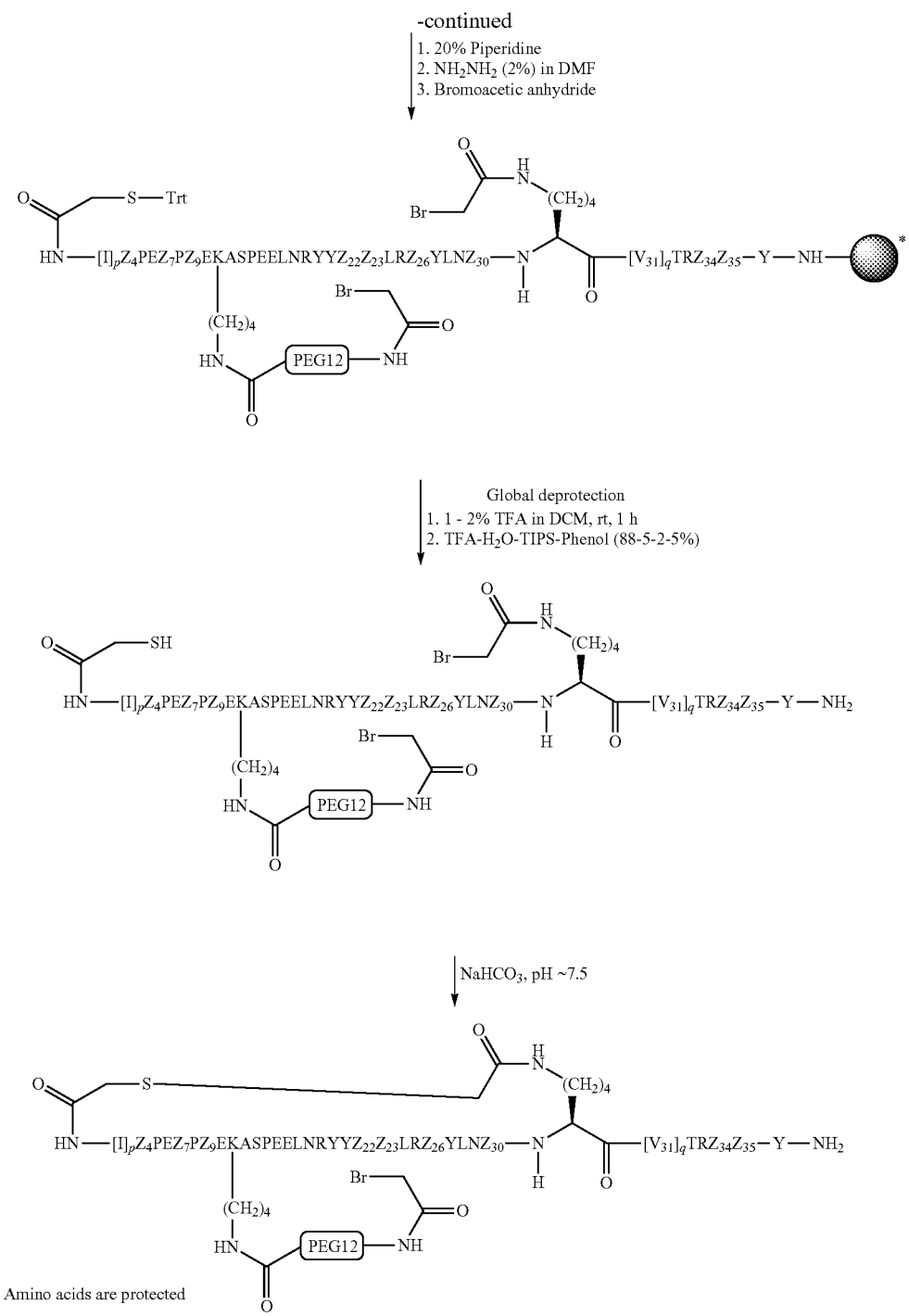

General Procedures for Synthesis of Bromoacetylated Cyclic-Lactam Peptides

The cyclic lactam peptides may be synthesized according to the procedures shown in Scheme 12. Cyclic lactam peptide is first synthesized according to Scheme 7 wherein only one of $Z_4$, $Z_7$, $Z_9$, $Z_{11}$, $Z_{22}$, $Z_{23}$, or $Z_{30}$ is lysine. The lysine is then bromoacetylated using bromoacetic acid N-hydroxysuccinimide ester (3-7 eq) in 10% ACN/water at pH 10, RT, 20 mins. The final bromoacetylated peptide may be purified by RP-HPLC as outlined for the cyclic-thioether peptides.

Scheme 12. Synthesis of bromoacetylated cycluc-lactam C-terminal amide peptides

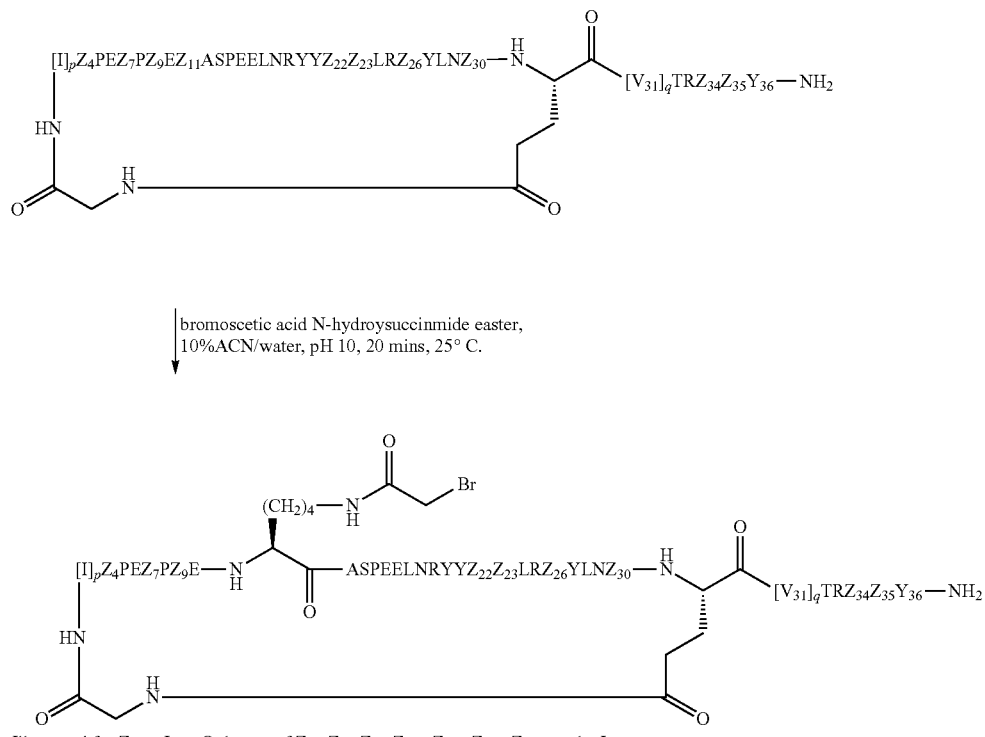

Illustrated for $Z_{11}$ = Lys, Only one of $Z_4$, $Z_7$, $Z_9$, $Z_{11}$, $Z_{22}$, $Z_{23}$, $Z_{30}$ may be Lys General Procedures for Synthesis of Bromoacetylated Cyclic Triazole-Linked Peptides The bromoacetylated cyclic triazole-linked peptides may be synthesized according to the procedure shown in Scheme 13. The linear protected peptide on resin may be synthesized in a similar manner as described for the cyclic-thioether peptides in Scheme 10 except that L-azido-lysine may be incorporated for triazole formation and the N-terminal residue may be 4-pentynoic acid. The Fmoc may be removed with 20% piperidine in DMF and then reacted with bromoacetic anhydride. The linear sequence may be globally deprotected (TFA/TIPS/water:95%/2.5%/2.5%) and the crude peptide precipitated into cold ether, collected by centrifugation, and purified by preparative RP-HPLC. The purified linear peptide may be cyclized in the presence of CuSO4/TBTA and NaASrb in buffer solution (HEPES, MOPS, etc.) to give cyclic triazole-linked peptides, which may be purified by preparative RP-HPLC as described in Scheme 1, step E.

An alternative class of cyclic triazole-linked peptides can synthesized by persons skilled in the art beginning with a linear sequence in which the N-terminal residue is an azido carboxylic acid (for example, 5-azido pentanoic acid) and the residue in position 30 or 31 is an alkynyl amino acid (for example, 2-amino-7-octynoic acid) in a similar fashion as described above.

Scheme 13. Synthesis of bromoacetylated cyclic triazole-linked C-terminal amide peptides.

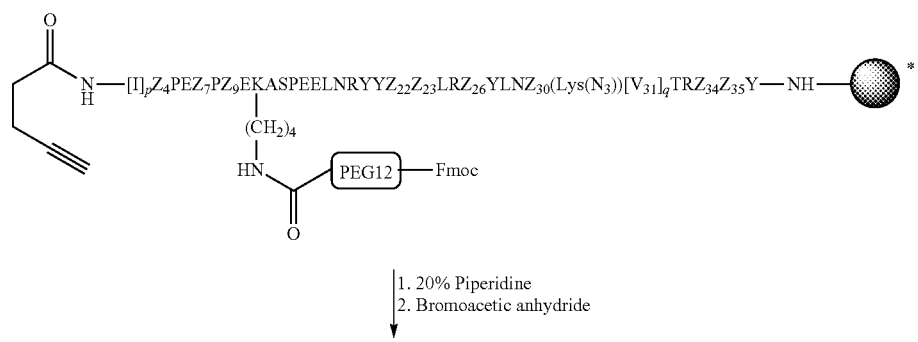

-continued

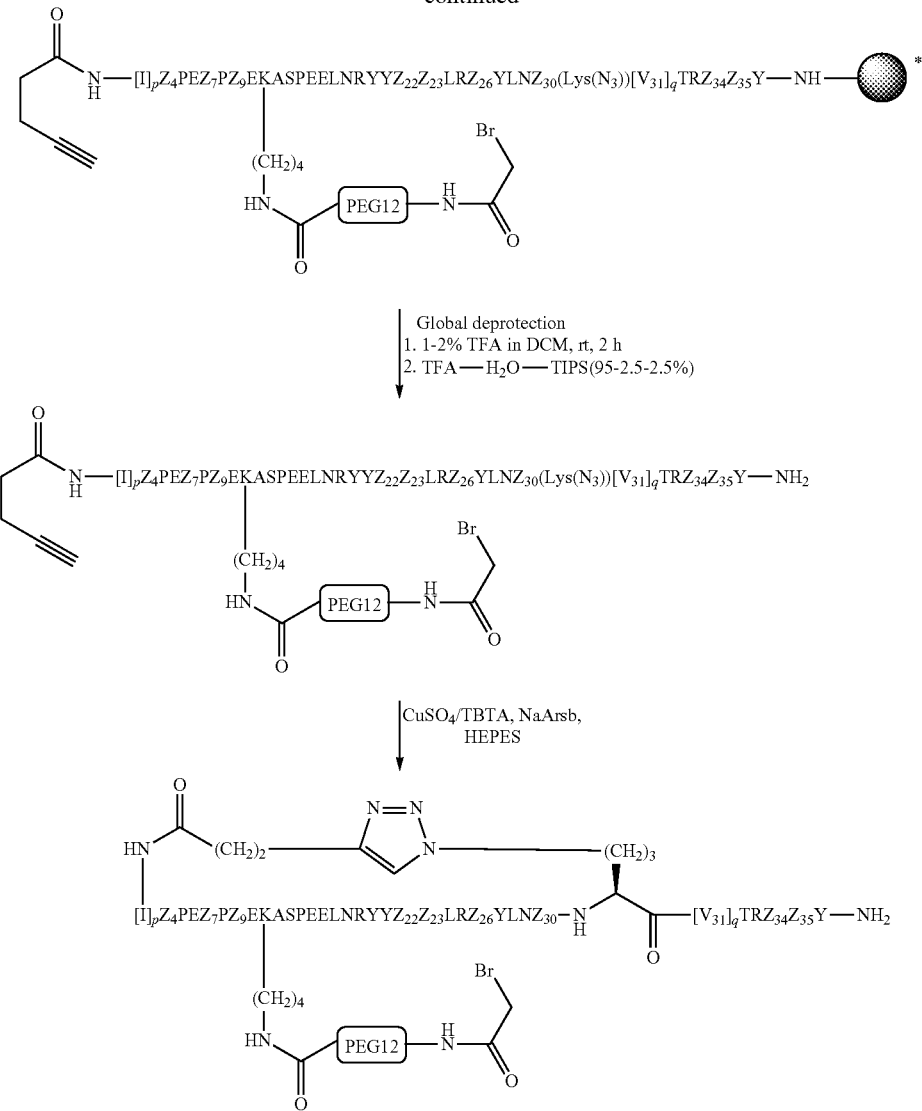

*Amino acids are protected.

Peptide Analysis and Characterization

Purified peptides were analyzed by LC/MS on a Hewlett Packard Series 1100 MSD system configured with an HP 1100 series HPLC using a Waters Atlantis T3 C18 (4.6×250 mm, 300 Å, 5 μm) column. Depending on the polar/non-polar nature of the peptide, one of three gradients was used (buffers A and B as above) at a flow rate of 1 mL/min and a column temperature of 35° C.: Method 1) 15-60% B over 22 min; Method 2) 30-60% B over 22 min; Method 3) 40-90% B over 22 min. Electrospray analysis (ES-API, positive ion scan) provided mass analysis for each peptide. In all cases, multiple charged species were observed with $1/3[M+3]^+$ and $1/4[M+4]^+$ ions being the characteristic, most prominently observed ions. All products yielded their expected multi-charged ions within acceptable limits. Results of the mass spectral analyses of the peptides and observed LC retention times (RT) are shown in Table 1:

TABLE 1

Analytical data for NTSC-PYY Compounds.

| Seq. I.D. No. | Mol. Formula | MW | $1/3[M+3]^+$ (Calc'd) | $1/3[M+3]^+$ (Found) | $1/4[M+4]^+$ (Calc'd) | $1/4[M+4]^+$ (Found) | HPLC Meth. | RT (min) |
|---|---|---|---|---|---|---|---|---|
| 1 | $C_{215}H_{345}BrN_{56}O_{67}S$ | 4898.41 | 1633.80 | 1633.8 | 1225.60 | 1225.4 | 1 | 12.48 |
| 2 | $C_{187}H_{281}N_{53}O_{55}S$ | 4183.66 | 1395.55 | 1395.4 | 1046.92 | 1046.6 | 1 | 11.7 |
| 3 | $C_{186}H_{284}N_{56}O_{55}$ | 4184.63 | 1395.88 | 1395.6 | 1047.16 | 1047.0 | 1 | 11.1 |
| 4 | $C_{210}H_{325}N_{53}O_{57}S$ | 4564.27 | 1522.42 | 1522.2 | 1142.07 | 1141.9 | 2 | 17.0 |

TABLE 1-continued

Analytical data for NTSC-PYY Compounds.

| Seq. I.D. No. | Mol. Formula | MW | 1/3[M + 3]$^+$ (Calc'd) | 1/3[M + 3]$^+$ (Found) | 1/4[M + 4]$^+$ (Calc'd) | 1/4M + 4]$^+$ (Found) | HPLC Meth. | RT (min) |
|---|---|---|---|---|---|---|---|---|
| 5 | $C_{225}H_{345}N_{55}O_{59}S$ | 4796.59 | 1599.86 | 1599.6 | 1200.15 | 1199.9 | 3 | 15.8 |
| 6 | $C_{224}H_{348}N_{58}O_{59}$ | 4797.56 | 1600.19 | 1600.1 | 1200.39 | 1200.3 | 3 | 15.7 |
| 7 | $C_{212}H_{327}N_{55}O_{59}S$ | 4622.31 | 1541.77 | 1541.8 | 1156.58 | 1156.7 | 2 | 15.8 |
| 8 | $C_{208}H_{319}N_{55}O_{59}S$ | 4566.20 | 1523.07 | 1522.8 | 1142.55 | 1142.4 | 2 | 14.7 |
| 9 | $C_{187}H_{283}N_{53}O_{54}S$ | 4169.68 | 1390.89 | 1390.6 | 1043.42 | 1043.3 | 1 | 11.3 |
| 10 | $C_{223}H_{339}N_{55}O_{61}S$ | 4798.52 | 1600.51 | 1600.4 | 1200.63 | 1200.6 | 3 | 13.4 |
| 11 | $C_{223}H_{341}N_{55}O_{60}S$ | 4784.54 | 1595.85 | 1595.7 | 1197.14 | 1197.1 | 3 | 12.8 |
| 12 | $C_{188}H_{283}N_{53}O_{55}S$ | 4197.69 | 1400.23 | 1400.2 | 1050.42 | 1050.3 | 1 | 11.9 |
| 13 | $C_{208}H_{321}N_{55}O_{58}S$ | 4552.22 | 1518.41 | 1518.2 | 1139.06 | 1139.0 | 2 | 13.8 |
| 14 | $C_{209}H_{321}N_{55}O_{59}S$ | 4580.23 | 1527.74 | 1527.8 | 1146.06 | 1145.9 | 2 | 15.2 |
| 15 | $C_{199}H_{309}N_{55}O_{59}S$ | 4448.02 | 1483.67 | 1483.7 | 1113.01 | 1112.9 | 2 | 14.1 |
| 16 | $C_{202}H_{308}N_{54}O_{58}S$ | 4453.04 | 1485.35 | 1485.1 | 1114.26 | 1114.2 | 2 | 13.9 |
| 17 | $C_{205}H_{312}N_{54}O_{59}S$ | 4509.10 | 1504.03 | 1503.9 | 1128.28 | 1128.2 | 2 | 16.6 |
| 18 | $C_{207}H_{314}N_{54}O_{61}S$ | 4567.14 | 1523.38 | 1523.2 | 1142.79 | 1142.7 | 2 | 16.4 |
| 19 | $C_{208}H_{319}N_{55}O_{59}S$ | 4566.20 | 1523.07 | 1523.1 | 1142.55 | 1142.5 | 2 | 15.0 |
| 20 | $C_{208}H_{319}N_{55}O_{59}S$ | 4566.20 | 1523.07 | 1522.8 | 1142.55 | 1142.4 | 2 | 15.1 |
| 21 | $C_{202}H_{310}N_{52}O_{59}S$ | 4443.04 | 1482.01 | 1481.9 | 1111.76 | 1111.6 | 2 | 17.2 |
| 22 | $C_{204}H_{312}N_{52}O_{61}S$ | 4501.08 | 1501.36 | 1501.2 | 1126.27 | 1126.2 | 2 | 16.8 |
| 23 | $C_{222}H_{349}N_{57}O_{66}S$ | 4900.57 | 1634.52 | 1634.4 | 1226.14 | 1225.9 | 2 | 16.7 |
| 24 | $C_{224}H_{349}N_{57}O_{66}S$ | 4928.62 | 1643.87 | 1643.4 | 1233.16 | 1233.0 | 2 | 18.4 |
| 25 | $C_{210}H_{325}N_{55}O_{58}S$ | 4580.27 | 1527.76 | 1527.7 | 1146.07 | 1146.1 | 2 | 17.0 |
| 26 | $C_{212}H_{329}N_{55}O_{58}S$ | 4608.32 | 1537.11 | 1537.1 | 1153.08 | 1153.0 | 2 | 19.7 |
| 27 | $C_{217}H_{338}N_{56}O_{63}S$ | 4771.45 | 1591.48 | 1591.3 | 1193.86 | 1193.8 | 2 | 12.0 |
| 28 | $C_{202}H_{310}N_{54}O_{57}S$ | 4439.06 | 1480.69 | 1480.6 | 1110.77 | 1110.8 | 2 | 13.3 |
| 29 | $C_{199}H_{311}N_{55}O_{58}S$ | 4434.04 | 1479.01 | 1478.9 | 1109.51 | 1109.3 | 2 | 13.7 |
| 30 | $C_{199}H_{311}N_{55}O_{58}S$ | 4434.04 | 1479.01 | 1479.0 | 1109.51 | 1109.3 | 2 | 14.2 |
| 31 | $C_{222}H_{347}N_{57}O_{64}S$ | 4870.58 | 1624.53 | 1624.6 | 1218.65 | 1218.6 | 2 | 18.5 |
| 32 | $C_{205}H_{314}N_{54}O_{58}S$ | 4495.12 | 1499.37 | 1499.3 | 1124.78 | 1124.8 | 2 | 15.9 |
| 33 | $C_{209}H_{323}N_{55}O_{58}S$ | 4566.24 | 1523.08 | 1522.9 | 1142.56 | 1142.4 | 2 | 14.6 |
| 34 | $C_{201}H_{315}N_{55}O_{58}S$ | 4462.09 | 1488.36 | 1488.0 | 1116.52 | 1116.4 | 2 | 13.9 |
| 35 | $C_{209}H_{323}N_{55}O_{58}S$ | 4566.24 | 1523.08 | 1522.8 | 1142.56 | 1142.5 | 2 | 14.4 |
| 36 | $C_{200}H_{313}N_{55}O_{58}S$ | 4448.07 | 1483.69 | 1483.5 | 1113.02 | 1112.9 | 2 | 13.8 |
| 37 | $C_{205}H_{322}N_{56}O_{59}S$ | 4547.20 | 1516.73 | 1516.6 | 1137.80 | 1137.7 | 2 | 14.2 |
| 38 | $C_{206}H_{324}N_{56}O_{59}S$ | 4561.22 | 1521.41 | 1521.7 | 1141.31 | 1141.3 | 2 | 13.7 |
| 39 | $C_{209}H_{322}N_{54}O_{59}S$ | 4567.23 | 1523.41 | 1523.2 | 1142.81 | 1142.7 | 3 | 10.3 |
| 40 | $C_{219}H_{346}N_{60}O_{64}$ | 4843.52 | 1615.50 | 1615.4 | 1211.9 | 1211.8 | 2 | 15.1 |
| 41 | $C_{207}H_{324}N_{58}O_{58}$ | 4553.20 | 1518.70 | 1518.4 | 1139.3 | 1139.3 | 2 | 13.6 |
| 42 | $C_{221}H_{348}N_{60}O_{66}$ | 4901.56 | 1634.90 | 1634.8 | 1226.4 | 1226.4 | 2 | 11.0 |
| 43 | $C_{220}H_{343}N_{57}O_{64}S$ | 4842.53 | 1615.18 | 1615.0 | 1211.63 | 1211.5 | 2 | 15.5 |
| 44 | $C_{224}H_{351}N_{57}O_{64}S$ | 4898.64 | 1633.88 | 1633.9 | 1225.66 | 1225.6 | 2 | 12.7 |
| 45 | $C_{261}H_{428}N_{56}O_{81}S$ | 5678.63 | 1893.88 | 1893.4 | 1420.66 | 1420.6 | 2 | 19.4 |
| 46 | $C_{205}H_{322}N_{56}O_{59}S$ | 4547.20 | 1516.73 | 1516.6 | 1137.80 | 1137.6 | 2 | 13.7 |
| 47 | $C_{225}H_{351}N_{57}O_{66}S$ | 4942.65 | 1648.55 | 1648.2 | 1236.66 | 1236.6 | 2 | 11.7 |
| 48 | $C_{225}H_{351}N_{57}O_{66}S$ | 4942.65 | 1648.55 | 1648.6 | 1236.66 | 1236.6 | 2 | 11.8 |
| 49 | $C_{208}H_{321}N_{55}O_{59}S$ | 4568.22 | 1523.74 | 1523.6 | 1143.06 | 1142.9 | 1 | 15.2 |
| 50 | $C_{225}H_{351}N_{57}O_{65}S$ | 4926.65 | 1643.22 | 1643.2 | 1232.66 | 1232.5 | 2 | 11.6 |
| 51 | $C_{205}H_{314}N_{54}O_{59}S$ | 4511.12 | 1504.71 | 1504.6 | 1128.78 | 1128.6 | 2 | 15.6 |
| 52 | $C_{237}H_{380}N_{56}O_{69}S$ | 5150.00 | 1717.67 | 1717.5 | 1288.50 | 1288.4 | 2 | 18.6 |
| 53 | $C_{234}H_{371}N_{59}O_{68}S$ | 5130.92 | 1711.31 | 1710.9 | 1283.73 | 1283.6 | 2 | 16.6 |
| 54 | $C_{222}H_{349}N_{57}O_{62}S$ | 4840.60 | 1614.53 | 1614.3 | 1211.15 | 1211.1 | 2 | 16.6 |
| 55 | $C_{223}H_{349}N_{57}O_{63}S$ | 4868.61 | 1623.87 | 1623.6 | 1218.15 | 1218.0 | 2 | 14.9 |
| 56 | $C_{206}H_{300}ClN_{55}O_{58}S$ | 4542.48 | 1515.16 | 1515.0 | 1136.62 | 1136.4 | 1 | 13.6 |
| 57 | $C_{207}H_{301}Cl_2N_{55}O_{59}S$ | 4606.95 | 1536.65 | 1536.3 | 1152.74 | 1152.5 | 1 | 14.5 |
| 58 | $C_{209}H_{314}FN_{55}O_{58}S$ | 4576.17 | 1526.39 | 1526.2 | 1145.04 | 1144.9 | 2 | 10.9 |
| 59 | $C_{223}H_{349}N_{57}O_{64}S$ | 4884.61 | 1629.20 | 1629.0 | 1222.15 | 1221.9 | 2 | 15.5 |
| 60 | $C_{223}H_{349}N_{57}O_{64}S$ | 4884.61 | 1629.20 | 1629.1 | 1222.15 | 1222.1 | 2 | 15.4 |
| 61 | $C_{210}H_{314}F_3N_{55}O_{58}S$ | 4626.18 | 1543.06 | 1542.7 | 1157.55 | 1157.4 | 2 | 12.7 |
| 62 | $C_{204}H_{310}F_3N_{55}O_{58}S$ | 4550.08 | 1517.69 | 1517.6 | 1138.52 | 1138.3 | 2 | 9.1 |
| 63 | $C_{207}H_{316}F_3N_{55}O_{58}S$ | 4592.16 | 1531.72 | 1531.7 | 1149.04 | 1149.0 | 2 | 12.1 |
| 64 | $C_{210}H_{325}N_{55}O_{59}S$ | 4596.27 | 1533.09 | 1532.7 | 1150.07 | 1150.0 | 2 | 11.8 |
| 65 | $C_{208}H_{312}D_9N_{55}O_{58}S$ | 4561.15 | 1521.38 | 1521.3 | 1141.29 | 1141.2 | 2 | 14.1 |
| 66 | $C_{211}H_{313}F_6N_{55}O_{58}S$ | 4694.17 | 1565.72 | 1565.4 | 1174.54 | 1174.6 | 2 | 14.1 |
| 67 | $C_{211}H_{313}F_6N_{55}O_{58}S$ | 4694.17 | 1565.72 | 1565.6 | 1174.54 | 1174.4 | 2 | 14.2 |
| 68 | $C_{219}H_{348}N_{58}O_{65}S$ | 4865.57 | 1622.86 | 1622.7 | 1217.39 | 1217.3 | 1 | 17.3 |
| 69 | $C_{181}H_{280}N_{54}O_{54}$ | 4076.53 | 1359.84 | 1359.7 | 1020.13 | 1020 | 1 | 11.4 |
| 70 | $C_{180}H_{278}N_{54}O_{54}$ | 4062.50 | 1355.17 | 1355 | 1016.63 | 1016.7 | 1 | 12.2 |
| 71 | $C_{181}H_{278}N_{54}O_{55}$ | 4090.51 | 1364.50 | 1364.4 | 1023.63 | 1023.5 | 1 | 12.8 |
| 72 | $C_{215}H_{339}N_{57}O_{66}$ | 4778.38 | 1593.79 | 1593.4 | 1195.60 | 1195.6 | 1 | 15.8 |
| 73 | $C_{203}H_{321}BrN_{56}O_{61}S$ | 4634.09 | 1545.70 | 1545.4 | 1159.52 | 1159.6 | 1 | 12.12 |
| 74 | $C_{188}H_{292}BrN_{55}O_{54}S$ | 4298.69 | 1433.90 | 1433.9 | 1075.67 | 1075.6 | 1 | 11.96 |
| 75 | $C_{211}H_{338}BrN_{55}O_{66}S$ | 4813.30 | 1605.43 | 1605.5 | 1204.32 | 1204.4 | 1 | 12.27 |
| 76 | $C_{249}H_{412}BrN_{57}O_{84}S$ | 5660.31 | 1887.77 | 1887.4 | 1416.08 | 1416.0 | 1 | 13.15 |
| 77 | $C_{214}H_{343}BrN_{56}O_{67}S$ | 4884.38 | 1629.13 | 1629.1 | 1222.09 | 1222.1 | 1 | 12.24 |
| 78 | $C_{216}H_{347}BrN_{56}O_{67}S$ | 4912.44 | 1638.48 | 1638.4 | 1229.11 | 1229.1 | 1 | 12.49 |

TABLE 1-continued

Analytical data for NTSC-PYY Compounds.

| Seq. I.D. No. | Mol. Formula | MW | 1/3[M + 3]+ (Calc'd) | 1/3[M + 3]+ (Found) | 1/4[M + 4]+ (Calc'd) | 1/4M + 4]+ (Found) | HPLC Meth. | RT (min) |
|---|---|---|---|---|---|---|---|---|
| 79 | $C_{216}H_{347}BrN_{56}O_{67}S$ | 4912.44 | 1638.48 | 1638.1 | 1229.11 | 1228.9 | 1 | 12.58 |
| 80 | $C_{220}H_{344}BrN_{59}O_{67}S$ | 4999.48 | 1667.49 | 1667.3 | 1250.87 | 1250.8 | 1 | 12.55 |
| 81 | $C_{220}H_{344}BrN_{59}O_{67}S$ | 4999.48 | 1667.49 | 1667.4 | 1250.87 | 1250.7 | 1 | 12.43 |
| 82 | $C_{211}H_{338}BrN_{55}O_{68}S$ | 4845.30 | 1616.10 | 1616.0 | 1212.32 | 1212.4 | 1 | 12.44 |
| 83 | $C_{217}H_{347}BrN_{58}O_{66}$ | 4904.39 | 1635.80 | 1635.9 | 1227.10 | 1227.0 | 1 | 12.55 |
| 84 | $C_{225}H_{354}BrN_{59}O_{66}S$ | 5053.61 | 1685.54 | 1685.4 | 1264.40 | 1264.3 | 1 | 12.80 |
| 85 | $C_{216}H_{345}BrN_{56}O_{68}S$ | 4926.42 | 1643.14 | 1642.9 | 1232.61 | 1232.6 | 1 | 11.72 |
| 86 | $C_{216}H_{345}BrN_{56}O_{69}S$ | 4942.42 | 1648.47 | 1648.3 | 1236.61 | 1236.5 | 1 | 11.92 |
| 87 | $C_{216}H_{345}BrN_{56}O_{69}S$ | 4942.42 | 1648.47 | 1648.3 | 1236.61 | 1236.4 | 1 | 11.82 |
| 88 | $C_{212}H_{339}BrN_{56}O_{67}S$ | 4856.33 | 1619.78 | 1619.5 | 1215.08 | 1214.9 | 1 | 12.43 |
| 89 | $C_{213}H_{339}BrN_{56}O_{68}S$ | 4884.32 | 1629.11 | 1629.0 | 1222.08 | 1222.0 | 1 | ND |
| 90 | $C_{214}H_{341}BrN_{56}O_{68}S$ | 4898.32 | 1633.77 | 1633.7 | 1225.58 | 1225.5 | 1 | ND |
| 91 | $C_{214}H_{341}BrN_{56}O_{68}S$ | 4898.32 | 1633.77 | 1633.3 | 1225.58 | 1225.5 | 1 | ND |
| 92 | $C_{216}H_{345}BrN_{56}O_{68}S$ | 4926.42 | 1643.14 | 1642.7 | 1232.61 | 1232.6 | 1 | ND |
| 93 | $C_{213}H_{341}BrN_{56}O_{67}S$ | 4870.35 | 1624.3 | 1624.1 | 1218.5 | 1218.4 | 1 | 12.67 |
| 94 | $C_{213}H_{341}BrN_{56}O_{67}S$ | 4870.35 | 1624.3 | 1624.3 | 1218.5 | 1218.4 | 1 | 12.42 |
| 95 | $C_{182}H_{279}BrN_{54}O_{55}$ | 4183.45 | 1395.5 | 1395.3 | 1046.9 | 1046.7 | 1 | 13.41 |
| 96 | $C_{239}H_{393}BrN_{56}O_{79}S$ | 5427.04 | 1810.0 | 1809.7 | 1357.8 | 1357.8 | 1 | 12.44 |
| 97 | $C_{214}H_{343}BrN_{56}O_{67}S$ | 4884.4 | 1629.1 | 1628.8 | 1222.1 | 1221.9 | 1 | 11.74 |
| 98 | $C_{186}H_{286}BrN_{55}O_{55}S$ | 4284.6 | 1429.2 | 1428.9 | 1072.1 | 1071.9 | 1 | 12.28 |
| 99 | $C_{187}H_{288}BrN_{55}O_{55}S$ | 4298.6 | 1433.9 | 1433.6 | 1075.6 | 1075.6 | 1 | 12.03 |
| 100 | $C_{186}H_{288}BrN_{55}O_{54}S$ | 4270.6 | 1424.5 | 1424.3 | 1068.6 | 1068.6 | 1 | 12.59 |

INTERMEDIATES

It is understood that the following examples and embodiments described herein are for illustrative purposes only and that various modifications or changes in light thereof will be suggestive to persons skilled in the art and are to be included within the spirit and purview of this application and the scope of the appended claims. All publications, patents, and patent applications cited herein are hereby incorporate by reference in their entirety for all purposes.

Intermediate 1

Synthesis of α-Tocopheryloxyacetic Acid (AcVitE) (8)

A) tert-Butyl α-tocopheryloxyacetate (7)

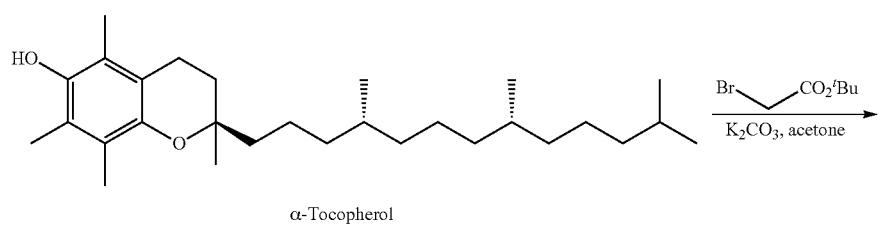

α-Tocopherol

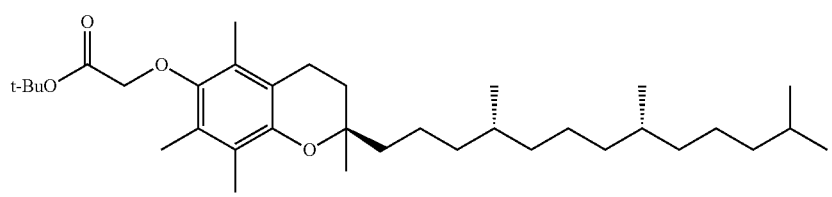

7

A mixture of α-tocopherol (1.14 g, 2.65 mmol), tert-butyl bromoacetate (470 μL, 3.18 mmol) and K₂CO₃ (1.1 g, 7.94 mmol) in acetone (10 mL) was stirred at rt for 2-3 d. The mixture was then filtered through a small plug of K₂CO₃ and the filtrate was concentrated under reduced pressure. The resultant residue was purified by silica gel chromatography eluting with EtOAc/heptanes (0-5%) to afford tert-butyl α-tocopheryloxyacetate (7) as a colorless oil. ¹H NMR (CDCl₃) δ 4.17 (s, 2H), 2.56 (t, J=6.57 Hz, 2H), 2.18 (s, 3H), 2.14 (s, 3H), 2.07 (s, 3H), 1.65-1.86 (m, 2H), 1.52 (s, 9H), 0.98-1.46 (m, 22H), 0.80-0.90 (m, 14H).

B) α-Tocopheryloxyacetic Acid (AcVitE) (8)

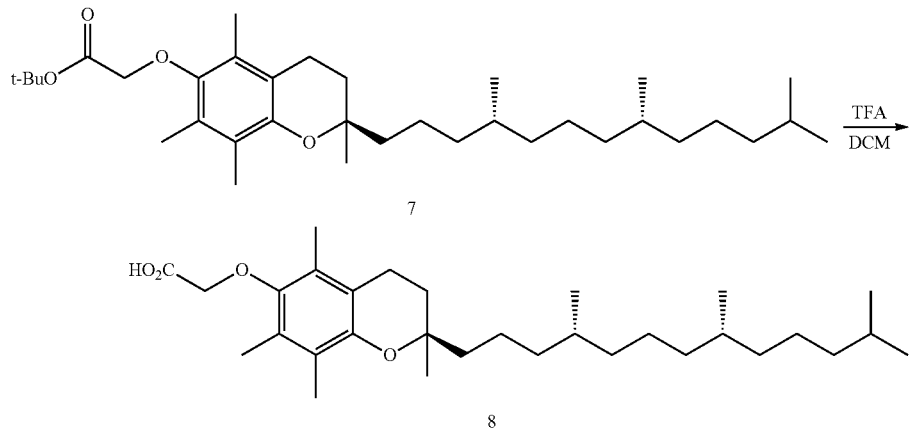

To a solution of tert-butyl α-tocopheryloxyacetate (7) (1.4 g, 2.57 mmol) in DCM (12 mL) was added TFA (6 mL), and the resulting solution was stirred at rt. After 2 h, the solution was concentrated under reduced pressure and the resultant dark oil was purified by silica gel chromatography eluting with MeOH/DCM (0-2.5% containing 0.5% HOAc) to afford α-tocopheryloxyacetic acid (AcVitE) (8) as an amber-colored syrup which slowly solidified under vacuum. ¹H NMR (CDCl₃) δ 4.34 (s, 2H), 2.57 (t, J=6.82 Hz, 2H), 2.16 (s, 3H), 2.12 (s, 3H), 2.08 (s, 3H), 1.79 (qt, J=6.76, 13.01 Hz, 2H), 1.48-1.59 (m, 3H), 1.18-1.48 (m, 12H), 1.01-1.17 (m, 7H), 0.77-0.93 (m, 14H). LC/MS: mass calcd. for C₃₁H₅₂O₄: 488.75; found: 489.5 [M+H]⁺.

Intermediate 2

1. Synthesis of (S)-22-(tert-butoxycarbonyl)-43,43-dimethyl-10,19,24,41-tetraoxo-3,6,12,15,42-pentaoxa-9,18,23-triazatetratetracontan-1-oic acid (16)

A) Benzyl 2,2-dimethyl-4-oxo-3,8,11-trioxa-5-azatridecan-13-oate (9)

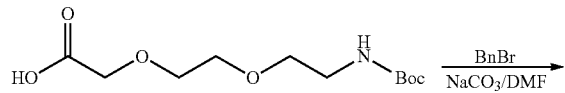

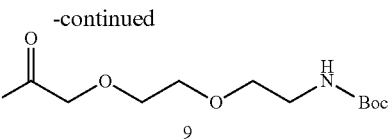

Into a 100-mL round-bottom flask, was placed 2,2-dimethyl-4-oxo-3,8,11-trioxa-5-azatridecan-13-oic acid (18 g, 68.366 mmol), benzyl bromide (23.386 g, 136.732 mmol), potassium carbonate (28.346 g, 205.099 mmol) and DMF (200 mL). The resulting solution was stirred at rt overnight and diluted with EtOAc (500 mL). The mixture was washed with water (300 mL) and brine (150 mL×2). The organic phase was evaporated and purified with silica gel column (EtOAc/propyl ether, 1:5) to give benzyl 2,2-dimethyl-4-oxo-3,8,11-trioxa-5-azatridecan-13-oate as colorless oil (9). LC/MS: mass calcd. for C₁₈H₂₇NO₆: 353.2, found: 354.05 [M+H]⁺.

B) Benzyl 2-(2-(2-aminoethoxy)ethoxy)acetate (10)

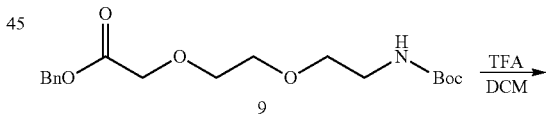

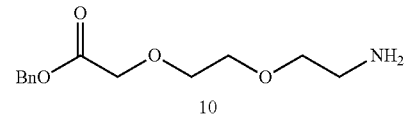

Into a 500-mL round-bottom flask, was placed benzyl 2,2-dimethyl-4-oxo-3,8,11-trioxa-5-azatridecan-13-oate (12 g, 33.955 mmol), TFA (19.358 g, 169.774 mmol) and DCM (150 mL). The resulting solution was stirred at rt overnight. The mixture was evaporated and dried to give benzyl 2-(2-(2-aminoethoxy)ethoxy)acetate as light-yellow oil (10). LC/MS: mass calcd. for C₁₃H₁₉NO₄: 253.13, found: 254.05 [M+H]⁺.

C). Benzyl 2,2-dimethyl-4,13-dioxo-3,8,11,17,20-pentaoxa-5,14-diazadocosan-22-oate (11)

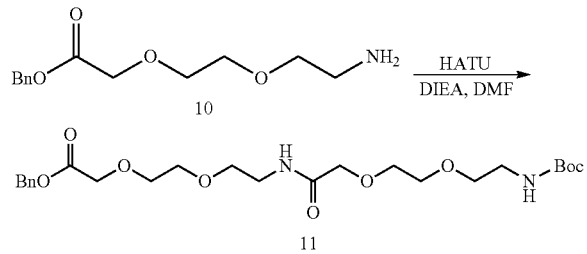

Into a 250-mL round-bottom flask, was placed 2,2-dimethyl-4-oxo-3,8,11-trioxa-5-azatridecan-13-oic acid (8.835 g, 33.558 mmol), benzyl 2-(2-(2-aminoethoxy)ethoxy)acetate (8.5 g, 33.558 mmol), HATU (15.312 g, 40.270 mmol), DIEA (8.674 g, 67.116 mmol) and DMF (100 mL). The resulting solution was stirred at rt overnight and diluted with EtOAc (500 mL). The organic phase was washed with water (200 mL) and brine (100 mL×2). The organic phase was evaporated and purified with silica gel column (DCM/MeOH, 10:1) to give benzyl 2,2-dimethyl-4,13-dioxo-3,8,11,17,20-pentaoxa-5,14-diazadocosan-22-oate as light-yellow oil (11). LC/MS: mass calcd. for $C_{24}H_{38}N_2O_9$: 498.26, found: 499.50 $[M+H]^+$.

D) Benzyl 17-amino-10-oxo-3,6,12,15-tetraoxa-9-azaheptadecan-1-oate (12)

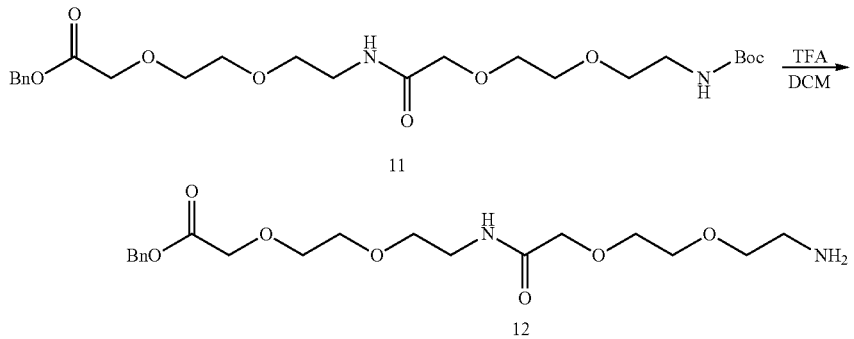

Into a 500-mL round-bottom flask, was placed benzyl 2,2-dimethyl-4,13-dioxo-3,8,11,17,20-pentaoxa-5,14-diazadocosan-22-oate (15 g, 30.086 mmol), TFA (17.153 g, 150.431 mmol) and DCM (200 mL). The resulting solution was stirred at rt overnight. The mixture was evaporated and dried to give benzyl 17-amino-10-oxo-3,6,12,15-tetraoxa-9-azaheptadecan-1-oate as light-yellow oil (12). LC/MS: mass calcd. for $C_{19}H_{30}N_2O_7$: 398.21, found: 399.2 $[M+H]^+$.

E) (S) 1-Benzyl 23-tert-butyl 22-(((9H-fluoren-9-yl)methoxy)carbonylamino)-10,19-dioxo-3,6,12,15-tetraoxa-9,18-diazatricosane-1,23-dioate (13)

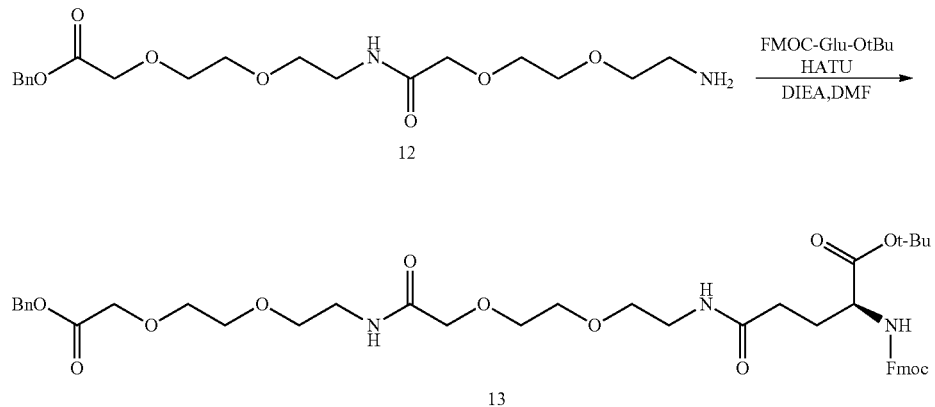

Into a 250-mL round-bottom flask, was placed benzyl 17-amino-10-oxo-3,6,12,15-tetraoxa-9-azaheptadecan-1-oate (11 g, 27.607 mmol), (S)-4-(((9H-fluoren-9-yl)methoxy)carbonylamino)-5-tert-butoxy-5-oxopentanoic acid (11.746 g, 27.607 mmol), HATU (12.596 g, 33.128 mmol), DIEA (7.136 g, 55.214 mmol) and DMF (100 mL). The resulting solution was stirred at rt overnight and diluted with EtOAc (500 mL). The organic phase was washed with water (200 mL×2) and brine (200 mL). The organic phase was evaporated and purified by silica gel chromatography (DCM/MeOH, 10:1) to give (S)-1-benzyl 23-tert-butyl 22-(((9H-fluoren-9-yl)methoxy)carbonylamino)-10,19-dioxo-3,6,12,15-tetraoxa-9,18-diazatricosane-1,23-dioate as light-yellow oil (13). LC/MS: mass calcd. for $C_{43}H_{55}N_3O_{12}$: 805.38, found: 806.80 $[M+H]^+$.

F) (S)-1-benzyl 23-tert-butyl 22-amino-10,19-dioxo-3,6,12,15-tetraoxa-9,18-diazatricosane-1,23-dioate (14)

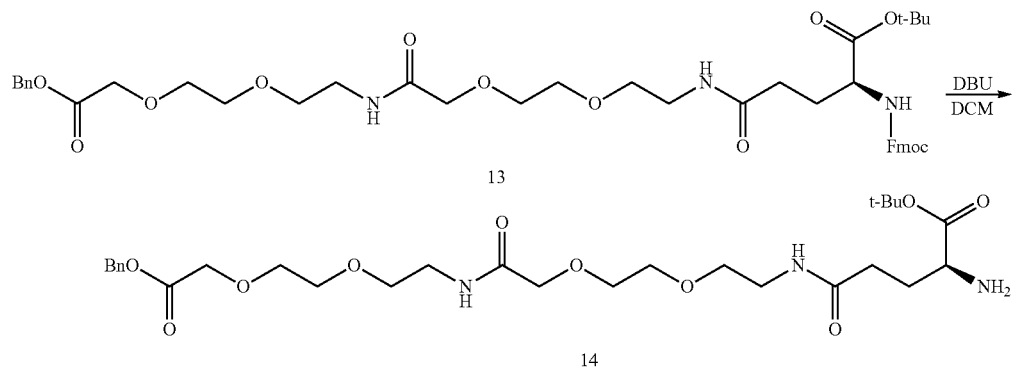

Into a 250-mL round-bottom flask, was placed (S)-1-benzyl 23-tert-butyl 22-(((9H-fluoren-9-yl)methoxy)carbonylamino)-10,19-dioxo-3,6,12,15-tetraoxa-9,18-diazatricosane-1,23-dioate (10 g, 12.408 mmol) and DBU in DCM (3%, 100 mL). The resulting solution was stirred at rt overnight, then washed with water (200 mL×2). The organic phase was concentrated. The residue was dissolved with water (200 mL) and extracted with ether (200 mL×2). The aqueous phase was extracted with DCM (200 mL). The organic phase was evaporated and dried to give of (S)-1-benzyl 23-tert-butyl 22-amino-10,19-dioxo-3,6,12,15-tetraoxa-9,18-diazatricosane-1,23-dioate as light-yellow oil (14). LC/MS: mass calcd. for $C_{28}H_{45}N_3O_{10}$: 583.31, found: 584.65 $[M+H]^+$.

G) (S)-1-benzyl 21,39-di-tert-butyl 9,18,23-trioxo-2,5,11,14-tetraoxa-8,17,22-triazanonatriacontane-1,21,39-tricarboxylate (15)

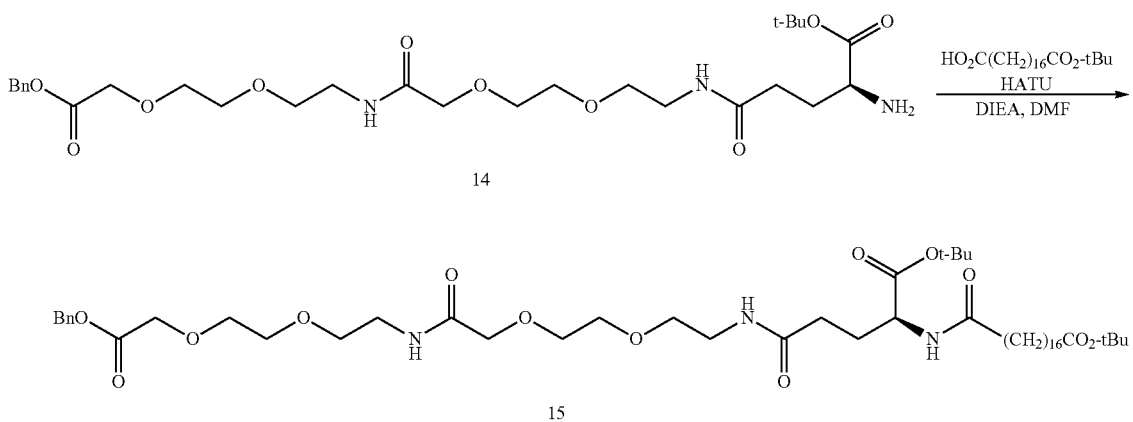

Into a 50-mL round-bottom flask, was placed (S)-1-benzyl 23-tert-butyl 22-amino-10,19-dioxo-3,6,12,15-tetraoxa-9,18-diazatricosane-1,23-dioate (1.575 g, 2.699 mmol), 18-tert-butoxy-18-oxooctadecanoic acid (1 g, 2.699 mmol), HATU (1.231 g, 3.239 mmol), DIEA (697.654 mg, 5.398 mmol, 2 equiv) and DMF (15 mL). The resulting solution was stirred at rt overnight and diluted with EtOAc (200 mL). The organic phase was washed with water (100 mL×2) and brine (100 mL). The organic phase was concentrated and purified by silica gel chromatography (DCM/MeOH, 10:1) to give (S)-1-benzyl 21,39-di-tert-butyl 9,18,23-trioxo-2,5,11,14-tetraoxa-8,17,22-triazanonatriacontane-1,21,39-tricarboxylate as light-yellow oil (15). LC/MS: mass calcd. for $C_{50}H_{55}N_5O_{13}$: 935.61, found: 936.6 $[M+H]^+$.

H) (S)-22-(tert-butoxycarbonyl)-43,43-dimethyl-10,19,24,41-tetraoxo-3,6,12,15,42-pentaoxa-9,18,23-triazatetratetracontan-1-oic acid (16)

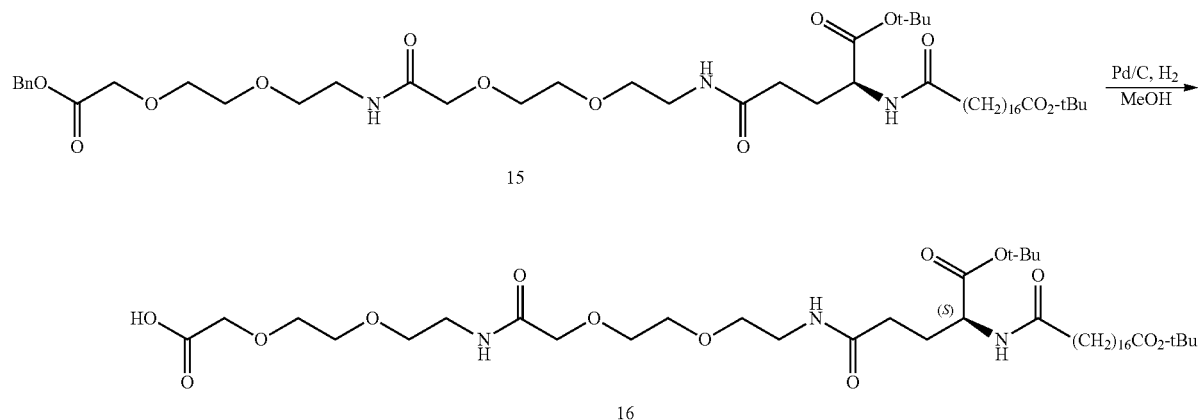

Into a 100-mL round-bottom flask, was placed (S)-1-benzyl 21,39-di-tert-butyl 9,18,23-trioxo-2,5,11,14-tetraoxa-8,17,22-triazanonatriacontane-1,21,39-tricarboxylate (2.5 g, 3.041 mmol), Pd/C (10% wt, 500 mg) and MeOH (50 mL). The resulting solution was stirred at rt overnight under H2 (3.5 atm). The residue was filtered, concentrated and purified by reverse phase silica gel chromatography (NH4HCO3/H2O, 0.05%) to give (S)-22-(tert-butoxycarbonyl)-43,43-dimethyl-10,19,24,41-tetraoxo-3,6,12,15,42-pentaoxa-9,18,23-triazatetratetracontan-1-oic acid as a light-yellow semi-solid (16). LC/MS: mass calcd. for C43H79N3O13: 845.56, found: 846.55 [M+H]+. 1H NMR (300 MHz, CD3OD) δ: 4.24-4.29 (m, 1H), 4.07 (s, 2H), 4.03 (s, 2H), 3.69-3.72 (m, 8H), 3.57-3.67 (m, 4H), 3.45-3.49 (m, 2H), 3.34-3.42 (m, 2H), 2.23-2.35 (m, 6H), 2.12-2.21 (m, 1H), 1.93-1.96 (m, 1H), 1.52-1.70 (m, 4H), 1.45-1.51 (m, 18H), 1.33 (s, 24H).

EXAMPLES

Compounds of the present invention can be prepared by methods known to those who are skilled in the art. The following examples are only meant to represent examples of the invention and are in no way meant to be a limit of the invention.

Example 1: Synthesis of Cyclic PYY Analog SEQ ID NO:1

Scheme 14. Synthesis of Fmoc-psi-[Arg(Pbf)-(N-Boc)Tyr(tBu)]-OH

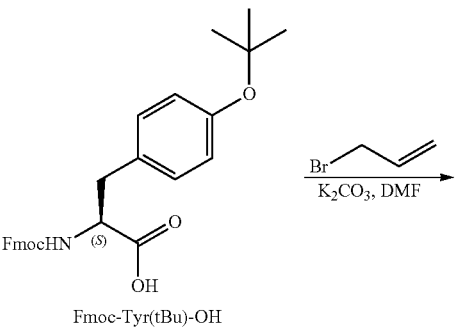

Fmoc-Tyr(tBu)-OH

-continued

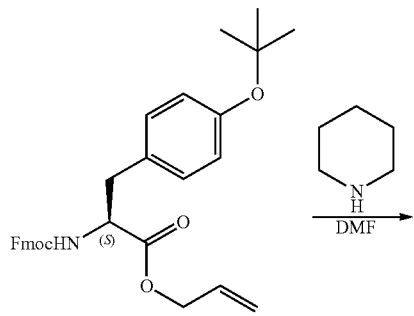

Fmoc-Tyr(tBu)-OAll

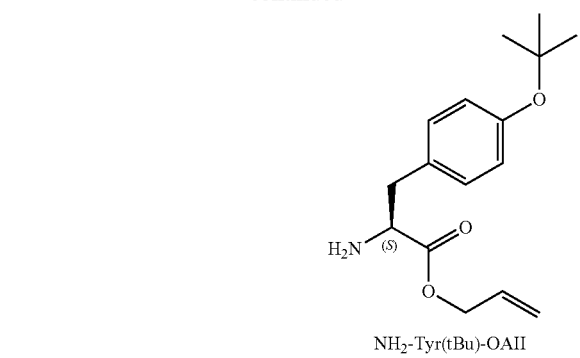
NH$_2$-Tyr(tBu)-OAll
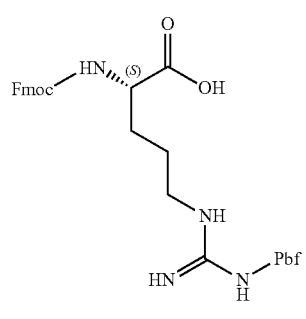
1
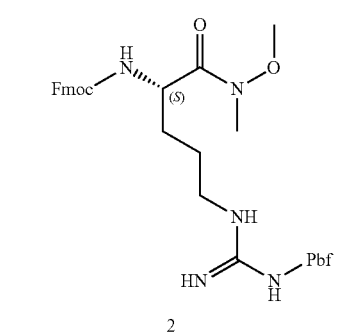
2
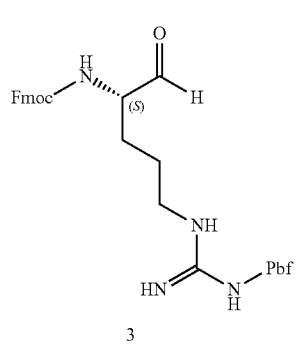
3
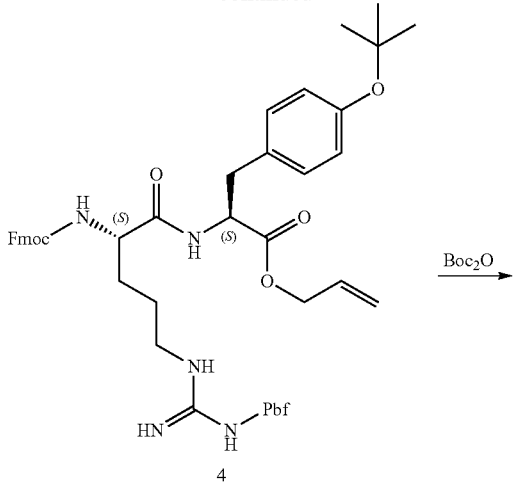
4
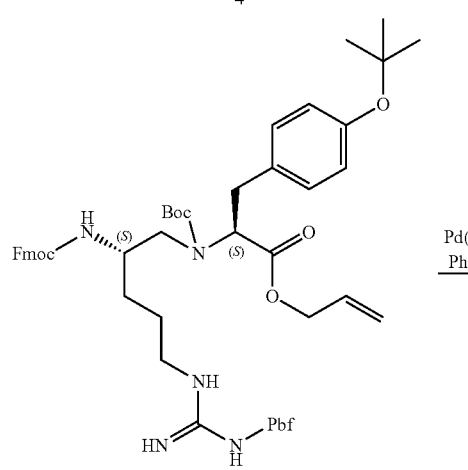
5
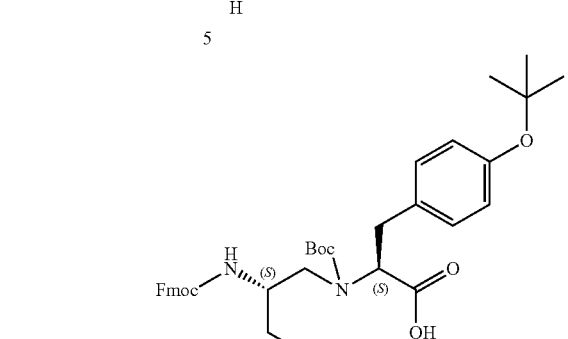
6
1. Synthesis of Fmoc-psi-[Arg(Pbf)-(N-Boc)Tyr(tBu)]-OH
A. Synthesis of H$_2$N-Tyr(tBu)-OAll
To an ice-cooled solution of Fmoc-Tyr(tBu)-0 (69 g, 150.15 mmol) and K2CO3 (62 g, 445.36 mmol) in DMF (500 mL) was added allylbromide (72 g, 595.16 mmol), and the resultant mixture was stirred for 3 h. Ice/water (1 L) was then added and the mixture was extracted with EtOAc. The combined organic extracts were dried (Na$_2$SO$_4$) and concentrated under reduced pressure to afford Fmoc-Tyr(tBu)-OAll as a yellow oil. To an ice-cooled solution of Fmoc-Tyr(tBu)-OAll (70 g, 140.1 mmol) in DMF (600 mL) was added piperidine (150 mL) in drop-wise fashion over a period of 20 min. After 3 h the reaction solution was poured into water/ice (1 L), and extracted with EtOAc (2×2 L). The combined organic extracts were dried (Na$_2$SO$_4$) and concentrated under reduced pressure. The residue thus obtained was purified by silica gel chromatography, eluting with EtOAc/petroleum ether (10:1) to afford 34 g of H$_2$N-Tyr(tBu)-OAll as a yellow oil.

B. Synthesis of Fmoc-Arg(Pbf)-N(Me)OMe (2)

To an ice-cooled mixture of Fmoc-Arg(Pbf)-OH (1) (64.8 g, 99.88 mmol), N,O-dimethylhydroxylamine hydrochloride (20 g, 206.2 mmol) and HATU (57 g, 149.91 mmol) in DCM (500 mL) was added DIEA (52 g, 402.2 mmol) in drop-wise fashion over a period of 10 min, and the resulting mixture was allowed to stir at room temperature overnight. The reaction was then poured into water/ice (1 L) and extracted with DCM (1 L). The organic extracts were dried (Na$_2$SO$_4$) and concentrated under reduced pressure to afford 70 g of crude Fmoc-Arg(Pbf)-N(Me)OMe (2) as a yellow solid, which was used without further purification.

C. Synthesis of Fmoc-Arg(Pbf)-CHO (3)

To a cooled (−78° C.) solution of LAH in THF (1M, 107 mL, 0.107 mmol) under an inert atmosphere of nitrogen was added through a cannula a cooled (−50° C.) solution of Fmoc-Arg(Pbf)-N(Me)OMe (2) (50 g, 72.3 mmol) in THF (100 mL) in a drop-wise fashion over a period of 1 h. After stirring at −78° C. for 5 h, the mixture was poured into 1N HCl solution (300 mL), and additional 1N HCl was added as necessary to adjust the pH to 4, and then extracted with EtOAc (2×2 L). The combined organic extracts were dried (Na$_2$SO$_4$) and concentrated under reduced pressure to afford 45 g of crude Fmoc-Arg(Pbf)-CHO (3) as a yellow solid, which was used without further purification.

D. Synthesis of Fmoc-psi-[Arg(Pbf)-Tyr(tBu)]-OAll (4)

To an ice-cooled solution of Fmoc-Arg(Pbf)-CHO (3) from step C (45 g, 71.12 mmol) and H$_2$N-Tyr(tBu)-OAll from step A (32 g, 115.37 mmol) in THF (200 mL), MeOH (200 mL) and HOAc (15 mL) was added sodium cyanoborohydride (18.0 g, 286.4 mmol) in portions over a period of 30 min, and the resulting solution was stirred at room temperature overnight. The reaction was quenched by addition of saturated aqueous NaHCO$_3$ (500 mL) solution and the mixture was extracted with EtOAc (2×2 L). The combined organic extracts were dried (Na$_2$SO$_4$) and concentrated under reduced pressure. The residue was purified by silica gel chromatography eluting with EtOAc/petroleum ether (10:1) to afford 40 g of Fmoc-psi-[Arg(Pbf)-Tyr(tBu)]-OAll (4) as a yellow solid.

E. Synthesis of Fmoc-psi-[Arg(Pbf)-N(Boc)Tyr(tBu)]-OAll (5)

To a solution of Fmoc-psi-[Arg(Pbf)-Tyr(tBu)-OAll] (4) (53 g, 59.28 mmol) in MeCN (240 mL) was added di-tert-butyl dicarbonate (20 g, 91.3 mmol), and the resulting solution was stirred at 50° C. overnight. The mixture was then concentrated under reduced pressure and the residue was purified by silica gel chromatography eluting with EtOAc/petroleum ether (1:1) to afford 32 g of Fmoc-psi-[Arg(Pbf)-N(Boc)Tyr(tBu)]-OAll (5) as a yellow solid.

F. Synthesis of Fmoc-psi-[Arg(Pbf)-N(Boc)Tyr(tBu)]-OH (6)

To a cooled (−30° C.) solution of Fmoc-psi-[Arg(Pbf)-N(Boc)Tyr(tBu)]-OAll (5) (32 g, 32 mmol) in DCM (600 mL) under an inert atmosphere of nitrogen was added Pd(PPh$_3$)$_4$ (3.0 g, 4.33 mmol), followed by drop-wise addition of N-methylaniline (10 g, 93 mmol) over a period of 30 min. The resulting mixture was stirred at room temperature for 2 h, and then concentrated under reduced pressure. The residue was purified by silica gel chromatography eluting with EtOAc/petroleum ether (1:1) to afford 26.8 g of Fmoc-/psi-[Arg(Pbf)-N(Boc)Tyr(tBu)]-OH (6) as a yellowish solid. $^1$H NMR (300 MHz, CD$_3$OD) δ 7.75-7.77 (2H, m), 7.59-7.60 (2H, m), 7.32-7.33 (4H, m), 7.09-7.11 (2H, m), 6.87-7.00 (2H, m), 4.27-4.50 (3H, m), 3.30-3.50 (4H, m), 3.02-3.23 (3H, m), 2.75-2.98 (3H, m), 2.57 (3H, s), 2.48 (3H, s), 2.00 (3H, s), 1.31-1.41 (28H, m). LC/MS (ES, m/z): mass calcd. for C$_{52}$H$_{67}$N$_5$O$_{10}$S: 953.46, found: 954.55 [M+H]$^+$.

2. Loading of the Dipeptide Fmoc-psi-(R35-N(Boc)-Y36) onto Sieber Resin

In a fritted microwave reaction vessel (supplied by CEM Corporation), NovaSyn TG Sieber resin (supplied by Novabiochem) (0.2 mmol) was treated with 20% piperidine in DMF (10 mL) and heated at 50° C. for 2.5 min in a CEM microwave reactor. The reaction was drained and the resin was washed with DMF and treated again with 20% piperidine in DMF at 50° C. for 5 min in a CEM microwave reactor. After draining and washing the resin with DMF, the deprotection treatment was repeated one more time. The resin was then treated with a solution of Fmoc-psi-[Arg(Pbf)-(N-Boc)Tyr(tBu)]-OH obtained from above (3-5 eq.), HATU (2.75-4.8 eq.) and DIEA (6-10 eq.) in DMF (4 mL) and mixed at rt for 6 to 24 h. The mixture was drained and the resin was washed extensively with DMF, and then capped by treatment with 20% Ac$_2$O in DMF (5 mL) under microwave conditions at 50° C. for 5 min. The reaction was drained and the resin was washed extensively with DMF and DCM.

3. Synthesis of Fmoc-βA-IKPEAPGEK(Alloc)AS-PEELNRYYASLRHYLNL(hC) TRQ(psi-R35Y36)-Sieber Resin Amino acid extensions onto the pre-loaded (psi-R35, Y36)-Sieber resin (0.2 mmol) were performed on a CEM Liberty Blue Microwave peptide synthesizer. Standard α-Fmoc-protected amino acids were double-coupled in 3.8-fold excess relative to the initial resin loading at 50° C. for 15 min using HBTU/DIEA as the coupling agents. Fmoc-Arg(Pbf)-OH was double-coupled using a two-stage protocol: 25 min at rt followed by 15 min at 50° C., and Fmoc-His(Trt)-OH was double-coupled using a two-stage protocol: 4 min at rt followed by 8 min at 50° C.

4. Synthesis of Fmoc-βA-IKPEAPGEK(NH$_2$)AS-PEELNRYYASLRHYLNL(hC) TRQ(psi-R35Y36)-Sieber Resin: Alloc Deprotection The resulting resin from above was treated with a solution of phenylsilane (25 eq.) in deoxygenated DCM (10 mL).

After stirring for 2 min, a solution of the Pd(PPh₃)₄ (0.5 eq.) in DCM (10 mL) was added and the resin mixture was stirred for 30 min under argon. The reaction was drained and the resin was washed with deoxygenated DCM. The deprotection was repeated with fresh reagents, after which the reaction was drained and the resin was washed extensively with DCM and DMF.

5. Synthesis of Fmoc-βA-IKPEAPGEK(NH-dPEG₁₂-NHFmoc)ASPEELNRYY ASLRHYLNL(hC)TRQ(psi-R35Y36)-Sieber Resin: Coupling N-Fmoc dPEG₁₂ Carboxylic Acids onto 11K The Alloc-deprotected peptide-Sieber resin from above was treated with a solution of the N-Fmoc-dPEG12-carboxylic acid (5 eq), HBTU (4.8 eq.) and DIEA (10 eq.) in DMF (7 mL) in a CEM microwave reactor at 50° C. for 15 min, by which time the reaction showed a negative Kaiser test. The reaction was drained and the resin was washed extensively with DMF and DCM.

6. Synthesis of BrCH₂COHN-βA-IKPEAPGEK(NH-dPEG₁₂-NHCOCH₂Br)ASPEEL NRYYASLRHYLNL(hC)TRQ(psi-R35Y36)-Sieber Resin: bis-bromoacetylation at PA and dPEG₁₂

The above resin was subjected to Fmoc-deprotection using fresh 20% piperidine in DMF at 50° C. for 5 min in a CEM microwave reactor. The deprotection was repeated twice. The Fmoc-deprotected peptide-resin thus obtained was treated with a solution of bromoacetic anhydride (20 eq.) in DMF (5 mL) in a CEM microwave reactor at 50° C. for 10 min, by which time the reaction showed a negative Kaiser test. The reaction was drained, and the resin was washed extensively with DMF and DCM, and then dried.

7. Synthesis of BrCH₂COHN-βA-IKPEAPGEK(NH-dPEG₁₂-NHCOCH₂Br)ASPEEL NRYYASLRHYLNL(hC)TRQ(psi-R35Y36)-CONH₂: Cleavage from Resin and Global Deprotection The dried resin was treated with a solution of 1.5% TFA in DCM (10 mL) and mixed for 5 to 10 min, then filtered. This treatment was repeated for 9 additional times using fresh cocktail for each treatment. The combined filtrates were then combined and concentrated to afford the crude protected peptide as a yellow foam. This foam was treated with 20 mL of cleavage cocktail (TFA/phenol/H₂O/TIPS=88/5/5/2) at room temperature for 2.5 h and then concentrated under a stream of nitrogen to a volume of 2.5 mL, cold ether (40 mL) was then added to precipitate the peptide. The mixture was centrifuged (5 min; 5000 rpm) and decanted. This process was repeated for 2 more times to give the crude peptide as an off-white powder.

Alternatively, the resin was treated with cleavage cocktail without prior treating with 1-2% TFA in DCM to afford the fully deprotected peptide.

8. Cyclic PYY Analog SEQ ID NO: 1: Cyclization Procedure A and Purification

The crude peptide from above was dissolved in deoxygenated 50% MeCN/water (5-10 mg/mL), EDTA (1 mM) was added optionally. The pH of the reaction solution was then raised to about 8 through the addition of 7.5 w/v % NaHCO₃ solution. The resulting solution was stirred at rt for 0.5 to 2.5 h, and then acidified to pH<1 by addition of TFA. The solution was then concentrated under reduced pressure at rt to about half of the original volume (~24 mL). The resultant solution was purified by reverse phase preparative HPLC. Purifications were performed on a Gilson HPLC 2020 Personal Purification System using a Varian Pursuit XRs C18 column (30×250 mm, 100 Å, 5 μm). The mobile phase consisted of gradient elution of Buffer A (0.1% TFA in water) and Buffer B (0.1% TFA in MeCN) ranging from an initial concentration of 20% B to final concentration of 50% B over 36 min. UV detection was monitored at 220 and 254 nm. Product-containing fractions were analyzed by analytical HPLC on an Agilent 1100 HPLC system using the same column type as above (4.6×250 mm, 5 μm). Pure fractions were combined, and then lyophilized to give the product as a cotton-like solid. LCMS: 1225.5 (M+4H)/4, 1633.4 (M+3H)/3 and 2450.0 (M+2H)/2 for the product peak at 12.27 min (LC: Atlantis T3 C18 column, 5 um, 4.6×250 mm, 1.0 mL/min, 15-60% gradient).

Example 2: Synthesis of Cyclic PYY Analog SEQ ID NO:2

1. Synthesis of H₂N-IKPEAPGEDASPEELNRYYASLRHYLNL(hC)TRQRY-PAL-PEG Resin

The protected peptidyl resin was synthesized using Fmoc strategy as described above on a CEM Liberty Blue Microwave peptide synthesizer using low loading Rink amide resins, preferably, Fmoc-PAL-PEG PS resin (ca., 0.16-0.2 meq/g, supplied by Applied Biosystems) on a scale of 0.1 mmol, as depicted in Scheme 1. Standard Fmoc-protected amino acids were coupled in 5-fold excess relative to resin loading using DIC/Oxyma as the coupling agents and a reaction temperature of ca., 90° C. for 4 min. Fmoc-Arg(Pbf)-OH was double coupled at 90° C. for 4 min each and Fmoc-His(Trt)-OH was coupled using a two-stage protocol: 4 min at rt followed by 8 min at 50° C. Single Fmoc deprotections were carried out using 20% piperidine in DMF (deprotection solution) at 90° C. for 1.5 min.

2. Synthesis of m-BrCH₂PhCOHN-IKPEAPGE-DASPEELNRYYASLRHYLNL(hC) TRQRY-PAL-PEG Resin The Fmoc-deprotected peptide-resin (0.1 mmol) from above was treated with a solution of m-bromomethylbenzoic acid (20 eq.) and DIC (10 eq.) in DMF (4 mL) in a microwave reactor at 75° C. for 15 min, by which time the reaction was generally determined to be complete, as per a Kaiser ninhydrin test (Kaiser, et al., Anal. Biochem., 1970, 34, 595-598). In cases where the coupling was determined to be incomplete, the coupling was repeated with fresh reagents. The reaction was drained, and the resin was washed extensively with DMF and DCM.

3. Synthesis of m-BrCH₂PhCOHN-IKPEAPGE-DASPEELNRYYASLRHYLNL(hC) TRQRY-CONH₂: Deprotection and Cleavage from Resin The resin from above was then treated with a cleavage cocktail (10 mL/0.1 mmol scale) consisting of TFA/water/phenol/TIPS (88:5:5:2) and heated in a microwave reactor at 38° C. for 40 min, then filtered. The resin was washed with TFA and the combined filtrates were concentrated under a stream of nitrogen to a volume of ca. 2.5 mL and the peptide was precipitated by the addition of cold diethyl ether (40 mL). The peptide/ether suspension was centrifuged and the ether layer was decanted. The peptide pellet was re-suspended in ether, centrifuged and decanted, and this process was repeated a third time. The crude peptide thus obtained was dried under a mild nitrogen stream.

4. Cyclic PYY Analog SEQ ID NO: 2: Cyclization Procedure A and Purification

The crude peptide from above was dissolved in deoxygenated MeCN/water (60% MeCN) at a concentration of ≤4 mg/mL. The pH of the peptide solution was then raised to ca. 7-9 through the addition of aq. $NH_4OAc$ (200 mM, pH 8.4) and the resulting solution was stirred at rt until the cyclization was complete, as per LCMS (typically, 3-4 h). The cyclization reaction mixture was acidified to pH 1.5-3 by the addition of TFA, and the solution was concentrated to remove most of the organic co-solvent to a point where slight clouding occurred. A minimal amount of the MeCN was added back as necessary to render the mixture homogeneous and the resultant solution was then purified directly by preparative HPLC in multiple injections using a C18 Varian Pursuit XRs C18 (21×250 mm, 100 Å, 5 μm) column. The mobile phase consisted of gradient elutions of buffer A (0.1% TFA in water) and Buffer B (0.1% TFA in MeCN) ranging from an initial concentration of 20% B to a final concentration of 40% B over 45 min. UV detection was monitored at 220 and 254 nm. Product-containing fractions were analyzed by analytical HPLC on an Agilent 1100 HPLC system using an appropriate column as listed in Table 1. Pure fractions were combined, concentrated to remove most of the organic phase, and then lyophilized.

Example 3: Synthesis of Cyclic PYY Analog SEQ ID NO:3

1. Synthesis of ($H_2N$)-IKPEAPGEDASPEELNRYYASLRHYLNL-(azido-norLeu)-TRQRYPAL-PEG Resin The resin-bound peptide was prepared on a 0.1 mmol scale according to the method described in Example 2, step 1, substituting Fmoc-azidonorLeu-OH in place of Fmoc-hCys(trt)-OH at position 31.

Synthesis of (HCCH($CH_2$)$_2$CONH)-IKPEAPGEDASPEELNRYYASLRHYLNL-(azido-norLeu)-TRQRYPAL-PEG Resin 4-Pentynoic acid was coupled onto the above resin under microwave conditions using a DIC/HOBT protocol (75° C. 10 min). The reaction was drained and the resin was washed extensively with DMF and DCM.

Synthesis of (HCCH($CH_2$)$_2$CONH)-IKPEAPGEDASPEELNRYYASLRHYLNL-(azido-norLeu)-TRQRYPAL-$CONH_2$ The above resin was treated with 10 mL cleavage cocktail consisting of TFA/DODT/$H_2O$/TIS (92.5:2.5:2.5:2.5) under microwave conditions (38° C. 40 min). The reaction was drained and the resin was washed with TFA (10 mL). The combined filtrate was then concentrated under a stream of nitrogen to a volume of ~2.5 mL. Cold ether (40 mL) was then added to precipitate the peptide and the mixture was centrifuged (5 min; 5000 rpm) and decanted. This process was repeated for 2 more times to give the crude peptide as an off-white powder.

4. Cyclic PYY Analog SEQ ID NO: 3

Prepare 7 mg of CuSO4 in 2 mL deoxygenated H2O. Prepare 30 mg of TBTA in 5.4 mL of EtOH and 0.6 mL of MeCN. Premix 0.94 mL of CuSO4 solution and 4.8 mL TBTA solution. Prepare 30 mg of Na Ascorbate in 3 mL of deoxygenated H2O.

To a solution of the crude azido-containing peptide from Step 3 (100 mg) in 20 mL of deoxygenated water was added the premixed $CuSO_4$/TBTA solution followed by 2.4 mL of Na ascorbate solution (solution immediately became milky). The mixture was warmed to 40° C. and stirred for 1.5 h, at which time LCMS analysis indicated a complete reaction. The mixture was diluted to ~40 mL with water (0.1% TFA); the mixture was centrifuged, and the supernatant was purified by reverse phase preparative HPLC. Purifications were performed using a Varian Pursuit XRs C18 column (21×250 mm, 100 Å, 5 μm) at 35° C. The mobile phase consisted of a gradient elution of Buffer A (0.1% TFA in water) and Buffer B (0.1% TFA in MeCN) ranging from an initial concentration of 10% B to an intermediate concentration of 18% B (21 mpm) and then to a final concentration of 33% B (10.5 mpm) over 35 min. UV detection was monitored at 220 and 254 nm. Product-containing fractions were analyzed by analytical HPLC on an Agilent 1100 HPLC system using the same column type as above (4.6×250 mm, 5 μm). Pure fractions were combined, and then lyophilized to give the product as a cotton-like solid.

Example 4: Synthesis of Cyclic PYY Analog SEQ ID NO:4

1. Synthesis of (Dde)K($NH_2$)ASPEELNRYYASLRHYLNL(hC)TRQRY-PAL-PEG Resin

The resin-bound peptide was prepared using the method described in Example 2, step 1.

2. Synthesis of (Dde)K(NH-Glu-(OtBu)$NH_2$)ASPEELNRYYASLRHYLNL(hC) TRQRY-PAL-PEG Resin Fmoc-Glu-OtBu (5 eq.) was coupled onto the above resin under microwave conditions using DIC/Oxyma coupling methods (90° C. 6 min; dc). The resin was drained and washed with DMF. Fmoc deprotection was then carried out using 20% piperidine in DMF using a 3-stage protocol (75° C. for 0.5 min; 75° C. for 3 min; 75° C. for 3 min) with DMF washings at each stage.

3. Synthesis of (Dde)K(NH-Glu-(OtBu)NH-Pal) ASPEELNRYYASLRHYLNL(hC) TRQRY-PAL-PEG Resin Palmitic acid (5 eq.) was coupled onto the above resin under microwave conditions using DIC/Oxyma coupling methods (90° C., 5 min). The resin was drained and washed with extensively with DMF and DCM.

4. Synthesis of ($H_2N$)K(NH-Glu-(OtBu)NH-Pal) ASPEELNRYYASLRHYLNL(hC) TRQRY-PAL-PEG Resin After washing the above resin with DMF, it was treated with a solution of 2% hydrazine in DMF (6 mL/0.1 mmol resin) at rt for 5 min, then drained and washed with DMF. The treatment was repeated 5 additional times.

5. Synthesis of (H$_2$N)IKPEAPGEK(NH-Glu-(OtBu)NH-Pal)ASPEELNRYYASLRHYLNL(hC)TRQRY-PAL-PEG Resin The remaining amino acid couplings were carried out using the method described in Example 2, step 1.
Cyclic PYY Analog SEQ ID NO: 4
The remainder of the synthesis was carried out using the methods described in Example 2, steps 2-4. Product purification was performed using a Varian Pursuit XRS C18 column (21×250 mm, 100 Å, 5 µm) at rt. The mobile phase consisted of a gradient elution of Buffer A (0.1% TFA in water) and Buffer B (0.1% TFA in MeCN) ranging from 23% B to an intermediate concentration of 33% B (21 mpm) over 5 min, and then to a final concentration of 48% B (10.5 mpm) over 55 min.

Example 5: Synthesis of Cyclic PYY Analog SEQ ID NO:5

The title compound was prepared according to the procedure as described in Example 4 substituting α-Tocopheryloxyacetic Acid (AcVitE) (8) in place of palmitic acid in step 3. Product purification was performed using an Agilent 300SB C8 column (21×250 mm, 100 Å, 5 µm) at rt. The mobile phase consisted of a gradient elution of Buffer A (0.1% TFA in water) and Buffer B (0.1% TFA in MeCN) ranging from an initial concentration of 35% B to an intermediate concentration of 45% B (21 mpm) over 5 min, and then to a final concentration of 60% B (10.5 mpm) over 60 min.

Example 6: Synthesis of Cyclic PYY Analog SEQ ID NO:6

1. Synthesis of (HCCH(CH$_2$)$_2$CONH)-IKPEAPGE-DASPEELNRYYASLRHYLNK(Dde)-(azido-nor-Leu)-TRQRY-PAL-PEG Resin The resin-bound peptide was prepared as described in Example 3, step 1, substituting Fmoc-Lys(Dde)-OH in place of Fmoc-Leu-OH at position 30 and incorporating the 4-pentynoic acid (double coupled) in this step at position 2, following Fmoc-Ile-OH at position 3.

2. Synthesis of (HCCH(CH$_2$)$_2$CONH)-IKPEAPGE-DASPEELNRYYASLRHYLNK(NH$_2$)-(azido-nor-Leu)-TRQRY-PAL-PEG Resin The above resin was treated with 3% hydrazine in DMF (8 mL/0.1 mmol scale) for 5 min at rt and then the mixture was drained and washed with DMF. This procedure was repeated ca. 5×, after which the resin was washed extensively with DMF and then DCM.

3. Synthesis of (HCCH(CH$_2$)$_2$CONH)-IKPEAPGE-DASPEELNRYYASLRHYLNK(NH-γ-Glu-AcVitE)-(azido-norLeu)-TRQRY-PAL-PEG Resin Fmoc-Glu-OtBu was coupled onto the above resin using the coupling protocol described in Example 2, step 1 with a 5 min coupling time. The resin was deprotected by treatment with 20% piperidine in DMF using a 3-stage microwave protocol (75° C. 0.5 min; 75° C., 3 min; 75° C., 3 min), after which the resin was washed extensively with DMF and DCM. α-Tocopheryloxyacetic Acid (AcVitE) (8) was then coupled onto the resin using the same procedure used for coupling Fmoc-Glu-OtBu.

4. Synthesis of (HCCH(CH$_2$)$_2$CONH)-IKPEAPGE-DASPEELNRYYASLRHYLNK(NH-γ-Glu-AcVitE)-(azido-norLeu)-TRQRY-CONH$_2$ Cleavage and precipitation of the peptide from the above resin was carried out using the procedure described in Example 3, step 3.
Cyclic PYY Analog SEQ ID NO: 6
The title compound was prepared using the procedure described in Example 3, step 4. Product purification was performed on a Varian Pursuit XRs C8 column (21×250 mm, 100 Å, 5 µm) at 35° C. The mobile phase consisted of a gradient elution of Buffer A (0.1% TFA in water) and Buffer B (0.1% TFA in MeCN) ranging from an initial concentration of 35% B to an intermediate concentration of 48% B (21 mpm) over 5 min, and then to a final concentration of 63% B (10.5 mpm) over 40 min.

Example 7: Synthesis of Cyclic PYY Analog SEQ ID NO:7

The title compound was prepared according to the procedure as described in Example 4 with the K(NH-γ-Glu-Pal) residue installed at position 9 instead of position 11. Product purification was performed using an Agilent 300SB C8 column (21×250 mm, 100 Å, 5 µm) at rt. The mobile phase consisted of a gradient elution of Buffer A (0.1% TFA in water) and Buffer B (0.1% TFA in MeCN) ranging from an initial concentration of 23% B to an intermediate concentration of 43% B (21 mpm) and then to a final concentration of 43% B (10.5 mpm) over 40 min. Impure product-containing fractions were re-purified on a Waters T3 C18 column (250×19 mm, 100 Å, 5 µm) at rt using a gradient from an initial concentration of 25% B to an intermediate concentration of 35% B (21 mpm) and then to a final concentration of 45% B (10.5 mpm) over 80 min.

Example 8: Synthesis of Cyclic PYY Analoγ SEQ ID NO:8

The title compound was prepared according to the procedure as described in Example 4 with the K(NH-γ-Glu-Pal) residue installed at position 30 instead of position 11. Product purification was performed using an Agilent 300SB C8 column (21×250 mm, 100 Å, 5 µm) at 35° C. The mobile phase consisted of a gradient elution of Buffer A (0.1% TFA in water) and Buffer B (0.1% TFA in MeCN) ranging from an initial concentration of 21% B to an intermediate concentration of 31% B (21 mpm) and then to a final concentration of 41% B (10.5 mpm) over 40 min. Impure product-containing fractions were re-purified on a Waters T3 C18 column (250×19 mm, 100 Å, 5 µm) at rt using a gradient from an initial concentration of 21% B to an intermediate concentration of 31% B (21 mpm) and then to a final concentration of 40% B (10.5 mpm) over 80 min.

Example 9: Synthesis of Cyclic PYY Analog SEQ ID NO:9

Synthesis of H$_2$N-IKPEAPGEDASPEELNRYYASLRHYLNL(hC)TRQ(psi-R35Y36)-Sieber Resin Amino acid extensions onto the pre-loaded (psi-R35, Y36)-Sieber resin from Example 1, step 2 (0.1 mmol) were performed as described in Example 1, step 3 with the modification of using a 5-fold excess of protected amino acids.

Synthesis of m-BrCH$_2$PhCOHN-IKPEAPGE-DASPEELNRYYASLRHYLNL(hC) TRQ(psi-R35Y36)-Sieber Resin m-Bromomethylbenzoic acid was coupled onto the above resin according to the procedure described in Example 1, step, with the modification that the coupling was carried out at 50° C. instead of 75° C.

3. Cyclic PYY Analog SEQ ID NO: 9

The title compound was prepared from the above resin following the procedures described in Example 1, steps 7 and 8. Product purification was performed using a Varian Pursuit XRs C18 column (21×250 mm, 100 Å, 5 µm) at 35° C. The mobile phase consisted of a gradient elution of Buffer A (0.1% TFA in water) and Buffer B (0.1% TFA in MeCN) ranging from an initial concentration of 10% B to an intermediate concentration of 18% B (21 mpm) over 10 min, and then to a final concentration of 33% B (10.5 mpm) over 35 min.

Example 10: Synthesis of Cyclic PYY Analog SEQ ID NO: 10

The title compound was prepared according to the procedure as described in Example 4 substituting Dde-Lys(Fmoc)-OH in place of Fmoc-Leu-OH at position 30 and α-Tocopheryloxyacetic Acid (AcVitE) (8) in place of palmitic acid in step 3. Product purification was performed using an Agilent 300SB C8 column (21×250 mm, 100 Å, 5 µm) at rt. The mobile phase consisted of a gradient elution of Buffer A (0.1% TFA in water) and Buffer B (0.1% TFA in MeCN) ranging from an initial concentration of 30% B to an intermediate concentration of 40% B (21 mpm) over 10 min, and then to a final concentration of 55% B (21 mpm) over 35 min. Impure product-containing fractions were re-purified using a modified gradient from an initial concentration of 35% B to an intermediate concentration of 43% B (21 mpm) over 5 min, and then to a final concentration of 58% B (10.5 mpm) over 40 min.

Example 11: Synthesis of Cyclic PYY Analog SEQ ID NO:11

1. Synthesis of (Alloc)K(NH$_2$)-(hC)-TRQ(psi-R35Y36)-Sieber Resin

The above resin was prepared following the procedure described in Example 9, step 1 using Alloc-Lys(Fmoc)-OH in place of Fmoc-Leu-OH at position 30.

2. Synthesis of (Alloc)K(NH-γ-Glu-AcVitE)-(hC)-TRQ(psi-R35Y36)-Sieber Resin

Fmoc-Glu-OtBu and α-Tocopheryloxyacetic Acid (AcVitE) (8) (5 eq. each) were sequentially coupled onto the above resin using HBTU/DIEA-mediated couplings under microwave conditions at 50° C. for 15-20 min.

3. Synthesis of H$_2$N—K(NH-γ-Glu-AcVitE)-(hC)-TRQ(psi-R35Y36)-Sieber Resin

The alloc protecting group was removed following the procedure described in Example 1, step 4.

4. Cyclic PYY Analog SEQ ID NO: 11

The title compound was prepared from the above resin following the procedures described in Example 9, steps 1-3, with the modification that a 1M TRIS/HCl buffer, pH 7.5 was used in place of the NH$_4$OAc buffer to effect cyclization. Product purification was performed using a Varian Pursuit XRs C18 column (21×250 mm, 100 Å, 5 µm) at 35° C. The mobile phase consisted of a gradient elution of Buffer A (0.1% TFA in water) and Buffer B (0.1% TFA in MeCN) ranging from an initial concentration of 10% B to an intermediate concentration of 18% B (21 mpm) over 10 min, and then to a final concentration of 33% B (10.5 mpm) over 35 min.

Example 12: Synthesis of Cyclic PYY Analog SEQ ID NO: 12

The title compound was prepared according to the procedure as described in Example 2 substituting Fmoc-N-Me-Arg(pbf)-OH in place of Fmoc-Arg(pbf)-OH at position 35 in step 1 and with the modification that a 1M NaHCO$_3$ buffer was used in place of the NH$_4$OAc buffer to effect cyclization. Product purification was performed using a Varian Pursuit XRs C18 column (30×250 mm, 100 Å, 5 µm) at rt. The mobile phase consisted of a gradient elution of Buffer A (0.1% TFA in water) and Buffer B (0.1% TFA in MeCN) ranging from 10-60% B (30 mpm) over 36 min.

Example 13: Synthesis of Cyclic PYY Analog SEQ ID NO: 13

The title compound was prepared according to the procedures described in Example 11, using palmitic acid in place of α-Tocopheryloxyacetic Acid (AcVitE) (8) in step 2, and with the modifications that 60% EtOH/H$_2$O was used as solvent in place of MeCN/H$_2$O and sat'd aq. NaHCO$_3$ was used in place of the NH$_4$OAc buffer to effect cyclization. Product purification was performed using a Waters XBridge C18 OBD column (50×250 mm, 5 µm) at rt. The mobile phase consisted of a gradient elution of Buffer A (10 mM NH$_4$OH in water, pH~9) and Buffer B (MeCN) ranging from an initial concentration of 15% B to an intermediate concentration of 20% B (100 mpm) over 5 min, and then to a final concentration of 35% B (100 mpm) over 40 min.

Example 14: Synthesis of Cyclic PYY Analog SEQ ID NO: 14

The title compound was prepared according to the procedure as described in Example 4 with the Lys(NH-γ-Glu-Pal) residue installed at position 30 instead of position 11 and with Fmoc-N-Me-Arg(pbf)-OH in place of Fmoc-Arg(pbf)-OH at position 35 in step 1 and with the modification that a 1M NaHCO$_3$ buffer was used in place of the NH$_4$OAc buffer in step 6, to effect cyclization. Product purification was performed using a Varian Pursuit XRs C18 column (30×250 mm, 100 Å, 5 µm) at rt. The mobile phase consisted of a gradient elution of Buffer A (0.1% TFA in water) and Buffer B (0.1% TFA in MeCN) ranging from 20-70% B (30 mpm) over 36 min. Impure fractions were re-purified on a Varian Pursuit XRs diphenyl column (30×100 mm, 100 Å, 5 μm) at rt using a gradient of 30-50% B (30 mpm) over 25 min.

Example 15: Synthesis of Cyclic PYY Analog SEQ ID NO: 15

The title compound was prepared according to the procedure as described in Example 4 with the Lys(NH-γ-Glu-Pal) residue installed at position 30 instead of position 11, substituting Fmoc-βAla-OH in place of Fmoc-Ile-OH coupling at position 3, and with the modifications that a 1M NaHCO$_3$ buffer was used in place of the NH$_4$OAc buffer to effect cyclization, and coupling with bromoacetic anhydride was used in place of m-bromomethylbenzoic acid in step 6 (step 2 from Example 2) using the following procedure: The Fmoc-deprotected peptide-resin (0.1 mmol) was treated with a solution of bromoacetic anhydride (10 eq.) in DMF (5 mL) in a microwave reactor at 50° C. for 5-10 min, by which time the reaction was generally determined to be complete as per a Kaiser ninhydrin test. In cases where the coupling was determined to be incomplete, the coupling was repeated with fresh reagents. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-60% B (30 mpm) over 36 min. Impure fractions were re-purified on a Varian Pursuit XRs diphenyl column (30×100 mm, 100 Å, 5 μm) at rt using a gradient of 30-50% B (30 mpm) over 25 min.

Example 16: Synthesis of Cyclic PYY Analog SEQ ID NO: 16

The title compound was prepared according to the procedure as described in Example 4 with the Lys(NH-γ-Glu-Pal) residue installed at position 30 instead of position 11, omitting the Fmoc-Ile-OH coupling at position 3, and using p-bromomethylbenzoic acid in place of m-bromomethylbenzoic acid in step 6 (step 2 from Example 2). Additionally, a 1M NaHCO$_3$ buffer was used in place of the NH$_4$OAc buffer, to effect cyclization. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-70% B (30 mpm) over 36 min. Impure fractions were re-purified on a Varian Pursuit XRs diphenyl column (30×100 mm, 100 Å, 5 μm) at rt using a gradient of 30-50% B (30 mpm) over 25 min.

Example 17: Synthesis of Cyclic PYY Analog SEQ ID NO: 17

The title compound was prepared according to the procedure as described in Example 4 with the Lys(NH-γ-Glu-Pal) residue installed at position 30 instead of position 11 and Fmoc-Ala-OH used in place of Fmoc-Lys(Boc)-OH at position 4 in step 1. TRIS/HCl buffer (1M, pH 7.5) was used in place of the NH$_4$OAc buffer in step 6 to effect cyclization. Product purification was performed using an Agilent Polaris C18-A column (30×250 mm, 100 Å, 5 μm) at rt. The mobile phase consisted of a gradient elution of Buffer A (0.1% TFA in water) and Buffer B (0.1% TFA in MeCN) ranging from an initial concentration of 20% B to an intermediate concentration of 35% B (40 mpm) over 5 min, and then to a final concentration of 45% B (40 mpm) over 40 min.

Example 18: Synthesis of Cyclic PYY Analog SEQ ID NO: 18

The title compound was prepared according to the procedure as described in Example 4 with the Lys(NH-γ-Glu-Pal) residue installed at position 30 instead of position 11 and Fmoc-Glu(OtBu)-OH used in place of Fmoc-Lys(Boc)-OH at position 4 in step 1. TRIS/HCl buffer (1M, pH 7.5) was used in place of the NH$_4$OAc buffer in step 6 to effect cyclization. Product purification was performed using an Agilent Polaris C18-A column (30×250 mm, 100 Å, 5 μm) at rt. The mobile phase consisted of a gradient elution of Buffer A (0.1% TFA in water) and Buffer B (0.1% TFA in MeCN) ranging from an initial concentration of 20% B to an intermediate concentration of 35% B (40 mpm) over 5 min, and then to a final concentration of 45% B (40 mpm) over 40 min.

Example 19: Synthesis of Cyclic PYY Analog SEQ ID NO: 19

The title compound was prepared according to the procedure as described in Example 4 with the Lys(NH-γ-Glu-Pal) residue installed at position 30 instead of position 11, Fmoc-N-Me-Arg(pbf)-OH in place of Fmoc-Arg(pbf)-OH at position 35 in step 1, Fmoc-Cys(trt)-OH in place of Fmoc-hCys(trt)-OH, and using p-bromomethyl benzoic acid in place of m-bromomethylbenzoic acid in step 6 (step 2 from Example 2).

The following modification was made to step 6 (steps 3 and 4 from Example 2): The crude peptide obtained prior to cyclization was purified using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-70% B (30 mpm) over 36 min. Product-containing fractions were combined and treated with solid NaHCO$_3$ to raise the pH to ~7-8; the resulting solution was stirred at rt for 4 h, then acidified to pH 4 with TFA. The solution was concentrated to a volume of 5-10 mL and MeCN was added to solubilize any precipitate. Product purification was performed as above, with a gradient of 20-60% B (30 mpm) over 36 min.

Example 20: Synthesis of Cyclic PYY Analog SEQ ID NO:20

The title compound was prepared according to the procedure as described in Example 4 with the Lys(NH-γ-Glu-Pal) residue installed at position 30 instead of position 11, Fmoc-N-Me-Arg(pbf)-OH in place of Fmoc-Arg(pbf)-OH at position 35 in step 1 and Fmoc-Cys(trt)-OH in place of Fmoc-hCys(trt)-OH. The crude linear peptide was purified and cyclized according to the modification described in Example 19. Final product purification was performed using a gradient of 20-60% B (30 mpm) over 36 min.

Example 21: Synthesis of Cyclic PYY Analog SEQ ID NO:21

The title compound was prepared according to the procedure as described in Example 4 with the Lys(NH-γ-Glu-Pal) residue installed at position 30 instead of position 11, Fmoc-Ala-OH used in place of Fmoc-His(trt)-OH at position 26 and Fmoc-Ala-OH used in place of Fmoc-Lys(Boc)-OH at position 4 in step 1. TRIS/HCl buffer, (1M, pH 7.5) was used in place of the NH$_4$OAc buffer in step 6 to effect cyclization. Product purification was performed using an Agilent Polaris C18-A column (30×250 mm, 100 Å, 5 µm) at rt. The mobile phase consisted of a gradient elution of Buffer A (0.1% TFA in water) and Buffer B (0.1% TFA in MeCN) ranging from an initial concentration of 20% B to an intermediate concentration of 35% B (40 mpm) over 5 min, and then to a final concentration of 45% B (40 mpm) over 40 min.

Example 22: Synthesis of Cyclic PYY Analog SEQ ID NO:22

The title compound was prepared according to the procedure as described in Example 4 with the Lys(NH-γ-Glu-Pal) residue installed at position 30 instead of position 11, Fmoc-Ala-OH used in place of Fmoc-His(trt)-OH at position 26 and Fmoc-Glu(OtBu)-OH used in place of Fmoc-Lys(Boc)-OH at position 4 in step 1. TRIS/HCl buffer, (1M, pH 7.5) was used in place of the NH$_4$OAC buffer in step 6 to effect cyclization. Product purification was performed using an Agilent Polaris C18-A column (30×250 mm, 100 Å, 5 µm) at rt. The mobile phase consisted of a gradient elution of Buffer A (0.1% TFA in water) and Buffer B (0.1% TFA in MeCN) ranging from an initial concentration of 20% B to an intermediate concentration of 33% B (40 mpm) over 5 min, and then to a final concentration of 43% B (40 mpm) over 40 min.

Example 23: Synthesis of Cyclic PYY Analog SEQ ID NO:23

The title compound was prepared according to the procedures described in Example 11, using octadecanedioic acid, mono-tert-butyl ester (available from AstaTech, Inc.) in place of α-Tocopheryloxyacetic Acid (AcVitE) (8), a coupling protocol employing HATU/DIEA at 50° C. for 30 min and NMP as solvent in place of DMF in step 2, and coupling two units of Fmoc-OEG-OH in tandem prior to coupling Fmoc-Glu-OtBu, in step 2. The crude linear peptide was purified and cyclized according to the modification described in Example 19, using a gradient of 20-60% B. Final product purification was performed using a gradient of 20-70% B (30 mpm) over 36 min.

Example 24: Synthesis of Cyclic PYY Analog SEQ ID NO:24

The title compound was prepared according to the procedures described in Example 23, using 20-(tert-butoxy)-20-oxoicosanoic acid (available from Key Organics, Inc.) in place of octadecanedioic acid, mono-tert-butyl ester. The crude linear peptide was purified and cyclized according to the modification described in Example 19, using a gradient of 20-60% B. Final product purification was performed using a gradient of 20-60% B (30 mpm) over 36 min.

Example 25: Synthesis of Cyclic PYY Analog SEQ ID NO:25

The title compound was prepared according to the procedures described in Example 11, using stearic acid in place of α-Tocopheryloxyacetic Acid (AcVitE) (8), a coupling protocol employing HATU/DIEA at 50° C. for 30 min and NMP as solvent in place of DMF in step 2. The crude linear peptide was purified and cyclized according to the modification described in Example 19, using a gradient of 20-80% B. Final product purification was performed using a gradient of 20-80% B (30 mpm) over 36 min.

Example 26: Synthesis of Cyclic PYY Analog SEQ ID NO:26

The title compound was prepared according to the procedures described in Example 11, using arachidic acid in place of α-Tocopheryloxyacetic Acid (AcVitE) (8), a coupling protocol employing HATU/DIEA at 50° C. for 30 min and NMP as solvent in place of DMF in step 2. The crude linear peptide was purified and cyclized according to the modification described in Example 19, using a gradient of 20-90% B. Final product purification was performed using a gradient of 20-90% B (30 mpm) over 36 min.

Example 27: Synthesis of Cyclic PYY Analog SEQ ID NO:27

The title compound was prepared according to the procedures described in Example 23, but omitting the coupling of Fmoc-Glu-OtBu after the tandem Fmoc-OEG-OH couplings. The crude linear peptide was purified and cyclized according to the modification described in Example 19, using a gradient of 20-60% B. Final product purification was performed using a gradient of 20-60% B (30 mpm) over 36 min.

Example 28: Synthesis of Cyclic PYY Analog SEQ ID NO:28

The title compound was prepared according to the procedures described in Example 11, using palmitic acid in place of α-Tocopheryloxyacetic Acid (AcVitE) (8), omitting the coupling of Fmoc-Ile-OH at position 3, and using p-bromomethylbenzoic acid in place of m-bromomethylbenzoic acid in step 4 (Example 9, step 2). The crude linear peptide was purified and cyclized according to the modification described in Example 19, using a gradient of 20-60% B. Final product purification was performed using a gradient of 20-60% B (30 mpm) over 36 min.

Example 29: Synthesis of Cyclic PYY Analog SEQ ID NO:29

The title compound was prepared according to the procedures described in Example 11, using palmitic acid in place of α-Tocopheryloxyacetic Acid (AcVitE) (8), substituting Fmoc-3Ala-OH in place of Fmoc-Ile-OH at position 3, and coupling bromoacetic anhydride in place of m-bromomethylbenzoic acid in step 4 (Example 9, step 2), using the modification described in Example 15. The crude linear peptide was purified and cyclized according to the modification described in Example 19, using a gradient of 20-60% B. Final product purification was performed using a gradient of 20-60% B (30 mpm) over 36 min.

Example 30: Synthesis of Cyclic PYY Analog SEQ ID NO:30

The title compound was prepared according to the procedures described in Example 11, using palmitic acid in place of α-Tocopheryloxyacetic Acid (AcVitE) (8), substituting Fmoc-Aβυ-OH in place of Fmoc-Ile-OH at position 3, and coupling bromoacetic anhydride in place of m-bromomethylbenzoic acid in step 4 (Example 9, step 2), using the modification described in Example 15. The crude linear peptide was purified and cyclized according to the modification described in Example 19, using a gradient of 20-60% B. Final product purification was performed using a gradient of 20-60% B (30 mpm) over 36 min.

Example 31: Synthesis of Cyclic PYY Analog SEQ ID NO:31

The title compound was prepared according to the procedures described in Example 23, using stearic acid in place of octadecanedioic acid, mono-tert-butyl ester. The crude linear peptide was purified and cyclized according to the modification described in Example 19, using a gradient of 20-60% B. Final product purification was performed using a gradient of 20-60% B (30 mpm) over 36 min.

Example 32: Synthesis of Cyclic PYY Analog SEQ ID NO:32

The title compound was prepared according to the procedures described in Example 11, using palmitic acid in place of α-Tocopheryloxyacetic Acid (AcVitE) (8) in step 2, Fmoc-Ala-OH used in place of Fmoc-His(trt)-OH at position 26 and Fmoc-Ala-OH used in place of Fmoc-Lys(Boc)-OH at position 4 in step 4 (Example 9, step 1). TRIS/HCl buffer, (1M, pH 7.5) was used in place of the NH$_4$OAc buffer in step 6 to effect cyclization. Product purification was performed using an Agilent Polaris C18-A column (30×250 mm, 100 Å, 5 µm) at rt. The mobile phase consisted of a gradient elution of Buffer A (0.1% TFA in water) and Buffer B (0.1% TFA in MeCN) ranging from an initial concentration of 20% B to an intermediate concentration of 35% B (40 mpm) over 5 min, and then to a final concentration of 45% B (40 mpm) over 40 min.

Example 33: Synthesis of Cyclic PYY Analog SEQ ID NO:33

The title compound was prepared according to the procedures described in Example 11, using palmitic acid in place of α-Tocopheryloxyacetic Acid (AcVitE) (8) in step 2 and Fmoc-N(Me)-Gln(trt)-OH in place of Fmoc-Gln(trt)-OH at position 34 in step 4 (Example 9, step 1). In this case, couplings were carried out at rt using NMP as solvent and an HATU/DIEA protocol (1 h, single coupling); Fmoc-N (Me)-Gln(trt)-OH and Fmoc-Arg(pbf)-OH were double coupled. A two-stage Fmoc deprotection protocol was used throughout (20% piperidine in DMF; rt; 10 min, 15 min). The crude linear peptide was purified and cyclized according to the modification described in Example 19, using a gradient of 20-70% B. Final product purification was performed using a gradient of 20-70% B (30 mpm) over 36 min.

Example 34: Synthesis of Cyclic PYY Analog SEQ ID NO:34

The title compound was prepared according to the procedures described in Example 11, using palmitic acid in place of α-Tocopheryloxyacetic Acid (AcVitE) (8), substituting Fmoc-Cys(trt)-OH in place of Fmoc-hCys(trt)-OH at position 31, 6-Fmoc-aminohexanoic acid in place of Fmoc-Ile-OH at position 3, and coupling bromoacetic anhydride in place of m-bromomethylbenzoic acid in step 4 (Example 9, step 2), using the modification described in Example 15. Aq. NaHCO$_3$ (2N) was used in place of the NH$_4$OAc buffer to effect cyclization. Product purification was performed using a Varian Pursuit XRs C18 column (30×250 mm, 100 Å, 5 µm) at rt. The mobile phase consisted of a gradient elution of Buffer A (0.1% TFA in water) and Buffer B (0.1% TFA in MeCN) ranging from 20-70% B (30 mpm) over 36 min.

Example 35: Synthesis of Cyclic PYY Analog SEQ ID NO:35

The title compound was prepared according to the procedures described in Example 9, with the following modifications: Fmoc-psi-[N-Me-Arg(Pbf)-N(Boc)Tyr(tBu)]-OH, prepared from Fmoc-N-Me-Arg(pbf)-OH in place of Fmoc-Arg(Pbf)-OH, according to the procedure described in Example 1, step 1, was used in place of Fmoc-psi-[Arg(Pbf)-N(Boc)Tyr(tBu)]-OH (6) to prepare the loaded Sieber resin used herein; Fmoc-Lys(Pal-Glu-OtBu)-OH (from Active Peptide) was used in place of Leu at position 30; m-chloromethylbenzoic acid was used in place of m-bromomethylbenzoic acid in step 2; couplings were carried out at rt using NMP as solvent and an HATU/DIEA protocol (1 h, single coupling) was used; Fmoc-Arg(pbf)-OH was double coupled. A two-stage Fmoc deprotection protocol was used throughout (20% piperidine in DMF; rt; 10 min, 15 min). The crude linear peptide was purified and cyclized according to the modification described in Example 19, using a gradient of 20-70% B. Final product purification was performed using a gradient of 20-70% B (30 mpm) over 36 min.

Example 36: Synthesis of Cyclic PYY Analog SEQ ID NO:36

The title compound was prepared according to the procedures described in Example 35, substituting Fmoc-βAla-OH in place of Fmoc-Ile-OH at position 3, and coupling bromoacetic anhydride in place of m-bromomethyl benzoic acid in step 4 (Example 9, step 2), using the modification described in Example 15. The modified workup of Example 19 was omitted. Fmoc-βAla-OH was coupled under microwave conditions at 50° C. for 20 min. Sat'd aq. NaHCO$_3$ was used in place of the NH$_4$OAc buffer to effect cyclization. Product purification was performed using a Varian Pursuit XRs C18 column (30×250 mm, 100 Å, 5 µm) at rt. The mobile phase consisted of a gradient elution of Buffer A (0.1% TFA in water) and Buffer B (0.1% TFA in MeCN) ranging from 20-70% B (30 mpm) over 36 min.

Example 37: Synthesis of Cyclic PYY Analog SEQ ID NO:37

The title compound was prepared according to the procedures described in Example 9, substituting Fmoc-Cys(trt)-OH in place of Fmoc-hCys(trt)-OH at position 31 and Fmoc-Lys(Pal-Glu-OtBu)-OH (from Active Peptide) in place of Fmoc-Leu-OH at position 30. In addition, Fmoc-Abu-OH was appended onto the sequence at position 2, in step 1, and coupling with bromoacetic anhydride was used in place of m-bromomethylbenzoic acid in step 2, using the modification described in Example 15. Sat'd aq. NaHCO$_3$ was used in place of the NH$_4$OAc buffer in step 3 to effect cyclization. Product purification was performed using a Varian Pursuit XRs C18 column (30×250 mm, 100 Å, 5 µm) at rt. The mobile phase consisted of a gradient elution of Buffer A (0.1% TFA in water) and Buffer B (0.1% TFA in MeCN) ranging from 20-70% B (30 mpm) over 36 min.

Example 38: Synthesis of Cyclic PYY Analog SEQ ID NO:38

The title compound was prepared according to the procedures described in Example 35, with the following modifications: Fmoc-βAla-OH was appended onto the sequence at position 2, following step 1 using microwave conditions at 50° C. for 20 min, and coupling with bromoacetic anhydride was used in place of m-bromomethylbenzoic acid in step 2, using the modification described in Example 15. Sat'd aq. NaHCO$_3$ was used in place of the NH$_4$OAc buffer to effect cyclization. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-80% B (30 mpm) over 36 min.

Example 39: Synthesis of Cyclic PYY Analog SEQ ID NO:39

The title compound was prepared according to the procedures described in Example 11, using arachidic acid in place of α-Tocopheryloxyacetic Acid (AcVitE) (8) in step 2. Fmoc-Ser(tBu)-OH was used in place of Fmoc-Lys(Boc)-OH at position 4 in step 4 (Example 9, step 1) and m-chloromethylbenzoic acid was used in place of m-bromomethylbenzoic acid in step 4 (Example 9, step 2). 60% EtOH/H$_2$O was used as solvent in place of MeCN/H$_2$O and sat'd aq. NaHCO$_3$ was used in place of the NH$_4$OAc buffer in step 4 to effect cyclization. Product purification was performed using a Waters XBridge C18 OBD column (50×250 mm, 5 μm) at rt. The mobile phase consisted of a gradient elution of Buffer A (10 mM NH$_4$OH in water, pH 9) and Buffer B (MeCN) ranging from an initial concentration of 20% B to an intermediate concentration of 25% B (100 mpm) over 5 min, and then to a final concentration of 40% B (100 mpm) over 40 min.

Example 40: Synthesis of Cyclic PYY Analog SEQ ID NO:40

Synthesis of (HCCH(CH$_2$)$_2$CONH)-IKPEAPGE-DASPEELNRYYASLRHYLNK(Dde)-(azido-norLeu)-TRQ(psi-R35Y36)-Sieber Resin Amino acid extensions onto the pre-loaded (psi-R35, Y36)-Sieber resin from Example 1, step 2 (0.1 mmol) were carried out at rt using NMP as solvent, a 5-fold excess of protected amino acids and an HATU/DIEA protocol (1 h, single coupling); Fmoc-Arg(pbf)-OH and Fmoc-His(trt)-OH were double coupled. A two-stage Fmoc deprotection protocol was used throughout (20% piperidine in DMF; rt; 10 min, 15 min).

Synthesis of (HCCH(CH$_2$)$_2$CONH)-IKPEAPGE-DASPEELNRYYASLRHYLNK(NH$_2$)-(azido-norLeu)-TRQ(psi-R35Y36)-Sieber Resin The above resin was treated with 2% hydrazine in DMF (12 mL/0.2 mmol scale) for 2 min at rt and then the mixture was drained. This procedure was repeated ca. 4×, after which the resin was washed extensively with DMF and then DCM.

Synthesis of (HCCH(CH$_2$)$_2$CONH)-IKPEAPGE-DASPEELNRYYASLRHYLNK((OEG)$_2$-γ-Glu-Pal)-(azido-norLeu)-TRQ(psi-R35Y36)-Sieber Resin The above resin was coupled with (S)-10,19-dioxo-22-palmitamido-3,6,12,15-tetraoxa-9,18-diazatricosanedioic acid (5 eq,) [prepared according to the procedure described for synthesis of intermediate 3, by substituting palmitic acid in place of 18-tert-butoxy-18-oxooctadecanoic acid in step G], using an HBTU/DIEA protocol at it for 1.5 h. The resin was drained and washed extensively with DMF and DCM.

Synthesis of (HCCH(CH$_2$)$_2$CONH)-IKPEAPGE-DASPEELNRYYASLRHYLNK((OEG)$_2$-γ-Glu-Pal)-(azido-norLeu)-TRQ(psi-R35Y36)-CONH$_2$ The dried resin was treated with a solution of 2% TFA in DCM (20 mL) and mixed for 20 min, then filtered. This treatment was repeated for 2 additional times using fresh cocktail for each treatment. The combined filtrates were then combined and concentrated to afford the crude protected peptide as a yellow foam. This foam was treated with 20 mL of cleavage cocktail (TFA/H$_2$O/TIPS=95/2.5/2.5) at rt for 2.5 h and then concentrated under a stream of nitrogen to a volume of about 2.5 mL. Cold ether (40 mL) was then added to precipitate the peptide and the mixture was centrifuged (5 min; 5000 rpm) and decanted. This process was repeated for 2 more times to give the crude peptide as an off-white powder.

Alternatively, the resin was treated with cleavage cocktail without prior treatment with 1-2% TFA in DCM, to afford the fully deprotected peptide directly.

The crude peptide was purified by reverse phase preparative HPLC using a Varian Pursuit XRs C18 column (30×250 mm, 100 Å, 5 μm). The mobile phase consisted of gradient elution of Buffer A (0.1% TFA in water) and Buffer B (0.1% TFA in MeCN) ranging from 20-70% B over 36 min. UV detection was monitored at 220 and 254 nm. Product-containing fractions were analyzed by analytical HPLC on an Agilent 1100 HPLC system using the same column type as above (4.6×250 mm, 5 μm). Pure fractions were combined, and then lyophilized to give the product as a cotton-like solid. LCMS: 1211.8 (M+4H)/4, 1615.4 (M+3H)/3 and 2422.9 (M+2H)/2 for the product peak at 16.87 min (LC: Atlantis T3 C18 column, 5 μm, 4.6×250 mm, 1.0 mL/min, 30-60% gradient).

Cyclic PYY Analog SEQ ID NO: 40

Prepare 5.1 mg of CuSO$_4$ in 1 mL H$_2$O. Prepare 10.4 mg of TBTA in 3 mL of EtOH. Premix 400 μL of CuSO$_4$ solution and 3 mL TBTA solution. Prepare 13 mg of Na Ascorbate in 2 mL of H$_2$O.

To a solution of the purified azido-containing peptide from Step 4 (37 mg) in 4 mL of HEPES (0.1M, pH 7.4) was added 1.7 mL of the premixed CuSO$_4$/TBTA solution followed by 1 mL of Na Ascorbate solution. Adjust EtOH/H$_2$O ratio until the reaction solution turned clear. The mixture was stirred at rt and monitored by HPLC. After 30 min, the reaction was completed. The mixture was adjusted to pH 4 and purified by reverse phase preparative HPLC. Purifications were performed using a Varian Pursuit XRs C18 column (30×250 mm, 100 Å, 5 μm). The mobile phase consisted of gradient elution of Buffer A (0.1% TFA in water) and Buffer B (0.1% TFA in MeCN) ranging from 20-60% B over 36 min. UV detection was monitored at 220 and 254 nm. Product-containing fractions were analyzed by analytical HPLC on an Agilent 1100 HPLC system using the same column type as above (4.6×250 mm, 5 μm). Pure fractions were combined, and then lyophilized to give the product as a cotton-like solid.

Example 41: Synthesis of Cyclic PYY Analog SEQ ID NO:41

The title compound was prepared according to the procedure described in Example 40, substituting L-Glutamic acid, N-(1-oxohexadecyl)-, 1-(1,1-dimethylethyl) ester in place of (S)-10,19-dioxo-22-palmitamido-3,6,12,15-tetraoxa-9,18-diazatricosanedioic acid, in step 3.

Example 42: Synthesis of Cyclic PYY Analog SEQ ID NO:42

The title compound was prepared according to the procedure described in Example 40, substituting (S)-22-(tert-butoxycarbonyl)-43,43-dimethyl-10,19,24,41-tetraoxo-3,6,12,15,42-pentaoxa-9,18,23-triazatetratetracontan-1-oic acid (16) (intermediate 2) in place of (S)-10,19-dioxo-22-palmitamido-3,6,12,15-tetraoxa-9,18-diazatricosanedioic acid, in step 3.

Example 43 Synthesis of Cyclic PYY Analog SEQ ID NO:43

Synthesis of (Alloc)Lys((OEG)$_2$-γ-Glu-NH$_2$)-(hC)-TRQ(psi-R35Y36)-Sieber Resin Amino acid extensions onto the pre-loaded (psi-R35,Y36)-Sieber resin from Example 1, step 2 (0.1 mmol) were carried out at rt using NMP as solvent, a 5-fold excess of protected amino acids and an HATU/DIEA protocol (1 h, single coupling); Fmoc-Arg(pbf)-OH was double coupled. A two-stage Fmoc deprotection protocol was used throughout (20% piperidine in DMF; rt; 10 min, 15 min).

Synthesis of (Alloc)Lys((OEG)$_2$-γ-Glu-Pal)-(hC)-TRQ(psi-R35Y36)-Sieber Resin

Palmitic acid was coupled onto the resin from step 1, using microwave conditions employing HATU/DIEA at 50° C. for 20-30 min and NMP as solvent.

Synthesis of (H$_2$N)Lys((OEG)$_2$-γ-Glu-Pal)-(hC)-TRQ(psi-R35Y36)-Sieber Resin

The alloc protecting group of the above resin was removed following the procedure described in Example 1, step 4.

4. Cyclic PYY Analog SEQ ID NO: 43

The title compound was prepared from the above resin following the procedures described in Example 9, steps 1-3, using m-chloromethylbenzoic acid in place of m-bromomethylbenzoic acid in step 2. The crude linear peptide was purified and cyclized according to the modification described in Example 19, using a gradient of 20-60% B. Final product purification was performed using a gradient of 20-60% B (30 mpm) over 36 min.

Example 44 Synthesis of Cyclic PYY Analog SEQ ID NO:44

The title compound was prepared according to the procedures described in Example 43, modified such that the tandem Fmoc-OEG-OH units and the Fmoc-Glu-OtBu unit were incorporated in step 2 instead of step 1. Octadecanedioic acid, mono-tert-butyl ester (AstaTech, Inc.) was used in place of palmitic acid in step 2 and the linker-lipid sequence was installed at position 11 instead of position 30. The crude linear peptide was purified and cyclized according to the modification described in Example 19, using a gradient of 20-70% B. Final product purification was performed using a gradient of 20-70% B (30 mpm) over 36 min.

Example 45 Synthesis of Cyclic PYY Analog SEQ ID NO:45

The title compound was prepared according to the procedures described in Example 43, modified such that Fmoc-dPEG24-carboxylic acid was used in place of the tandem Fmoc-OEG-OH units and were, along with palmitic acid, incorporated into step 2. The linker-lipid sequence was installed at position 11 instead of position 30. The crude linear peptide was purified and cyclized according to the modification described in Example 19, using a gradient of 20-90% B. Final product purification was performed using a gradient of 20-90% B (30 mpm) over 36 min.

Example 46 Synthesis of Cyclic PYY Analog SEQ ID NO:46

The title compound was prepared according to the procedures described in Example 9, using Fmoc-Lys(Pal-Glu-OtBu)-OH (from Active Peptide) in place of Leu at position 30. In addition, Fmoc-βAla-OH was appended onto the sequence at position 2, following step 1 using microwave conditions at 50° C. for 20 min, and coupling with bromoacetic anhydride was used in place of m-bromomethylbenzoic acid in step 2, using the modification described in Example 15. Solid The crude linear peptide was purified and cyclized according to the modification described in Example 19, using a gradient of 20-70% B. Final product purification was performed using a gradient of 20-70% B (30 mpm) over 36 min.

Example 47 Synthesis of Cyclic PYY Analog SEQ ID NO:47

The title compound was prepared according to the procedures described in Example 44, installing the linker-lipid sequence at position 7 instead of position 11. Product purification was performed using a Varian Pursuit XRs C18 column (30×250 mm, 100 Å, 5 μm) at rt. The crude linear peptide was purified and cyclized according to the modification described in Example 19, using a gradient of 20-60% B. Final product purification was performed using a gradient of 20-60% B (30 mpm) over 36 min.

Example 48 Synthesis of Cyclic PYY Analog SEQ ID NO:48

The title compound was prepared according to the procedures described in Example 43, using octadecanedioic acid, mono-tert-butyl ester (AstaTech, Inc.) in place of palmitic acid in step 2 with a coupling time of 30 min, and installing the linker-lipid sequence at position 22 instead of position 30. The crude linear peptide was purified and cyclized according to the modification described in Example 19, using a gradient of 20-70% B. Final product purification was performed using a gradient of 20-70% B (30 mpm) over 36 min.

Example 49 Synthesis of Cyclic PYY Analog SEQ ID NO:49

The title compound was prepared following the procedures described in Example 11, substituting 16-tetrahydropyran-2-yloxypalmitic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H$_2$O was used as solvent in place of MeCN/H$_2$O and sat'd aq. NaHCO$_3$ was used in place of the NH$_4$OAc buffer in step 4 to effect cyclization. Product purification was performed using a Waters XBridge C18 OBD column (50×250 mm, 5 μm) at rt. The mobile phase consisted of a gradient elution of Buffer A (10 mM NH$_4$OH in water, pH~9) and Buffer B (MeCN) ranging from an initial concentration of 20% B to an intermediate concentration of 10% B (100 mpm) over 5 min, and then to a final concentration of 30% B (100 mpm) over 40 min.

Example 50 Synthesis of Cyclic PYY Analog SEQ ID NO:50

The title compound was prepared according to the procedures described in Example 48, and installing the linker-lipid sequence at position 23 instead of position 30.

Example 51 Synthesis of Cyclic PYY Analog SEQ ID NO:51

The title compound was prepared according to the procedures described in Example 9, using Fmoc-Lys(Pal-Glu-OtBu)-OH (from Active Peptide) in place of Fmoc-Leu-OH at position 30 and Fmoc-Ser(tBu)-OH in place of Fmoc-Lys(Boc)-OH at position 4, in step 1. 60% EtOH/H$_2$O was used as solvent in place of MeCN/H$_2$O and sat'd aq. NaHCO$_3$ was used in place of the NH$_4$OAc buffer in step 4 to effect cyclization. Product purification was performed using a Waters XBridge C18 OBD column (50×250 mm, 5 μm) at rt. The mobile phase consisted of a gradient elution of Buffer A (10 mM NH$_4$OH in water, pH~9) and Buffer B (MeCN) ranging from an initial concentration of 10% B to an intermediate concentration of 20% B (100 mpm) over 5 min, and then to a final concentration of 30% B (100 mpm) over 40 min. Impure fractions were re-chromatographed using a gradient comprised of an initial concentration of 10% B to an intermediate concentration of 20% B (100 mpm) over 5 min, and then to a final concentration of 30% B (100 mpm) over 60 min.

Example 52 Synthesis of Cyclic PYY Analog SEQ ID NO:52

The title compound was prepared according to the procedures described in Example 43, using Fmoc-dPEG12-carboxylic acid in place of the tandem Fmoc-OEG-OH units and incorporating it along with Fmoc-Glu-OtBu and palmitic acid in step 2. The linker-lipid sequence was installed at position 11 instead of position 30. The crude linear peptide was purified and cyclized according to the modification described in Example 19, using a gradient of 20-70% B. Final product purification was performed using a gradient of 20-70% B (30 mpm) over 36 min.

Example 53 Synthesis of Cyclic PYY Analog SEQ ID NO:53

The title compound was prepared according to the procedures described in Example 52, using four units of Fmoc-OEG-OH in tandem in place of Fmoc-dPEG12-carboxylic acid.

Example 54 Synthesis of Cyclic PYY Analog SEQ ID NO:54

The title compound was prepared according to the procedures described in Example 53, installing two units of Fmoc-OEG-OH in tandem instead of two.

Example 55 Synthesis of Cyclic PYY Analog SEQ ID NO:55

The title compound was prepared according to the procedures described in Example 43, installing the linker-lipid sequence at position 23 instead of position 30. The crude linear peptide was purified and cyclized according to the modification described in Example 19, using a gradient of 20-70% B. Final product purification was performed using a gradient of 20-70% B (30 mpm) over 36 min

Example 56: Synthesis of Cyclic PYY Analog SEQ ID NO:56

The title compound was prepared using the methods described in Example 11, substituting (4'-chlorobiphenyl-4-yl)-acetic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H$_2$O was used as solvent in place of MeCN/H$_2$O and sat'd aq. NaHCO$_3$ was used in place of the NH$_4$OAc buffer in step 4 to effect cyclization. Product purification was performed using a Waters XBridge C18 OBD column (50×250 mm, 5 μm) at rt. The mobile phase consisted of a gradient elution of Buffer A (10 mM NH$_4$OH in water, pH~9) and Buffer B (MeCN) ranging from 10-28% B (100 mpm) over 40 min.

Example 57: Synthesis of Cyclic PYY Analog SEQ ID NO:57

The title compound was prepared following the procedures described in Example 11, substituting 3-[(2,4-dichlorophenoxy)phen-4-yl]propionic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H$_2$O was used as solvent in place of MeCN/H$_2$O and sat'd aq. NaHCO$_3$ was used in place of the NH$_4$OAc buffer in step 4 to effect cyclization. Product purification was performed using a Waters XBridge C18 OBD column (50×250 mm, 5 μm) at rt. The mobile phase consisted of a gradient elution of Buffer A (10 mM NH$_4$OH in water, pH 9) and Buffer B (MeCN) ranging from 10-30% B (80 mpm) over 40 min. Product-containing fractions were combined, acidified with TFA, concentrated and re-chromatographed on an Agilent Polaris C18-A column (30×250 mm, 100 Å, 5 μm) at rt. The mobile phase consisted of a gradient elution of Buffer A (0.1% TFA in water) and Buffer B (0.1% TFA in MeCN) ranging from an initial concentration of 20% B to an intermediate concentration of 15% B (40 mpm) to a final concentration of 45% B (40 mpm) over 45 min.

Example 58: Synthesis of Cyclic PYY Analog SEQ ID NO:58

The title compound was prepared following the procedures described in Example 11, substituting 11-(4-fluorophenyl}undecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 μm) at rt. The mobile phase consisted of a gradient elution of Buffer A (10 mM $NH_4OH$ in water, pH~9) and Buffer B (MeCN) ranging from 15-35% B (100 mpm) over 40 min.

Example 59: Synthesis of Cyclic PYY Analog SEQ ID NO:59

The title compound was prepared according to the procedures described in Example 43, omitting step 2 and incorporating the palmitic acid coupling into step 1. The linker-lipid sequence was installed at position 22 instead of position 11. The crude linear peptide was purified and cyclized according to the modification described in Example 19, using a gradient of 20-70% B. Final product purification was performed using a gradient of 20-70% B (30 mpm) over 36 min

Example 60: Synthesis of Cyclic PYY Analog SEQ ID NO:60

The title compound was prepared according to the procedures described in Example 53, incorporating two FMOC-OEG-OH units in tandem instead of four and installing the linker-lipid sequence was at position 7 instead of position 11. The crude linear peptide was purified and cyclized according to the modification described in Example 19, using a gradient of 20-80% B. Final product purification was performed using a gradient of 20-80% B (30 mpm) over 36 min.

Example 61: Synthesis of Cyclic PYY Analog SEQ ID NO:61

The title compound was prepared following the procedures described in Example 11, substituting 11-[(4-trifluoromethyl)phenyl]undecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 μm) at rt. The mobile phase consisted of a gradient elution of Buffer A (10 mM $NH_4OH$ in water, pH 9) and Buffer B (MeCN) ranging from 15-35% B (100 mpm) over 40 min.

Example 62: Synthesis of Cyclic PYY Analog SEQ ID NO:62

The title compound was prepared following the procedures described in Example 11, substituting 11,11,11-trifluoroundecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 μm) at rt. The mobile phase consisted of a gradient elution of Buffer A (10 mM $NH_4OH$ in water, pH~9) and Buffer B (MeCN) ranging from 10-28% B(100 mpm) over 40 min.

Example 63: Synthesis of Cyclic PYY Analog SEQ ID NO:63

The title compound was prepared following the procedures described in Example 11, substituting 15,15,15-trifluoropentadecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 μm) at rt. The mobile phase consisted of a gradient elution of Buffer A (10 mM $NH_4OH$ in water, pH~9) and Buffer B (MeCN) ranging from 15-30% B(100 mpm) over 40 min.

Example 64: Synthesis of Cyclic PYY Analog SEQ ID NO:64

The title compound was prepared following the procedures described in Example 11, substituting 16-ethoxypalmitic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 μm) at rt. The mobile phase consisted of a gradient elution of Buffer A (10 mM $NH_4OH$ in water, pH~9) and Buffer B (MeCN) ranging from 15-30% B (100 mpm) over 40 min.

Example 65: Synthesis of Cyclic PYY Analog SEQ ID NO:65

The title compound was prepared following the procedures described in Example 11, substituting 13,13,14,14,15,15,16,16,16-D9-palmitic acid (Cambridge Isotopes) in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50× 250 mm, 5 μm) at rt. The mobile phase consisted of a gradient elution of Buffer A (10 mM $NH_4OH$ in water, pH 9) and Buffer B (MeCN) ranging from 15-20% B (100 mpm) over 5 min, and then to 35% B (100 mpm) over 40 min.

Example 66: Synthesis of Cyclic PYY Analog SEQ ID NO:66

The title compound was prepared following the procedures described in Example 11, substituting 11-[(2,4-bis(trifluoromethyl)phenyl]undecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 μm) at rt. The mobile phase consisted of a gradient elution of Buffer A (10 mM NH$_4$OH in water, pH 9) and Buffer B (MeCN) ranging from 15-35% B (100 mpm) over 40 min.

Example 67: Synthesis of Cyclic PYY Analog SEQ ID NO:67

The title compound was prepared following the procedures described in Example 11, substituting 11-[(3,5-bis (trifluoromethyl)phenyl]undecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H$_2$O was used as solvent in place of MeCN/H$_2$O and sat'd aq. NaHCO$_3$ was used in place of the NH$_4$OAc buffer in step 4 to effect cyclization. Product purification was performed using a Waters XBridge C18 OBD column (50×250 mm, 5 μm) at rt. The mobile phase consisted of a gradient elution of Buffer A (10 mM NH$_4$OH in water, pH 9) and Buffer B (MeCN) ranging 15-35% B (100 mpm) over 40 min.

Example 68: Synthesis of Cyclic PYY Analog SEQ ID NO:68

1. Synthesis of (Fmoc)-βA-IKPEAPGEK(Alloc) ASPEELNRYYASLRHYLNCVTRQ(psi-R35Y36)-Sieber Resin Amino acid extensions onto the pre-loaded (psi-R35, Y36)-Sieber resin from Example 1, step 2 (0.1 mmol) were carried out at rt using DMF as solvent, a 6-fold excess of protected amino acids and an HATU/DIEA protocol (10 min, double coupling). A two-stage Fmoc deprotection protocol was used throughout (20% piperidine in DMF; rt; 10 min, 15 min).

2. Synthesis of (Fmoc)-βA-IKPEAPGEK((OEG)$_2$-γ-Glu-NHCO(CH$_2$)$_{16}$CO$_2$tBu)-ASPEELN-RYYASLRHYLNCVTRQ(psi-R35Y36)-Sieber Resin Deprotection of the above resin was carried out following the method described in Example 1, step 4, using modified reaction times of 10 min for each treatment. The resin was then coupled with intermediate 2 (15) (5 eq.), using an HATU/DIEA protocol in DMF (1 h, rt).

3. Synthesis of (BrAc)-βA-IKPEAPGEK((OEG)$_2$-γ-Glu-NHCO(CH$_2$)$_{16}$CO$_2$tBu)-ASPEELN-RYYASLRHYLNCVTRQ(psi-R35Y36)-Sieber Resin Following Fmoc deprotection (20% piperidine/DMF), the above resin was treated with bromoacetic anhydride (10 eq.; rt, 30 min) to provide the bromoacetylated resin.

4. Synthesis of (BrAc)-βA-IKPEAPGEK((OEG)$_2$-γ-Glu-NHCO(CH$_2$)$_{16}$CO$_2$tBu)-ASPEELN-RYYASLRHYLNCVTRQ(psi-R35Y36)-CONH$_2$ The above resin was treated with a cleavage cocktail consisting of TFA/H$_2$O/TIPS (95:2.5:2.5) for 1.5 h at rt. The crude peptide was precipitated with ether following the procedure described in Example 1, step 7.

5. Cyclic PYY Analog SEQ ID NO: 68

The crude peptide obtained above was dissolved at a concentration of 10 mg/mL in 10% MeCN/H$_2$O, and TEA was added to raise the solution pH to 8-9. After stirring at rt for ~20 min, TFA was added to lower the pH to 2, and the solution was purified directly by preparative HPLC on a Kinetics C18 Evo column (30×100 mm, 100 Å, 5 μm). The mobile phase consisted of gradient elution of Buffer A (0.1% TFA in water) and Buffer B (0.1% TFA in MeCN) ranging from 20-60% B over 22 min. UV detection was monitored at 220 and 254 nm. Pure fractions were combined, and then lyophilized to give the product as a cotton-like solid.

Example 69: Synthesis of Cyclic PYY Analog SEQ ID NO:69

1. Synthesis of (Boc)-G-ISPEAPGEK(dde)AS-PEELNRYYASLRHYLNLE(OAllyl)TRQ(psi-R35Y36)-Sieber Resin Amino acid extensions onto the pre-loaded (psi-R35, Y36)-Sieber resin from Example 1, step 2 (0.1 mmol) were carried out at rt using DMF as solvent, a 6-fold excess of protected amino acids and an HATU/NMM protocol (10 min, double coupling). A two-stage Fmoc deprotection protocol was used throughout (20% piperidine in DMF; rt; 10 min, 15 min).

2. Synthesis of (Boc)-G-ISPEAPGEK(dde)AS-PEELNRYYASLRHYLNLE(NHS)TRQ(psi-R35Y36)-Sieber Resin Alloc-deprotection of the above resin was carried out following the method described in Example 1, step 4, using modified reaction times of 10 min for each treatment. The resin was then coupled with NHS (10 eq.), using an HATU/DIEA protocol in DMF (1 h, rt, double coupling).

3. Synthesis of (NH$_2$)-G-ISPEAPGEK(dde)AS-PEELNRYYASLRHYLNLE(NHS)TRQ(psi-R35Y36)

The above resin was treated with a cleavage cocktail consisting of TFA/H$_2$O/TIPS (95:2.5:2.5) for 1.5 h at rt. The crude peptide was precipitated with ether following the procedure described in Example 1, step 7.

Cyclic PYY Analog SEQ ID NO: 69

The crude peptide obtained above was dissolved at a concentration of 80 mg/mL in DMSO, and TEA (25 eq.) was added to effect lactamization. After stirring at rt for ~30 min, the reaction was diluted 10-fold with 10% MeCN/water, the pH adjusted to 2 and the crude peptide purified directly by preparative HPLC on a Kinetics C18 Evo column (30×100 mm, 100 Å, 5 μm). The mobile phase consisted of gradient of Buffer A (0.1% TFA in water) and Buffer B (0.1% TFA in MeCN) ranging from 10-60% B over 22 min. UV detection was monitored at 220 and 254 nm. Pure fractions were combined, and then lyophilized to give the K(Dde)-protected peptide. The Dde protecting group was removed using 2% hydrazine/DMF (10 mg peptide/ml), 30 mins at rt. The reaction was diluted 10-fold with 10% MeCN/water, and the pH was adjusted to 2 with TFA and the crude peptide solution was purified as above to give the product as a cotton-like solid.

Example 70: Synthesis of Cyclic PYY Analog SEQ ID NO:70

The title compound was prepared according to the procedure in Example 69, substituting Fmoc-E(OAll)-OH for Fmoc-Leu-OH at position 30 and substituting Fmoc-Val-OH for Fmoc-E(OAll)-OH in position 31.

Example 71: Synthesis of Cyclic PYY Analog SEQ ID NO:71

1. Synthesis of (Boc)-G-ISPEAPGEK(dde)AS-PEELNRYYASLRHYLN E(OAllyl)VTRQ(N-Me-R)Y-NovaSyn TGR Resin Amino acid extensions onto a NovaSyn TGR resin (0.1 mmol) were carried out using the procedure described in Example 69, step 1.

2. Cyclic PYY Analog SEQ ID NO: 71

The title compound was prepared from the above resin according to the procedures described in Example 69, steps 2-4.

Example 72: Synthesis of Cyclic PYY Analog SEQ ID NO:72

1. Synthesis of (S)-22-(tert-butoxycarbonyl)-43,43-dimethyl-10,19,24,41-tetraoxo-3,6,12,15,42-pentaoxa-9,18,23-triazatetratetracontan-1-oic N-hydroxysuccinimide ester To a solution of (S)-22-(tert-butoxycarbonyl)-43,43-dimethyl-10,19,24,41-tetraoxo-3,6,12,15,42-pentaoxa-9,18,23-triazatetratetracontan-1-oic acid (Intermediate 2 (16)) (54.0 mg, 0.063 mmol), N-hydroxysuccinimide (14.6 mg, 0.127 mmol), and HATU (24.1 mg, 0.063 mmol) in 1.0 ml of DMF was added DIEA (0.022 ml, 0.127 mmol) and the mixture stirred for 30 mins at RT and used directly in the next step without further purification.

2. Synthesis of Cyclic PYY Analog SEQ ID NO:72

To a solution of [cyclo-(G2-E30), S4, K11, psi-(R35, Y36)]-PYY2-36 (prepared in Example 70) (4 mg, 0.96 µmol) in DMF (0.2 mL) was added 24 µL of the N-hydroxy ester solution (prepared in Step 1), and TEA (0.66 µL; 5 eq) and the mixture stirred overnight at rt. The reaction was diluted 10-fold with 10% MeCN/water, the pH adjusted to 2 with TFA and the crude peptide purified directly by preparative HPLC on a Kinetics C18 Evo column (30×100 mm, 100 Å, 5 µm). The mobile phase consisted of gradient elution of Buffer A (0.1% TFA in water) and Buffer B (0.1% TFA in MeCN) ranging from 10-60% B over 22 min. UV detection was monitored at 220 and 254 nm. Pure fractions were combined, and then lyophilized to give the t-butyl ester-protected peptide. The t-butyl ester protecting groups were removed using a mixture of TFA/H$_2$O/TIPS (95:2.5:2.5) for 1.5 h at rt. The mixture was concentrated and the peptide purified as above to give the product as a cotton-like solid.

Example 73: Synthesis of Cyclic PYY Analog SEQ ID NO:73

The title compound was prepared according to the procedure as described in Example 1 substituting N-Fmoc-dPEG6-carboxylic acid for N-Fmoc-dPEG12-carboxylic acid in step 5.

Example 74: Synthesis of Cyclic PYY Analog SEQ ID NO:74

The title compound was prepared according to the procedure as described in Example 1 but omitting the PEG linker coupling step 5.

Example 75: Synthesis of Cyclic PYY Analog SEQ ID NO:75

The title compound was prepared according to the procedure as described in Example 1 substituting Fmoc-Cys(trt)-OH for Fmoc-hCys(trt)-OH at position 31, and omitting the Fmoc-βAla-OH coupling step in step 3.

Example 76: Synthesis of Cyclic PYY Analog SEQ ID NO:76

The title compound was prepared according to the procedure as described in Example 1 with modified step 3 and step 4. In step 3, Fmoc-Lys(Alloc)-OH and Fmoc-Lys(dde)-OH were used for position 30 and position 11, respectively. After Alloc at position at 30 was deprotected with Pd(PPh$_3$)$_4$-phenylsilane, mPEG16-carboxylic acid was coupled with HATU-DIPEA. In step 4, dde at position 11 was removed with 2% hydrazine in DMF.

Example 77: Synthesis of Cyclic PYY Analog SEQ ID NO:77

The title compound was prepared according to the procedure as described in Example 76 substituting mPEG12-carboxylic acid for mPEG16-carboxylic acid in step 3, and omitting the Fmoc-dPEG12-carboxylic acid coupling step in step 5.

Example 78: Synthesis of Cyclic PYY Analog SEQ ID NO:78

The title compound was prepared according to the procedure as described in Example 1 substituting Fmoc-N-Me-Gln(trt)-OH for Fmoc-Gln(trt)-OH in step 3.

Example 79: Synthesis of Cyclic PYY Analog SEQ ID NO:79

The title compound was prepared according to the procedure as described in Example 1 substituting Fmoc-N-Me-Arg(pbf)-OH for Fmoc-Arg(pbf)-OH in step 1B.

Example 80: Synthesis of Cyclic PYY Analog SEQ ID NO:80

The title compound was prepared according to the procedure as described in Example 79 substituting Fmoc-Arg(pbf)-OH for Fmoc-Lys(Boc)-OH at position 4, and substituting Fmoc-Trp(Boc)-OH for Fmoc-Leu-OH at position 30 in step 3.

Example 81: Synthesis of Cyclic PYY Analog SEQ ID NO:81

The title compound was prepared according to the procedure as described in Example 80 substituting Fmoc-Cys(trt)-OH for Fmoc-hCys(trt)-OH at position 31, and substituting Fmoc-γ-aminobutanoic acid for Fmoc-βAla-OH in step 3.

Example 82: Synthesis of Cyclic PYY Analog SEQ ID NO:82

The title compound was prepared according to the procedure as described in Example 1 substituting Fmoc-PEG2-carboxylic acid for Fmoc-βAla-OH and Fmoc-Cys(trt)-OH for Fmoc-hCys(trt)-OH at position 31 as well as omitting the coupling of Fmoc-Ile-OH in step 3.

Example 83: Synthesis of Cyclic PYY Analog SEQ ID NO:83

The title compound was prepared according to the procedure as described in Example 1 substituting Fmoc-Lys (N3)-OH for Fmoc-hCys(trt)-OH at position 31, substituting pent-4-ynoic acid for Fmoc-βAla-OH in step 3, and following the cyclization procedure B as below.

Cyclization procedure B: To a solution of fully deprotected peptide with PEG12-AcBr installed at position 11 (38 mg, 0.0067 mmol) in 2 mL of HEPES (pH 7.4) was added 1.7 mL of the premixed $CuSO_4$/TBTA solution (the solution was prepared by mixing a solution of 2.2 mg of $CuSO_4$ in water (0.4 mL) with a solution of 11 mg of TBTA in EtOH), followed by addition of 7 mg of sodium ascorbate in water (1 mL). The clear reaction solution was left mixing at rt and monitored by HPLC. After 30 min, the reaction was completed, and the reaction mixture was adjusted to pH 4 using TFA and subjected to HPLC purification (Pursuit XRS 5 250×30 mm C18 column, running @30 mpm flow, monitoring 214 nM wavelength, with a gradient ranging from 20-60% MeCN-water/water both with 0.1% TFA over 36 minutes). The desired fraction was collected and lyophilized.

Example 84: Synthesis of Cyclic PYY Analog SEQ ID NO:84

The title compound was prepared according to the procedure as described in Example 1 omitting the Fmoc-βAla-OH coupling step, substituting N3-PEG8-carboxylic acid for Fmoc-dPEG12-carboxylic acid in step 5, and substituting 3-(bromomethyl)benzoic acid coupling with DIC for bromoacetic anhydride acylation in step 3, and following the cyclization procedure C as below.

Cyclization procedure C: To a solution of fully deprotected peptide (20 mg, 0.0035 mmol) in 5 mL of degassed water, aq. $NaHCO_3$ solution was added to adjust the reaction mixture to pH 6.4 or higher. After 20 min, the LCMS indicated the reaction was complete, and the reaction mixture was adjusted to pH 4 using TFA and subjected to HPLC purification (Pursuit XRS 5 250×30 mm C18 column, running @30 mpm flow, monitoring 214 nM wavelength, with a gradient ranging from 10-60% MeCN-water/water both with 0.1% TFA over 36 minutes). The desired fraction was collected and lyophilized.

After the cyclization, the cyclized intermediate was subjected to linker extension by click chemistry following the cyclization procedure B with N-(1-bromo-2-oxo-7,10,13-trioxa-3-azahexadecan-16-yl)pent-4-ynamide, which was prepared by coupling of N-Boc-PEG4-$NH_2$ with pent-4-ynoic acid using HATU-DIPEA, followed by deprotection of Boc with TFA and acylation with bromoacetic anhydride in the presence of TEA.

Example 85: Synthesis of Cyclic PYY Analog SEQ ID NO:85

The title compound was prepared according to the procedure as described in Example 1 with PEG12-AcBr linker installed at position 23 instead of position 11.

Example 86: Synthesis of Cyclic PYY Analog SEQ ID NO:86

The title compound was prepared according to the procedure as described in Example 1 with PEG12-AcBr linker installed at position 22 instead of position 11.

Example 87: Synthesis of Cyclic PYY Analog SEQ ID NO:87

The title compound was prepared according to the procedure as described in Example 1 with PEG12-AcBr linker installed at position 7 instead of position 11.

Example 88: Synthesis of Cyclic PYY Analog SEQ ID NO:88

The title compound was prepared according to the procedure as described in Example 1 substituting Fmoc-V-OH for Fmoc-hCys(trt)-OH at position 31, substituting Fmoc-Cys(trt)-OH for Fmoc-Leu-OH at position 30, and substituting Fmoc-Gly-OH for Fmoc-βAla-OH in step 3.

Example 89: Synthesis of Cyclic PYY Analog SEQ ID NO:89

The title compound was prepared according to the procedure as described in Example 88 omitting step 1 to make the reduced dipeptide, and substituting Fmoc-Tyr(tBu)-OH loading followed by coupling with Fmoc-(N-Me)Arg-OH for Fmoc-psi-(R35-N(Boc)-Y36)-OH loading in step 2.

Example 90: Synthesis of Cyclic PYY Analog SEQ ID NO:90

The title compound was prepared according to the procedure as described in Example 89 substituting Fmoc-βAla-OH for Fmoc-Gly-OH in step 3.

Example 91: Synthesis of Cyclic PYY Analog SEQ ID NO:91

The title compound was prepared according to the procedure as described in Example 89 substituting Fmoc-hCys(trt)-OH for Fmoc-Cys(trt)-OH at position 30 in step 3.

Example 92: Synthesis of Cyclic PYY Analog SEQ ID NO:92

The title compound was prepared according to the procedure as described in Example 90 substituting Fmoc-hCys(trt)-OH for Fmoc-Val-OH at position 31, and substituting Fmoc-Leu-OH for Fmoc-Cys(trt)-OH at position 30 in step 3.

Example 93: Synthesis of Cyclic PYY Analog SEQ ID NO:93

The title compound was prepared according to the procedure as described in Example 1 substituting Fmoc-Val-OH for Fmoc-hCys(trt)-OH at position 31, substituting Fmoc-Cys(trt)-OH for Fmoc-Leu-OH at position 30, and substituting Fmoc-Gly-OH for Fmoc-βAla-OH at the N-terminus in step 3.

Example 94: Synthesis of Cyclic PYY Analog SEQ ID NO:94

The title compound was prepared according to the procedure as described in Example 1 substituting Fmoc-Val-OH for Fmoc-hCys(trt)-OH at position 31 and substituting Fmoc-Cys(trt)-OH for Fmoc-Leu-OH at position 30 in step 3.

Example 95: Synthesis of Cyclic PYY Analog SEQ ID NO:95

The title compound was prepared (0.05 mmol scale) according to the procedures as described in Example 1 substituting Fmoc-Val-OH for Fmoc-hCys(trt)-OH at position 31, substituting Fmoc-Glu(OAlloc)-OH for Fmoc-Leu-OH at position 30, substituting Fmoc-Lys(Dde)-OH for Fmoc-Lys(Alloc)-OH at position 11, substituting Fmoc-Ser(tBu)-OH for Fmoc-Lys(Boc)-OH in position 4 and substituting Boc-Gly-OH for Fmoc-βAla-OH at the N-terminus in step 3.

To the resulting resin from above was added deoxygenated DCM (10 mL), phenylsilane (10 eq.) and a solution of the Pd(PPh$_3$)$_4$ (0.2 eq.) in DCM (1 mL) and the mixture was stirred for 10 mins. The reaction was drained and the resin was washed with deoxygenated DCM and the deprotection was repeated one time.

To the resulting resin from above was added DMF (10 ml), HATU (5 eq), and DIEA (10 eq) and the mixture stirred for 5 min then a solution of N-hydroxysuccinimide (10 eq) in DMF was added and stirred for an additional 20 min. The resin was filtered and the procedure repeated one time.

The resin from above was deprotected for 2 h at rt in TFA/TIPS/water (95/2.5/2.5) (10 ml). The cleavage cocktail was concentrated to approx. 1 ml and then added to 40 ml of ether. The resulting precipitate was collected by centrifugation and dried under N2.

The resulting material from above was dissolved in 9 mL of DMSO to which 10 eq of TEA was added and the reaction allowed to proceed for 3 h at rt. The resulting solution was diluted to 30 ml with water, the pH adjusted to 2 and purified by RP-HPLC on a 30 mm×250 mm C18 column eluting with a linear gradient of 20-40% MeCN in water (0.1% TFA) in 30 mins. The fractions containing product were lyophilized.

The resulting material from above was then treated with 1-2% hydrazine/DMF (1 mL) to remove the Dde from lysine. The resulting mixture was diluted to 10 ml with water, the pH adjusted to 2 and then purified by RP-HPLC as above.

The resulting product was then dissolved in 10% MeCN/water, the pH adjusted to 10, and a solution of bromoacetic N-hydroxysuccinimide ester (3 eq of 0.1M/DMF soln) was added and the reaction allowed to proceed for 10 min at rt. The resulting mixture was diluted to 10 ml with water, the pH adjusted to 2 and then purified by RP-HPLC as above to give the title product.

Example 96: Synthesis of Cyclic PYY Analog SEQ ID NO:96

The title compound was prepared according to the procedure as described in Example 1 substituting N-Fmoc-dPEG24-carboxylic acid for N-Fmoc-dPEG12-carboxylic acid in step 5.

Example 97: Synthesis of Cyclic PYY Analog SEQ ID NO:97

The title compound was prepared according to the procedure as described in Example 1 substituting Fmoc-Gly-OH for Fmoc-βAla-OH in step 3.

Example 98: Synthesis of Cyclic PYY Analog SEQ ID NO:98

The title compound was prepared according to the procedure as described in Example 89 but omitting the Fmoc-dPEG12-carboxylic acid coupling step in step 5.

Example 99: Synthesis of Cyclic PYY Analog SEQ ID NO:99

The title compound was prepared according to the procedure as described in Example 90 but omitting the Fmoc-dPEG12-carboxylic acid coupling step in step 5.

Example 100: Synthesis of Cyclic PYY Analog SEQ ID NO: 100

The title compound was prepared according to the procedure as described in Example 94 but omitting the Fmoc-dPEG12-carboxylic acid coupling step in step 5.

All of the following sequences are considered to be examples of the invention.

SEQUENCE LISTING

SEQ ID NO: 1
Name: [Cyclo-(βA2-COCH$_2$-hC31), K(PEG12-AcBr)11, psi-(35R, 36Y)]-PYY2-36
Structure:

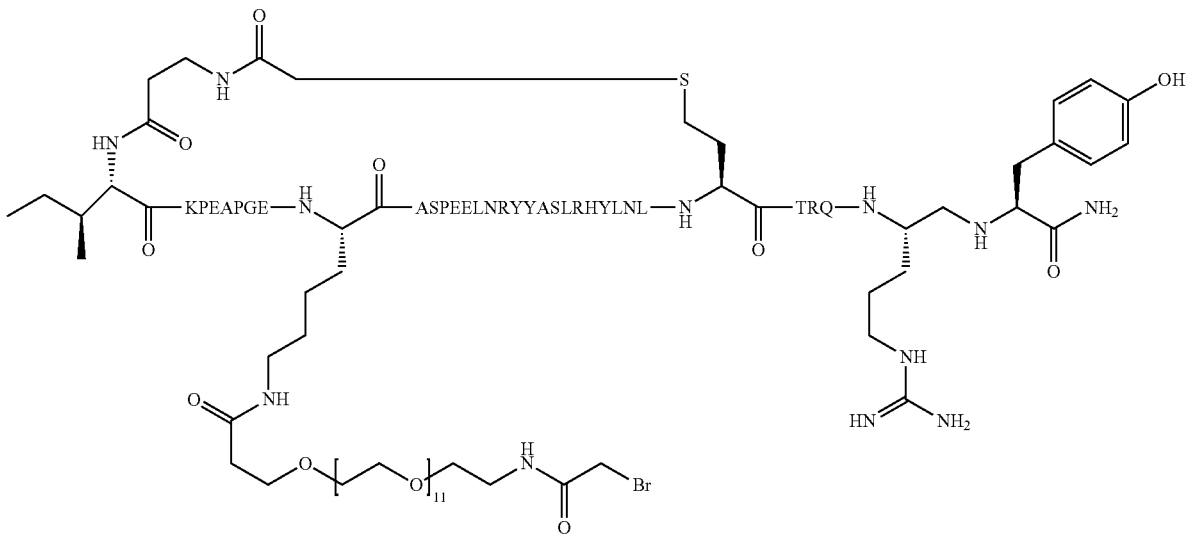

SEQ ID NO: 2
Name: [cyclo-(I3-m-COPhCH₂-hC31)]-PYY3-36
Structure:
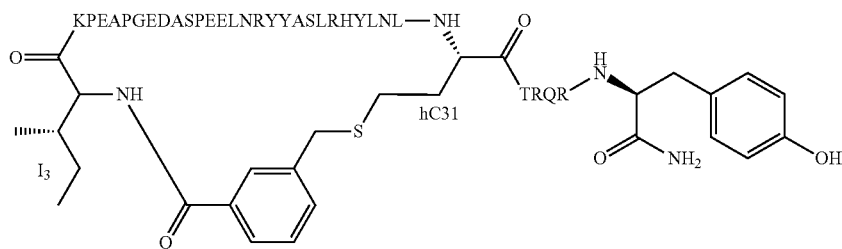
SEQ ID NO: 3
Name: [cyclo-(I3-CO(CH₂)₂triazolyl-Nle31)]-PYY3-36
Structure:
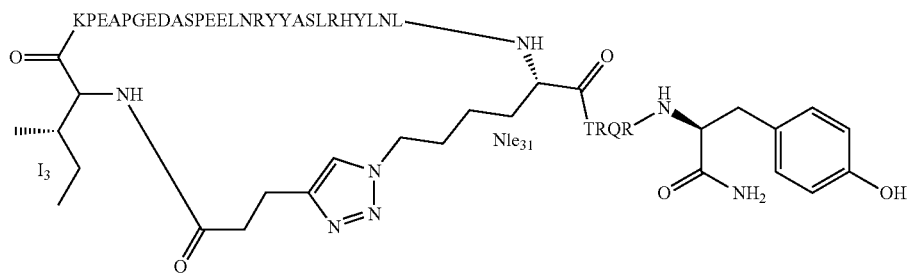
SEQ ID NO: 4
Name: [cyclo-(I3-m-COPhCH₂-hC31), K(γ-Glu-Pal)11]-PYY3-36
Structure:
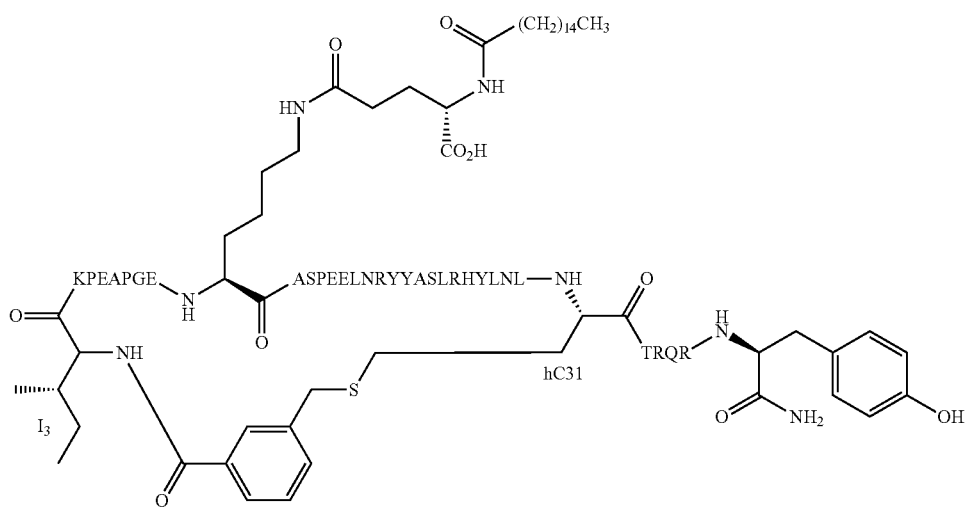

SEQ ID NO: 5
Name: [cyclo-(I3-m-COPhCH₂-hC31), K(γ-Glu-AcVitE)11]-PYY3-36
Structure:
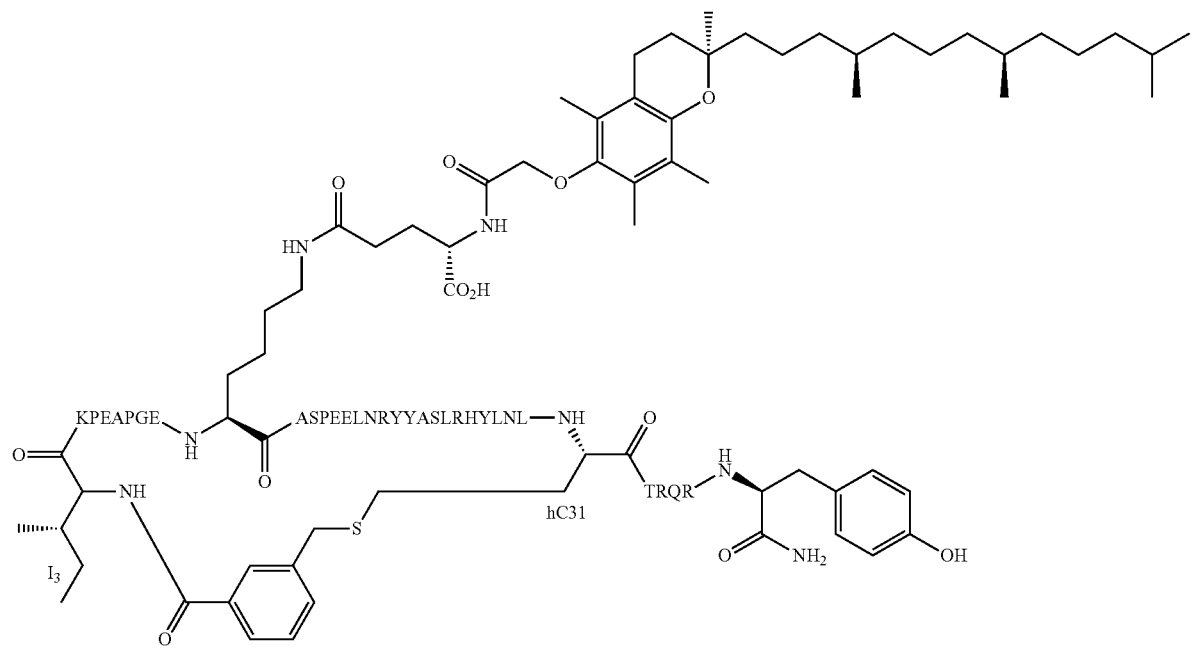
SEQ ID NO: 6
Name: [cyclo-(I3-CO(CH₂)₂triazolyl-Nle31), K(γ-Glu-AcVitE)11]-PYY3-36
Structure:
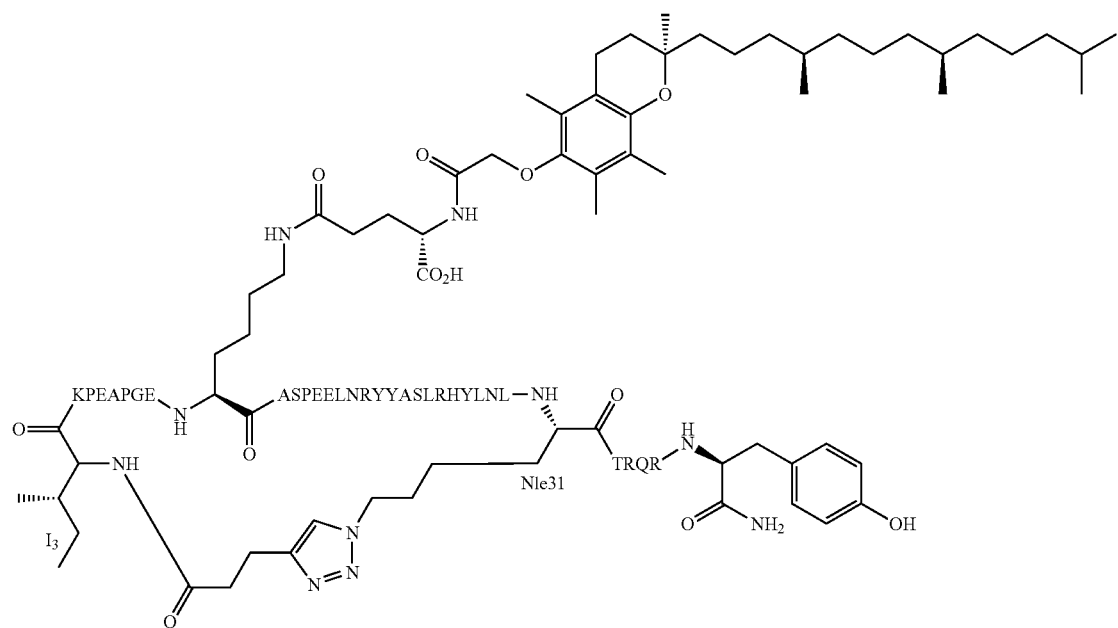

SEQ ID NO: 7
Name: [cyclo-(I3-m-COPhCH2-hC31), K(γ-Glu-Pal)9]-PYY3-36
Structure:
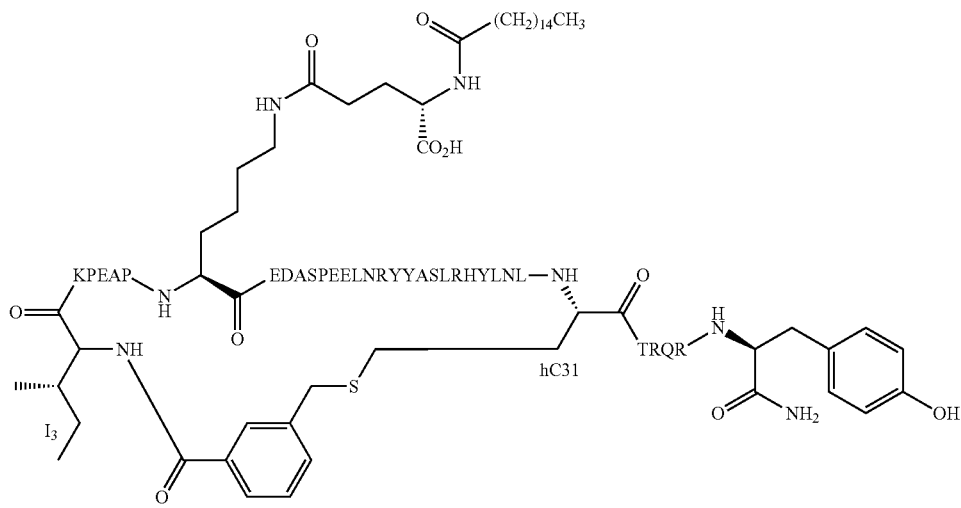
SEQ ID NO: 8
Name: [cyclo-(I3-m-COPhCH2-hC31), K(γ-Glu-Pal)30]-PYY3-36
Structure:
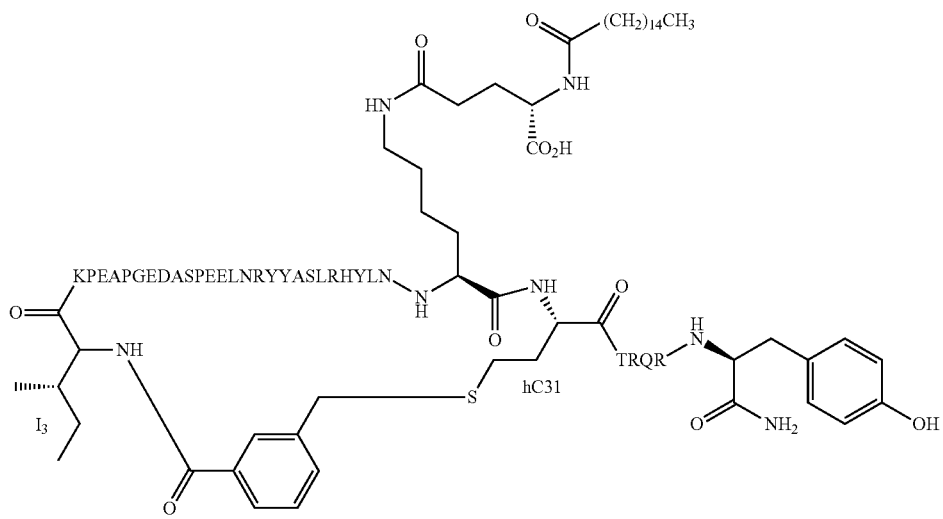
SEQ ID NO: 9
Name: [cyclo-(I3-m-COPhCH2-hC31), psi-(R35Y36)]-PYY3-36
Structure:
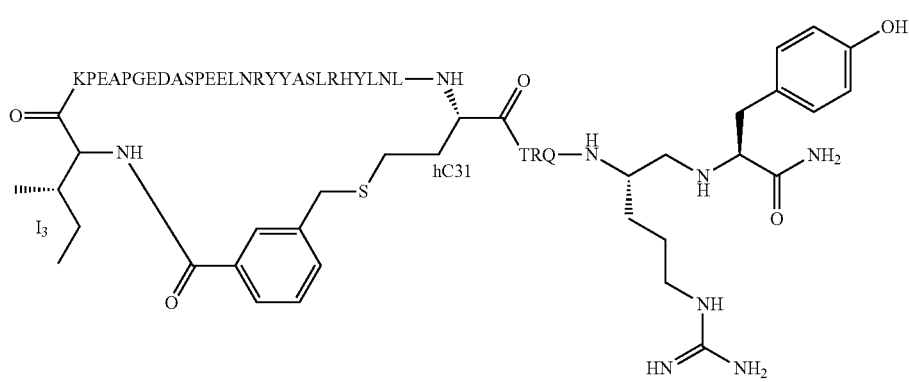

SEQ ID NO: 10
Name: [cyclo-(I3-m-COPhCH₂-hC31), K(γ-Glu-AcVitE)30]PYY3-36
Structure:
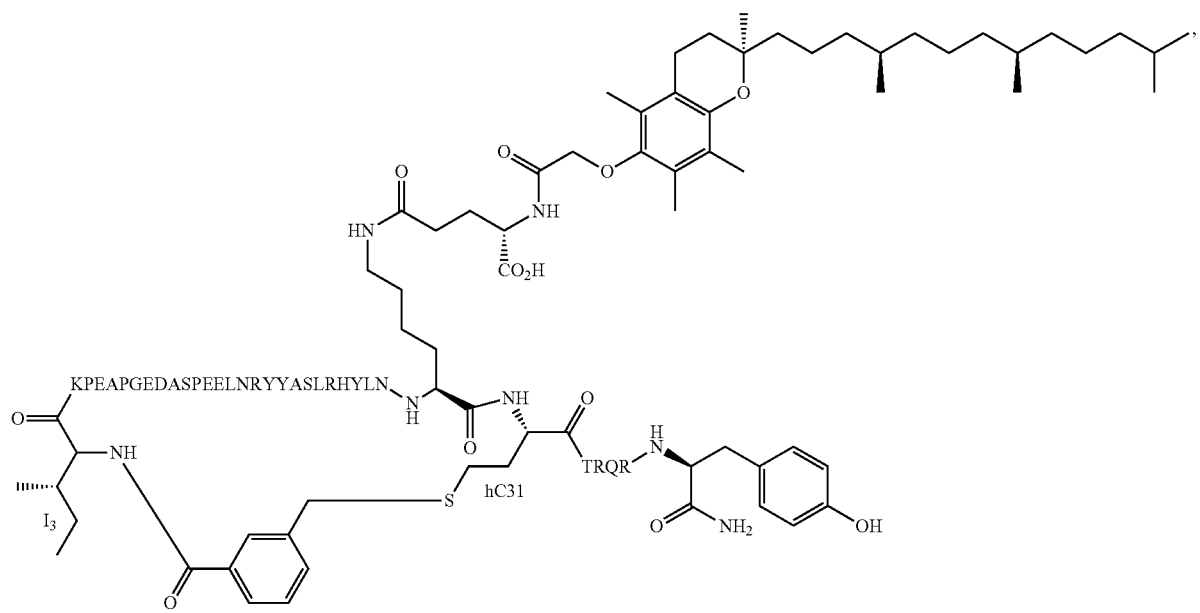
SEQ ID NO: 11
Name: [cyclo-(I3-m-COPhCH₂-hC31), K(γ-Glu-AcVitE)30, psi-(R35,Y36)]-PYY3-36
Structure:
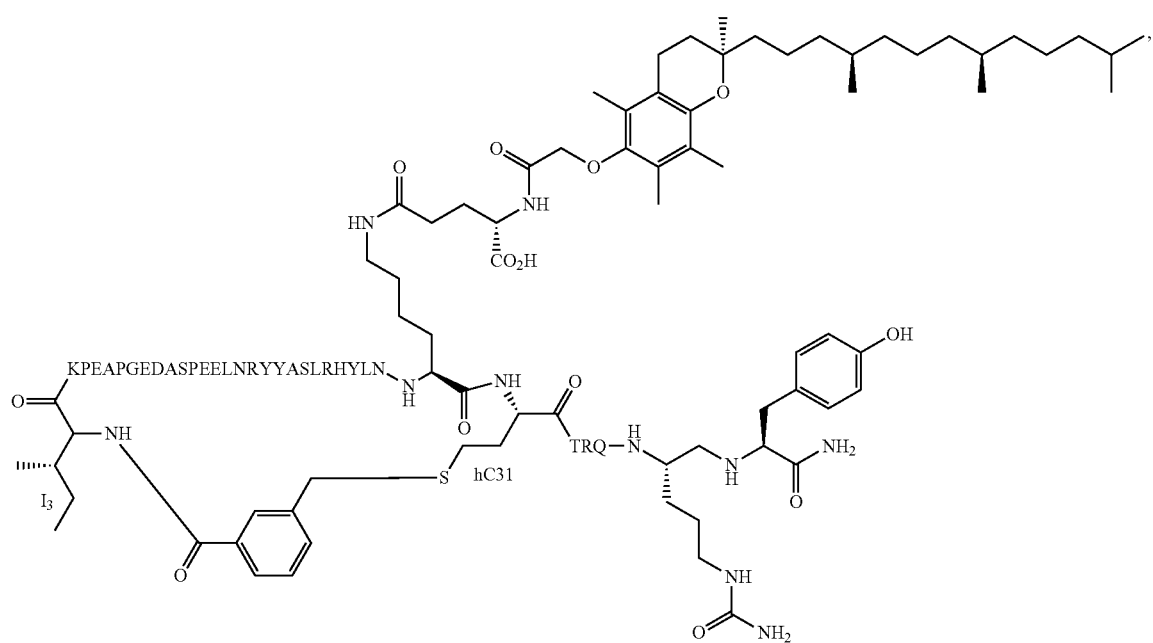

SEQ ID NO: 12
Name: [cyclo-(I3-m-COPhCH₂-hC31), (N-Me-R35)]-PYY3-36
Structure:
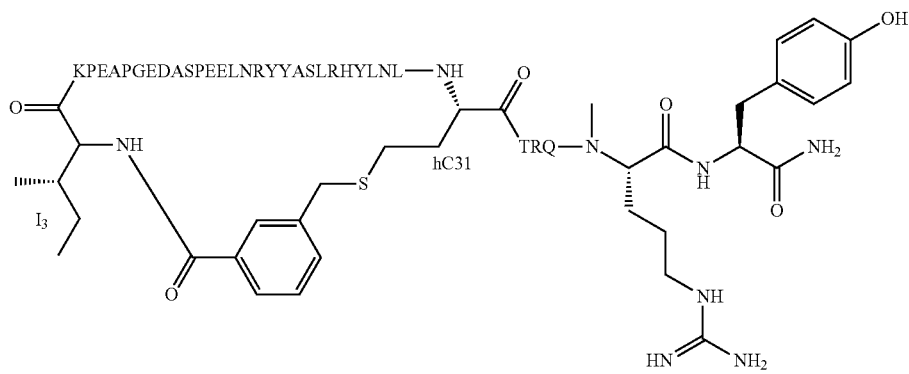
SEQ ID NO: 13
Name: [cyclo-(I3-m-COPhCH₂-hC31), K(γ-Glu-Pal)30, psi-(R35,Y36)]-PYY3-36
Structure:
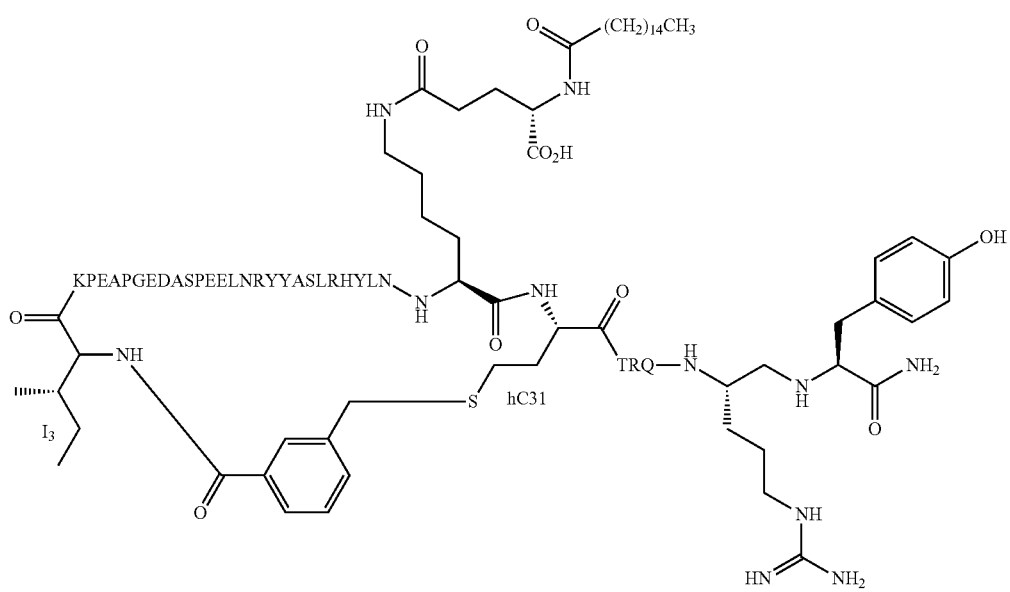

-continued
SEQ ID NO: 14
Name: [cyclo-(I3-m-COPhCH2-hC31), K(γ-Glu-Pal)30, (N-Me-R35)]-PYY3-36
Structure:
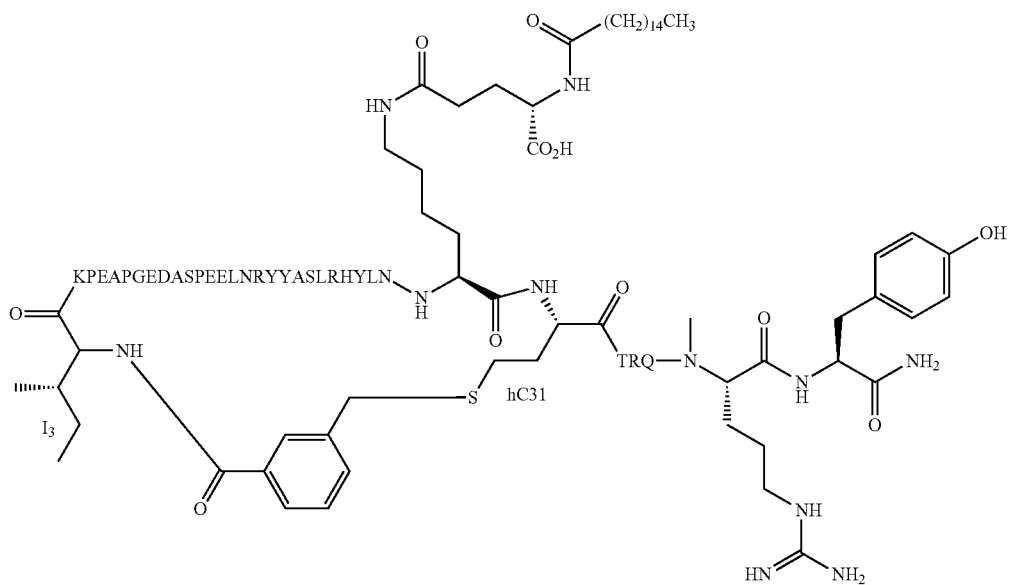
SEQ ID NO: 15
Name: [cyclo-(K4-CO(CH2)2NHCOCH2-hC31), K(γ-Glu-Pal)30]-PYY4-36
Structure:
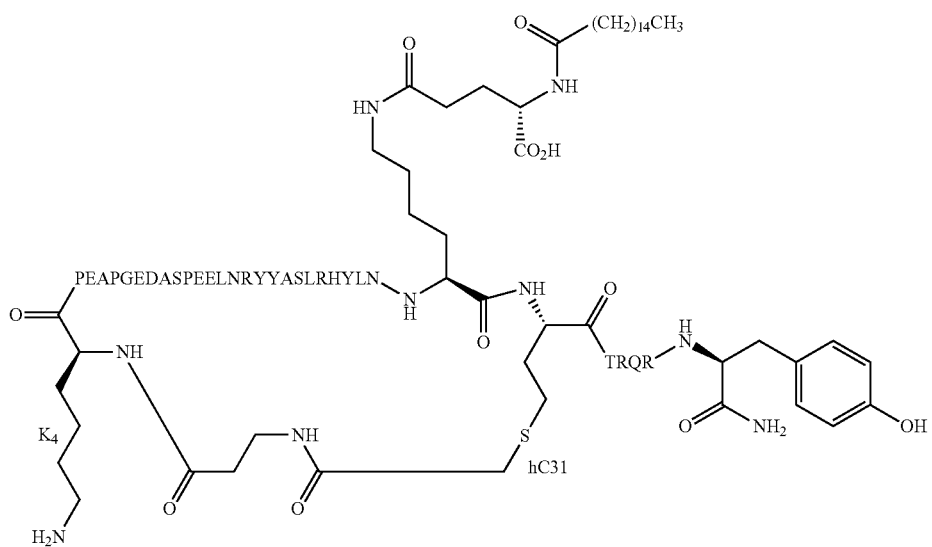

SEQ ID NO: 16
Name: [cyclo-(K4-p-COPhCH2-hC31), K(γ-Glu-Pal)30]-PYY4-36
Structure:
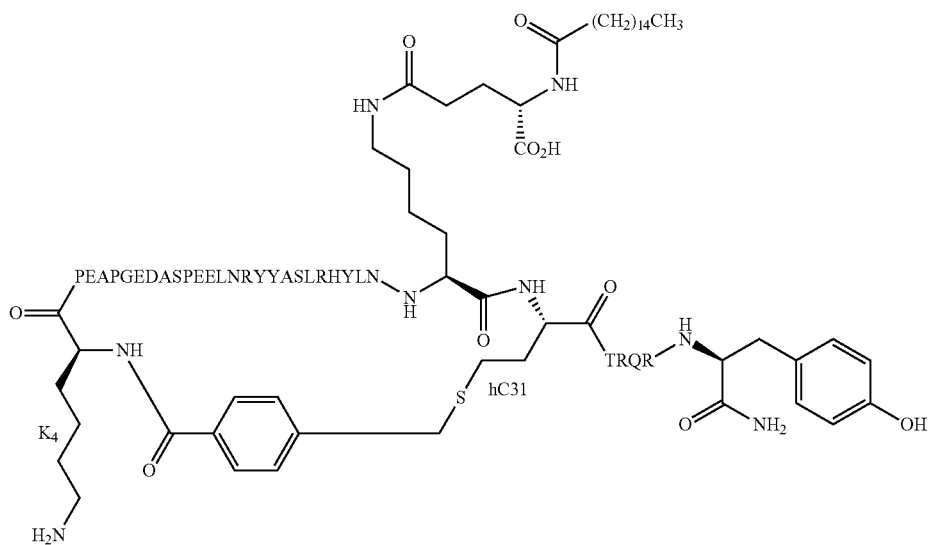
SEQ ID NO: 17
Name: [cyclo-(I3-m-COPhCH2-hC31), A4, K(γ-Glu-Pal)30]-PYY3-36
Structure:
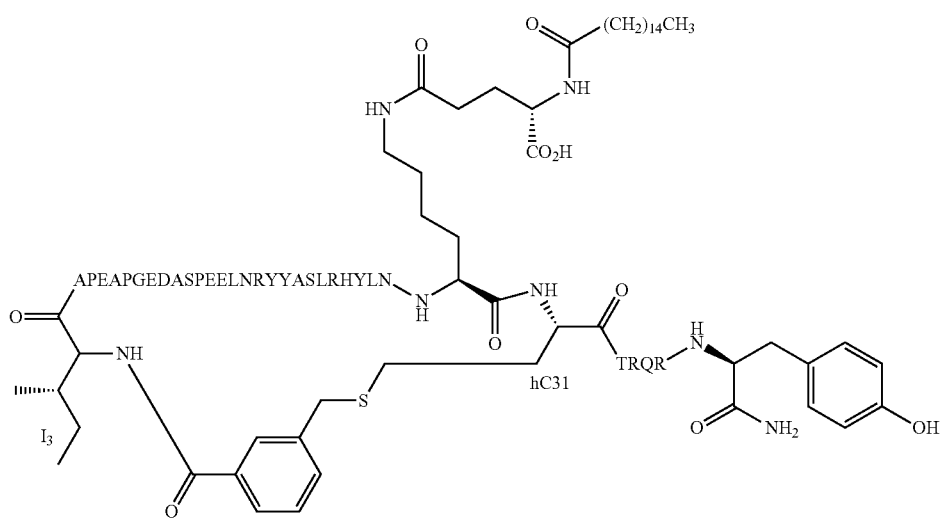

SEQ ID NO: 18
Name: [cyclo-(I3-m-COPhCH2-hC31), E4, K(γ-Glu-Pal)30]-PYY3-36
Structure:
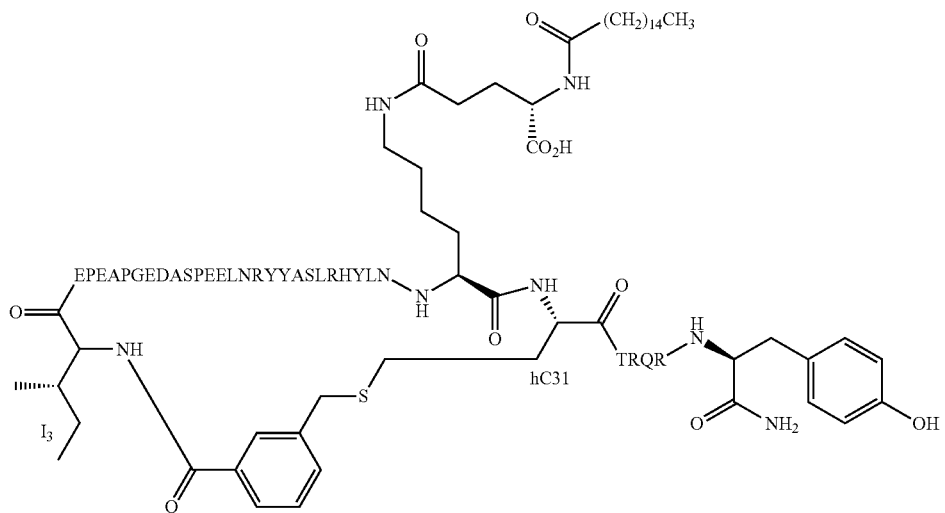
SEQ ID NO: 19
Name: [cyclo-(I3-p-COPhCH2-C31), K(γ-Glu-Pal)30, (N-Me-R35)]-PYY3-36
Structure:
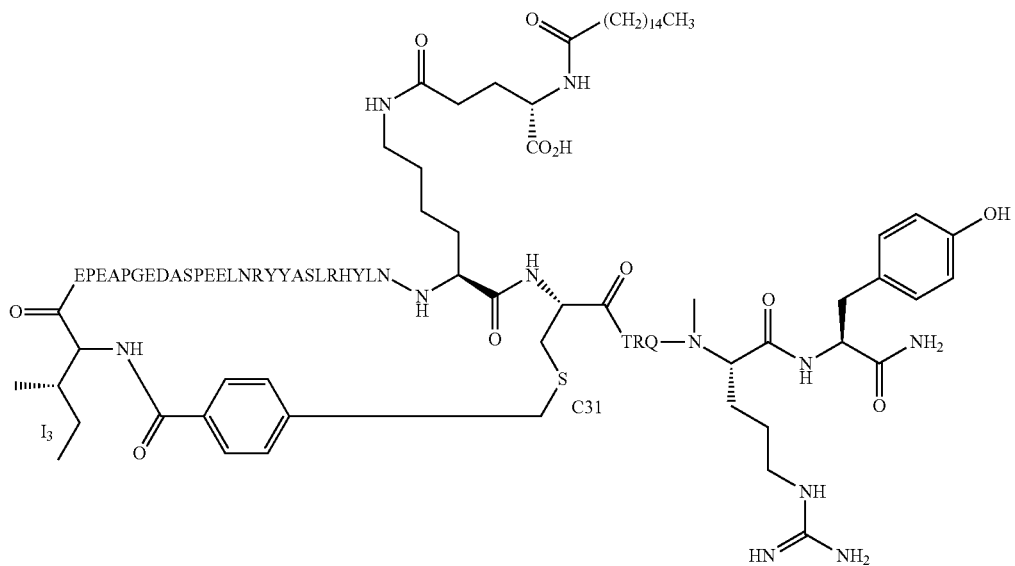

-continued
SEQ ID NO: 20
Name: [cyclo-(I3-p-COPhCH2-C31), K(γ-Glu-Pal)30, (N-Me-R35)]-PYY3-36
Structure:
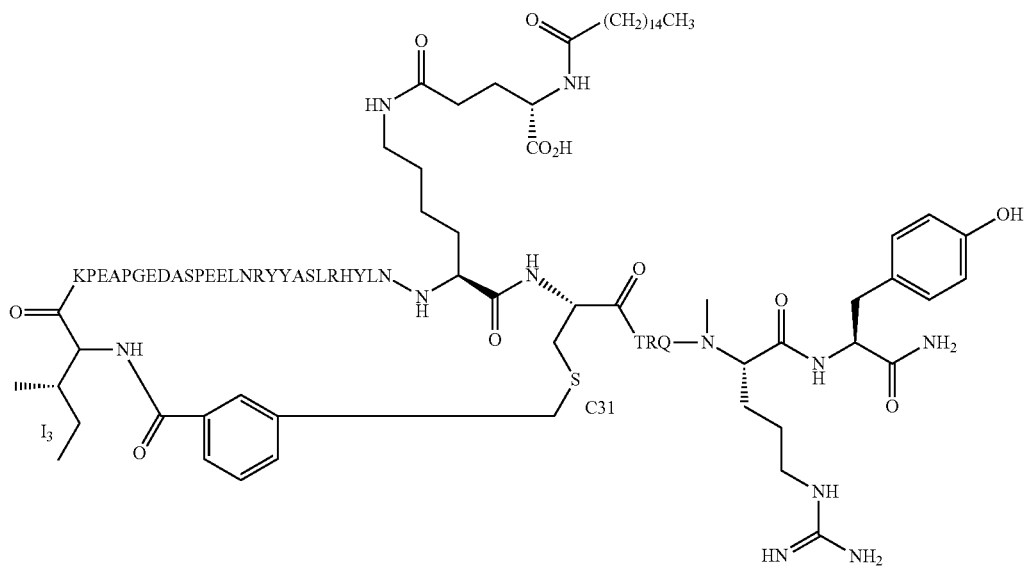
SEQ ID NO: 21
Name: [cyclo-(I3-m-COPhCH2-hC31), A4, A26, K(γ-Glu-Pal)30], PYY3-36
Structure:
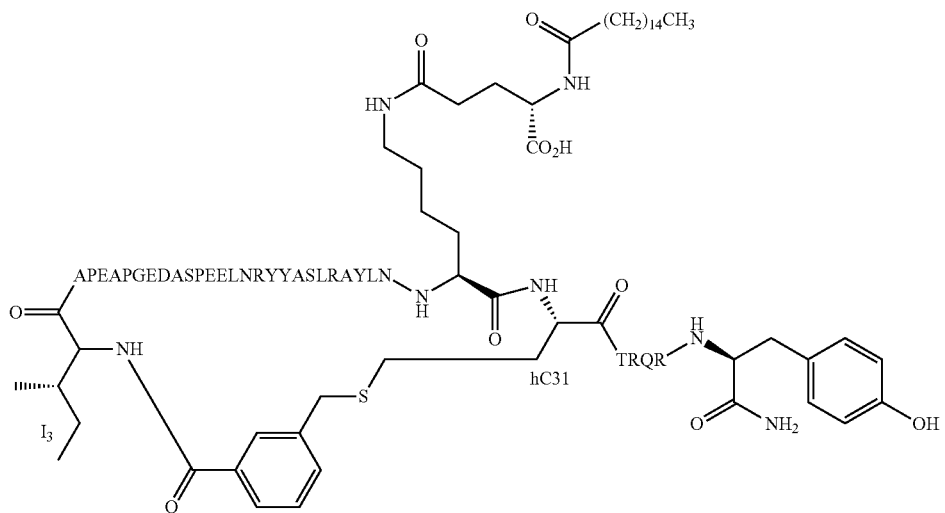

SEQ ID NO: 22
Name: [cyclo-(I3-m-COPhCH₂-hC31), E4, A26, K(γ-Glu-Pal)30]-PYY3-36
Structure:
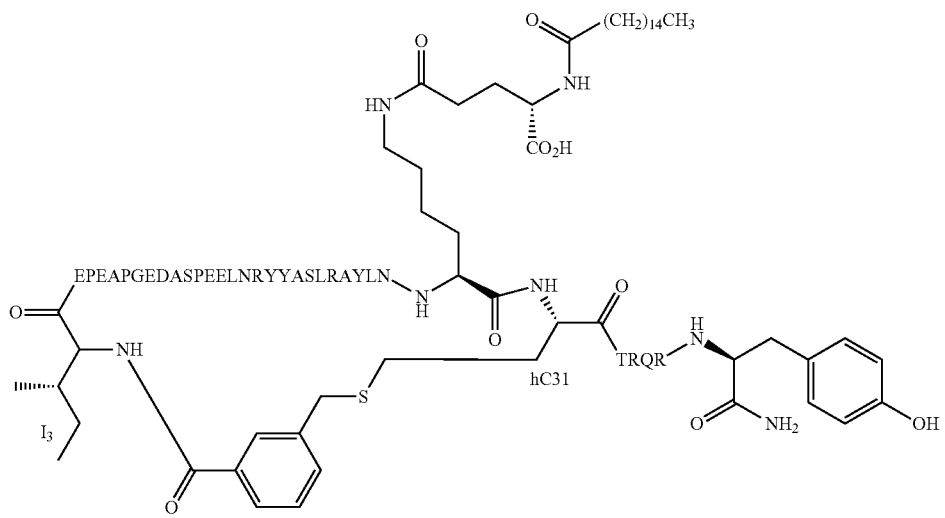
SEQ ID NO: 23
Name: [cyclo-(I3-m-COPhCH₂-hC31), K((OEG)₂-γ-Glu-COC₁₆CO₂H)30, psi-(R35,Y36)]-PYY3-36
Structure:
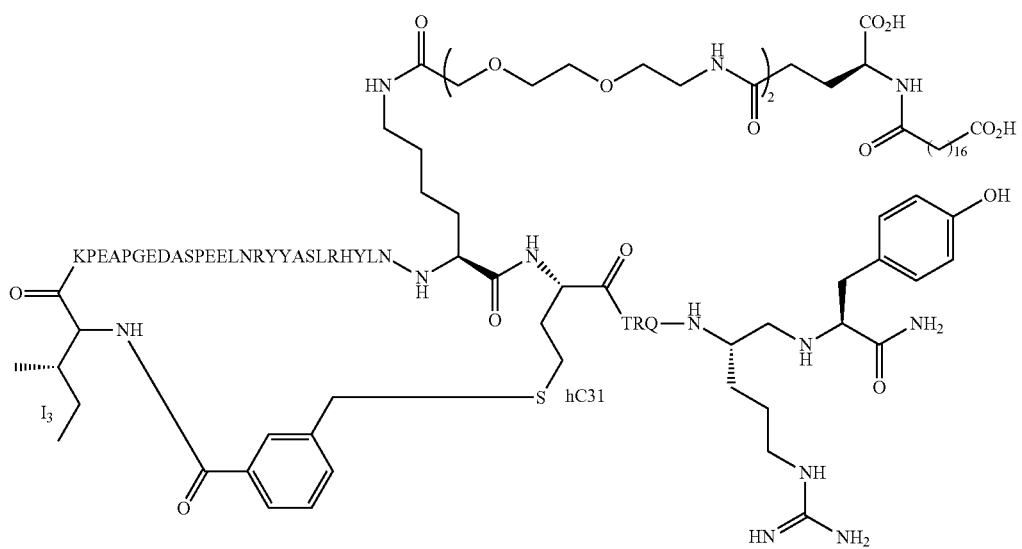

SEQ ID NO: 24
Name: [cyclo-(I3-m-COPhCH$_2$-hC31), K((OEG)$_2$-γ-Glu-COC$_{18}$CO$_2$H)30, psi-(R35,Y36)]-PYY3-36
Structure:
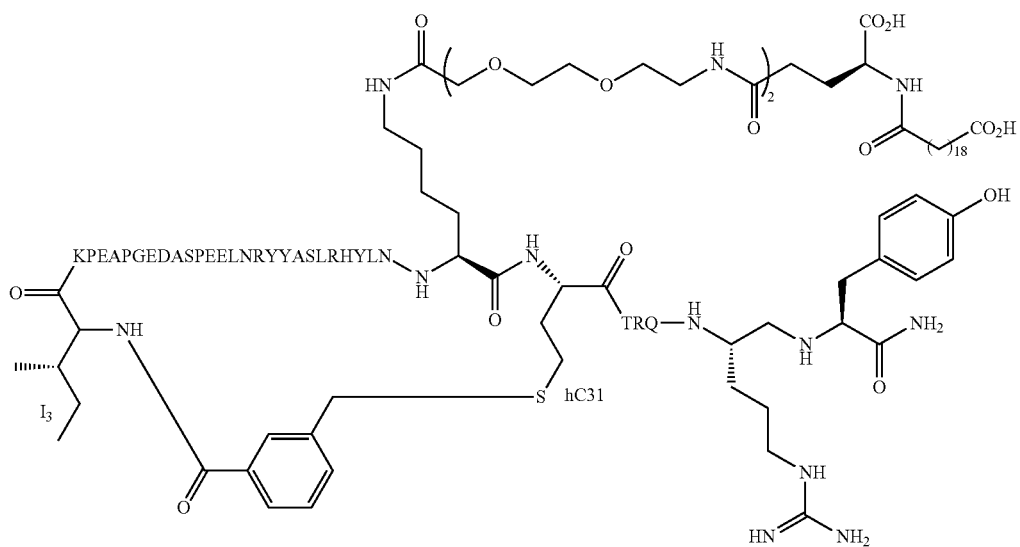
SEQ ID NO: 25
Name: [cyclo-(I3-m-COPhCH$_2$-hC31), K(γ-Glu-Stear)30, psi-(R35,Y36)]-PYY3-36
Structure:

SEQ ID NO: 26
Name: [cyclo-(I3-m-COPhCH2-hC31), K(γ-Glu-Arach)30, psi-(R35,Y36)]-PYY3-36
Structure:
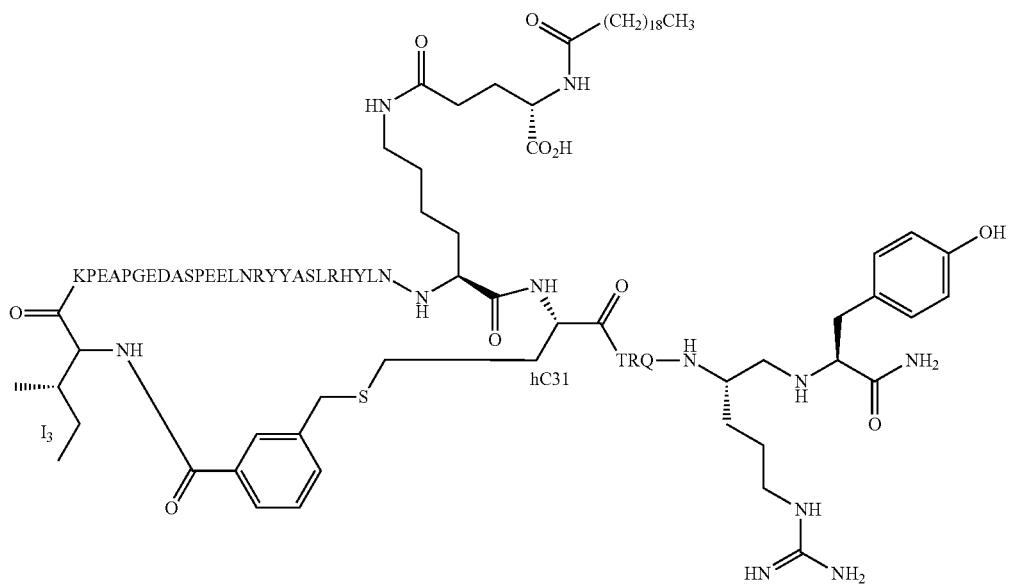
SEQ ID NO: 27
Name: [cyclo-(I3-m-COPhCH2-hC31), K((OEG)2-COC16CO2H)30, psi-(R35,Y36)]-PYY3-36
Structure:
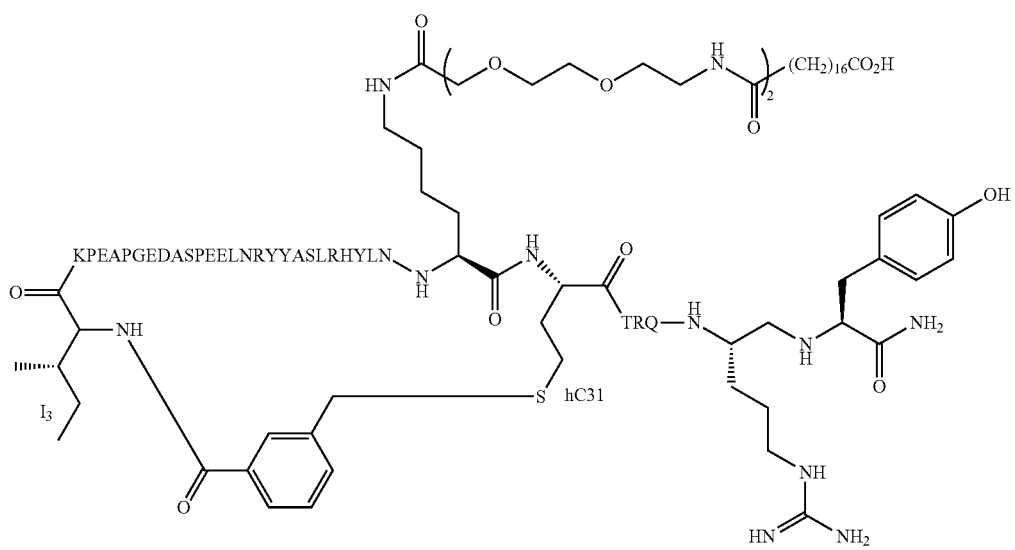

-continued
SEQ ID NO: 28
Name: [cyclo-(K4-p-COPhCH$_2$-hC31), K(γ-Glu-Pal)30, psi-(R35,Y36)]-PYY4-36
Structure:
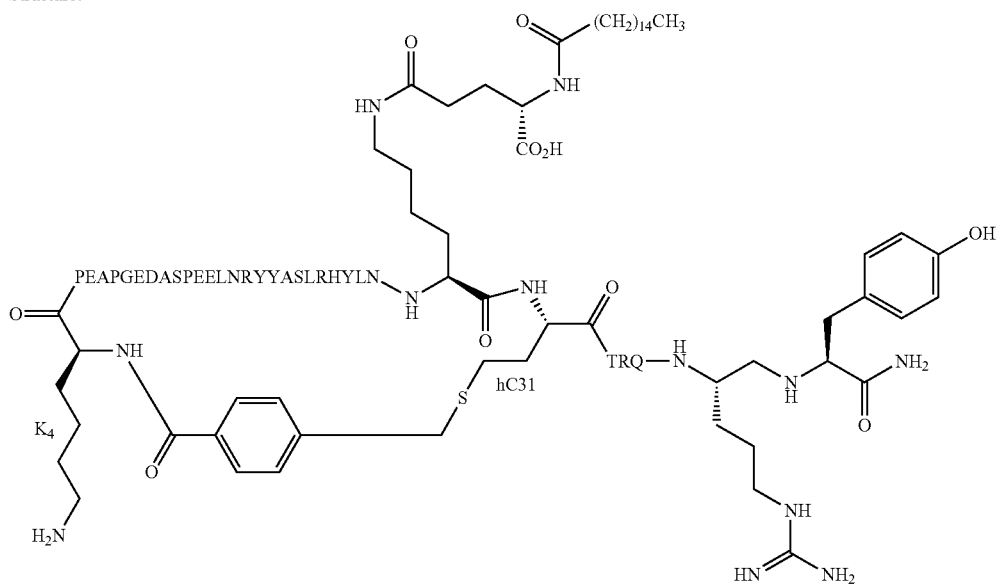
SEQ ID NO: 29
Name: [cyclo-(K4-COCH$_2$)$_2$NHCOCH$_2$-hC31), K(γ-Glu-Pal)30, psi-(R35,Y36)]-PYY4-36
Structure:
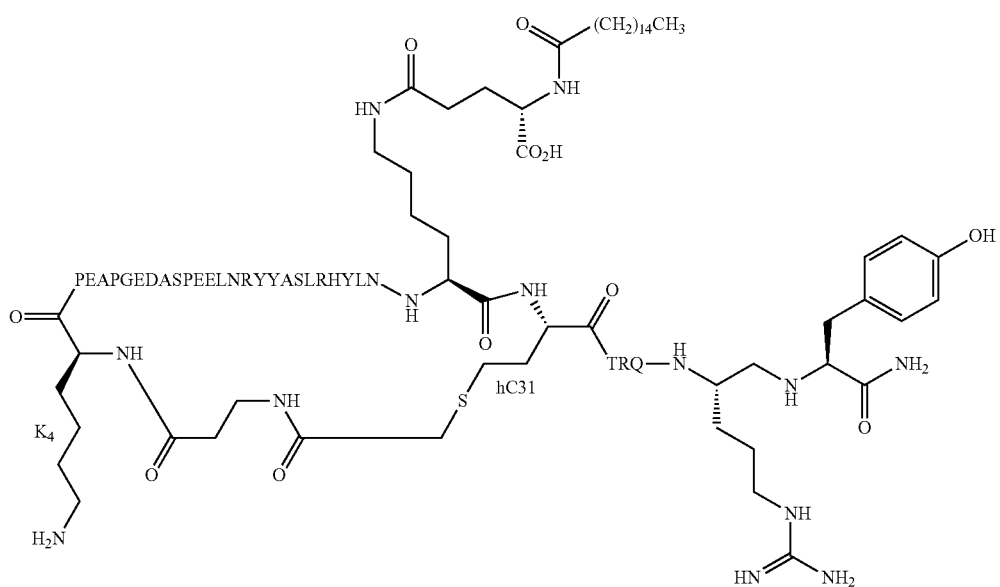

-continued
SEQ ID NO: 30
Name: [cyclo-(K4-COCH2)2NHCOCH2-C31), K(γ-Glu-Pal)30, psi-(R35,Y36)]-PYY4-36
Structure:
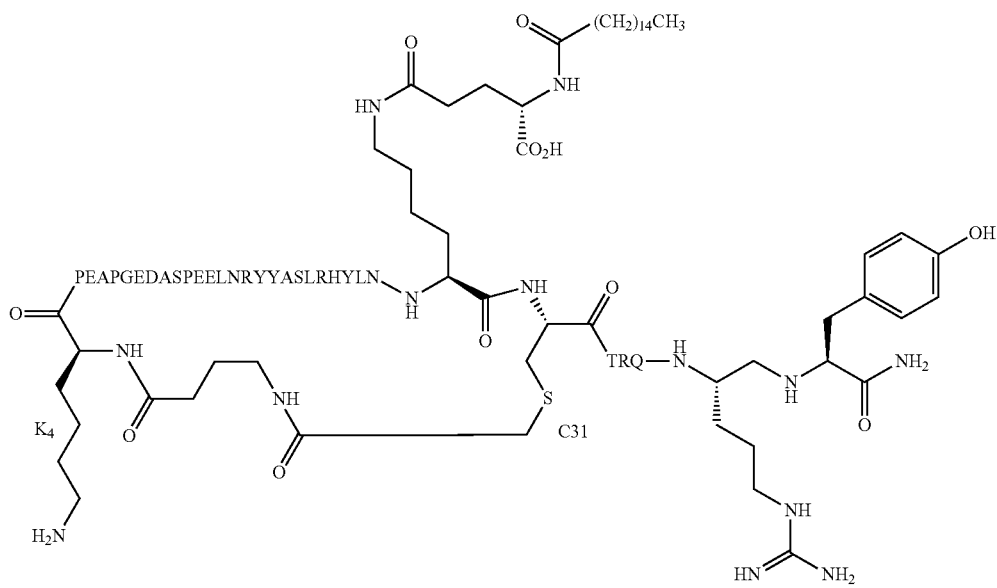
SEQ ID NO: 31
Name: [cyclo-(I3-m-COPhCH2-hC31), K((OEG)2-γ-Glu-Stear)30, psi-(R35,Y36)]-PYY3-36
Structure:
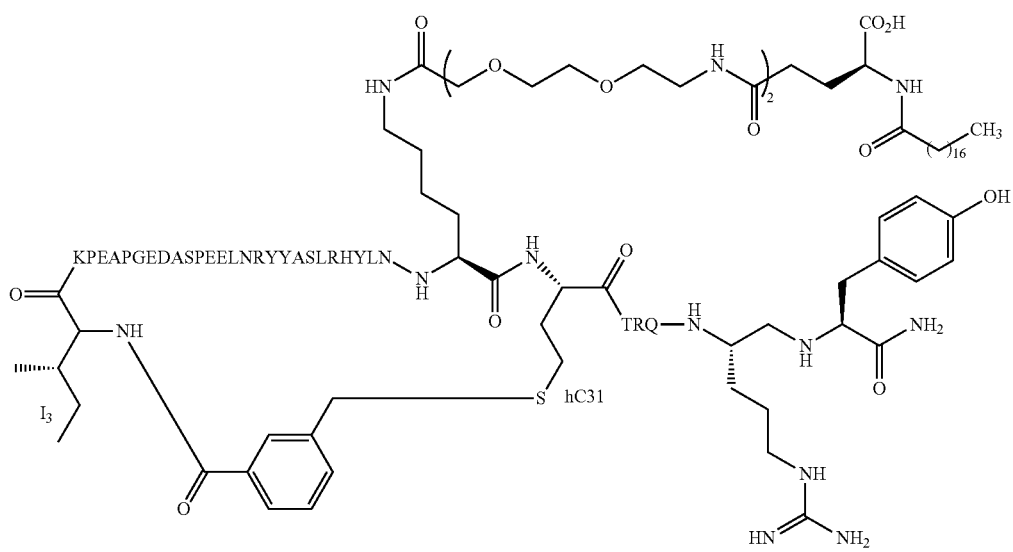

SEQ ID NO: 32
Name: [cyclo-(I3-m-COPhCH₂-hC31), A4, A26, K(γ-Glu-Pal)30, psi-(R35,Y36)]-PYY3-36
Structure:
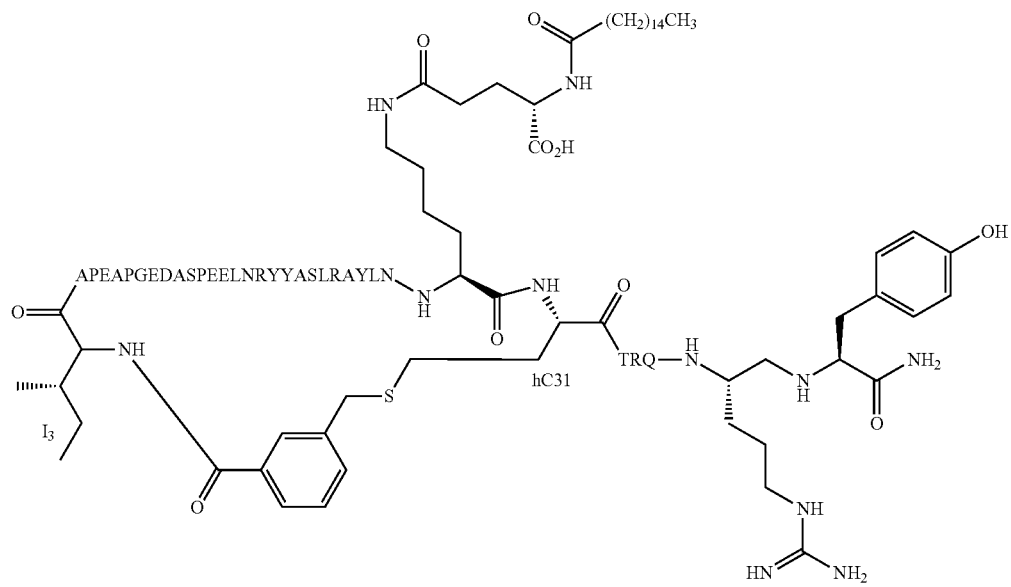
SEQ ID NO: 33
Name: [cyclo-(I3-m-COPhCH₂-hC31), K(γ-Glu-Pal)30, (N-Me-Q34), psi-(R35,Y36)]-PYY3-36
Structure:
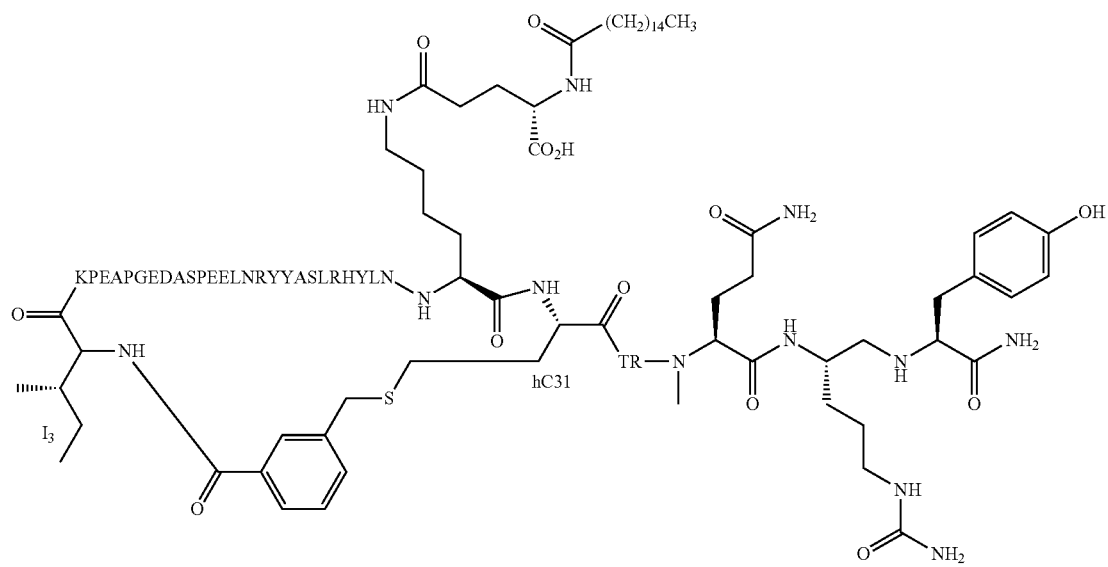

SEQ ID NO: 34
Name: [cyclo-(K4-CO(CH₂)₅NHCOCH₂-C31), K(γ-Glu-Pal)30, psi-(R35,Y36)]-PYY3-36
Structure:
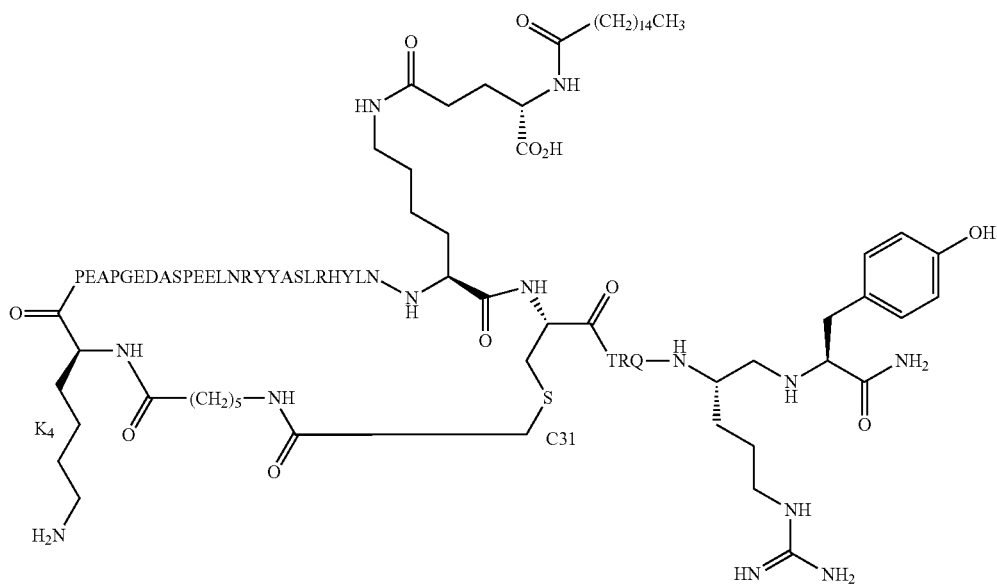
SEQ ID NO: 35
Name: [cyclo-(I3-m-COPhCH₂-hC31), K(γ-Glu-Pal)30, (N-Me-R35), psi-(R35,Y36)]-PYY3-36
Structure:
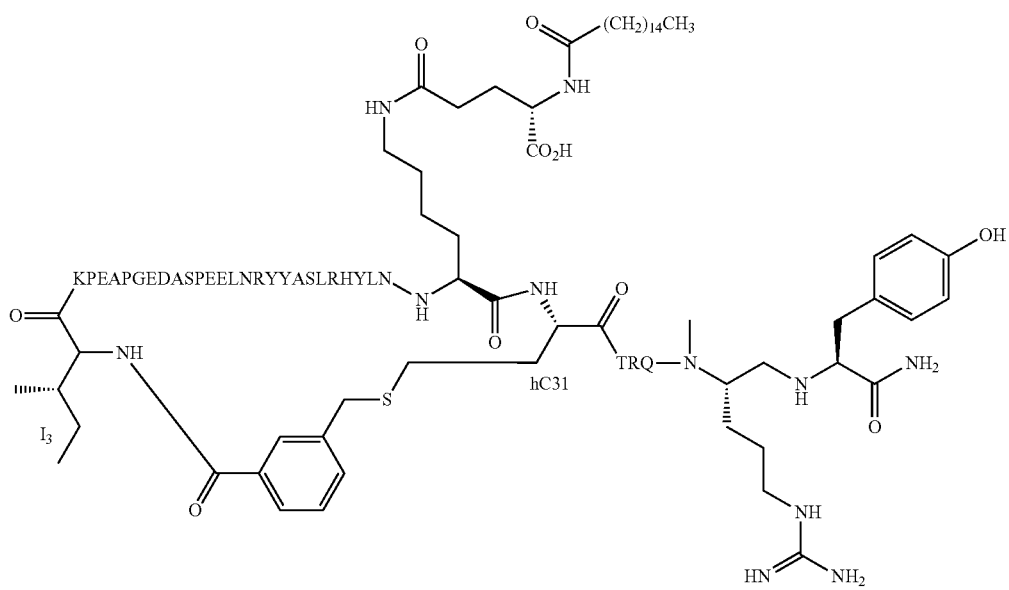

-continued
SEQ ID NO: 36
Name: [cyclo-(K4-CO(CH₂)₂NHCOCH₂-hC31), K(γ-Glu-Pal)30, (N-Me-R35), psi-(R35,Y36)]-PYY4-36
Structure:
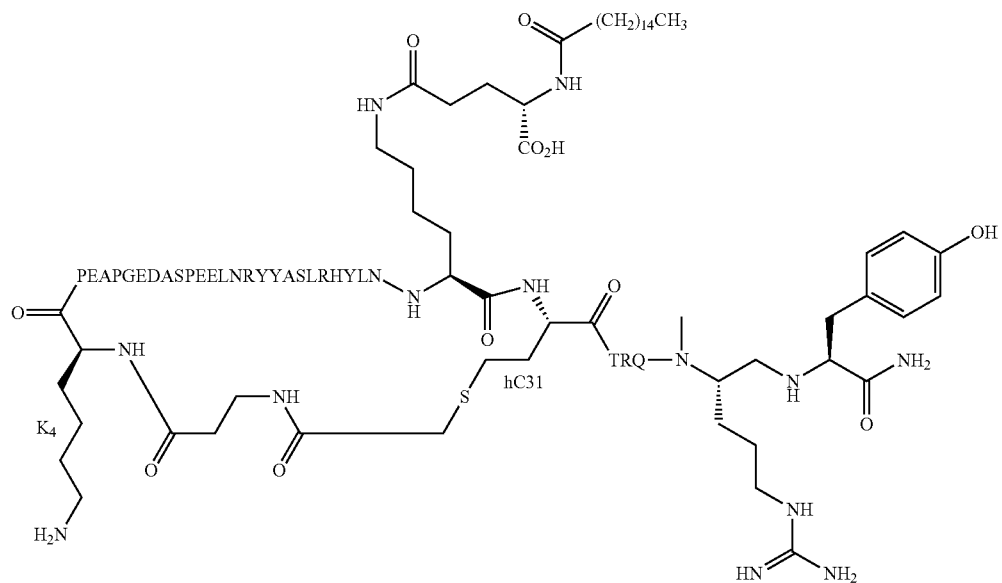
SEQ ID NO: 37
Name: [cyclo-(I3-CO(CH₂)₃NHCOCH₂-C31), K(γ-Glu-Pal)30, psi-(R35,Y36)]-PYY3-36
Structure:
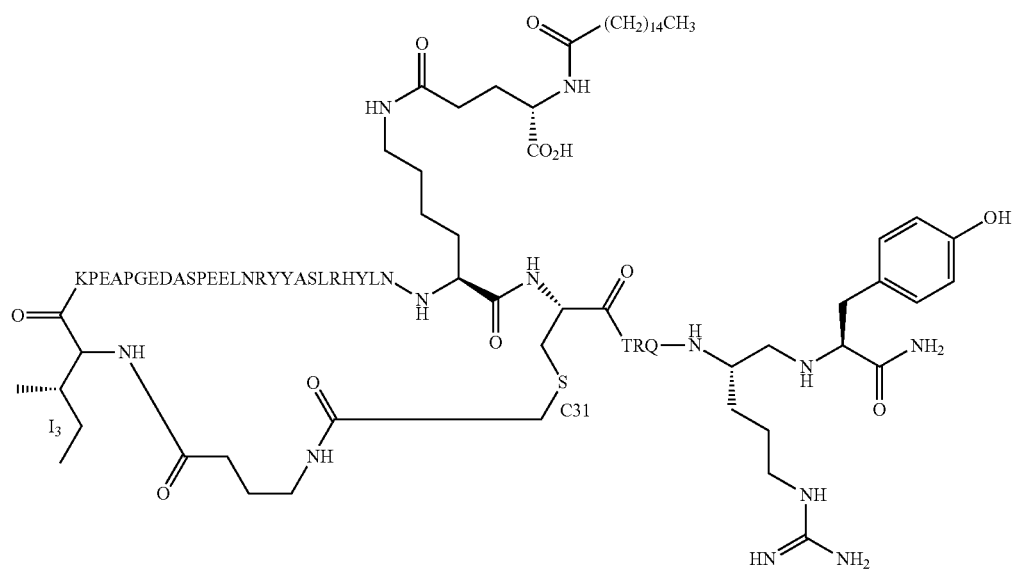

SEQ ID NO: 38
Name: [cyclo-(I3-CO(CH2)2NHCOCH2-hC31), K(γ-Glu-Pal)30, (N-Me-R35), psi-(R35,Y36)]-PYY3-36
Structure:
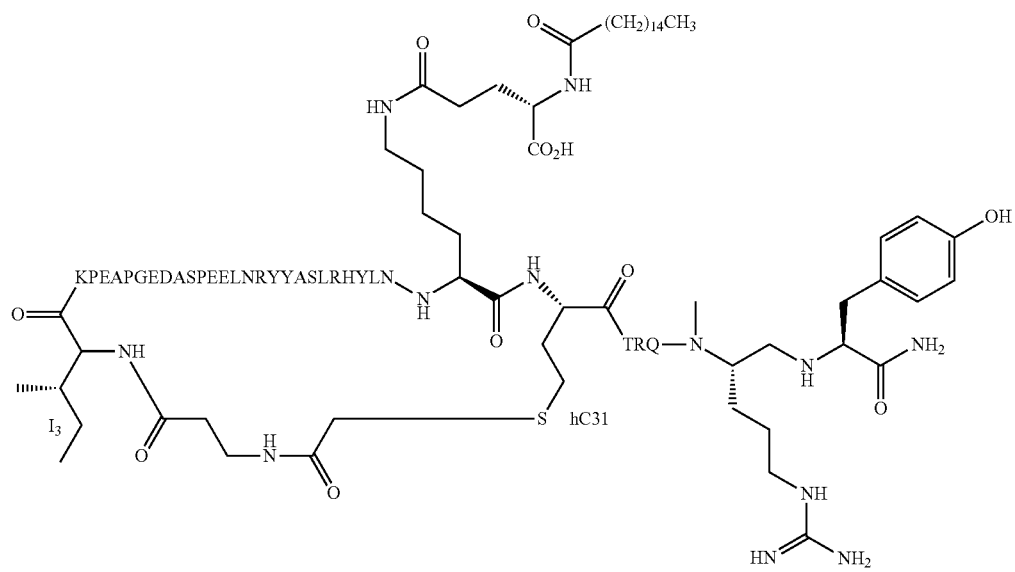
SEQ ID NO: 39
Name: [cyclo-(I3-m-COPhCH2-hC31), S4, K(γ-Glu-Arach)30, psi-(R35,Y36)]-PYY3-36
Structure:
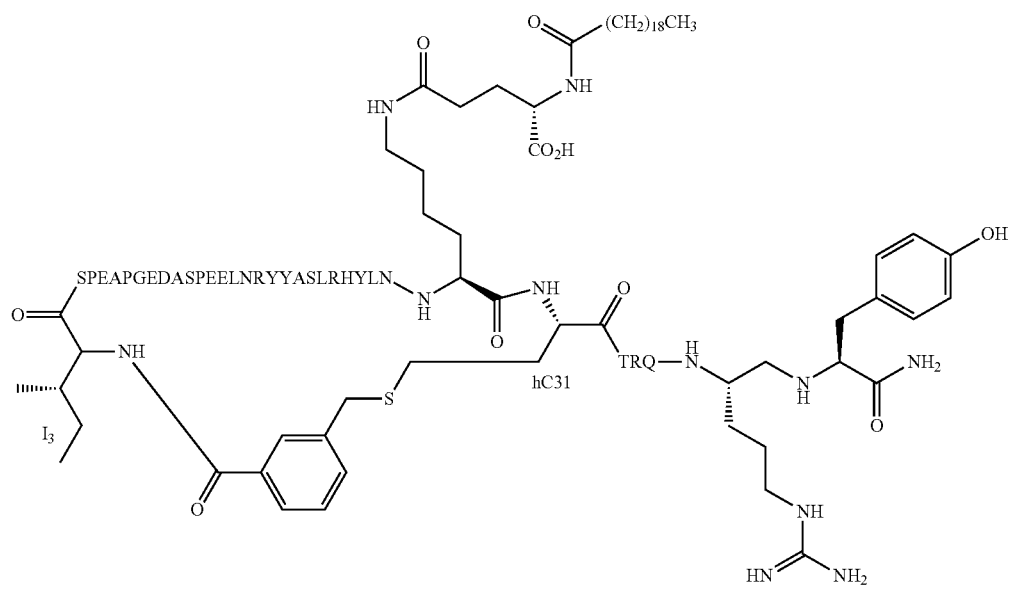

SEQ ID NO: 40
Name: [cyclo-(I3-CO(CH₂)₂triazolyl-Nle31), K((OEG)₂-γ-Glu-Pal)30, psi-(R35,Y36)]-PYY3-36
Structure:
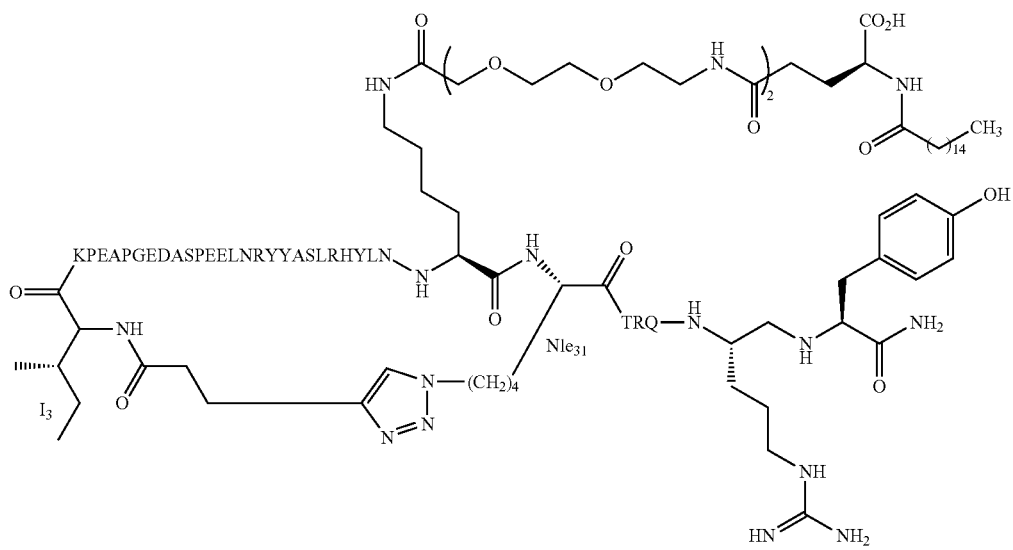
SEQ ID NO: 41
Name: [cyclo-(I3-CO(CH₂)₂triazolyl-Nle31), K(γ-Glu-Pal)30, psi-(R35,Y36)]-PYY3-36
Structure:
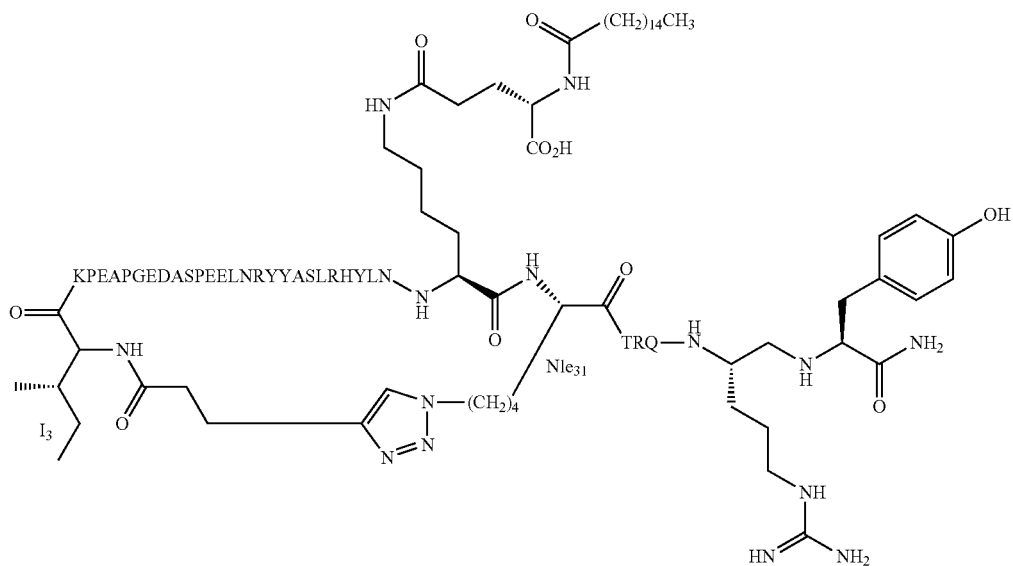

SEQ ID NO: 42
Name: [cyclo-(I3-CO(CH₂)₂triazolyl-Nle31), K((OEG)₂-γ-Glu-COC₁₆CO₂H)30, psi-(R35,Y36)]-PYY3-36
Structure:
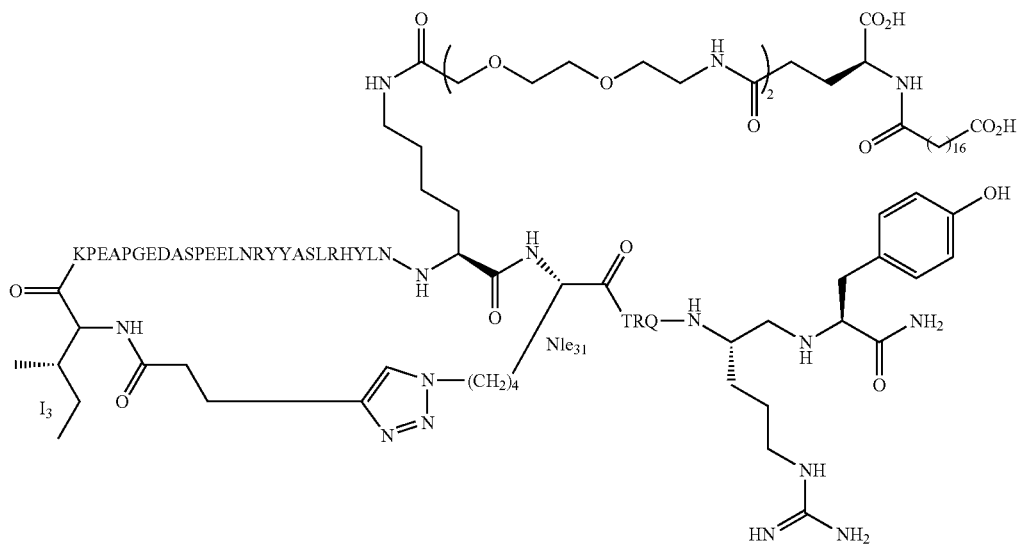
SEQ ID NO: 43
Name: [cyclo-(I3-m-COPhCH₂-hC31), K((OEG)₂-γ-Glu-Pal)30, psi-(R35,Y36)]-PYY3-36
Structure:
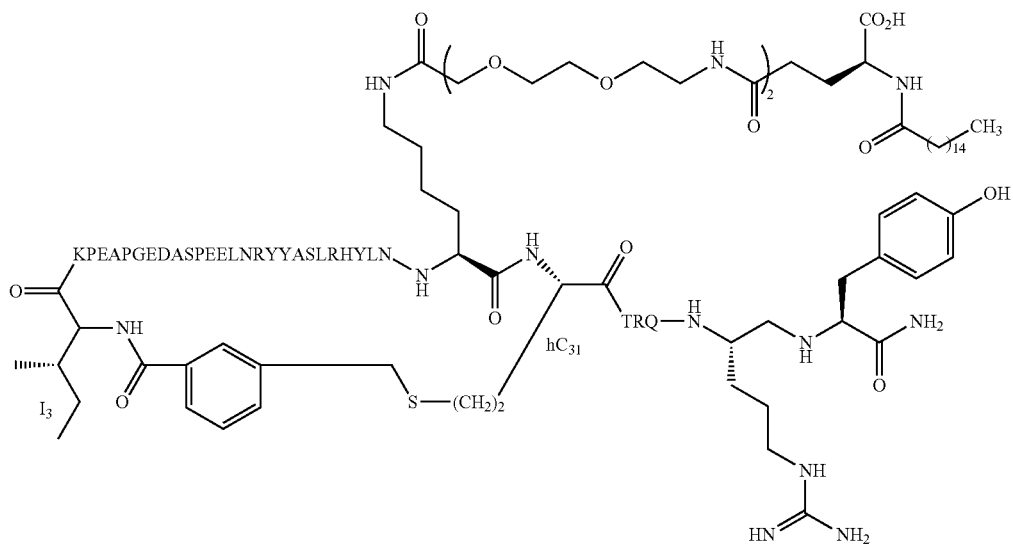

SEQ ID NO: 44
Name: [cyclo-(I3-m-COPhCH2-hC31), K((OEG)2-γ-Glu-COC16CO2H)11, psi-(R35,Y36)]-PYY3-36
Structure:
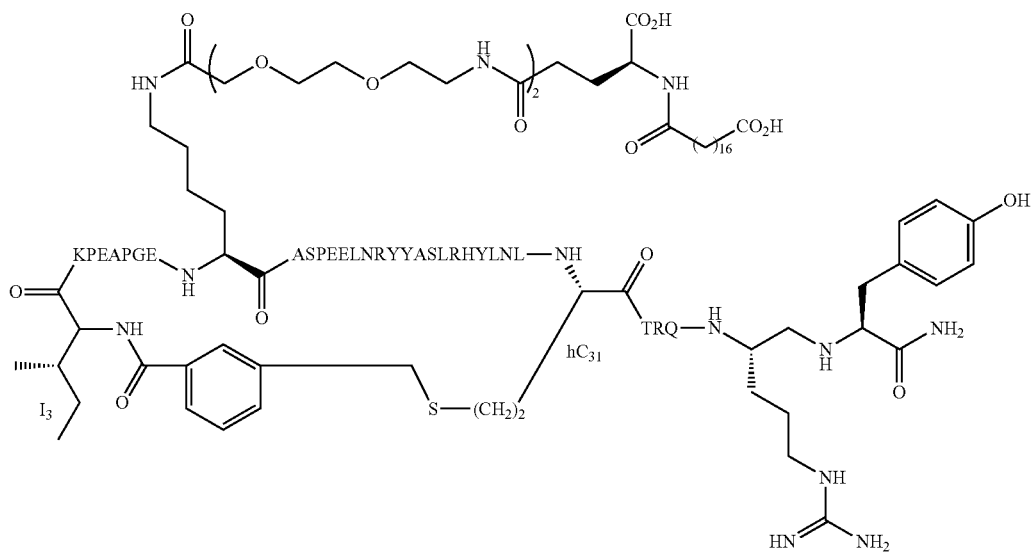
SEQ ID NO: 45
Name: [cyclo-(I3-m-COPhCH2-hC31), K(COCH2CH2(OCH2CH2)24NH-γ-Glu-Pal)11, psi-(R35,Y36)]-PYY3-36
Structure:
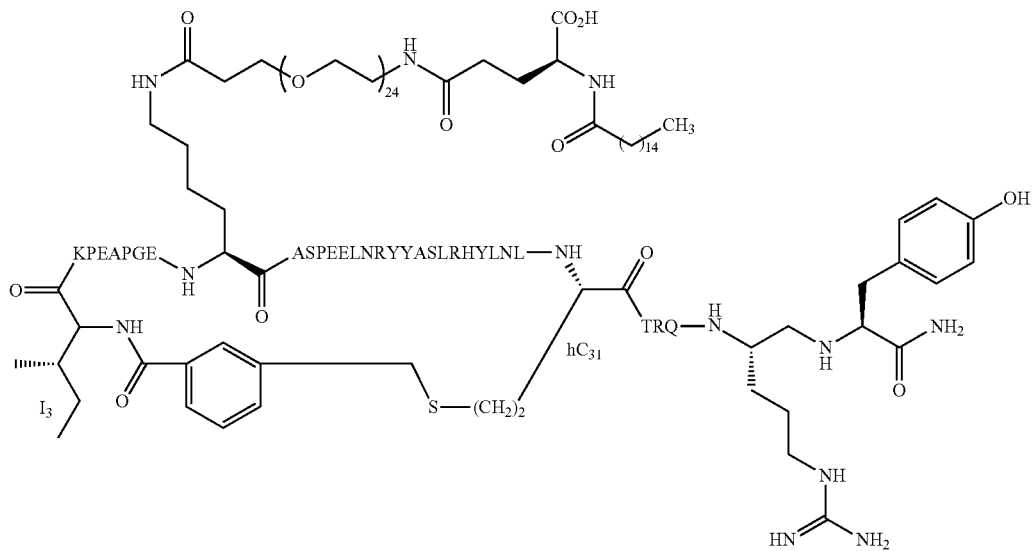

SEQ ID NO: 46
Name: [cyclo-(I3-CO(CH₂)₂NHCOCH₂-hC31), K(γ-Glu-Pal)30, psi-(R35,Y36)]-PYY3-36
Structure:
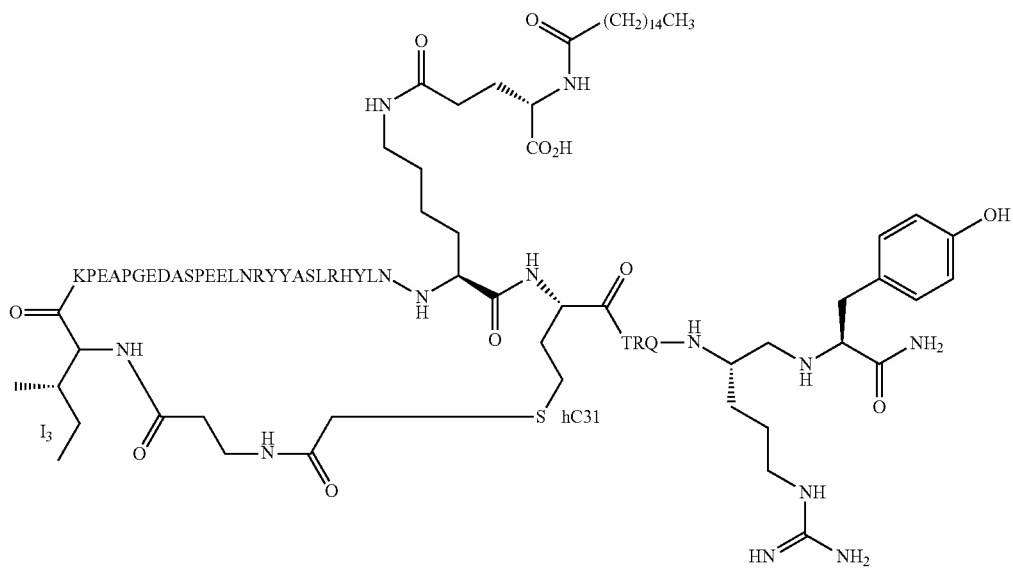
SEQ ID NO: 47
Name: [cyclo-(I3-m-COPhCH₂-hC31), K((OEG)₂-γ-Glu-COC₁₆CO₂H)7, psi-(R35,Y36)]-PYY3-36
Structure:
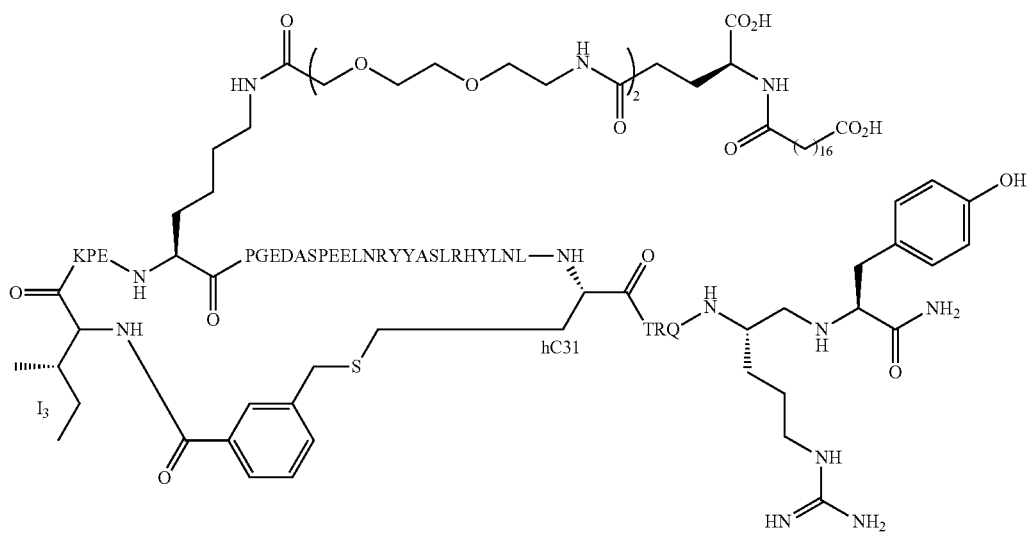

SEQ ID NO: 48
Name: [cyclo-(I3-m-COPhCH$_2$-hC31), K((OEG)$_2$-γ-Glu-COC$_{16}$CO$_2$H)22, psi-(R35,Y36)]-PYY3-36
Structure:
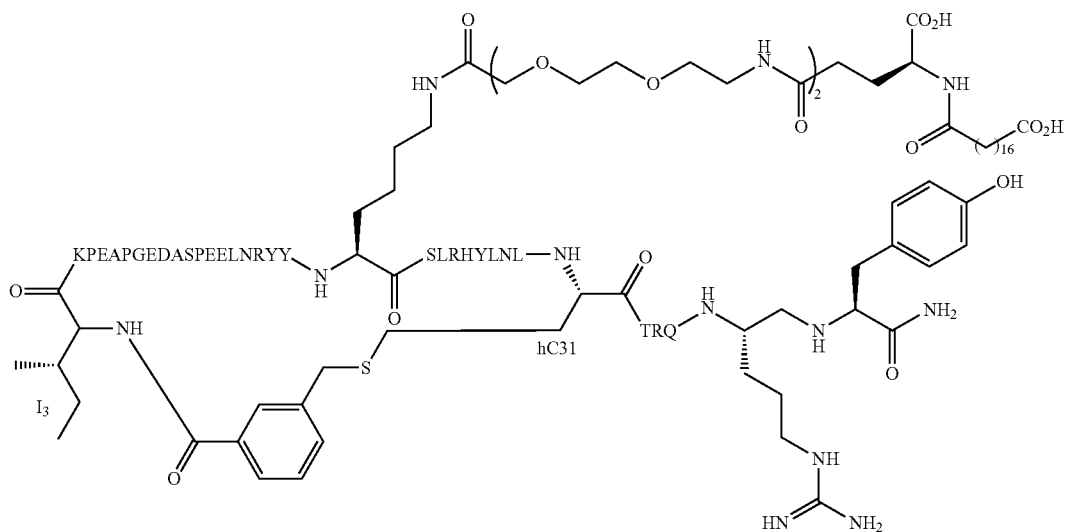
SEQ ID NO: 49
Name: [cyclo-(I3-m-COPhCH$_2$-hC31), K(γ-Glu-(Pal-16-OH))30, psi-(R35,Y36)]-PYY3-36
Structure:
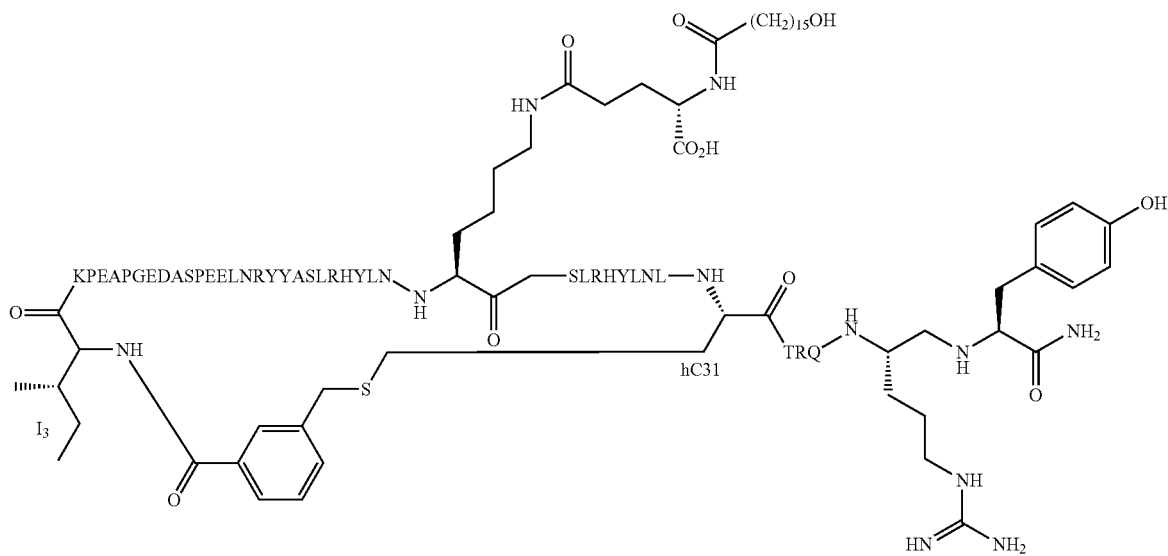

SEQ ID NO: 50
Name: [cyclo-(I3-m-COPhCH₂-hC31), K((OEG)₂-γ-Glu-COC₁₆CO₂H)23, psi-(R35,Y36)]-PYY3-36
Structure:
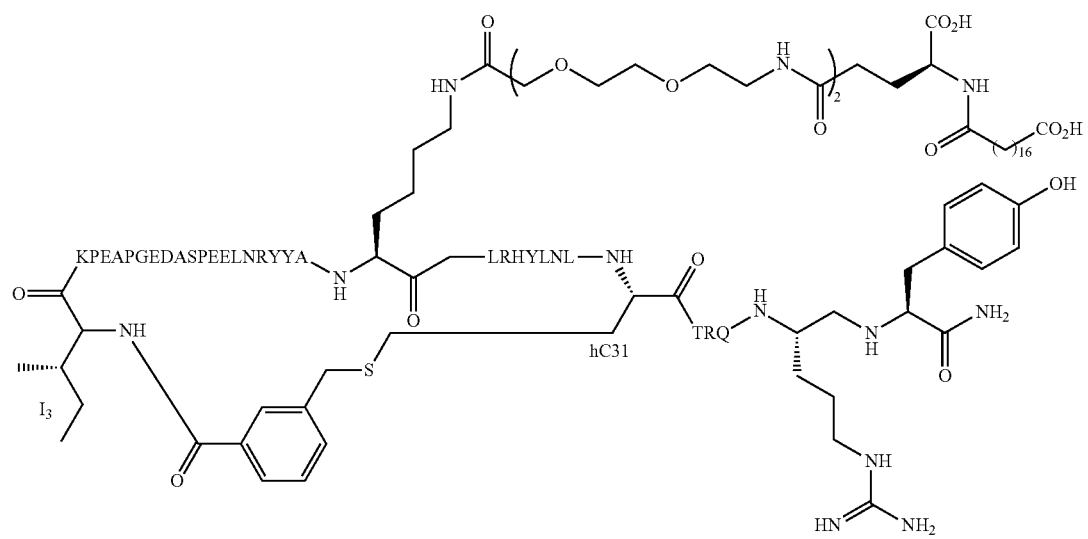
SEQ ID NO: 51
Name: [cyclo-(I3-m-COPhCH₂-hC31), S4, K(γ-Glu-Pal)30, psi-(R35,Y36)]-PYY3-36
Structure:
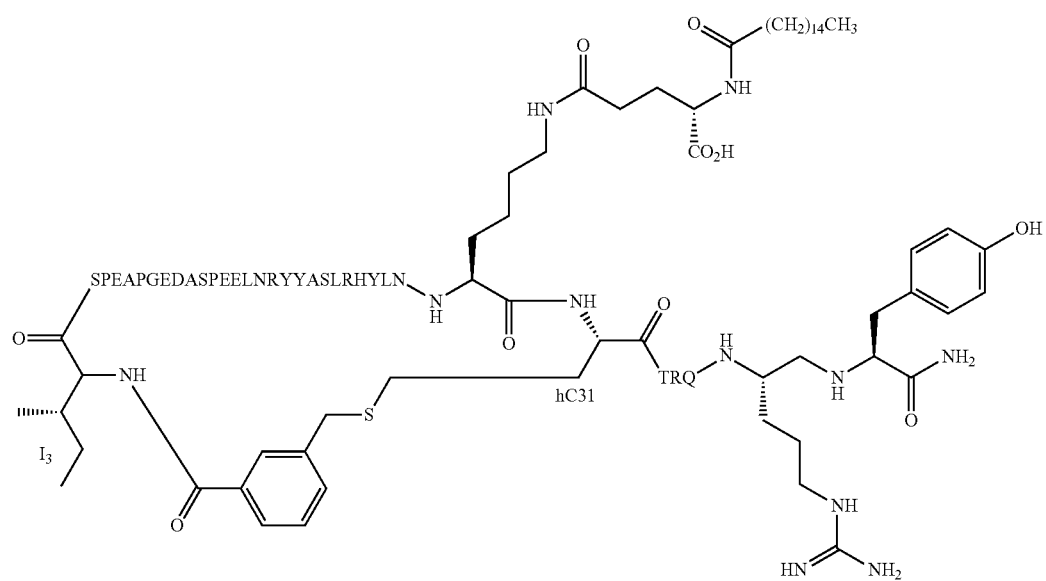

SEQ ID NO: 52
Name: [cyclo-(I3-m-COPhCH$_2$-hC31), K(COCH$_2$CH$_2$(OCH$_2$CH$_2$)$_{12}$NH-γ-Glu-Pal)11, psi-(R35,Y36)]-PYY3-36
Structure:
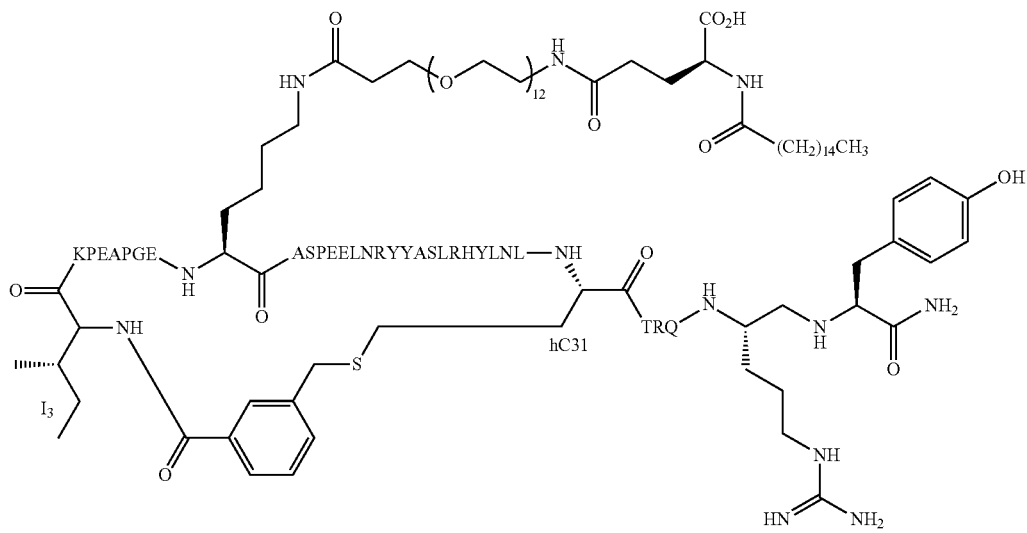
SEQ ID NO: 53
Name: [cyclo-(I3-m-COPhCH$_2$-hC31), K((OEG)$_4$-γ-Glu-Pal)11, psi-(R35,Y36)]-PYY3-36
Structure:
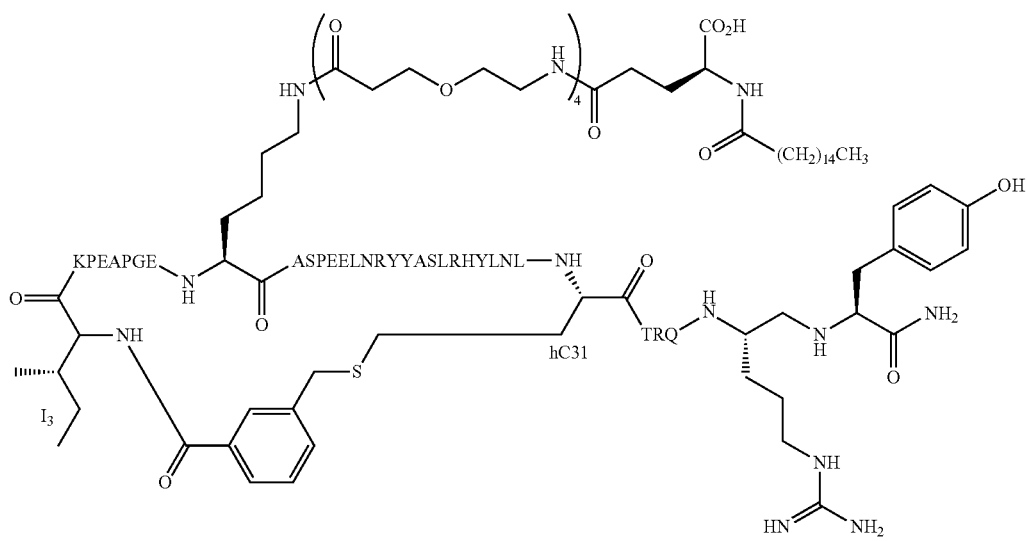

SEQ ID NO: 54
Name: [cyclo-(I3-m-COPhCH2-hC31), K((OEG)2-γ-Glu-Pal)11, psi-(R35,Y36)]-PYY3-36
Structure:
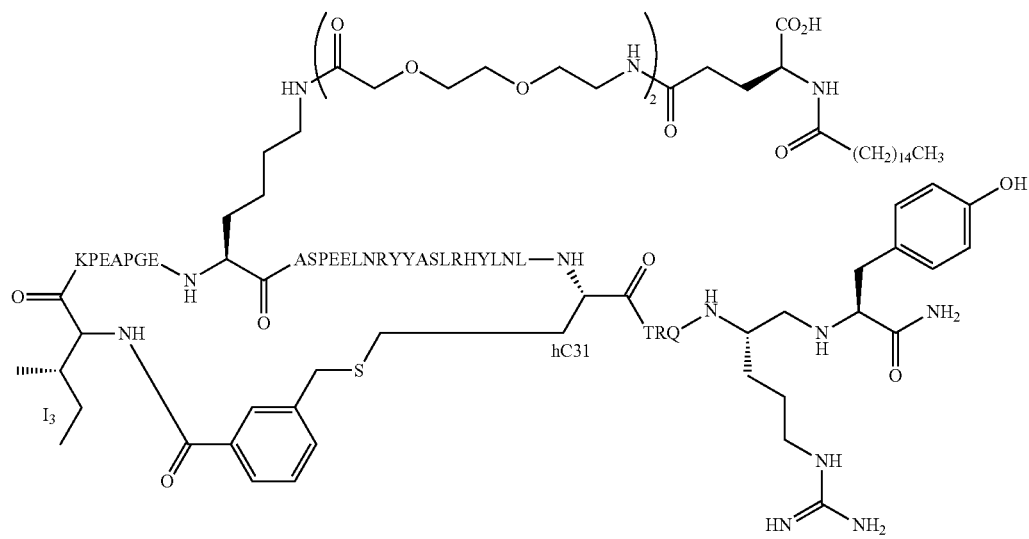
SEQ ID NO: 55
Name: [cyclo-(I3-m-COPhCH2-hC31), K((OEG)2-γ-Glu-Pal)23, psi-(R35,Y36)]-PYY3-36
Structure:
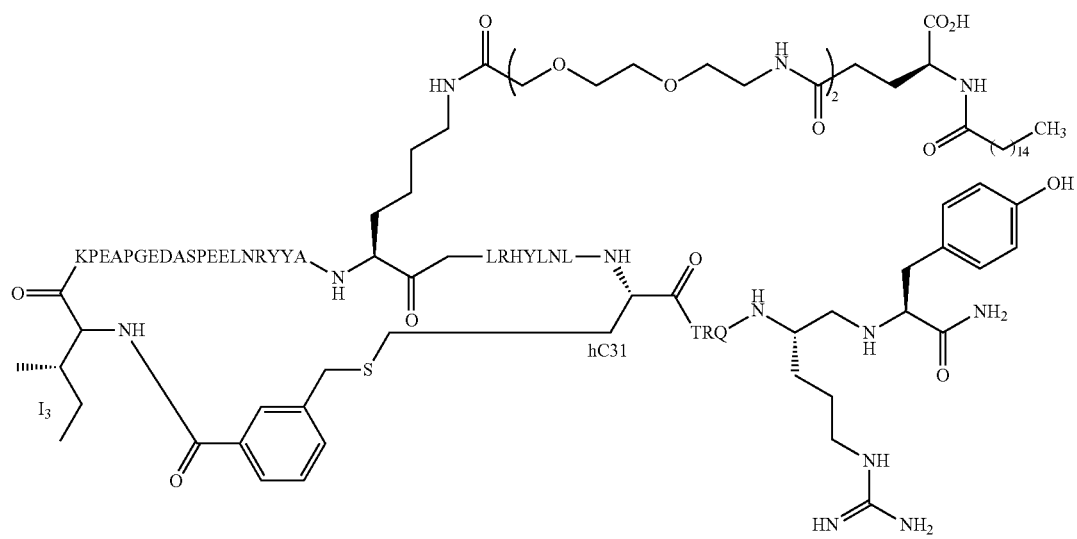

SEQ ID NO: 56
Name: [cyclo-(I3-m-COPhCH2-hC31), K(γ-Glu-COCH2Ph-(4-ClPh)30, psi-(R35,Y36)]-PYY3-36
Structure:
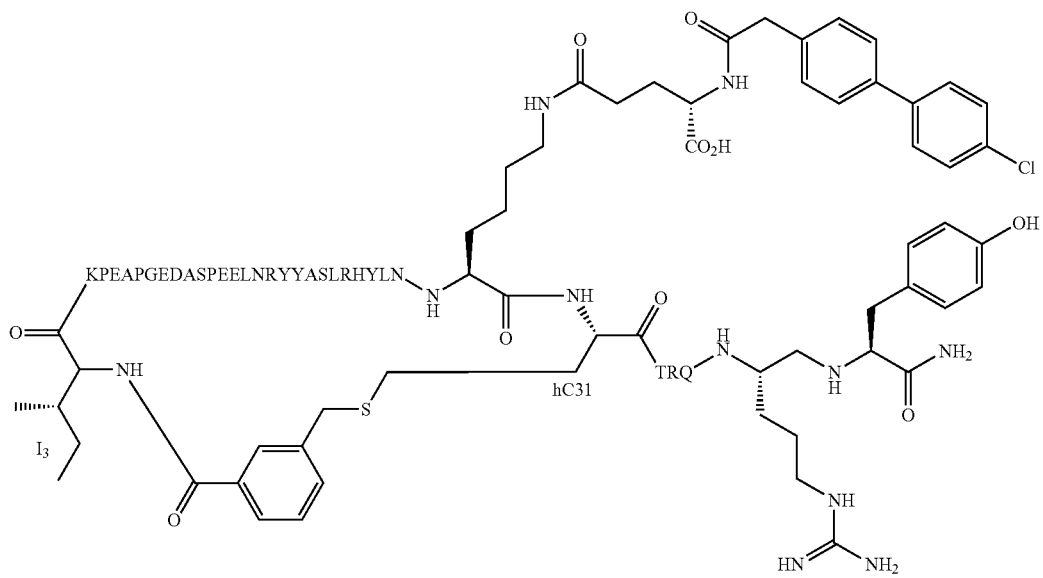
SEQ ID NO: 57
Name: [cyclo-(I3-m-COPhCH2-hC31), K(γ-Glu-CO(CH2)2PhO-(2,4-Cl2Ph)30, psi-(R35,Y36)]-PYY3-36
Structure:
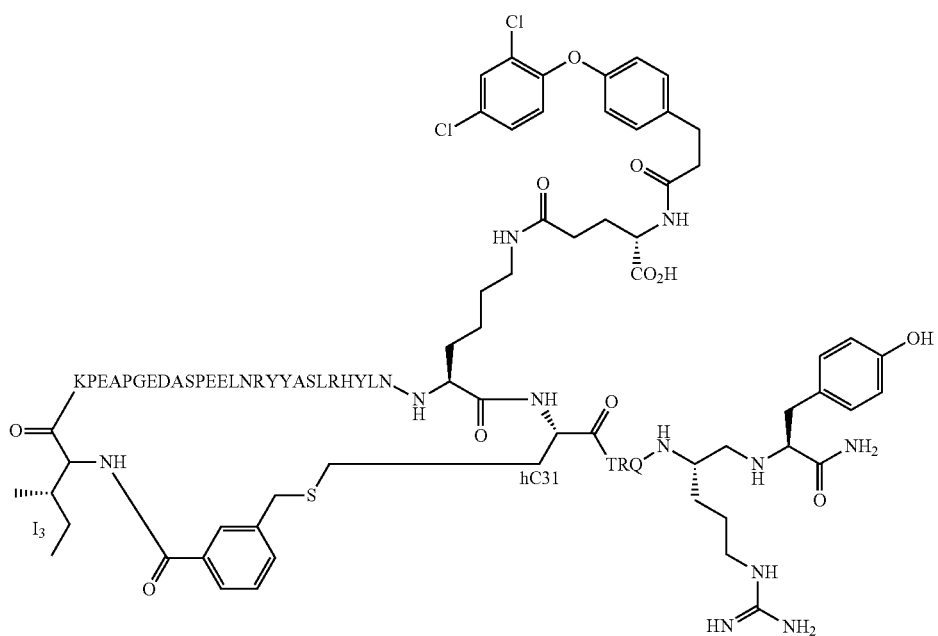

SEQ ID NO: 58
Name: [cyclo-(I3-m-COPhCH2-hC31), K(γ-Glu-CO(CH2)10-(4-F-Ph))30, psi-(R35,Y36)]-PYY3-36
Structure:
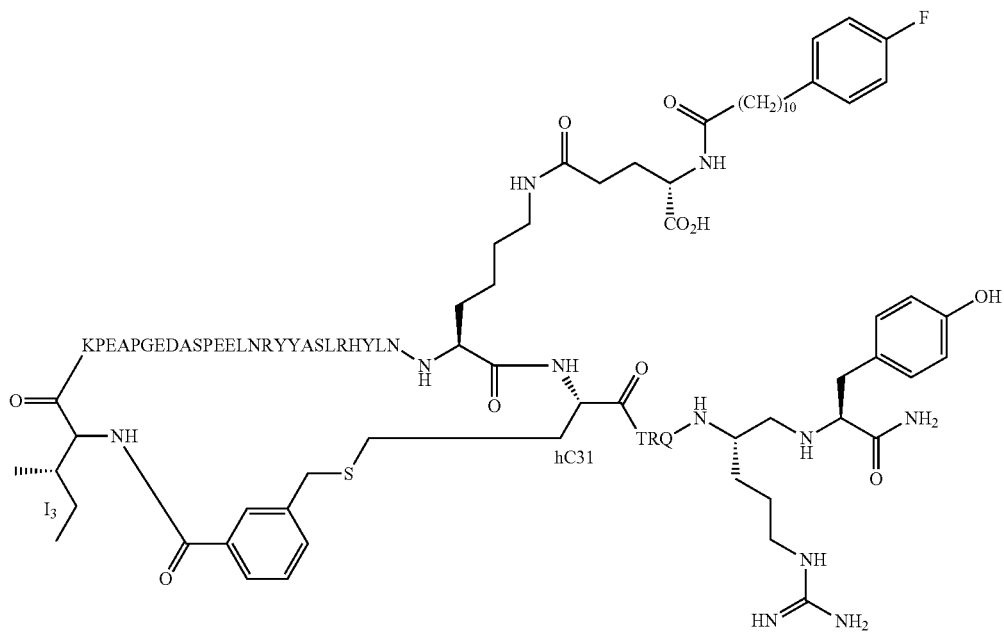
SEQ ID NO: 59
Name: [cyclo-(I3-m-COPhCH2-hC31), K((OEG)2-γ-Glu-Pal)22, psi-(R35,Y36)]-PYY3-36
Structure:
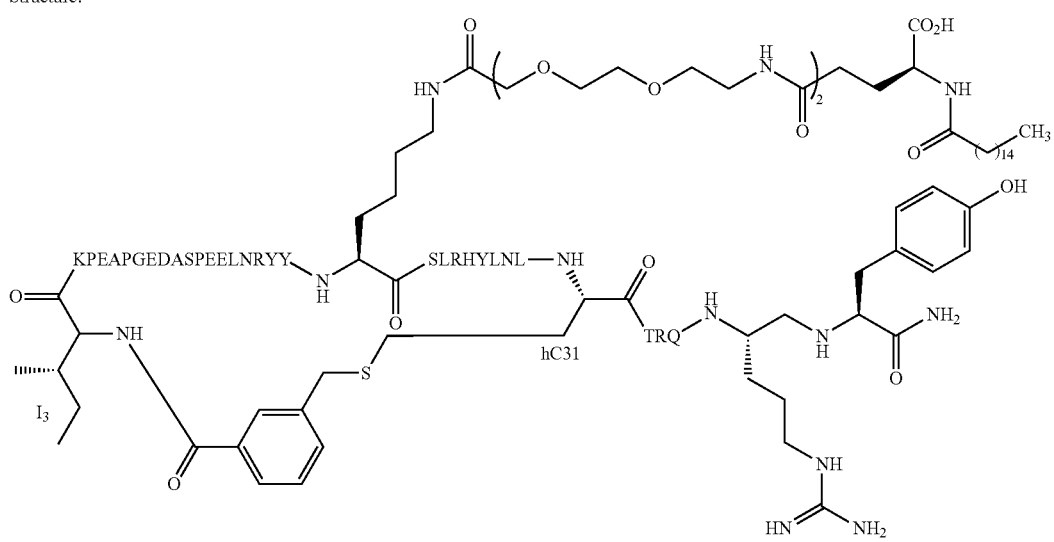

SEQ ID NO: 60
Name: [cyclo-(I3-m-COPhCH2-hC31), K((OEG)2-γ-Glu-Pal)7, psi-(R35,Y36)]-PYY3-36
Structure:
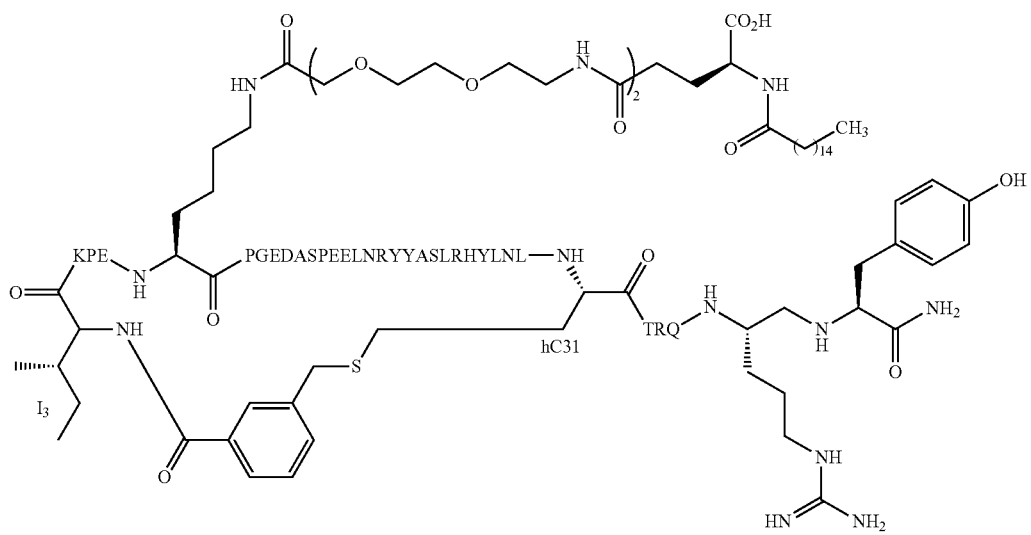
SEQ ID NO: 61
Name: [cyclo-(I3-m-COPhCH2-hC31), K(γ-Glu-CO(CH2)10-(4-F3C-Ph))30, psi-(R35,Y36)]-PYY3-36
Structure:
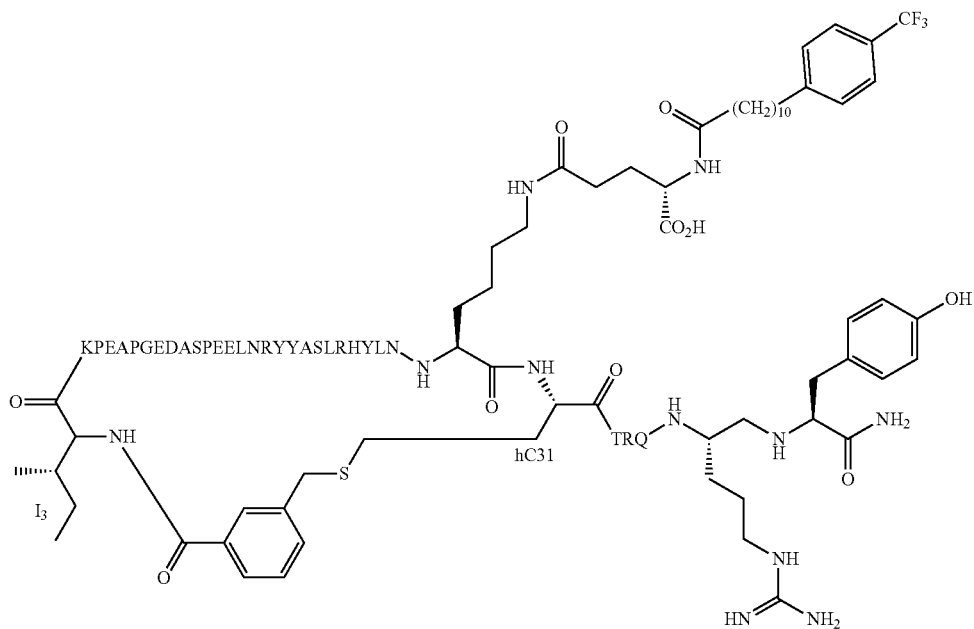

SEQ ID NO: 62
Name: [cyclo-(I3-m-COPhCH2-hC31), K(γ-Glu-CO(CH2)10-CF3)30, psi-(R35,Y36)]-PYY3-36
Structure:
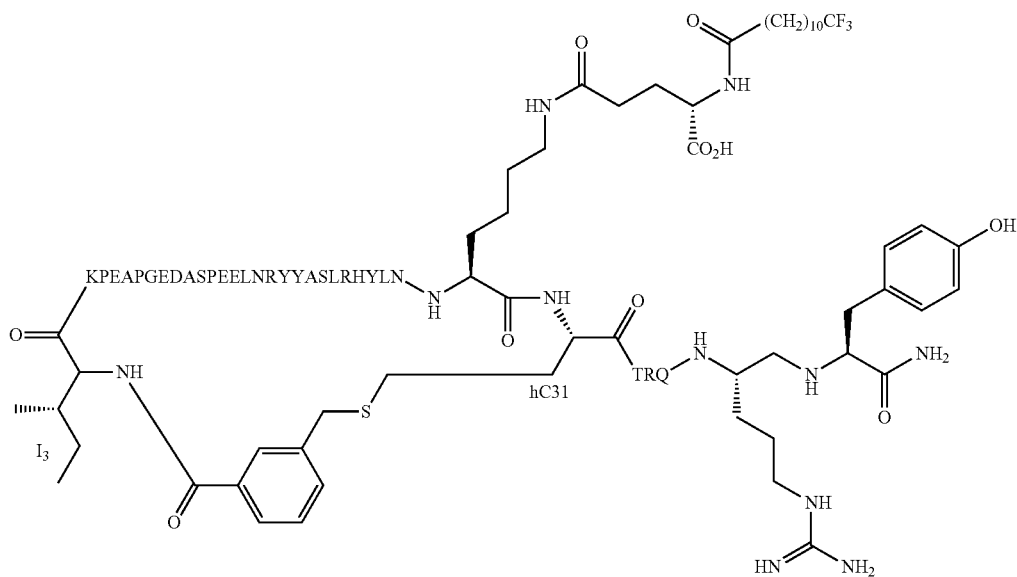
SEQ ID NO: 63
Name: [cyclo-(I3-m-COPhCH2-hC31), K(γ-Glu-CO(CH2)13-CF3)30, psi-(R35,Y36)]-PYY3-36
Structure:
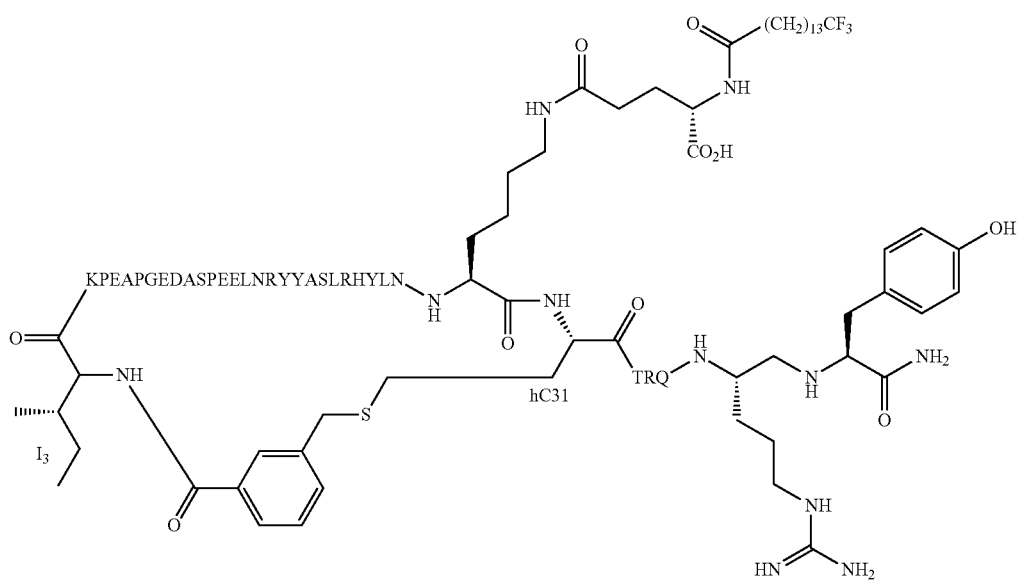

SEQ ID NO: 64
Name: [cyclo-(I3-m-COPhCH₂-hC31), K(γ-Glu-(Pal-16-OEt))30, psi-(R35,Y36)]-PYY3-36
Structure:
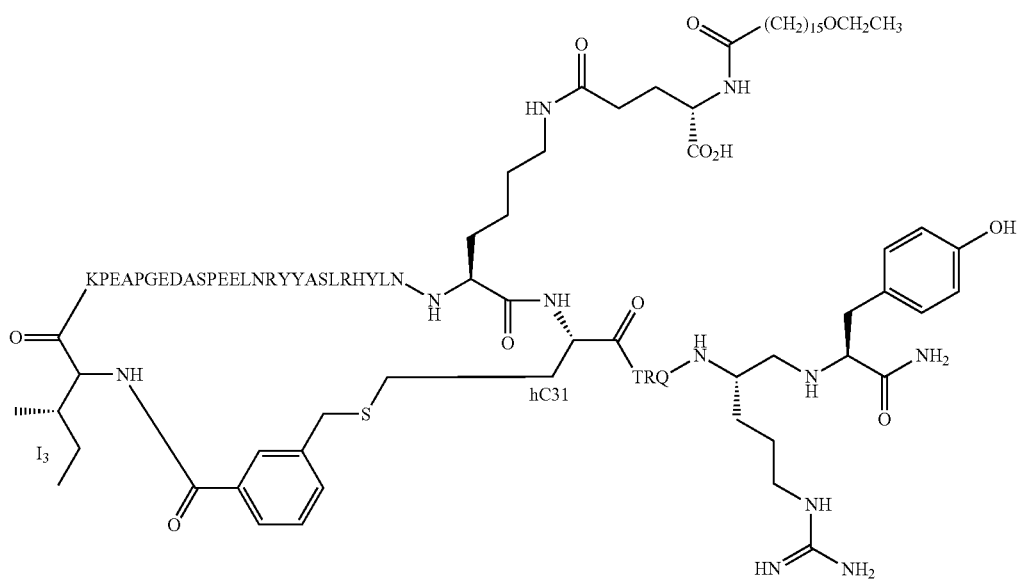
SEQ ID NO: 65
Name: [cyclo-(I3-m-COPhCH₂-hC31), K(γ-Glu-CO(CH₂)₁₁(CD₂)₃CD₃)30, psi-(R35,Y36)]-PYY3-36
Structure:
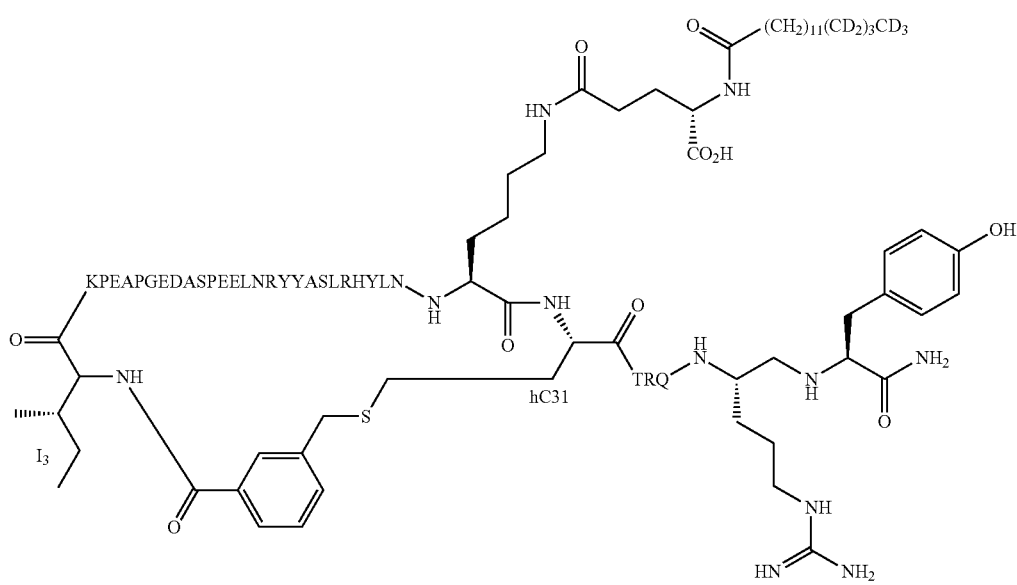

SEQ ID NO: 66
Name: [cyclo-(I3-m-COPhCH₂-hC31), K(γ-Glu-CO(CH₂)₁₀-(2,4-(CF₃)₂-PH))30, psi-(R35,Y36)]-PYY3-36
Structure:
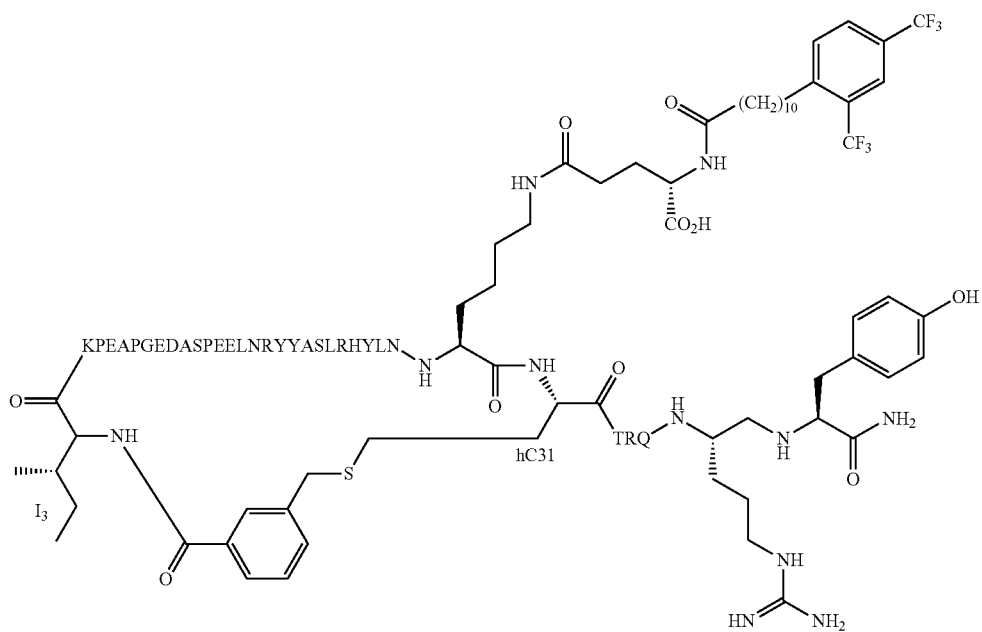
SEQ ID NO: 67
Name: [cyclo-(I3-m-COPhCH₂-hC31), K(γ-Glu-CO(CH₂)₁₀-(3,5-(CF₃)₂-Ph))30, psi-(R35,Y36)]-PYY3-36
Structure:
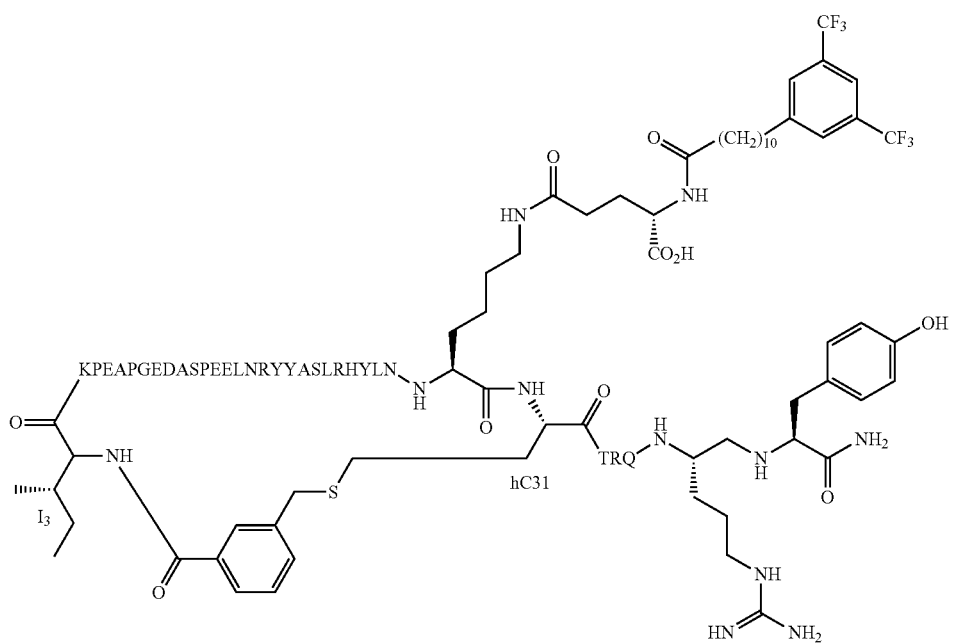

SEQ ID NO: 68
Name: [cyclo-(I3-CO(CH2)2NHCOCH2-C30), K((OEG)2-γ-Glu-COC16CO2H)11, psi-(R35,Y36)]-PYY3-36
Structure:
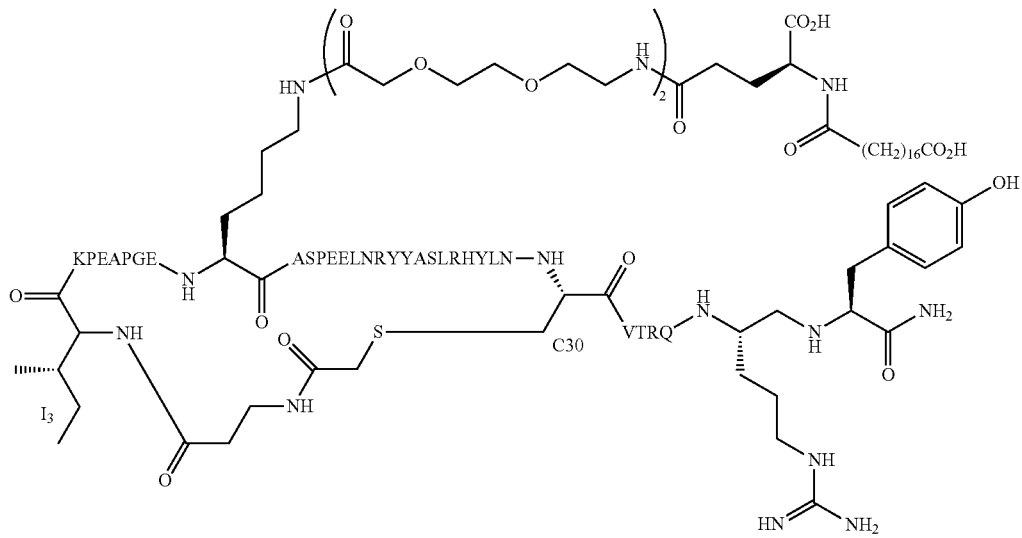
SEQ ID NO: 69
Name: [cyclo-(G2-E31), S4, K11, psi-(R35,Y36)]-PYY2-36
Structure:
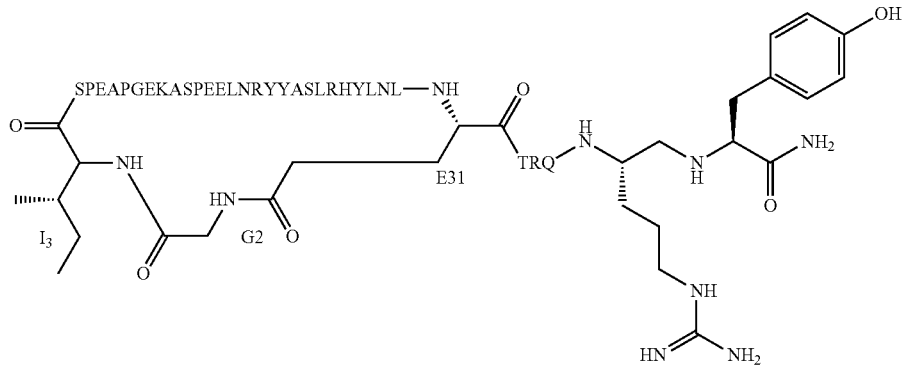
SEQ ID NO: 70
Name: [cyclo-(G2-E30), S4, K11, psi-(R35,Y36)]-PYY2-36
Structure:
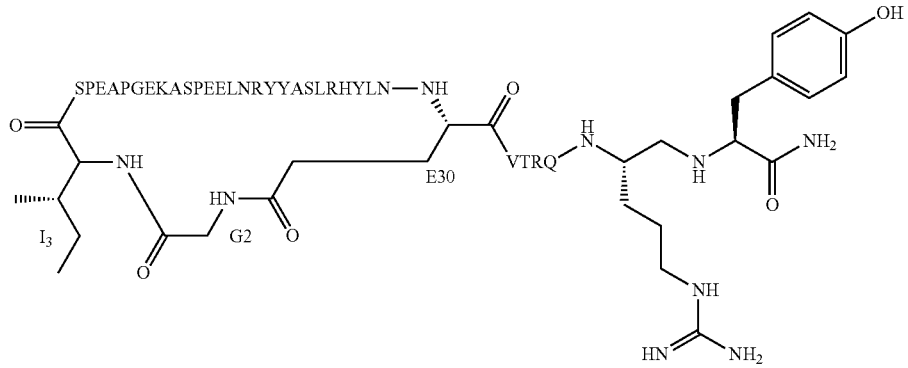

SEQ ID NO: 71
Name: [cyclo-(G2-E30), S4, K11, (N-Me-R35)]PYY3-36
Structure:
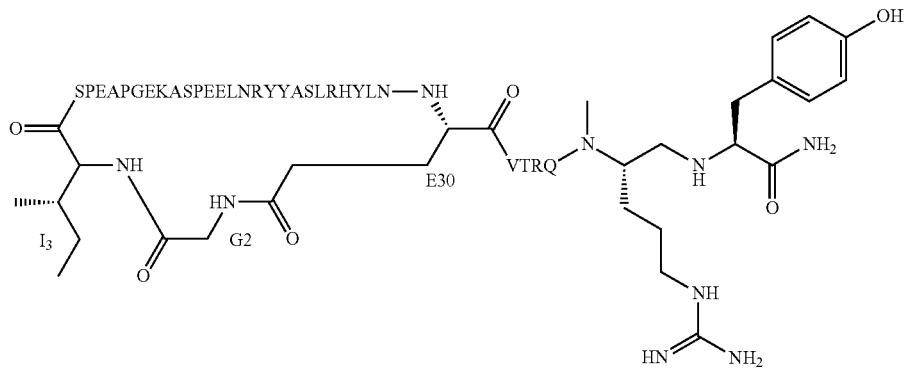
SEQ ID NO: 72
Name: [cyclo-(G2-E30), S4, K((OEG)2-γ-Glu-COC16CO2H)11, psi-(R35,Y36)]-PYY2-36
Structure:
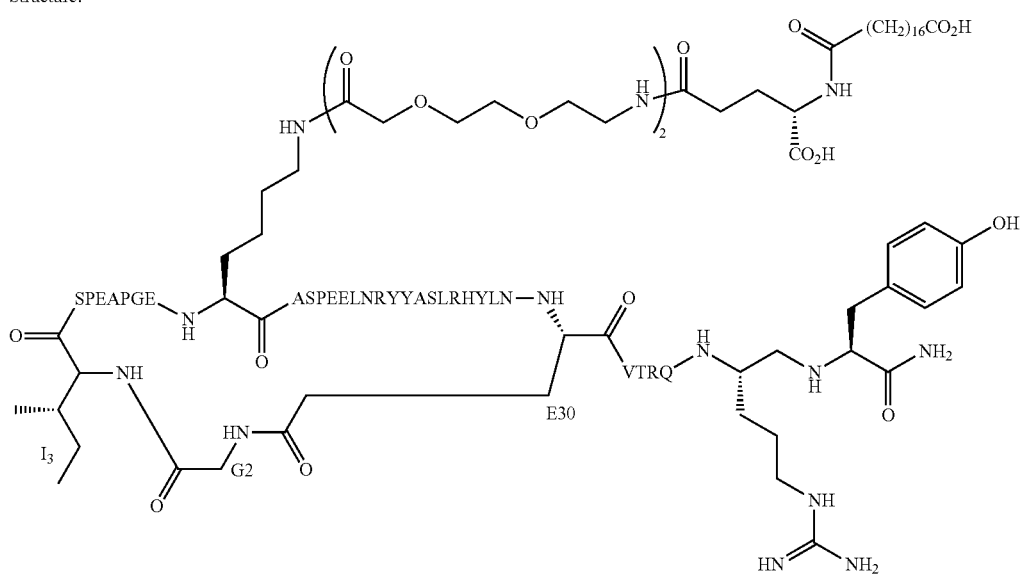
SEQ ID NO: 73
Name: [Cyclo-(βA2-COCH2-hC31), K(PEG6-AcBr)11, psi-(R35,Y36)]-PYY2-36
Structure:
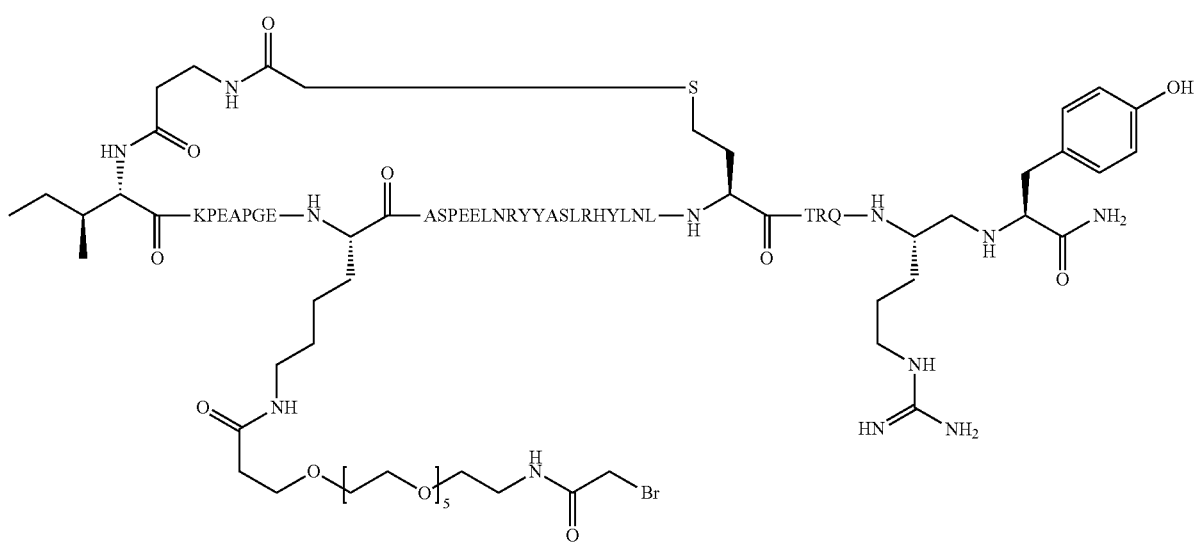

SEQ ID NO: 74
Name: [Cyclo-(βA2-COCH₂-hC31), K(AcBr)11, psi-(R35,Y36)]-PYY2-36
Structure:
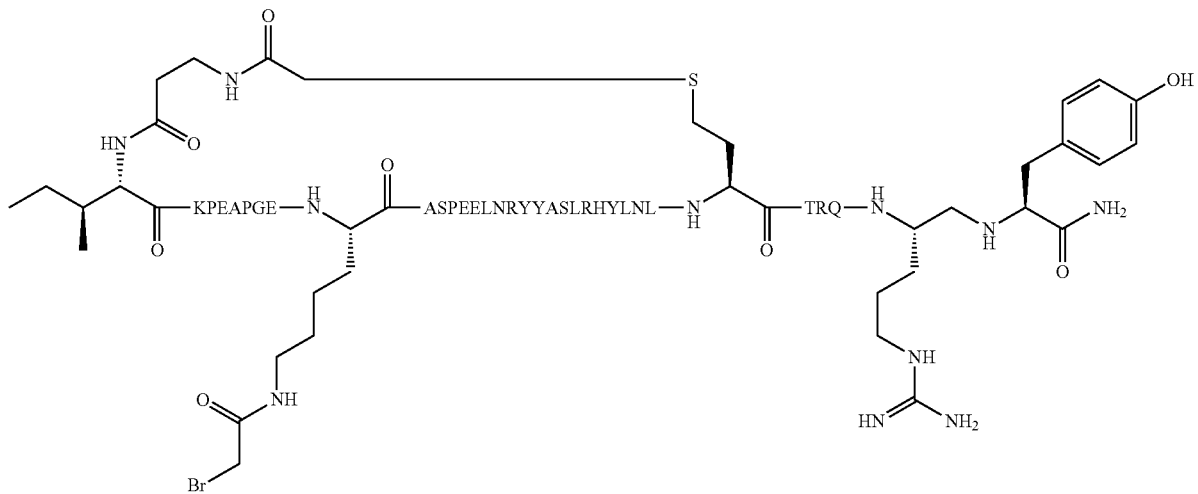
SEQ ID NO: 75
Name: [Cyclo-(I3-COCH₂-C31), K(PEG12-AcBr)11, psi-(R35,Y36)]-PYY2-36
Structure:
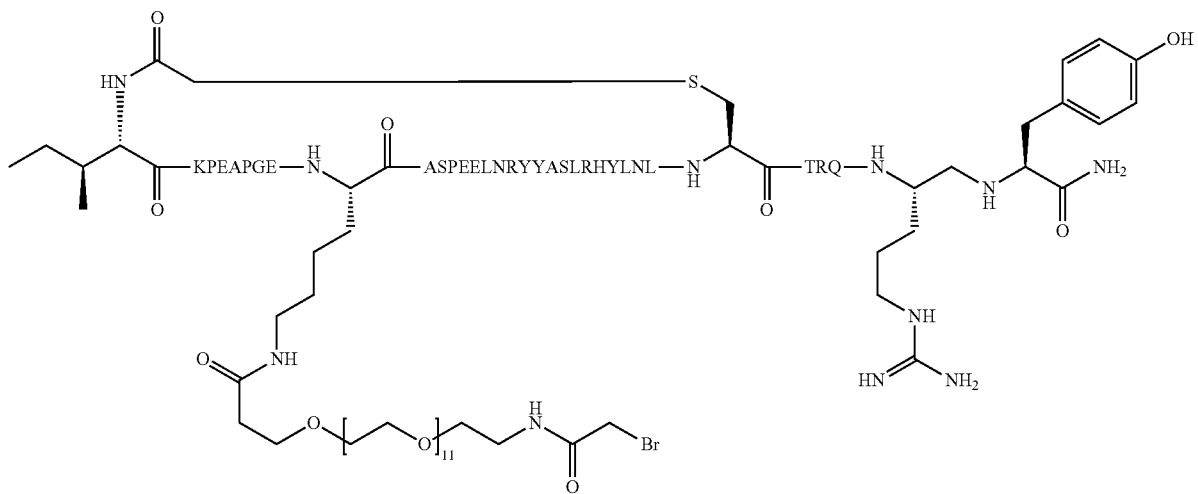
SEQ ID NO: 76
Name: [Cyclo-(βA2-COCH₂-hC31), K(PEG12-AcBr)11, K(mPEG16)30, psi-(R35,Y36)]-PYY2-36
Structure:
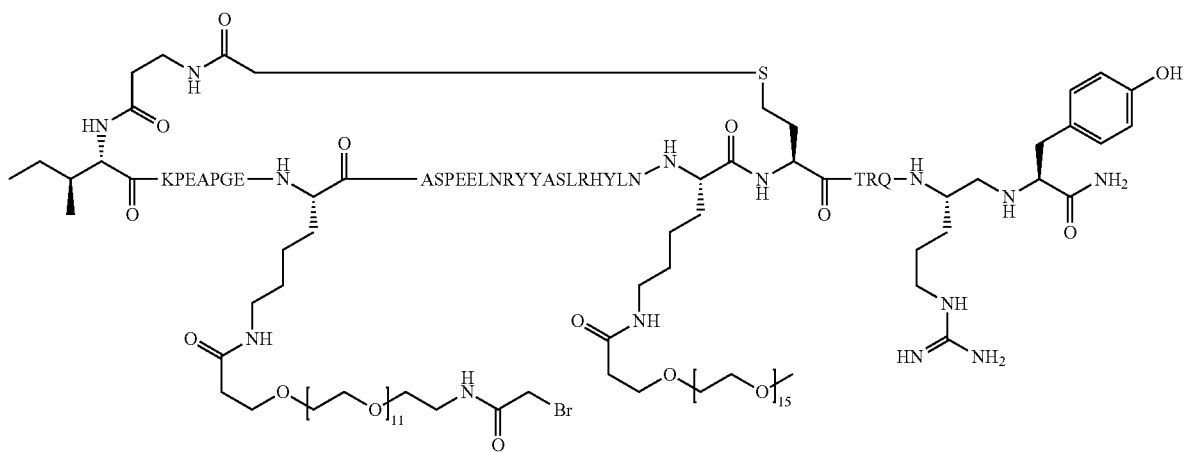

SEQ ID NO: 77
Name: [Cyclo-(βA2-COCH$_2$-hC31), K(AcBr)11, K(mPEG12)20, psi-(R35,Y36)]-PYY2-36
Structure:
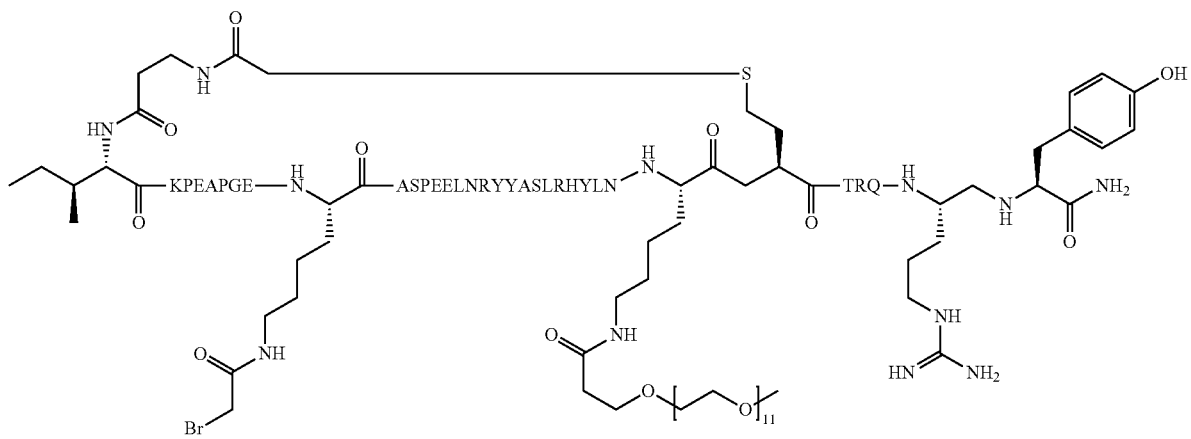
SEQ ID NO: 78
Name: [Cyclo-(βA2-COCH$_2$-hC31), K(PEG12-AcBr)11, (N-Me)Q34, psi-(R35,Y36)]-PYY2-36
Structure:
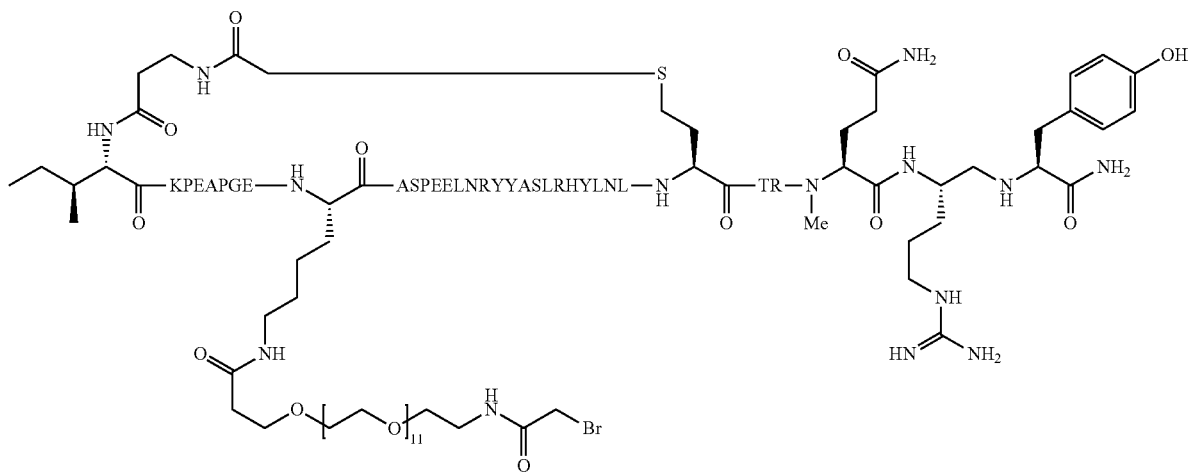
SEQ ID NO: 79
Name: [Cyclo-(βA2-COCH$_2$-hC31), K(PEG12-AcBr)11, N-Me-R35, psi-(R35,Y36)]-PYY2-36
Structure:
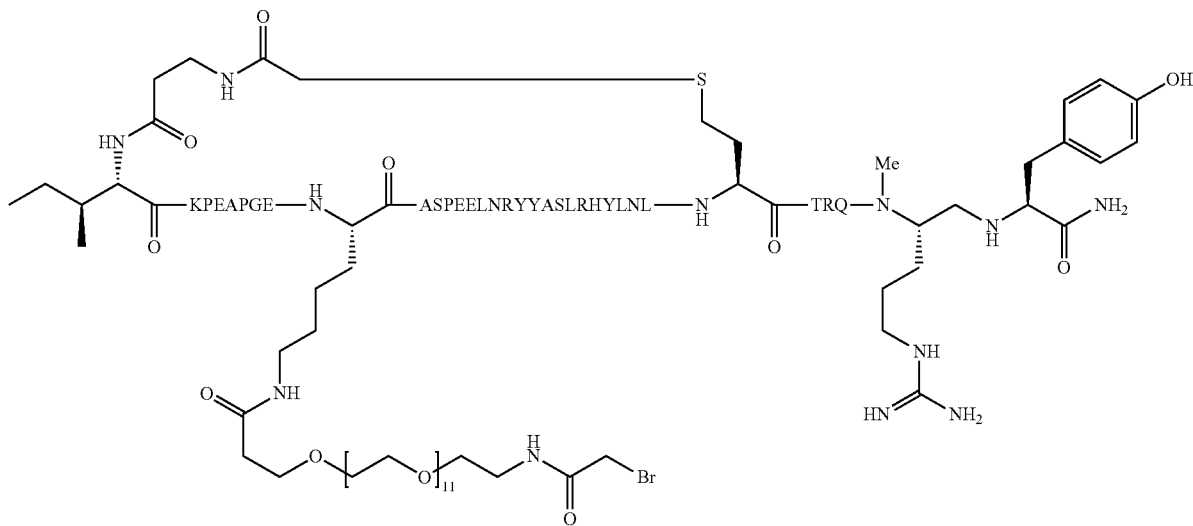

SEQ ID NO: 80
Name: [Cyclo-(βA2-COCH₂-hC31), R4, K(PEG12-AcBr)11, W30, psi-(R35,Y36)]-PYY2-36
Structure:
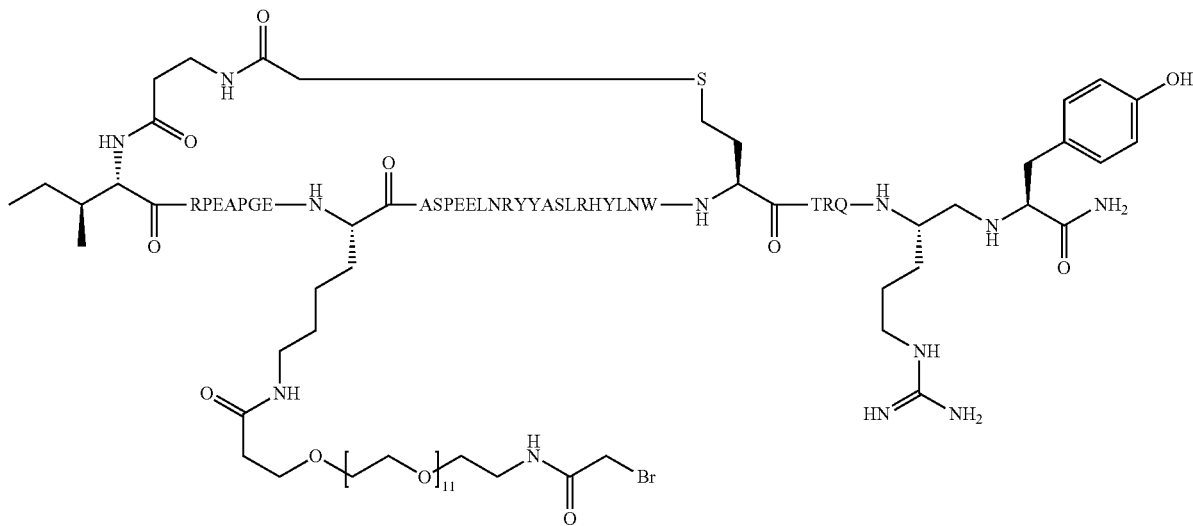
SEQ ID NO: 81
Name: [Cyclo-(3I-COCH₂CH₂CH₂NHCOCH₂-C31), R4, K(PEG12-AcBr)11, W30, psi-(R35,Y36)]-PYY3-36
Structure:
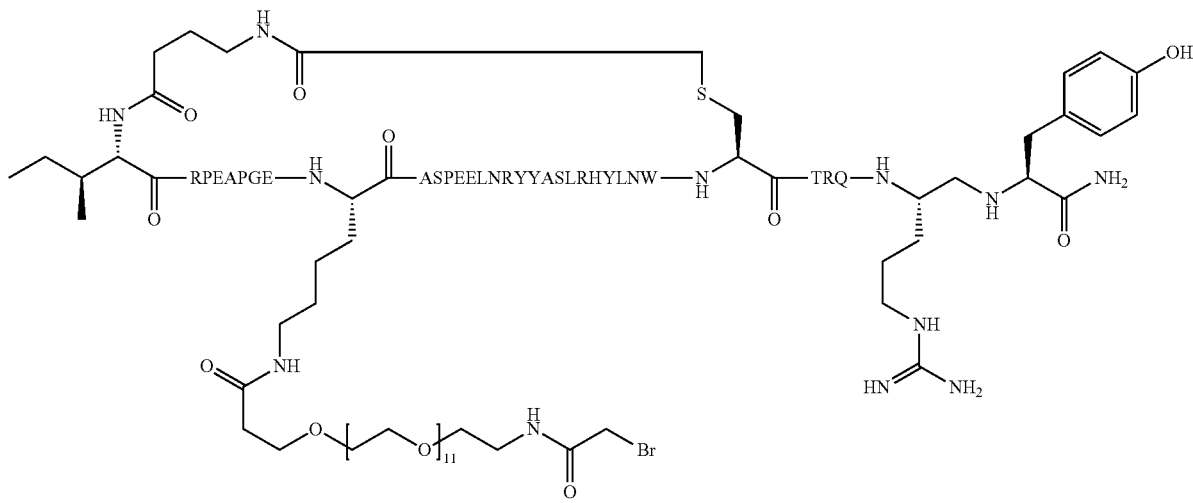

SEQ ID NO: 82
Name: [Cyclo-(K4-OEG-COCH₂-C31), K(PEG12-AcBr)11, psi-(R35,Y36)]-PYY4-36
Structure:
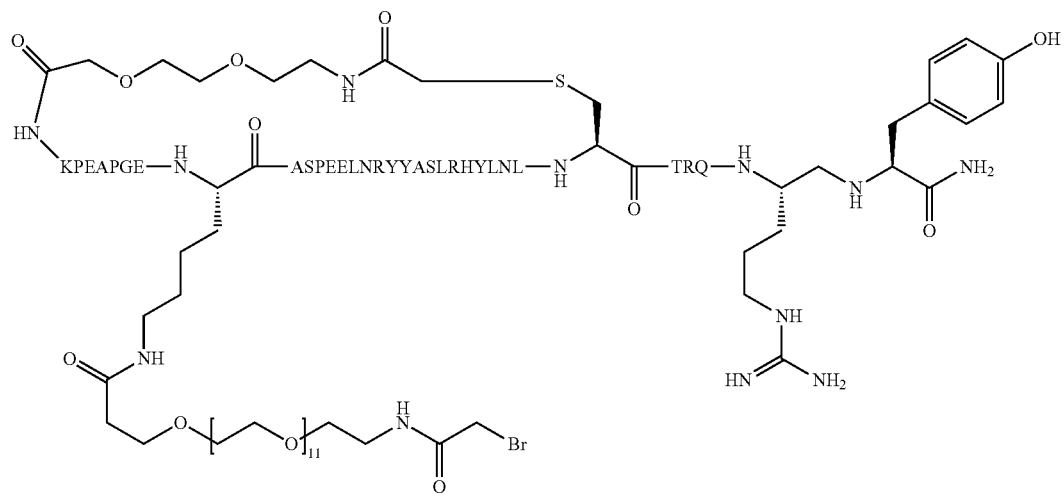
SEQ ID NO: 83
Name: [Cyclo-(I3-COCH₂CH₂triazolylNle31), K(PEG12-AcBr)11, psi-(R35,Y36)]-PYY3-36
Structure:
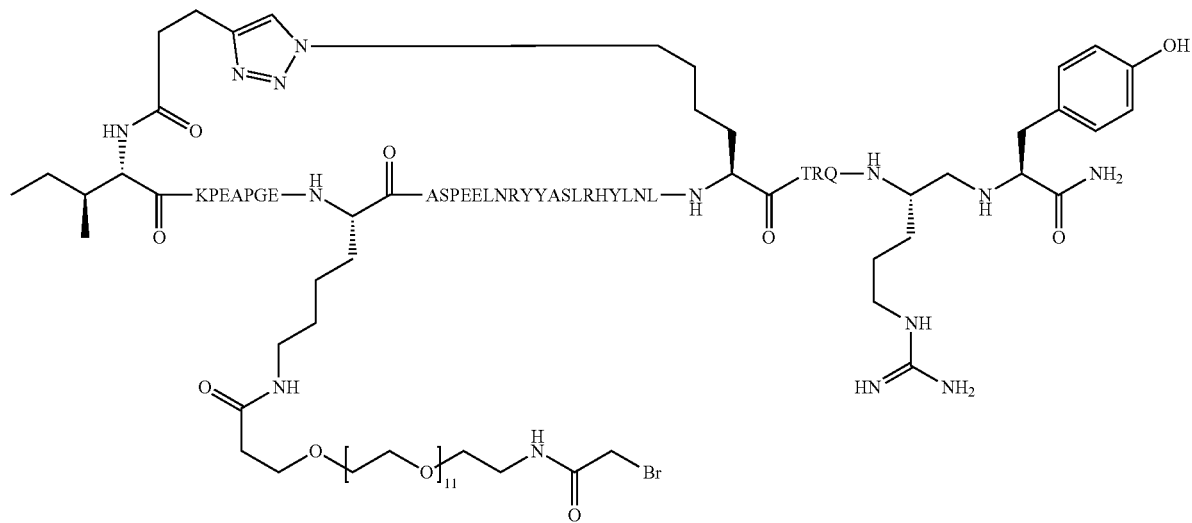

SEQ ID NO: 84
Name: [Cyclo-(I3-m-CO-benzyl-hC31), K(PEG8-triazolyl-CH2CH2CO-PEG4-AcBr)11, psi-(R35,Y36)]-PYY3-36
Structure:
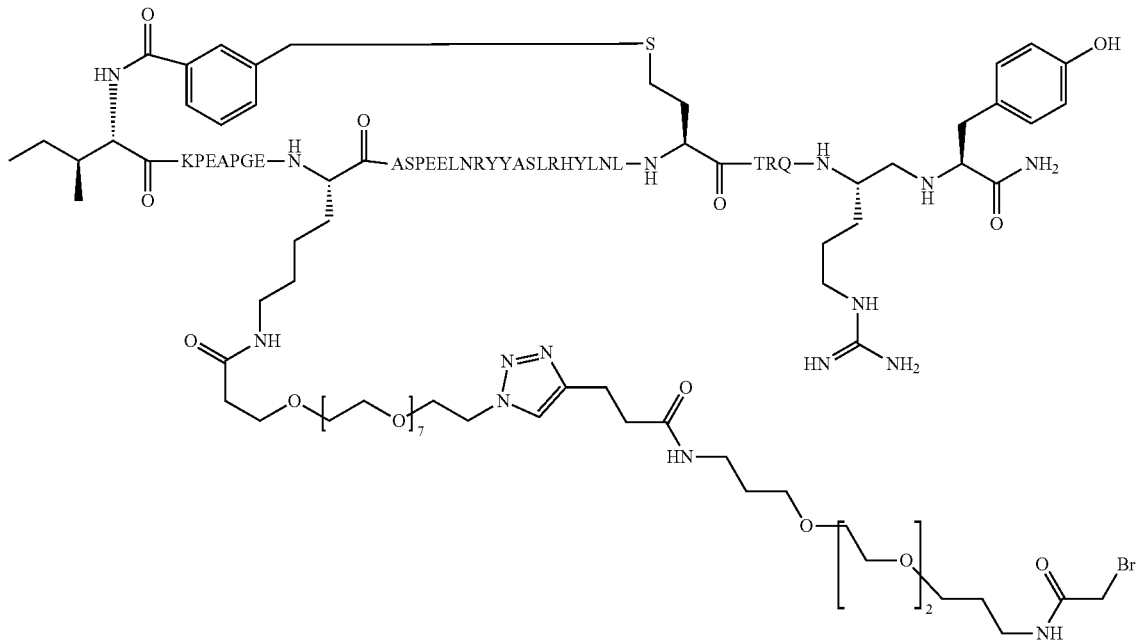
SEQ ID NO: 85
Name: [Cyclo-(βA2-COCH2-hC31), K(PEG12-AcBr)23, psi-(R35,Y36)]-PYY2-36
Structure:
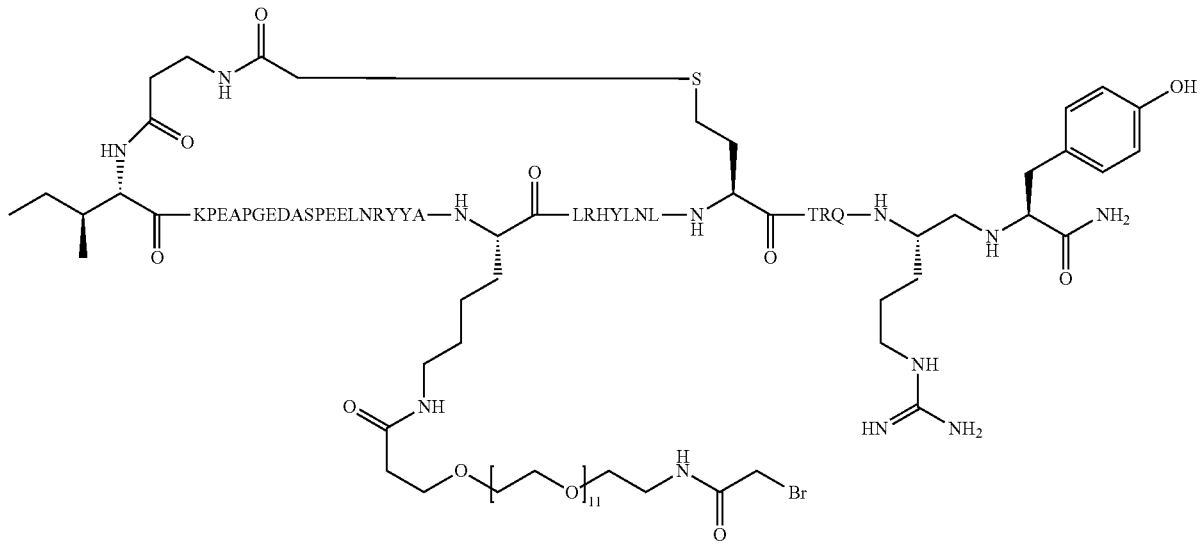

SEQ ID NO: 86
Name: [Cyclo-(βA2-COCH₂-hC31), K(PEG12-AcBr)22, psi-(R35,Y36)]-PYY2-36
Structure:
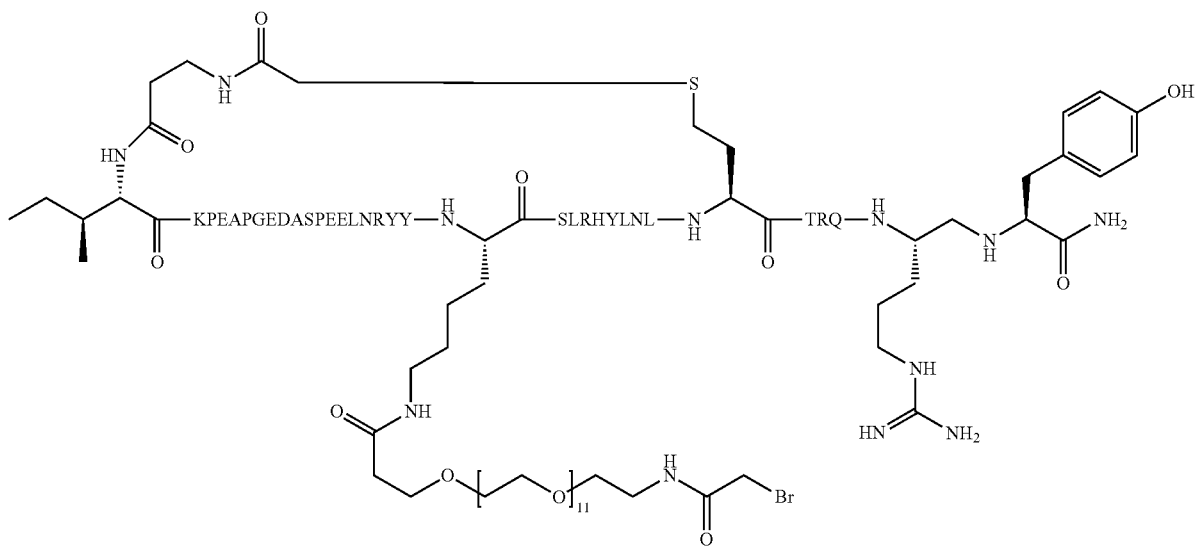
SEQ ID NO: 87
Name: [Cyclo-(βA2-COCH₂-hC31), K(PEG12-AcBr)7, psi-(R35,Y36)]-PYY2-36
Structure:
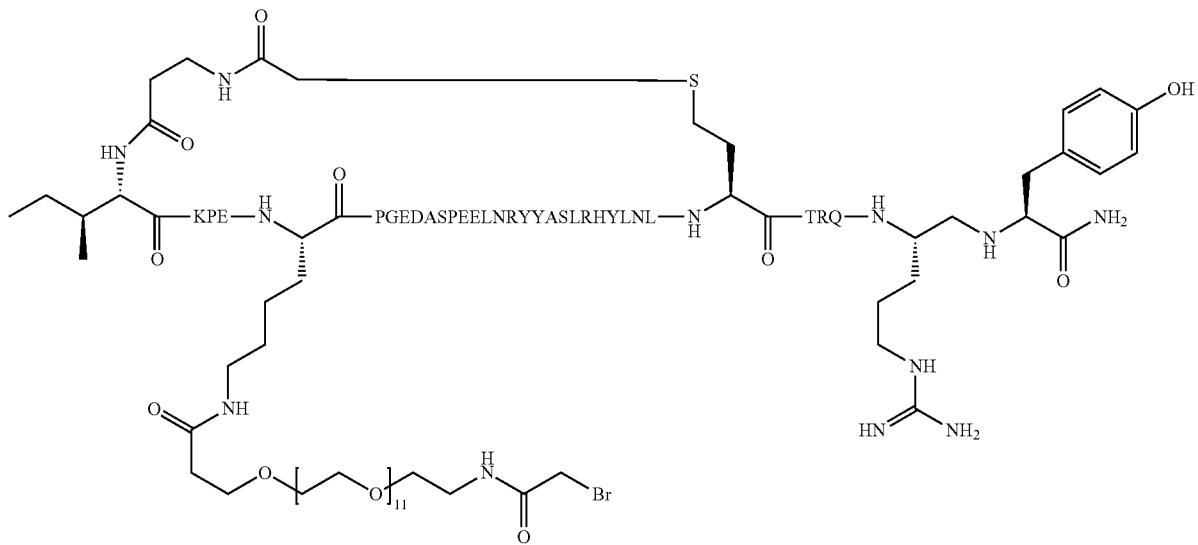

SEQ ID NO: 88
Name: [Cyclo-(G2-COCH₂-C30), K(PEG12-AcBr)11, psi-(R35,Y36)]-PYY2-36
Structure:
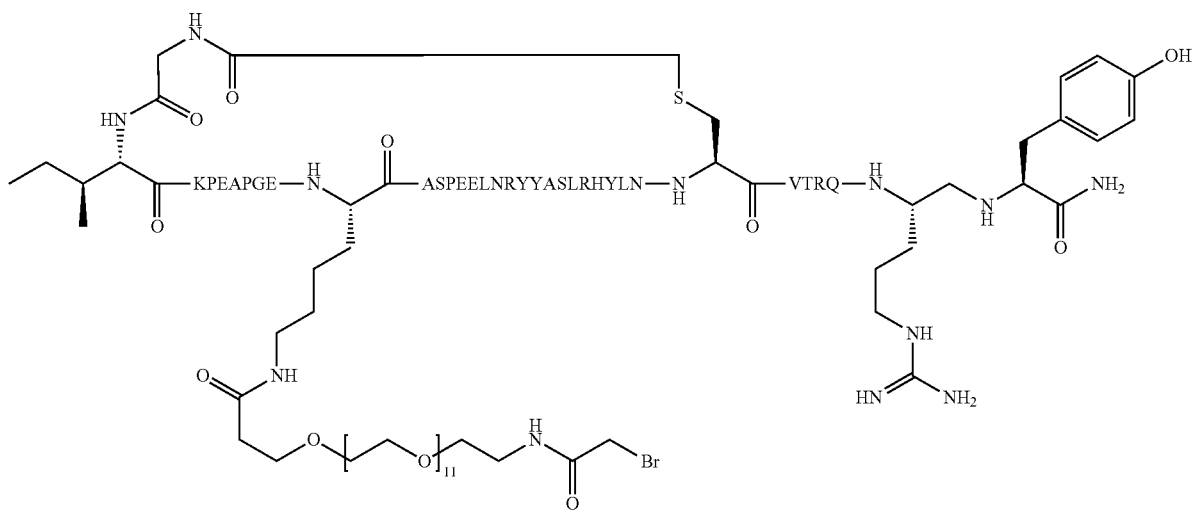
SEQ ID NO: 89
Name: [Cyclo-(G2-COCH₂-C30), K(PEG12-AcBr)11, N-Me-R35]-PYY2-36
Structure:
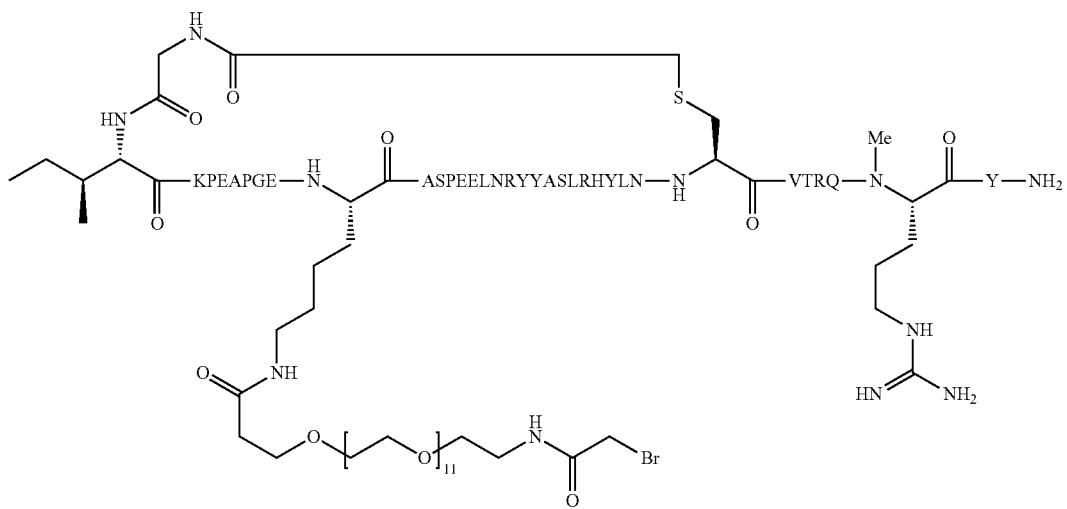

SEQ ID NO: 90
Name:[Cyclo-(βA2-COCH₂-C30), K(PEG12-AcBr)11, N-Me-R35]-PYY2-36
Structure:
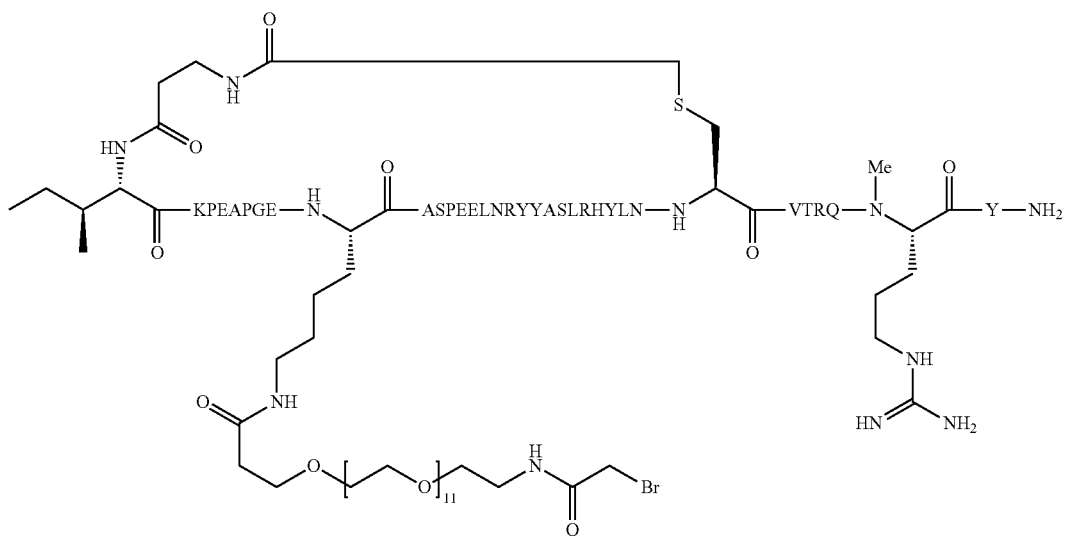
SEQ ID NO: 91
Name: [Cyclo-(G2-COCH₂-hC30), K(PEG12-AcBr)11, N-Me-R35]-PYY2-36
Structure:
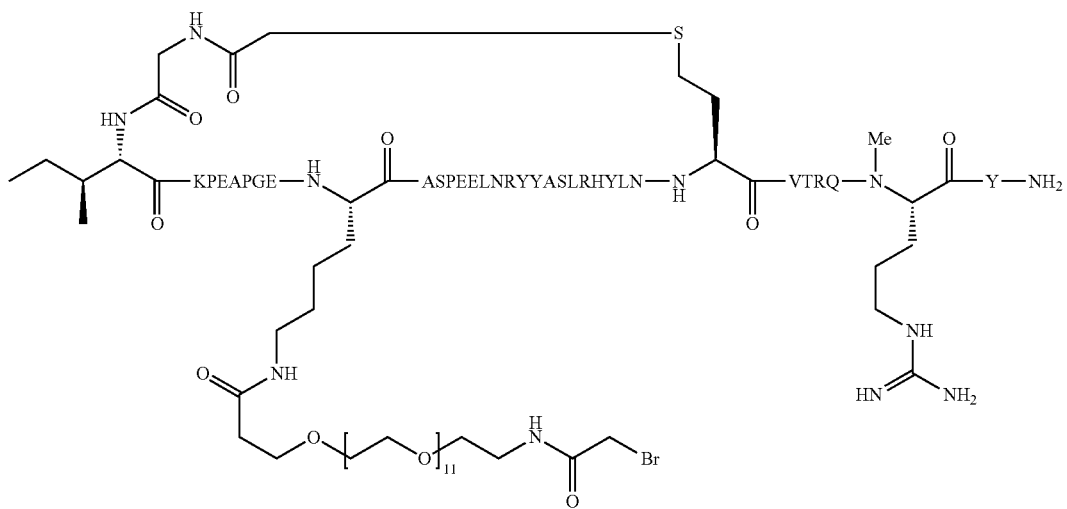

SEQ ID NO: 92
Name: [Cyclo-(βA2-COCH₂-hC30), K(PEG12-AcBr)11, N-Me-R35]PYY2-36
Structure:
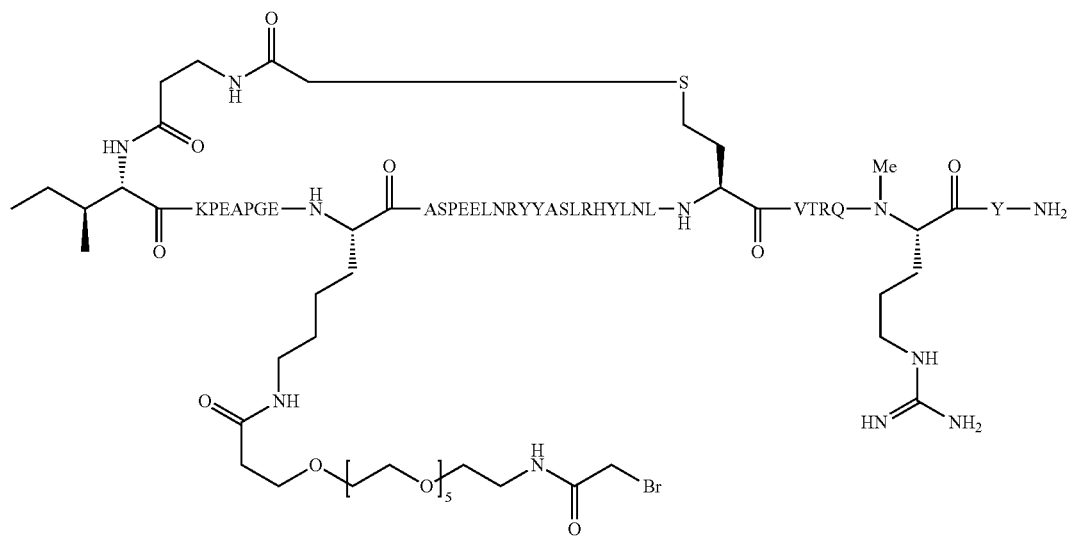
SEQ ID NO: 93
Name: [Cyclo-(G2-COCH₂-hC30), K(PEG12-AcBr)11, psi-(R35,Y36)]-PYY2-36
Structure:
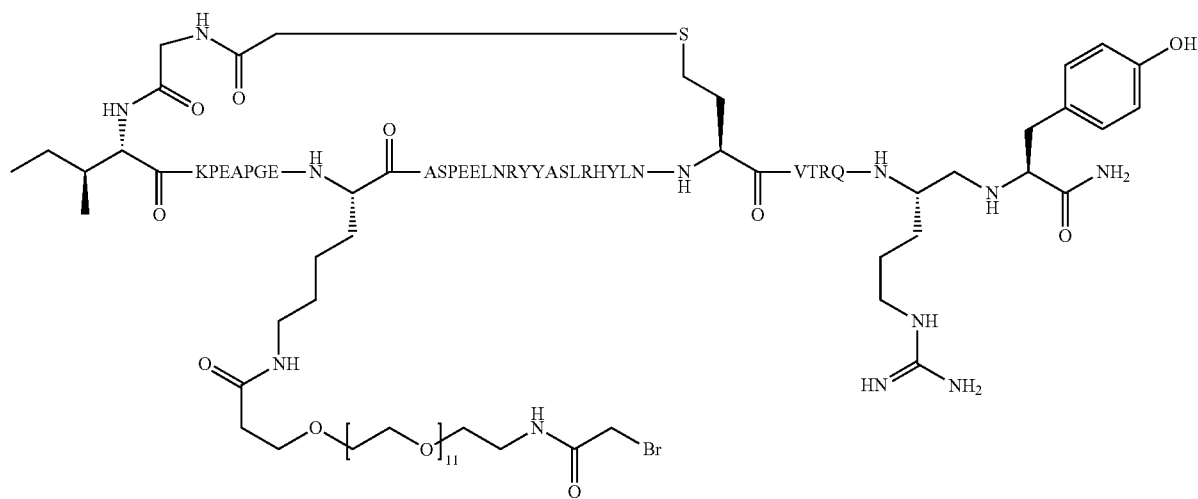

SEQ ID NO: 94
Name: [Cyclo-(βA2-COCH2-C30), K(PEG12-AcBr)11, psi-(R35,Y36)]-PYY2-36
Structure:
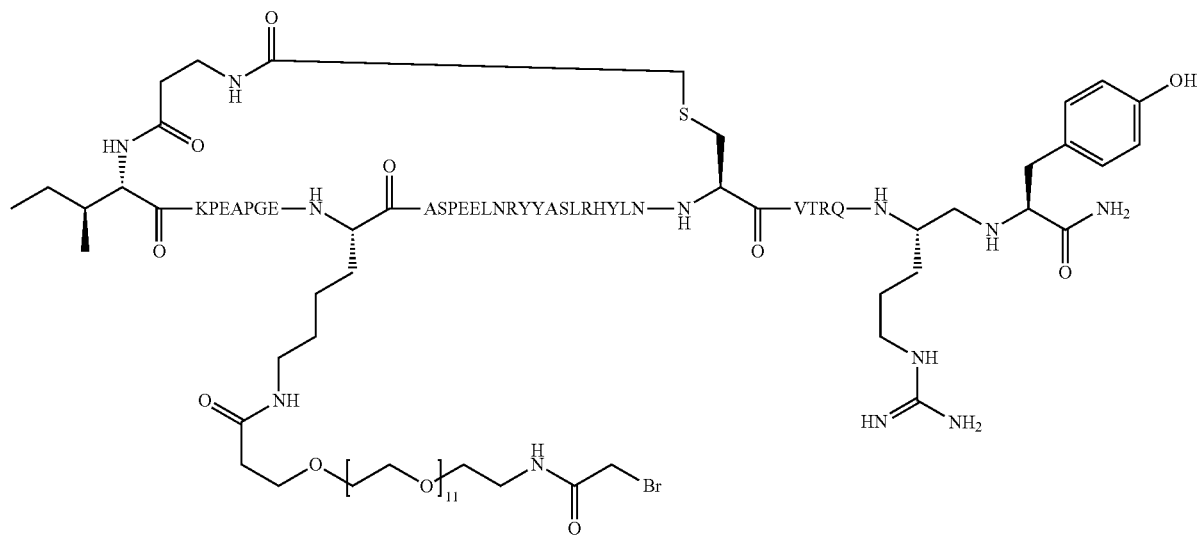
SEQ ID NO: 95
Name: [Cyclo-(G2-E30), S4, K(AcBr)11, psi-(R35,Y36)]-PYY2-36
Structure:
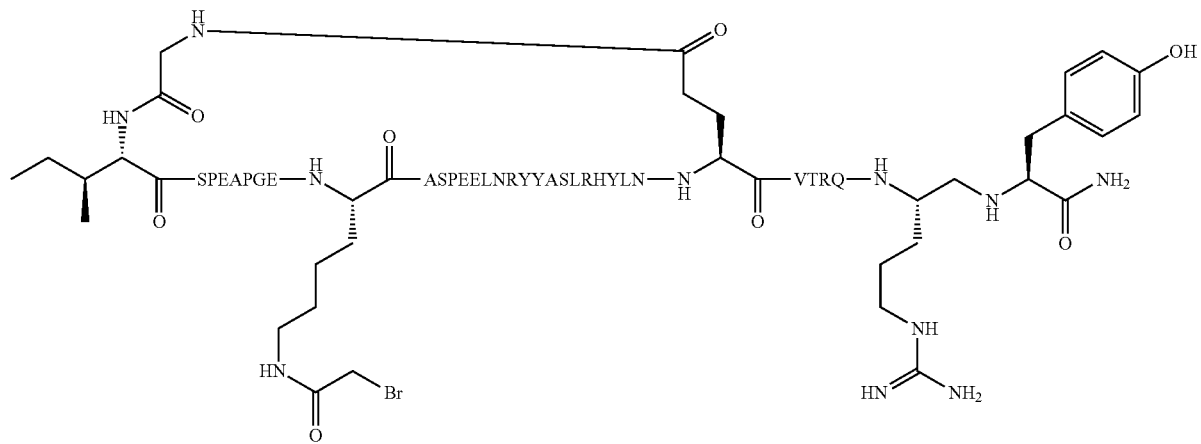

SEQ ID NO: 96
Name: [Cyclo-(βA2-COCH₂-hC31), K(PEG24-AcBr)11, psi-(R35,Y36)]-PYY2-36
Structure:
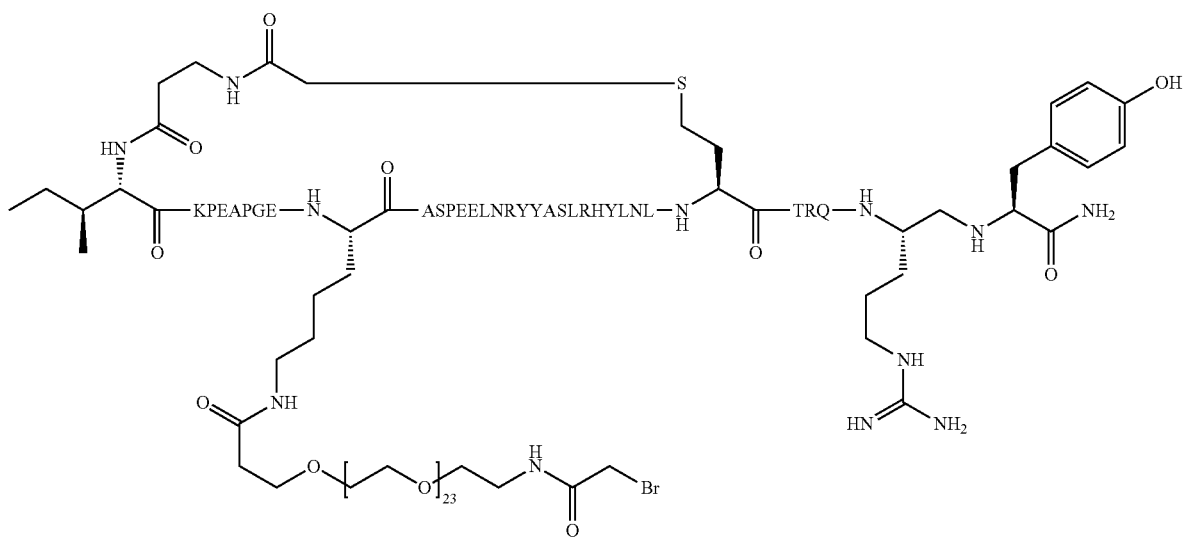
SEQ ID NO: 97
Name: [Cyclo-(G2-Ac-hC31), K(PEG12-AcBr)11, psi-(R35,Y36)]-PYY2-36
Structure:
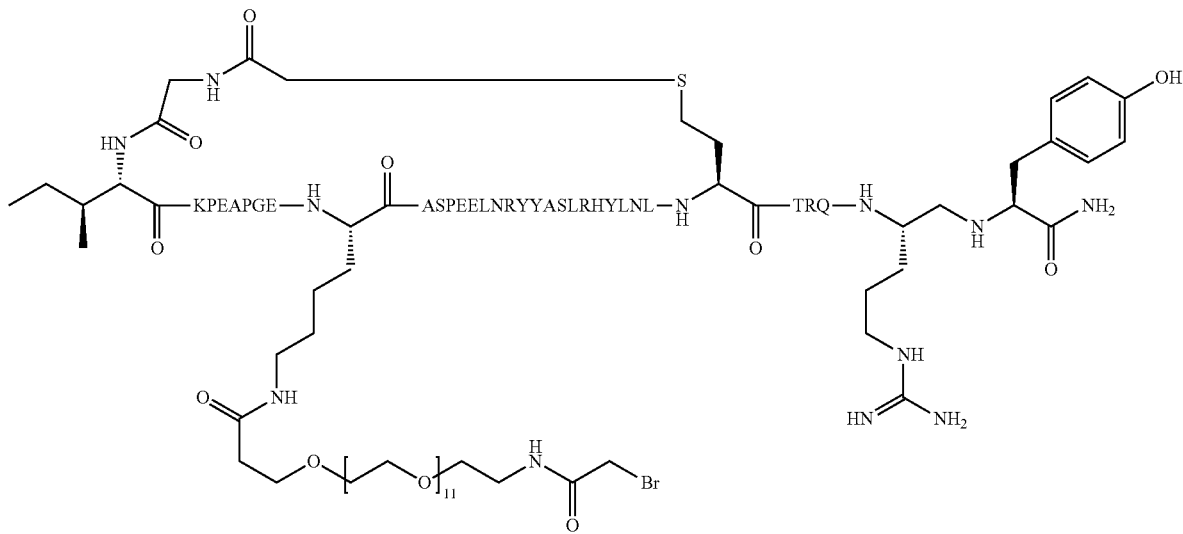

SEQ ID NO: 98
Name: [Cyclo-(G2-COCH₂-C30), K(AcBr)11, N-Me-R35]-PYY2-36
Structure:
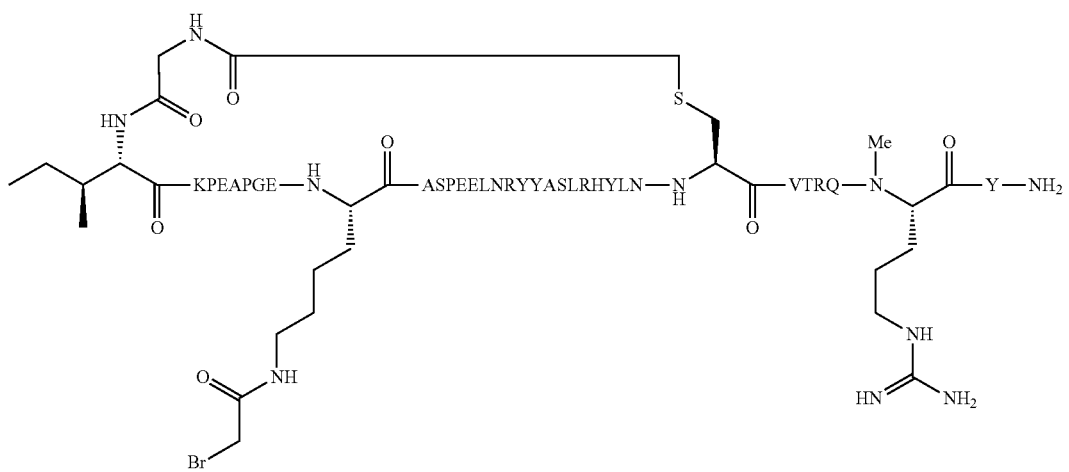
SEQ ID NO: 99
Name: [Cyclo-(βA2-COCH₂-C30), K(AcBr)11, N-Me-R35]-PYY2-36
Structure:
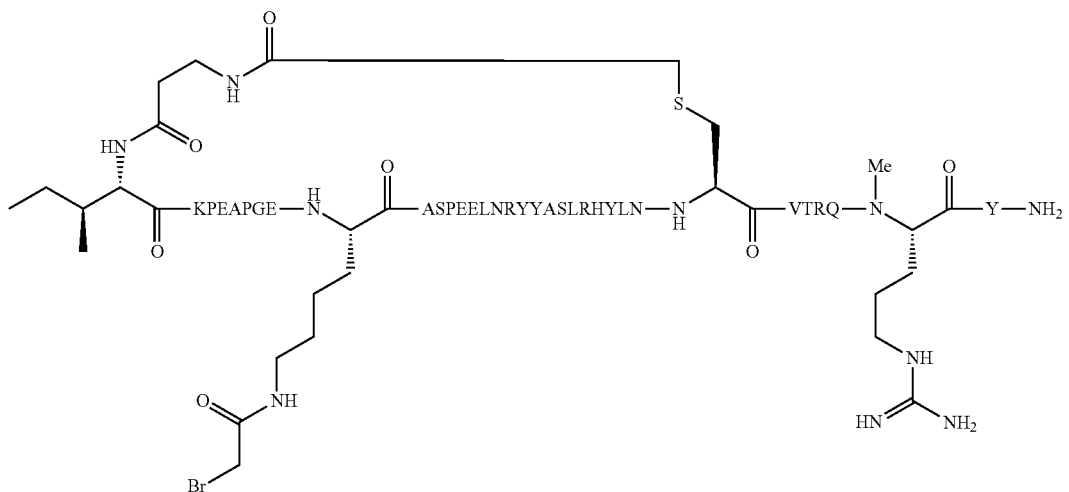
SEQ ID NO: 100
Name: [Cyclo-(βA2-COCH₂-C30), K(AcBr)11, psi-(R35,Y36)]-PYY2-36
Structure:
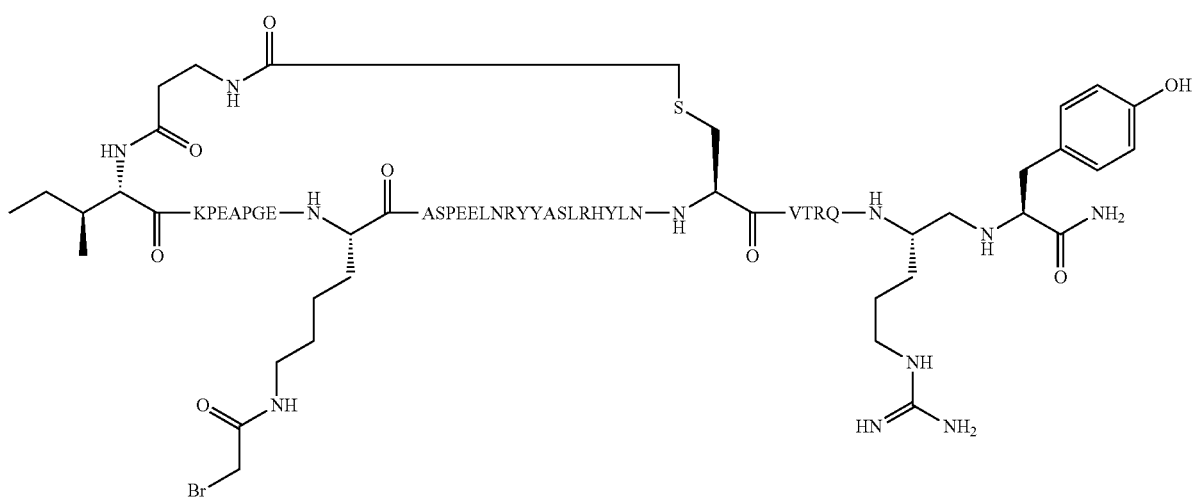

SEQ ID NO: 101
Name: [Cyclo-(βA2-COCH₂-hC31), psi-(R35,Y36)]-PYY2-36
Structure:
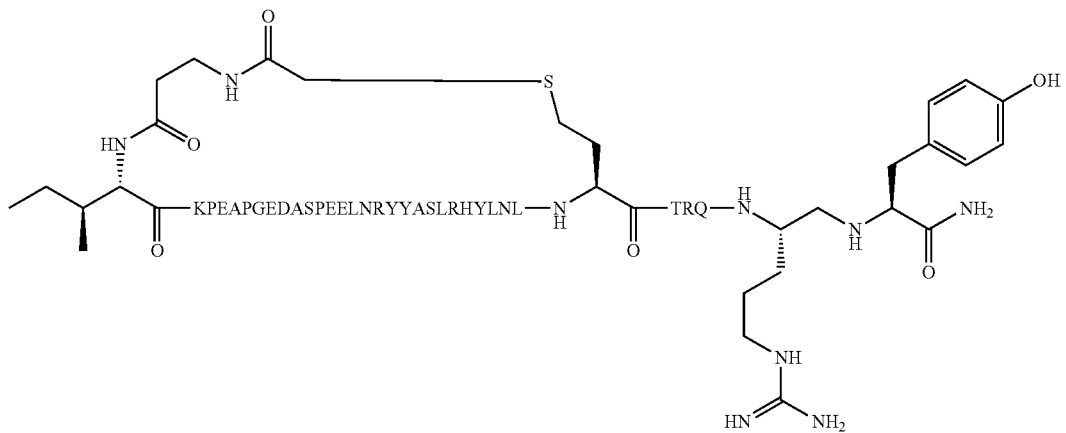
SEQ ID NO: 102
Name: [Cyclo-(βA2-COCH₂-hC31), K11, psi-(R35,Y36)]-PYY2-36
Structure:
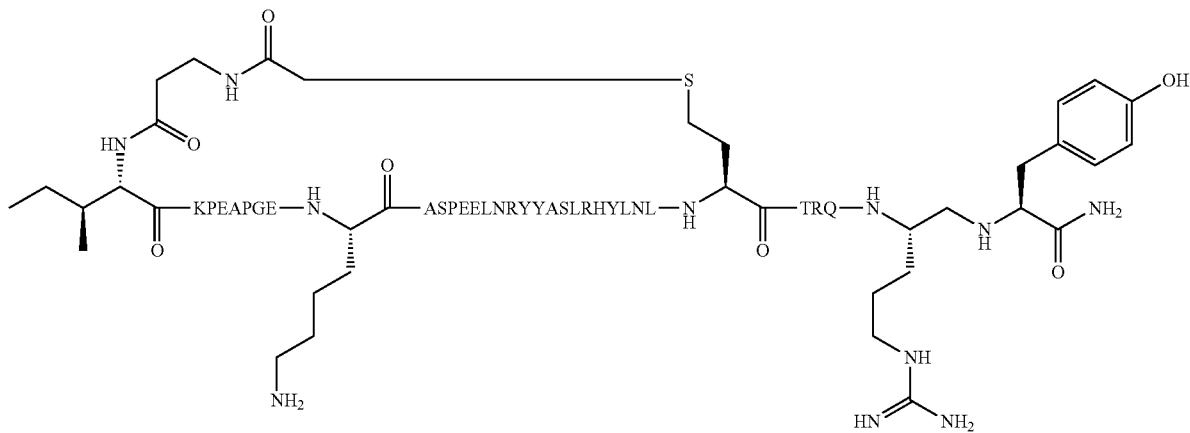
SEQ ID NO: 103
Name: [Cyclo-(G2-E30), S4, psi-(R35,Y36)]-PYY2-36
Structure:
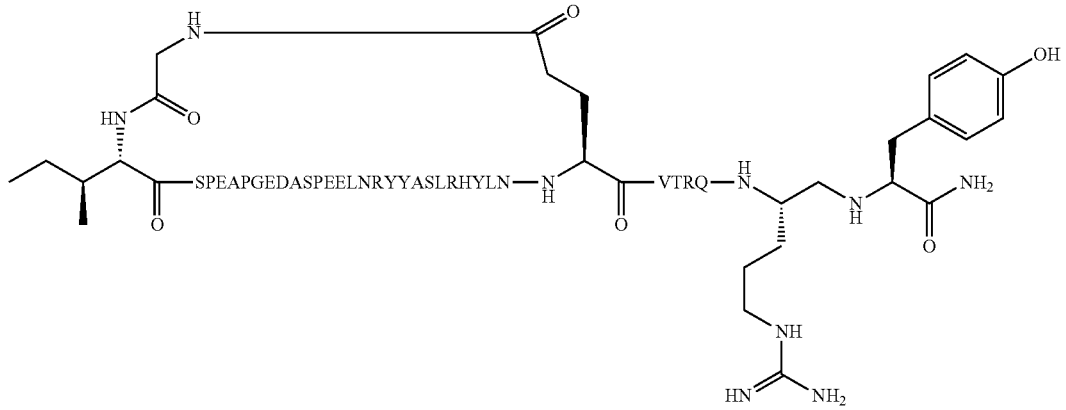

SEQ ID NO: 104
Name: [Cyclo-(G2-E30), S4, K11, psi-(R35,Y36)]-PYY2-36
Structure:
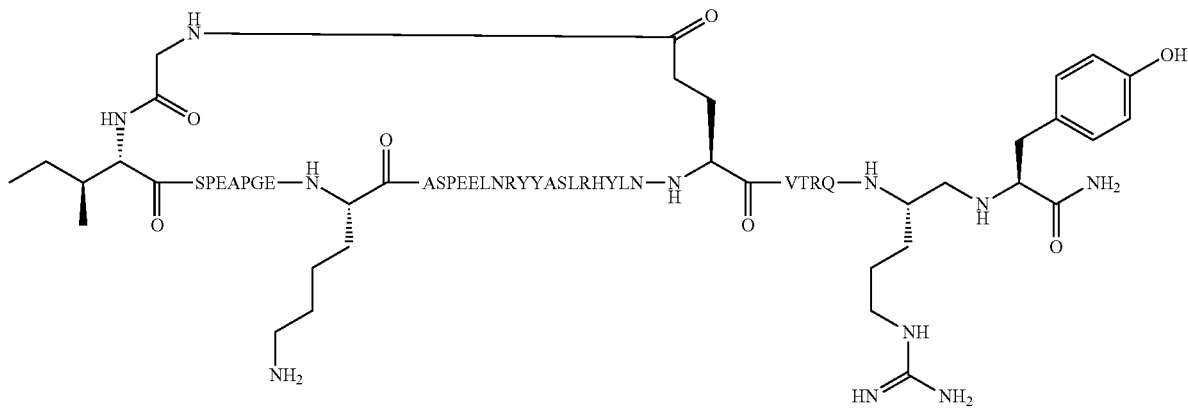
SEQ ID NO: 105
Name: [Cyclo-(G2-COCH₂-C30), N-Me-R35]-PYY2-36
Structure:
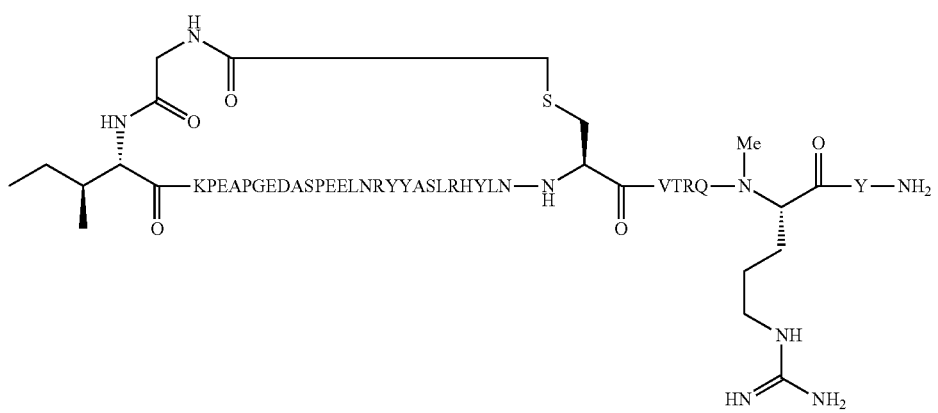
SEQ ID NO: 106
Name: [Cyclo-(G2-COCH₂-C30), K11, N-Me-R35]-PYY2-36
Structure:
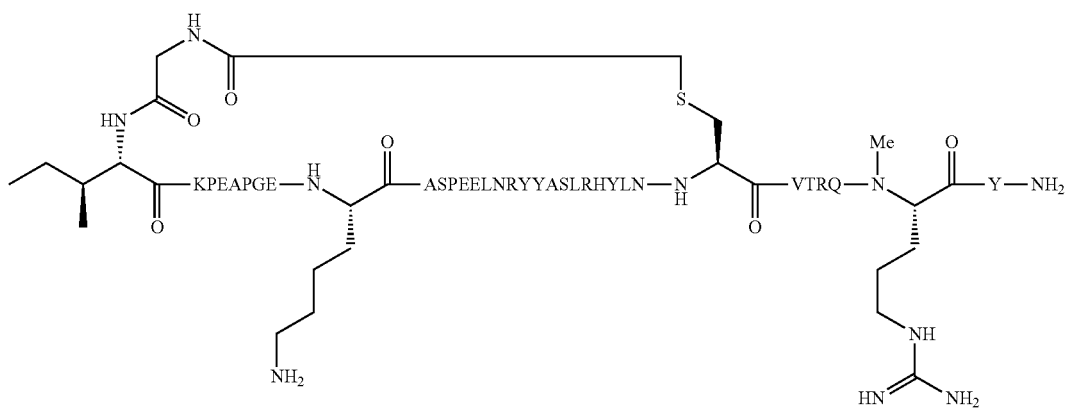

SEQ ID NO: 107
Name: [Cyclo-(βA2-COCH2-C30), N-Me-R35]-PYY2-36
Structure:
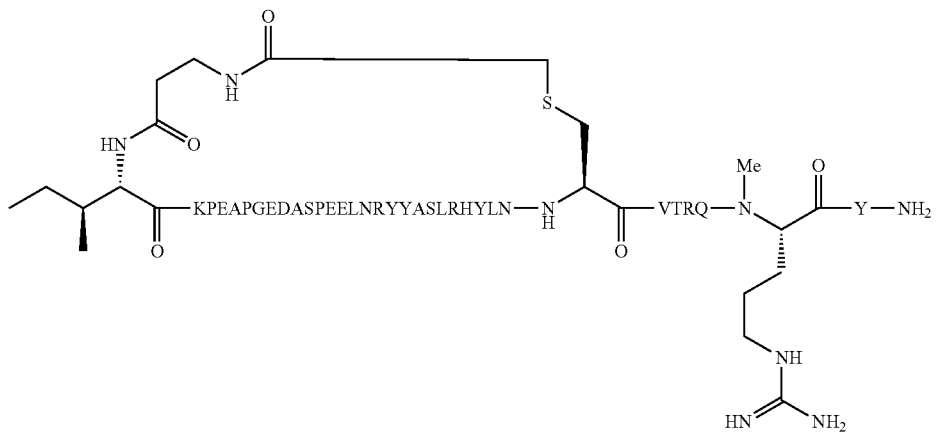
SEQ ID NO: 108
Name: [Cyclo-(βA2-COCH2-C30), K11, N-Me-R35]-PYY2-36
Structure:
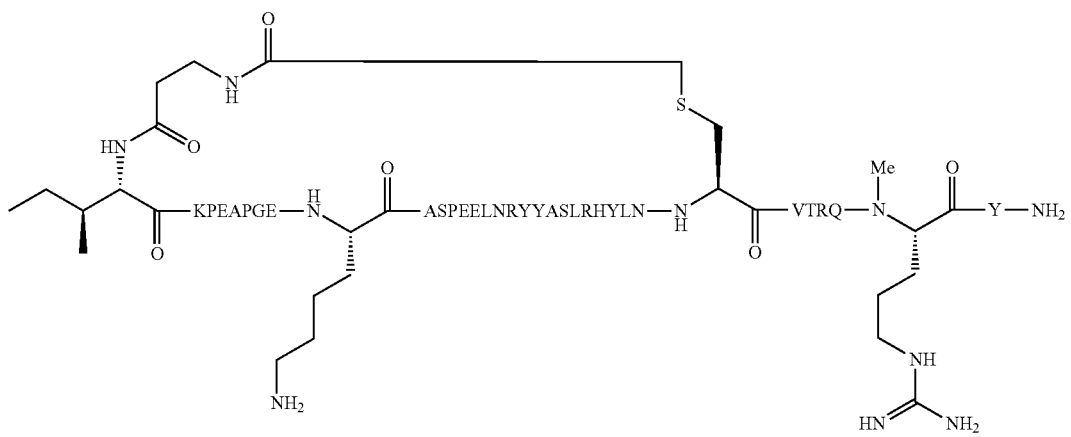
SEQ ID NO: 109
Name: [Cyclo-(βA2-COCH2-C30), psi-(R35,Y36)]-PYY2-36
Structure:
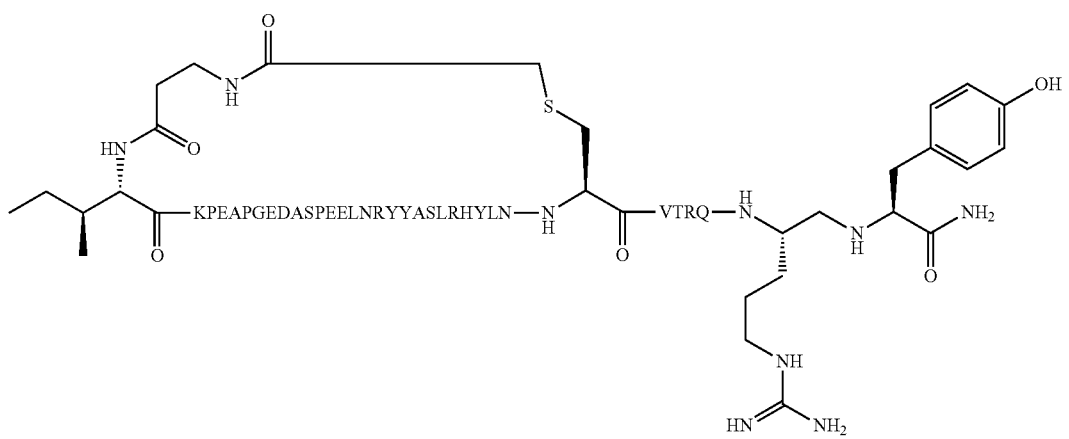

SEQ ID NO: 110
Name: [Cyclo-(βA2-COCH₂-C30), K11, psi-(R35,Y36)]-PYY2-36
Structure:

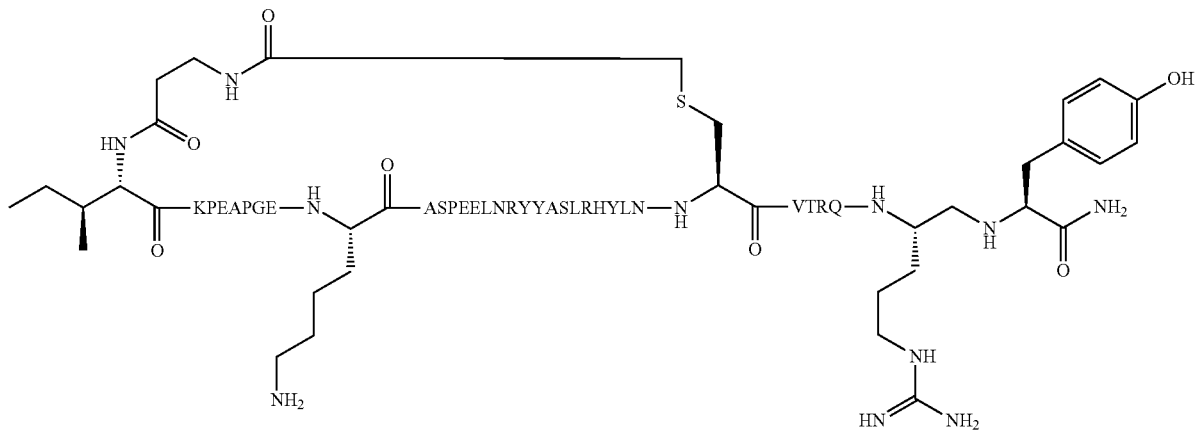

Example 111: Human NPY2R cAMP In Vitro Potency Assay (hY2 Assay)

The method used to test the potency of PYY analogs in vitro was a cell based assay designed to measure inhibition of forskolin-induced cAMP produced by adenylate cyclase through modulation of the human NPY2R Gi-protein coupled receptor. The forskolin-induced cAMP production in human NPY2R transfected HEK cells was reduced through activation of NPY2R by PYY analogs and controls in a dose-dependent manner, and measured in the LANCE FRET-based competitive cAMP immunoassay (PerkinElmer).

Cells were thawed from cryopreservation and added to 15 ml of cell media (DMEM/high glucose (Cellgro), 10% FBS (Hyclone), 1% Pen/Strep (Life Technologies), 1 L-Glutamine (Thermo Scientific), 1% Na Pyruvate (Thermo Scientific)). Cells were centrifuged at 450×g for 5 min, supernatants were aspirated, and cells were re-suspended in cell media at a density of 0.2×106 cells/ml. Cells were dispensed (25 μL/well) to a Biocoat collagen-coated white 384-well plate (Becton Dickinson) to a final density of 5000 cells/well, and incubated at 37° C., 5% $CO_2$ for 16 to 24 h. Supernatants in the assay plate were decanted. Dilutions of PYY analogs and controls were prepared in 1×HBSS (Cellgro), 5 mM HEPES (Cellgro), 0.1% BSA (PerkinElmer) and 0.5 mM 3-isobutyl-1-methylxanthine (Sigma), and 6 μL/well of each sample were added to designated wells. Lance cAMP antibody (PerkinElmer) was diluted 1:100 in 1×HBSS (Cellgro), 5 mM HEPES (Cellgro), 0.005 mM forskolin (Sigma), 0.1% BSA (PerkinElmer) and 0.5 mM 3-isobutyl-1-methylxanthine (Sigma), and 6 μL of the antibody mixture was added to the plate, which was then incubated at rt for 25 min. Then 12 μL/well LANCE cAMP detection reagent mix containing biotin-cAMP (1:750) and Europium-W8044 (1:2250) (PerkinElmer) was added to each assay plate, which was then incubated at rt for 2 h. Plates were read on a PerkinElmer Envision plate reader (excitation 320 nm, emission—615 nm and 665 nm), with relative fluorescence units (RFU) calculated as (615 nm/665 nm)×10,000. All samples were measured in triplicate. Data were analyzed using the Crucible in-house data analysis software, designed by Eudean Shaw. The unknown cAMP concentrations within each well were interpolated from the reference standards of known cAMP concentrations included within each plate. Parameters such as EC50, Log (EC50), HillSlope (nH), top, and bottom, were derived by plotting cAMP concentration values over log compound concentrations fitted with 4-P model using a non-linear weighted least squares application within R environment implemented by the Non-Clinical Statistics & Computing department at Janssen R&D.

The potencies of the NTSC-PYY analogues of the present invention relative to $PYY_{3-36}$, used as a control in the same assay are presented in Table 2 below:

TABLE 2 hY2 Receptor Potencies of NTSC-PYY Compounds and $PYY_{3-36}$ (SEQ ID NO: 111)

| SEQ ID NO. | Y2R $EC_{50}$ (nM) SEQ ID NO: 2-39 | Y2R $EC_{50}$ (nM) SEQ ID NO: 111 |
|---|---|---|
| 2 | 0.14 | 0.19 |
| 3 | 0.11 | 0.12 |
| 4 | 0.74 | 0.05 |
| 5 | 9.8 | 0.05 |
| 6 | 10.5 | 0.05 |
| 7 | 0.56 | 0.05 |
| 8 | 0.06 | 0.05 |
| 9 | 0.02 | 0.12 |
| 10 | 0.12 | 0.12 |
| 11 | 0.13 | 0.15 |
| 12 | 0.21 | 0.09 |
| 13 | 0.04 | 0.09 |
| 14 | 0.10 | 0.13 |
| 15 | 0.08 | 0.12 |
| 16 | 0.17 | 0.12 |
| 17 | 0.31 | 0.12 |
| 18 | 1.4 | 0.12 |
| 19 | 2.9 | 0.07 |
| 20 | 4.1 | 0.07 |
| 21 | 0.49 | 0.12 |
| 22 | 4.4 | 0.12 |
| 23 | 9.4 | 0.12 |
| 24 | 6.1 | 0.12 |
| 25 | 0.02 | 0.12 |
| 26 | 0.03 | 0.12 |
| 27 | 0.70 | 0.11 |
| 28 | 0.05 | 0.11 |
| 29 | 0.09 | 0.11 |
| 30 | 1.6 | 0.08 |

TABLE 2-continued hY2 Receptor Potencies of NTSC-PYY
Compounds and PYY$_{3-36}$ (SEQ ID NO: 111)

| SEQ ID NO. | Y2R EC$_{50}$ (nM) SEQ ID NO: 2-39 | Y2R EC$_{50}$ (nM) SEQ ID NO: 111 |
|---|---|---|
| 31 | 0.01 | 0.10 |
| 32 | 0.15 | 0.08 |
| 33 | 0.13 | 0.08 |
| 34 | 0.09 | 0.08 |
| 35 | 0.18 | 0.10 |
| 36 | 1.5 | 0.10 |
| 37 | 0.09 | 0.09 |
| 38 | 0.21 | 0.09 |
| 39 | 0.02 | 0.05 |
| 40 | 0.01 | 0.08 |
| 41 | 0.07 | 0.08 |
| 42 | 11.3 | 0.08 |
| 43 | 0.01 | 0.09 |
| 44 | 2.11 | 0.09 |
| 45 | 0.01 | 0.09 |
| 46 | 0.02 | 0.09 |
| 47 | 3.3 | 0.08 |
| 48 | 6.9 | 0.10 |
| 49 | 0.35 | 0.10 |
| 50 | 11.9 | 0.10 |
| 51 | 0.10 | 0.10 |
| 52 | 0.01 | 0.08 |
| 53 | 0.02 | 0.08 |
| 54 | 0.09 | 0.08 |
| 55 | 0.02 | 0.08 |
| 56 | 0.09 | 0.06 |
| 57 | 0.03 | 0.11 |
| 58 | 0.11 | 0.07 |
| 59 | 0.01 | 0.08 |
| 60 | 0.01 | 0.08 |
| 61 | 0.05 | 0.08 |
| 62 | 0.12 | 0.08 |
| 63 | 0.11 | 0.06 |
| 64 | 0.08 | 0.06 |
| 65 | 0.04 | 0.06 |
| 66 | 0.03 | 0.06 |
| 67 | 0.07 | 0.06 |
| 68 | 0.27 | 0.06 |
| 69 | 8.97 | 0.08 |
| 70 | 0.02 | 0.08 |
| 71 | 0.07 | 0.04 |
| 72 | 1.75 | 0.07 |

Example 112: Efficacy Studies In Vivo

A) Food Intake in Lean C57BL6N Mice: Acute Dosing

Male C57BL/6 mice (10-12 weeks of age) were obtained from Taconic Laboratory. Mice were housed one mouse per cage with AlphaDri bedding in a temperature-controlled room with 12-h light/dark cycle. Mice were allowed ad libitum access to water and maintained on their regular diet (Lab Diet Cat: 5001). Animals were acclimated in the BioDAQ cages (Research Diets, Inc., New Brunswick, N.J.) no less than 72 h prior to the start of the experiment.

Once acclimated in the BioDAQ cages, mice were grouped into cohorts of eight animals based on their individual food intake over the previous 24 h. At 4:00-5:00 μm, animals were weighed and treated with either vehicle (2.7 mM disodium phosphate, 61.33 mM propylene glycol, 19.5 mM phenol, pH 8.2) or test compound at a dose of 1 μmol/kg (500 nmol/mL) via subcutaneous administration. Following compound administration, changes in food weight for each cage were recorded continuously by the BioDAQ automated monitoring system for 24 h. Crumbs were removed daily from hoppers and the areas around the cages with a vacuum. Food was replenished as necessary. The percentage of mean cumulative food intake relative to vehicle over the 24 h period post compound administration was calculated and is reported in Table 3. Statistical analyses were performed using one-way ANOVA with Tukey's post-test in Prism. All data are presented as the mean.

B) Weight Loss in Diet-Induced Obese (DIO) Mice: Acute Dosing

Male DIO C57BL/6 mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet). Animals were acclimated to the facility for at least one week prior to the start of the experiment.

The day prior to dosing, mice were grouped into cohorts of eight animals based on individual body weights. At 3:00-4:00 μm the following day, animals were weighed and treated with either vehicle (2.7 mM disodium phosphate, 61.33 mM propylene glycol, 19.5 mM phenol, pH 8.2) or test compound at a dose of 100 nmol/kg (50 nmol/mL) via subcutaneous administration. Body weights were measured 24 h after dosing and the percentages of weight loss were calculated and are reported in Table 3. Statistical analyses were performed using one-way ANOVA with Tukey's post-test in Prism. All data are presented as the mean.

C) Weight Loss in Diet-Induced Obese Mice: Chronic Dosing

Male DIO C57BL/6 mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet). Animals were acclimated to the facility for at least one week prior to the start of the experiment.

The day prior to dosing, mice were grouped based on individual body weights. At 3:00-4:00 μm for each of the next 7 days, animals were weighed and then treated with either vehicle (2.7 mM disodium phosphate, 61.33 mM propylene glycol, 19.5 mM phenol, pH 8.2) or test compound at a dose of 100 nmol/kg (50 nmol/mL) via subcutaneous administration. After 7 days, body weights were measured and the percentages of weight loss were calculated and are reported in Table 3. Statistical analyses were performed using one-way ANOVA with Tukey's post-test in Prism. All data are presented as the mean.

TABLE 3

In Vivo Efficacy Studies of NTSC-PYY Compounds

| Seq. I.D. No. | Food Intake Lean Mice % of Vehicle (dose = 1 μM/kg) | Weight Loss Acute DIO Mice % Weight Change# (24 h) (dose = 100 nM/kg) | Weight Loss Chronic DIO Mice % Weight Change# (7 days) (dose = 100 nM/kg) |
|---|---|---|---|
| PYY3-36 | 84 | ND | ND |
| 2 | 65*** | ND | ND |
| 3 | 76* | ND | ND |
| 8 | 48*** | −4.95*** | −10.23*** |
| 9 | 83 | ND | ND |
| 10 | 26*** | −2.06** | ND |

TABLE 3-continued

In Vivo Efficacy Studies of NTSC-PYY Compounds

| Seq. I.D. No. | Food Intake Lean Mice % of Vehicle (dose = 1 µM/kg) | Weight Loss Acute DIO Mice % Weight Change# (24 h) (dose = 100 nM/kg) | Weight Loss Chronic DIO Mice % Weight Change# (7 days) (dose = 100 nM/kg) |
|---|---|---|---|
| 11 | ND | −5.10*** | −9.65*** |
| 13 | ND | −3.58*** | −10.20*** |
| 14 | ND | −2.56* | −5.66** |
| 25 | ND | −3.95*** | ND |
| 26 | ND | −4.69*** | ND |
| 39 | ND | −4.73*** | ND |
| 43 | ND | −1.96** | ND |
| 46 | ND | −2.86* | ND |
| 51 | ND | −4.16*** | ND |
| 68 | ND | −5.68*** | ND |

ND = not determined
% Weight Change relative to vehicle control animals
*$p < 0.05$;
**$p < 0.01$;
***$p < 0.001$ While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

We claim:
1. A pharmaceutical composition comprising:
   a. a compound of Formula I:

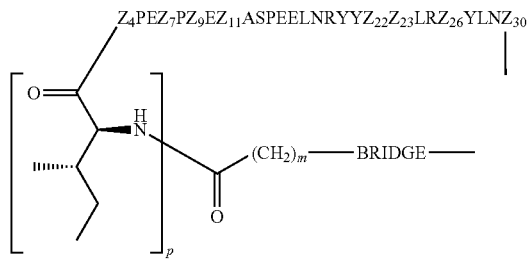

Formula I

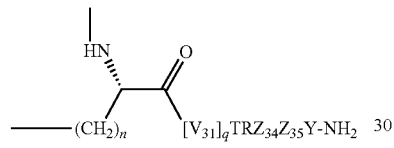

wherein
p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K;
$Z_9$ is G or K;
$Z_{11}$ is D or K;
$Z_{22}$ is A or K;
$Z_{23}$ is S or K;
$Z_{26}$ is A or H;
$Z_{30}$ is L, W, absent, or K;
provided that $Z_{30}$ is absent only when q is 1;
$Z_{34}$ is

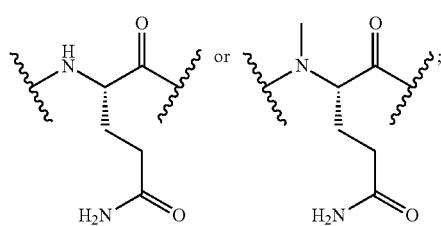 [SMILES: *N[C@@H](CCC(N)=O)C(*)=O ; *C(=O)[C@H](CCC(N)=O)N(*)C]

$Z_{35}$ is

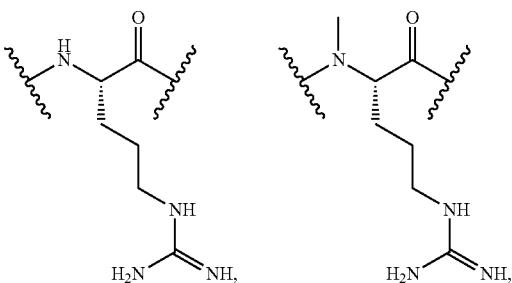

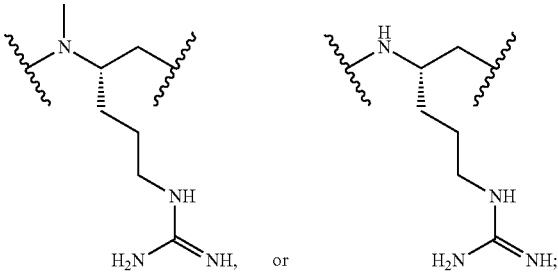

or a derivative thereof; wherein the derivative is the compound of Formula I that is modified by one or more processes comprising amidation, glycosylation, carbamylation, sulfation, phosphorylation, cyclization, lipidation, or pegylation; or a pharmaceutically acceptable salt thereof; and b. an additional compound selected from the group consisting of a biguanide, insulin, oxyntomodulin, a sulfonylurea, and a thiazolidinedione.

2. The pharmaceutical composition of claim 1, wherein the compound is a compound of Formula I or a compound of Formula I that is modified by one or more processes comprising amidation, lipidation, or pegylation; or a pharmaceutically acceptable salt thereof.

3. The pharmaceutical composition of claim 1, wherein BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
   $Z_7$ is A or K, wherein the amino side chain of said K is optionally substituted with

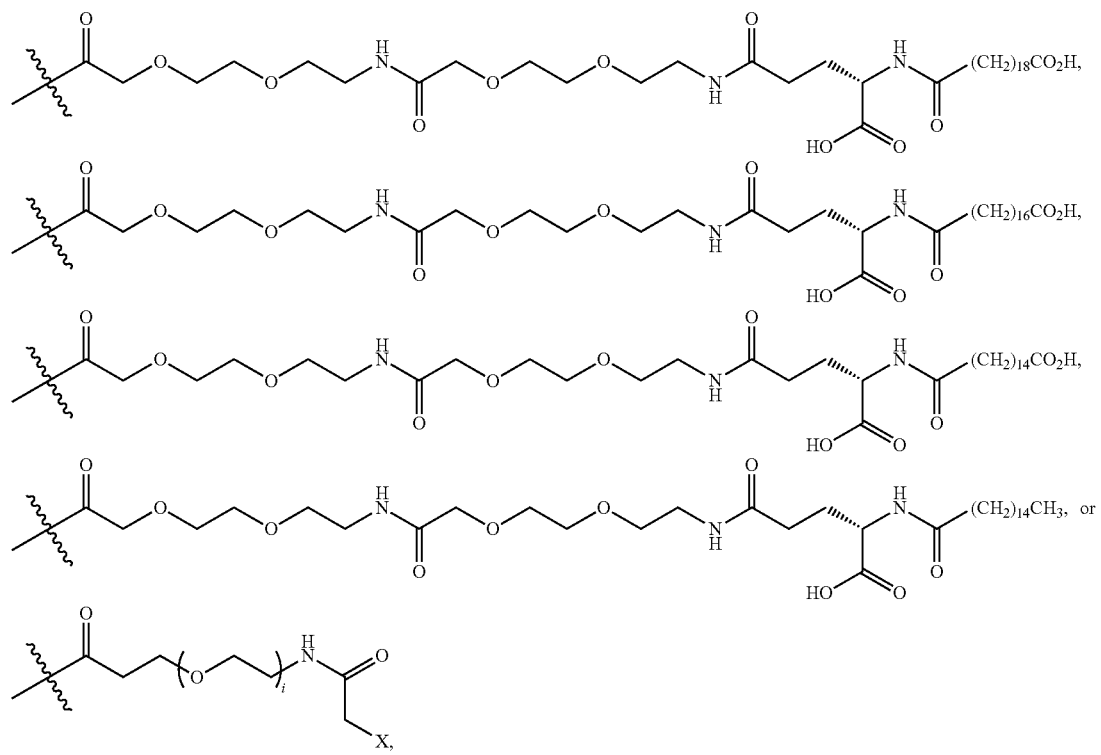
wherein i is an integer of 0 to 24, and X=Br, I or Cl, —C(O)CH$_2$Br, —C(O)CH$_2$I, or —C(O)CH$_2$Cl;
$Z_9$ is G or K, wherein the amino side chain of said K is optionally substituted with
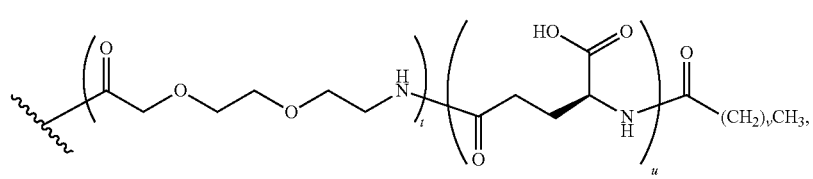
wherein t is 0, 1, or 2;
u is 0 or 1; and
v is 14, 16, or 18;
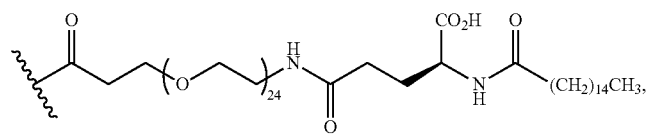
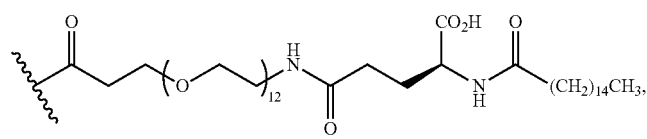

-continued
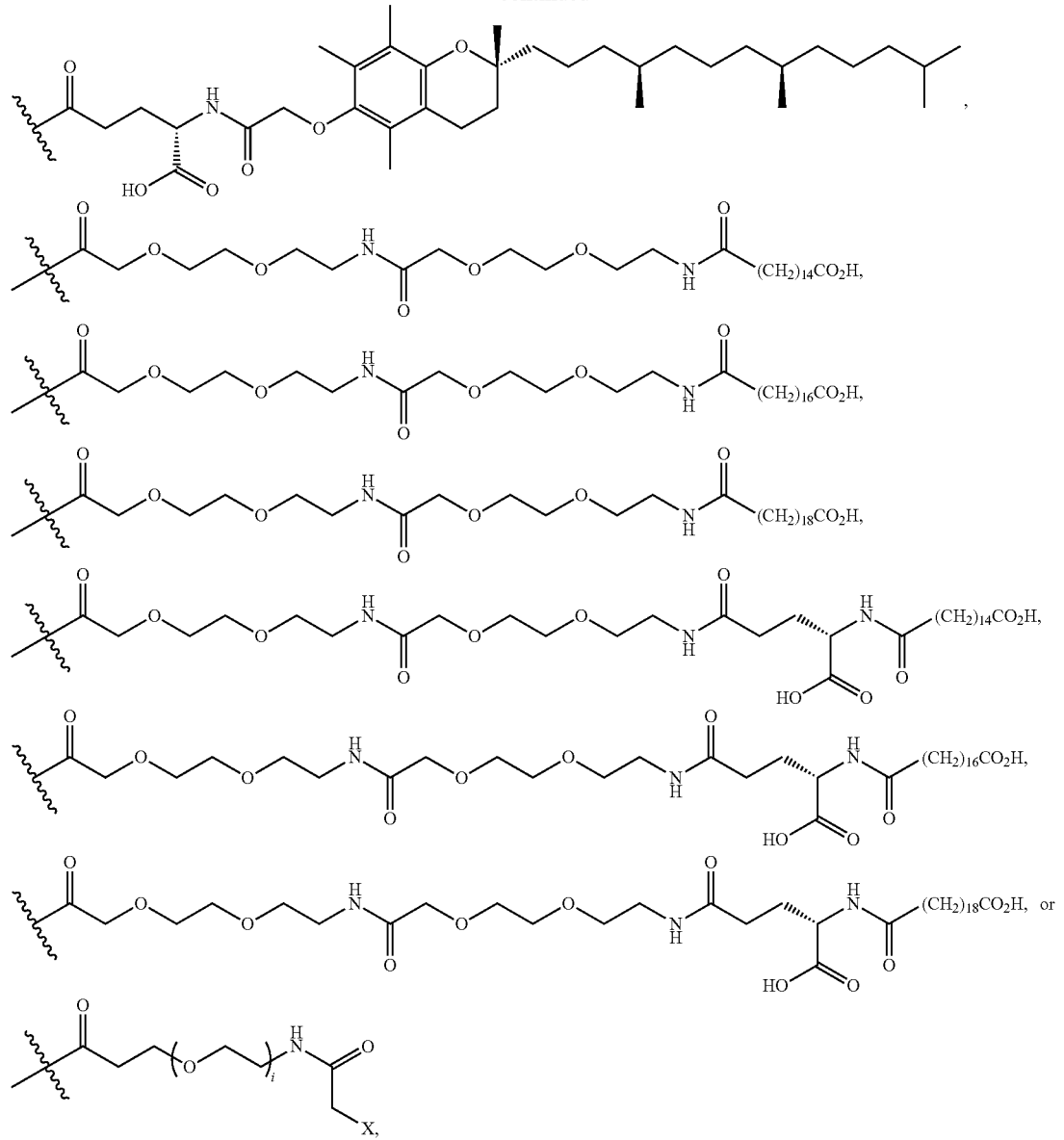
wherein i is an integer of 0 to 24, and X=Br, I or Cl, —C(O)CH$_2$Br, —C(O)CH$_2$I, or —C(O)CH$_2$Cl;
$Z_{11}$ is D or K, wherein the amino side chain of said K is optionally substituted with
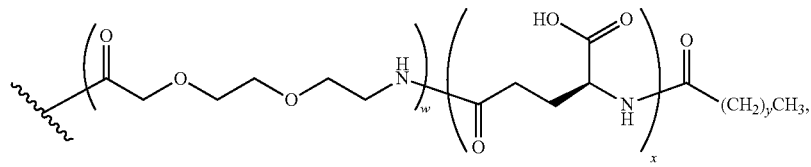
wherein w is 0, 1, 2, or 4;
x is 0 or 1; and
y is 14, 16, or 18;

367
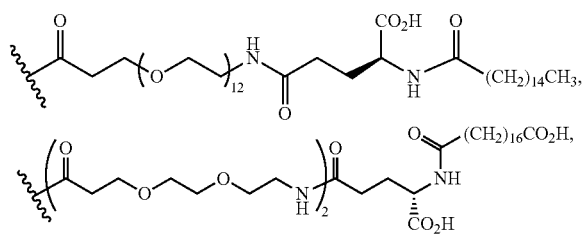
368
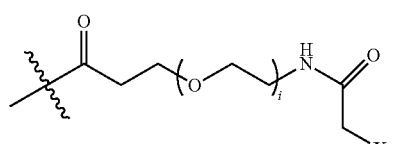
wherein i is an integer of 0 to 24, and X=Br, I or Cl,
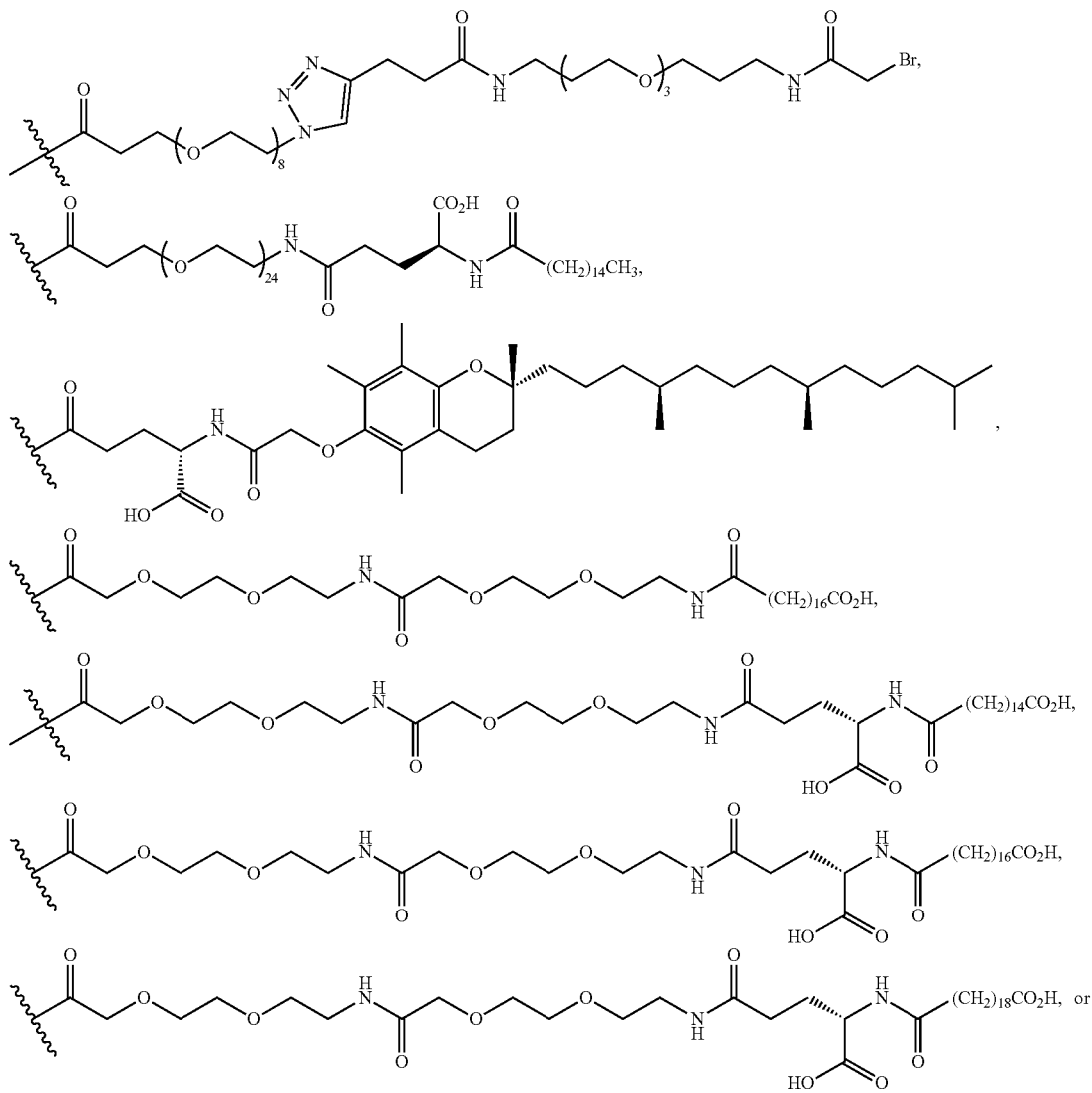
—C(O)CH$_2$Br, —C(O)CH$_2$I, or —C(O)CH$_2$Cl;
Z$_{22}$ is A or K, wherein the amino side chain of said K is optionally substituted with
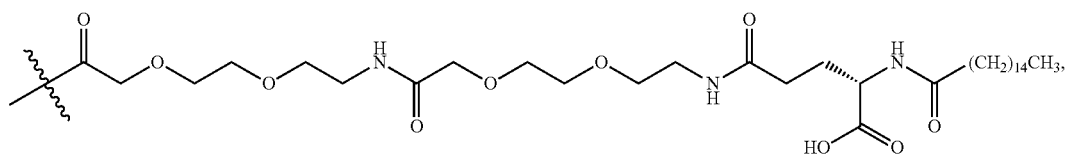

-continued

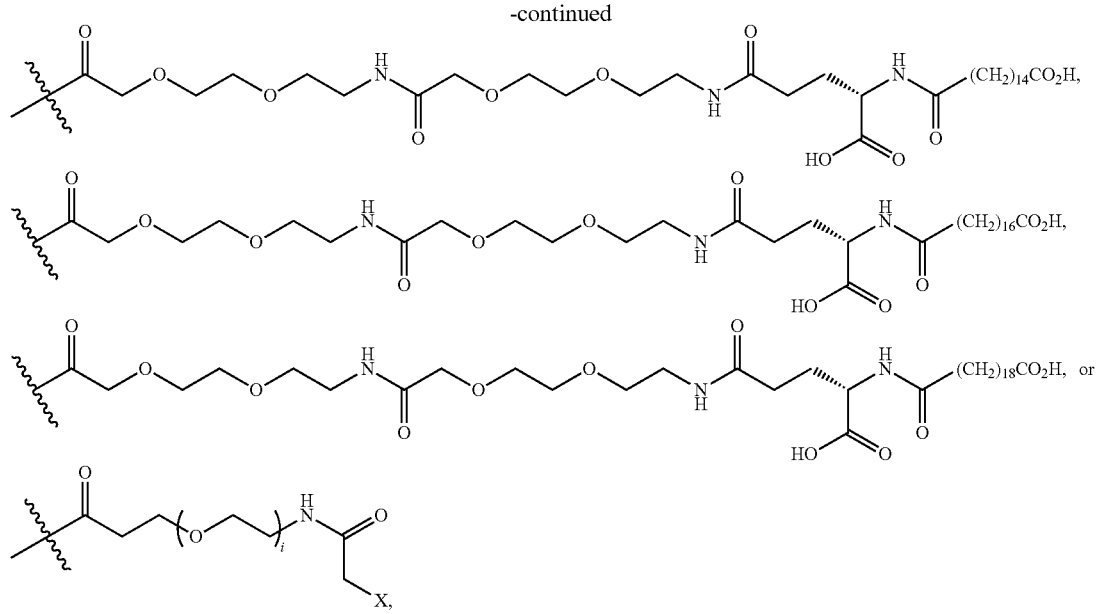

wherein i is an integer of 0 to 24, and X=Br, I or Cl, —C(O)CH$_2$Br, —C(O)CH$_2$I, or —C(O)CH$_2$Cl;

$Z_{23}$ is S or K, wherein the amino side chain of said K is optionally substituted with

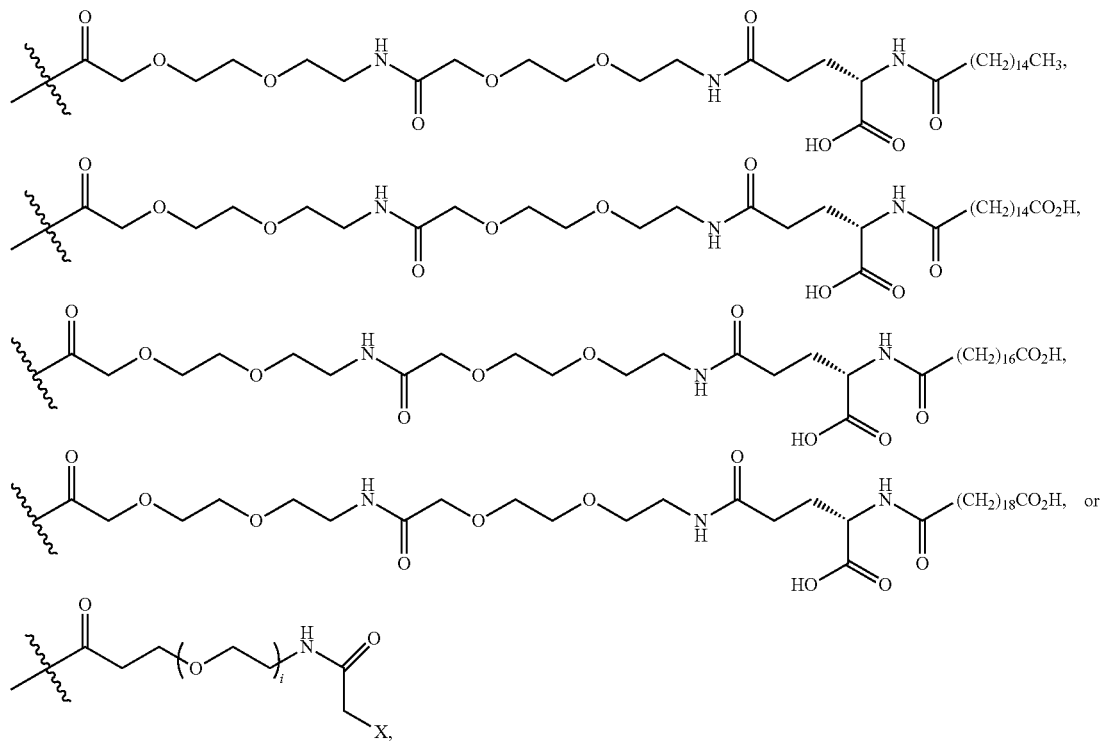

wherein i is an integer of 0 to 24, and X=Br, I or Cl, —C(O)CH$_2$Br, —C(O)CH$_2$I, or —C(O)CH$_2$Cl;

$Z_{30}$ is L, W, absent, or K, provided that $Z_{30}$ is absent only when q is 1, wherein the amino side chain of said K is optionally substituted with

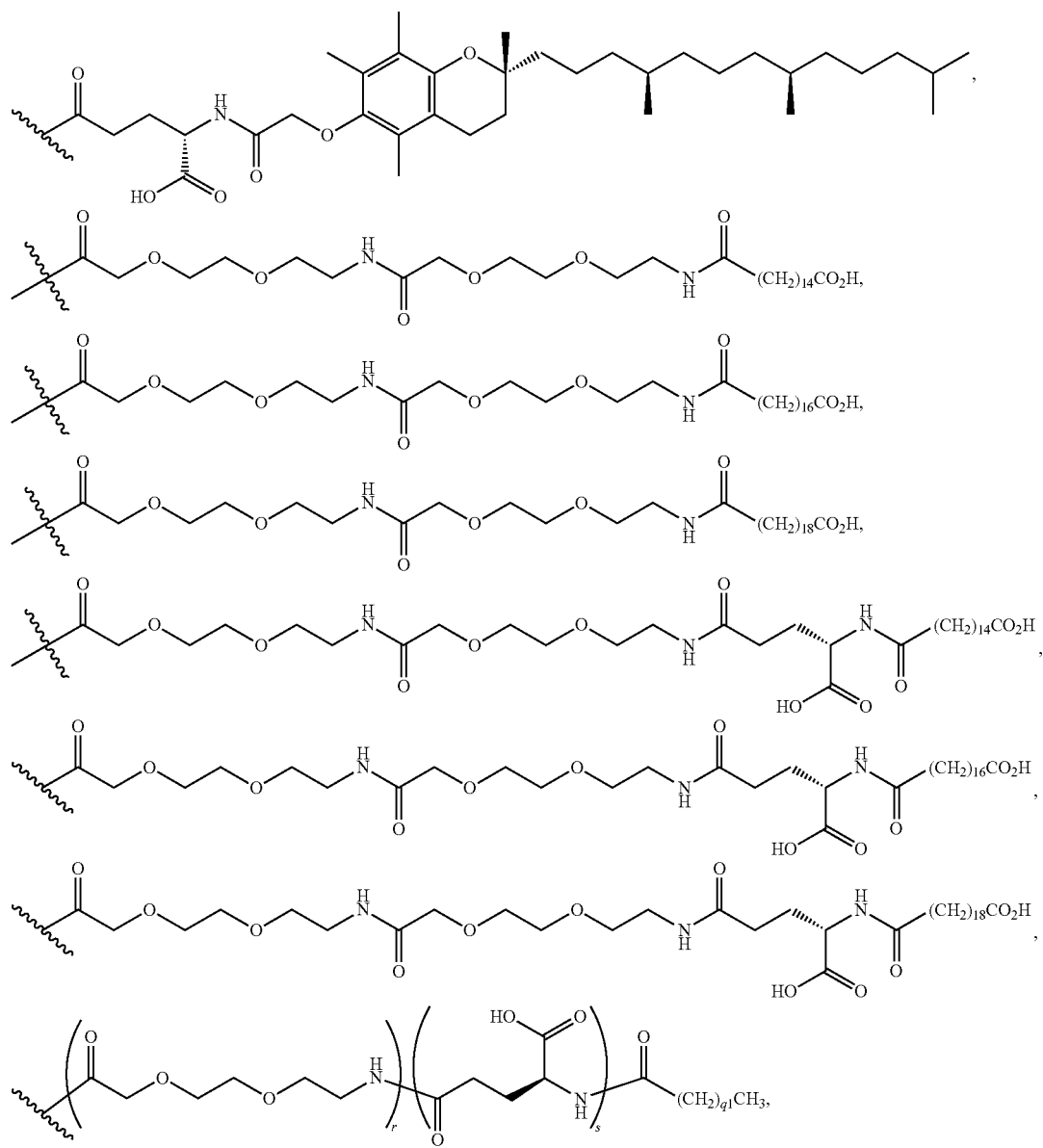
wherein r is 0, 1, or 2;
s is 0 or 1; and
$q_1$ is 14, 16, or 18;
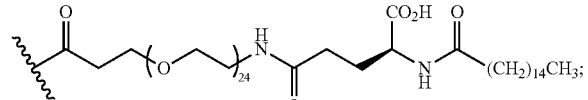
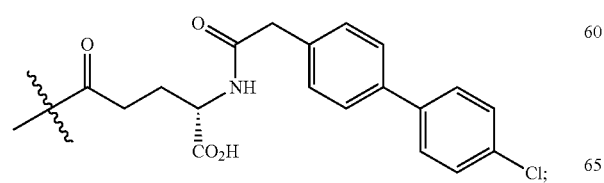
-continued
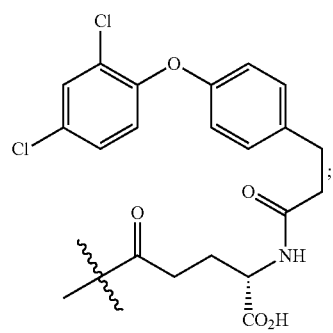

-continued
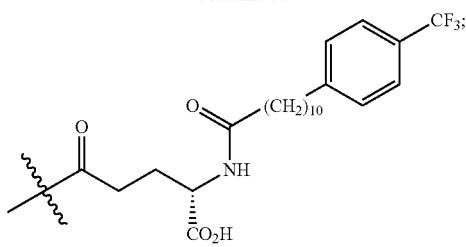
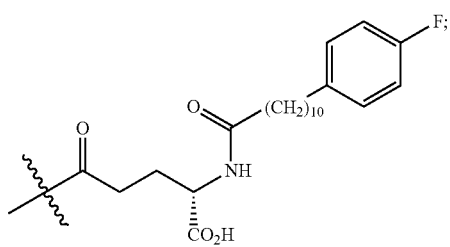
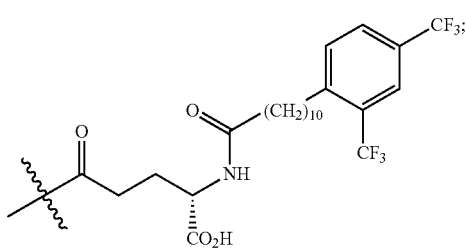
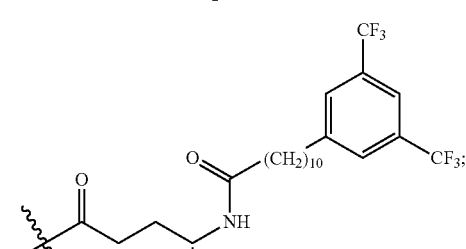
-continued
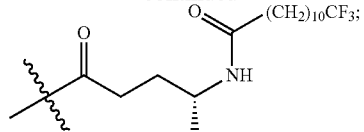
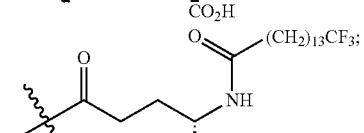
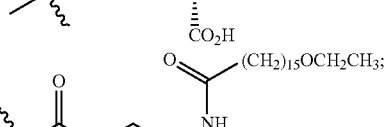
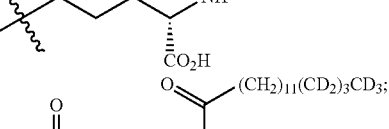
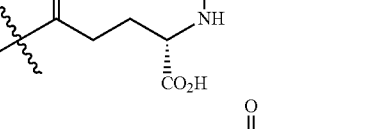
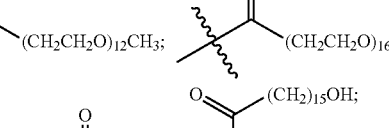
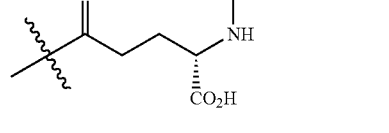
or a pharmaceutically acceptable salt thereof.
4. The pharmaceutical composition of claim 3 wherein
m is 0, 1, 2, 3, or 5;
n is 1, 2, or 4;
$Z_7$ is A or K, wherein the amino side chain of said K is optionally substituted with
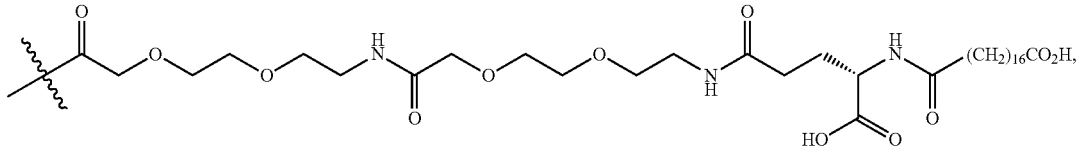
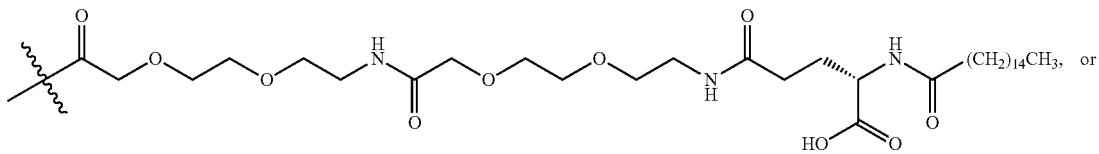
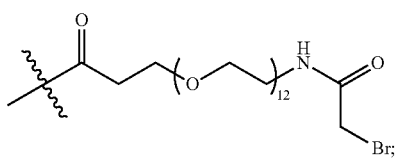

$Z_9$ is G or K, wherein the amino side chain of said K is optionally substituted with
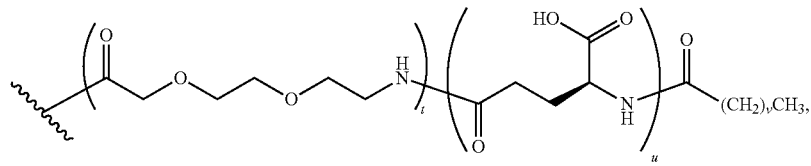
wherein t is 0;
u is 1; and
v is 14;
$Z_{11}$ is D or K, wherein the amino side chain of said K is optionally substituted with
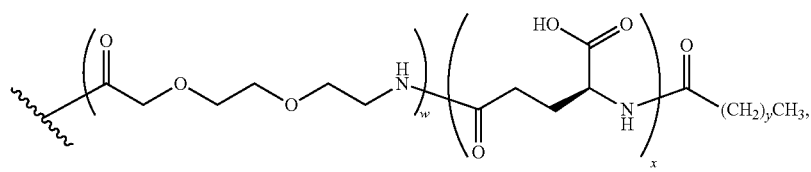
wherein w is 0, or 4;
x is 1; and
y is 14;
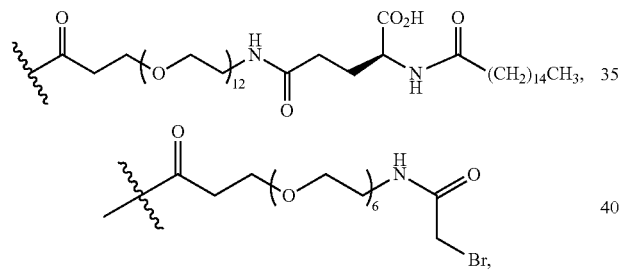
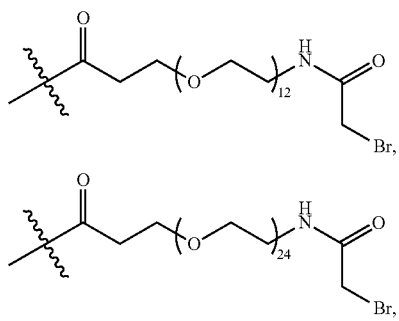
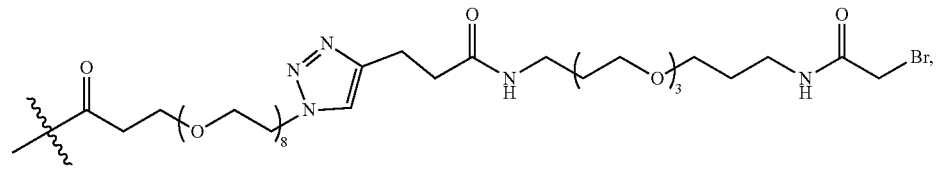
—C(O)CH$_2$Br,
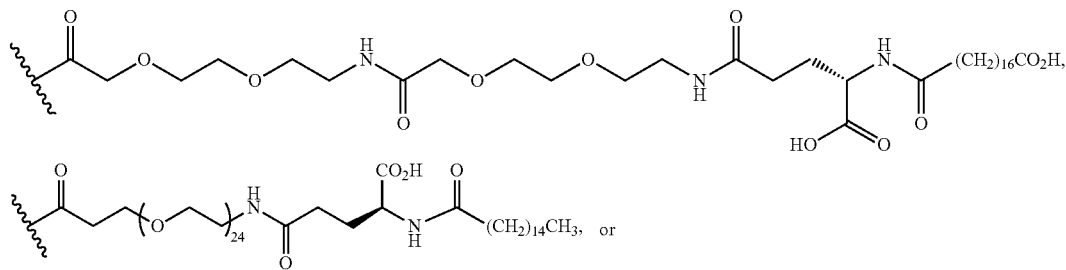

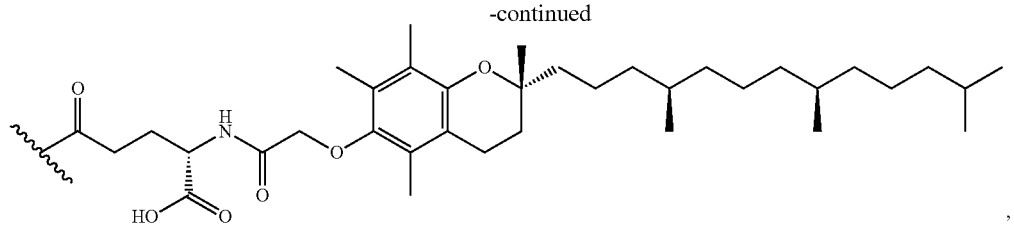
,
$Z_{22}$ is A or K, wherein the amino side chain of said K is optionally substituted with
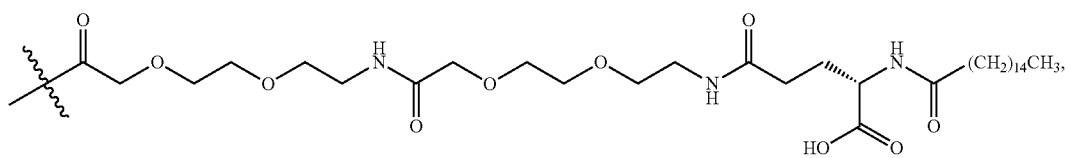
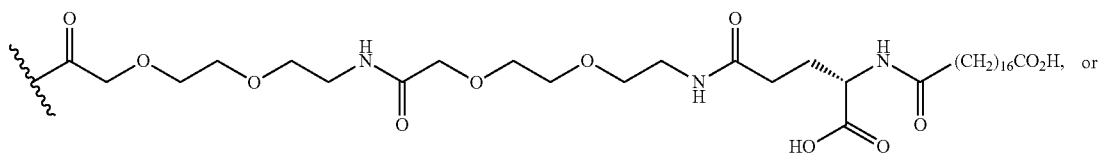
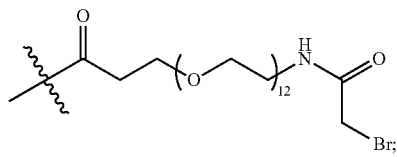
$Z_{23}$ is S or K, wherein the amino side chain of said K is optionally substituted with
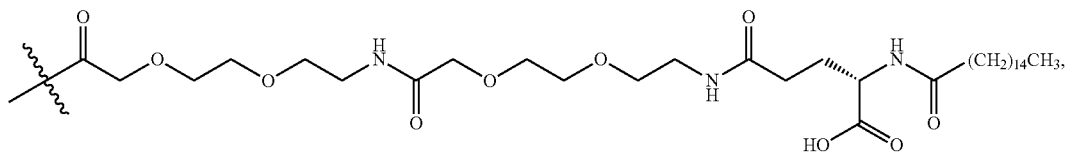
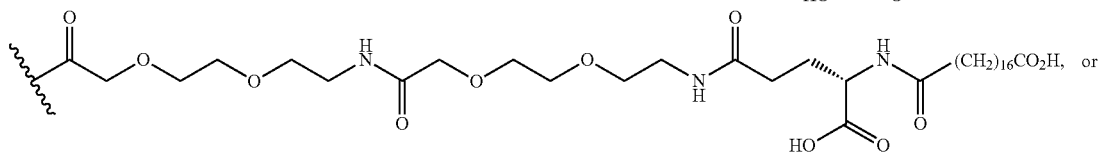
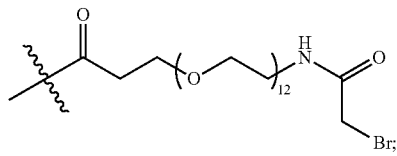
$Z_{30}$ is L, W, absent, or K, provided that $Z_{30}$ is absent only when q is 1, wherein the amino side chain of said K is optionally substituted with

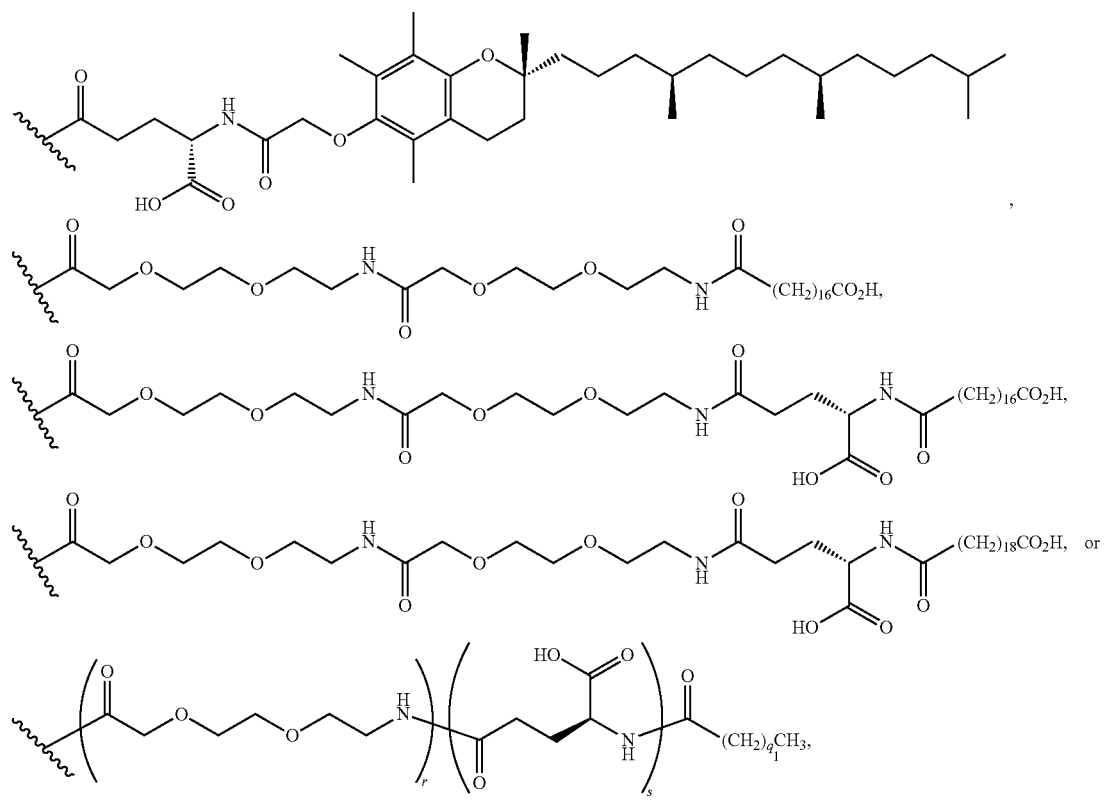
wherein r is 0, 1, or 2;
s is 1; and
$q_1$ is 14, 16, or 18;
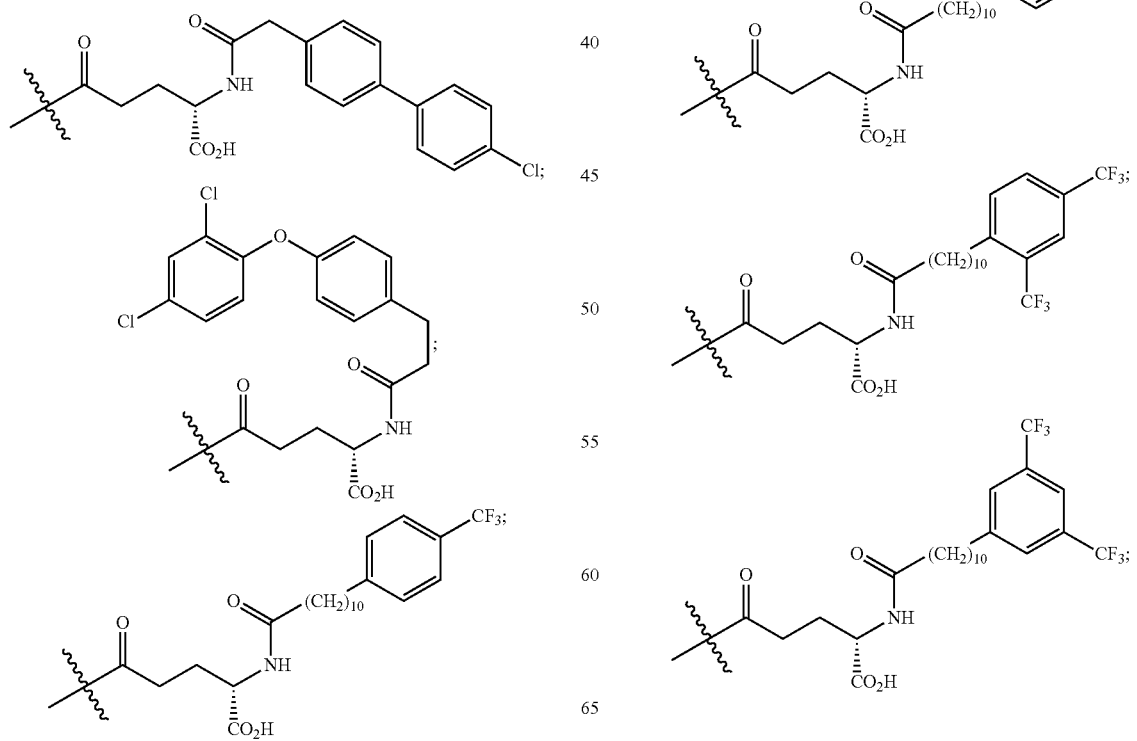

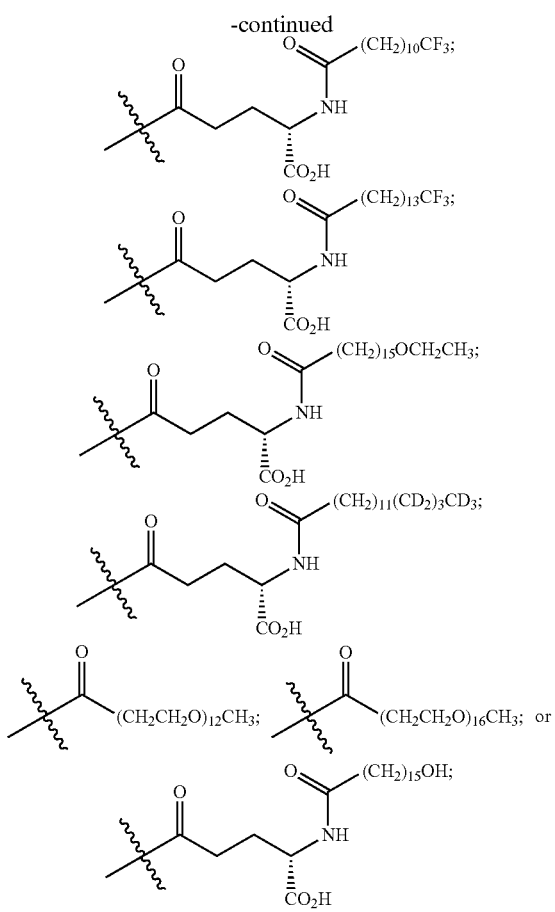

or a pharmaceutically acceptable salt thereof.

5. The pharmaceutical composition of claim 1, wherein the compound of Formula (I) is selected from the group consisting of SEQ ID NO: 1 to SEQ ID NO:110, or a pharmaceutically acceptable salt thereof.

6. The pharmaceutical composition of claim 1, wherein the compound is conjugated to a half-life extension moiety.

7. A pharmaceutical composition comprising the compound of claim 1, and a pharmaceutically acceptable carrier.

8. A method for treating or ameliorating obesity, comprising administering to a subject in need thereof an effective amount of the pharmaceutical composition of claim 1, or a form, composition or medicament thereof.

9. A method of treating or ameliorating a syndrome, disorder or disease, wherein said syndrome, disorder or disease is selected from the group consisting of obesity, type 2 diabetes, metabolic syndrome, and insulin resistance comprising administering to a subject in need thereof an effective amount of the pharmaceutical composition of claim 1, or a form, composition or medicament thereof.

10. The method of claim 9, wherein said syndrome, disorder or disease is type 2 diabetes.

11. A method of reducing food intake comprising administering to a subject in need thereof an effective amount of the pharmaceutical composition of claim 1, or a form, composition or medicament thereof.

12. A method of modulating Y2 receptor activity comprising administering to a subject in need thereof an effective amount of the pharmaceutical composition of claim 1, or a form, composition or medicament thereof.

13. A method of treating a disease, disorder or syndrome selected from the group consisting of obesity, type 2 diabetes, metabolic syndrome, and insulin resistance comprising administering to a subject in need thereof an effective amount of the pharmaceutical composition of claim 1, or a form, composition or medicament thereof in combination with at least one antidiabetic agent.

14. The method of claim 13, wherein said antidiabetic agent is a glucagon-like-peptide-1 receptor modulator.

15. The pharmaceutical composition of claim 1 wherein the additional compound is metformin, chlorpropamide, glimepiride, glipizide, glyburide, glibenclamide, glibornuride, glisoxepide, glyclopyramide, tolazamide, tolbutamide, acetohexamide, carbutamide, pioglitazone, rosiglitazone, lobeglitazone, ciglitazone, darglitazone, englitazone, netoglitazone, rivoglitazone, or troglitazone.

* * * * *

SEQUENCE LISTING

```
<160> NUMBER OF SEQ ID NOS: 111

<210> SEQ ID NO 1
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the Ala is a beta-alanine with a
      cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein Cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 1

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 2
<211> LENGTH: 34
<212> TYPE: PRT
<213> ORGANISM: Artificial Sequence
<220> FEATURE:
<223> OTHER INFORMATION: Cyclic PYY Peptide Compound
```

```
-continued

<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Cys
<222> LOCATION: (29)..(29)
<223> OTHER INFORMATION: Cys, wherein Cys is homocysteine with a cyclic
      modification

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 3
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Leu
<222> LOCATION: (29)..(29)
<223> OTHER INFORMATION: Leu, wherien Leu is a norleucine with a cyclic
      modification

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 4
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein cys is a homocysteine with a
      cyclic modification

<400> SEQUENCE: 4

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr
```

-continued

```
<210> SEQ ID NO 5
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a gamma-Glu-AcVitE chemical
      modification
<220> FEATURE:
<221> NAME/KEY: Cys
<222> LOCATION: (29)..(29)
<223> OTHER INFORMATION: Cys, wherein cys is homocysteine with a cyclic
      modification

<400> SEQUENCE: 5

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 6
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a gamma-Glu-AcVitE chemical
      modification
<220> FEATURE:
<221> NAME/KEY: Leu
<222> LOCATION: (29)..(29)
<223> OTHER INFORMATION: Leu, wherein the leu is norleucine with a
      cyclic modification

<400> SEQUENCE: 6

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 7
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (7)..(7)
<223> OTHER INFORMATION: Lys with a gamma-Glu-Pal chemical modification
<220> FEATURE:
```

```
<221> NAME/KEY: Cys
<222> LOCATION: (29)..(29)
<223> OTHER INFORMATION: Cys, wherein cys is homocysteine with a cyclic
      modification

<400> SEQUENCE: 7

Ile Lys Pro Glu Ala Pro Lys Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 8
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein cys is homocysteine with a cyclic
      modification

<400> SEQUENCE: 8

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 9
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Cys
<222> LOCATION: (29)..(29)
<223> OTHER INFORMATION: Cys, wherein cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 9

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30
```

Arg Tyr

```
<210> SEQ ID NO 10
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-AcVitE chemical
      modification
<220> FEATURE:
<221> NAME/KEY: Cys
<222> LOCATION: (29)..(29)
<223> OTHER INFORMATION: Cys, wherein cys is homocysteine with a cyclic
      modification

<400> SEQUENCE: 10
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Lys Cys Thr Arg
            20                  25                  30

Gln Arg Tyr
        35

```
<210> SEQ ID NO 11
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-AcVitE chemical
      modification
<220> FEATURE:
<221> NAME/KEY: Cys
<222> LOCATION: (29)..(29)
<223> OTHER INFORMATION: Cys, wherein cys is homocysteine with a cyclic
      modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 11
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Lys Cys Thr Arg
            20                  25                  30

Gln Arg Tyr
        35

```
<210> SEQ ID NO 12
<211> LENGTH: 34
```

-continued

```
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Cys
<222> LOCATION: (29)..(29)
<223> OTHER INFORMATION: Cys, wherein the cys is homocysteine with a
      cyclic modification
<220> FEATURE:
<221> NAME/KEY: Arg
<222> LOCATION: (33)..(33)
<223> OTHER INFORMATION: Arg with a N-Me chemical modification

<400> SEQUENCE: 12

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 13
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 13

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 14
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
```

```
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is homocysteine with a
      cyclic modification
<220> FEATURE:
<221> NAME/KEY: Arg
<222> LOCATION: (33)..(33)
<223> OTHER INFORMATION: Arg with a N-Me chemical modification

<400> SEQUENCE: 14

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 15
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein cys is homocysteine with a cyclic
      modification

<400> SEQUENCE: 15

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 16
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein the cys is homocysteine with a
      cyclic modification

<400> SEQUENCE: 16

Lys Pro Glu Ala Pro Gly Glu Asp Ala Ser Pro Glu Glu Leu Asn Arg
1               5                   10                  15
```

```
Tyr Tyr Ala Ser Leu Arg His Tyr Leu Asn Lys Cys Thr Arg Gln Arg
            20                  25                  30

Tyr

<210> SEQ ID NO 17
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification

<400> SEQUENCE: 17

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 18
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein cys is homocysteine with a cyclic
      modification

<400> SEQUENCE: 18

Ile Glu Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 19
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
```

```
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a N-Me chemical modification

<400> SEQUENCE: 19

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 20
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a N-Me chemical modification

<400> SEQUENCE: 20

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 21
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein cys is a homocysteine with a
      cyclic modification

<400> SEQUENCE: 21
```

Ile Ala Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Lys Cys Thr Arg Gln
        20                  25                  30

Arg Tyr

<210> SEQ ID NO 22
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification

<400> SEQUENCE: 22

Ile Glu Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Lys Cys Thr Arg Gln
        20                  25                  30

Arg Tyr

<210> SEQ ID NO 23
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-COC16CO2H chemical
      modification
<220> FEATURE:
<221> NAME/KEY: Cys
<222> LOCATION: (29)..(29)
<223> OTHER INFORMATION: Cys, wherein cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 23

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
        20                  25                  30

Arg Tyr

<210> SEQ ID NO 24
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-COC18CO2H chemical
      modification
<220> FEATURE:
<221> NAME/KEY: Cys
<222> LOCATION: (29)..(29)
<223> OTHER INFORMATION: Cys, wherein cys is homocysteine with a cyclic
      modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 24

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 25
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Stear chemical
      modification
<220> FEATURE:
<221> NAME/KEY: Cys
<222> LOCATION: (29)..(29)
<223> OTHER INFORMATION: Cys, wherein cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 25

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

```
<210> SEQ ID NO 26
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Arach chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 26
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

```
<210> SEQ ID NO 27
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-COC16CO2H chemical
      modification
<220> FEATURE:
<221> NAME/KEY: Cys
<222> LOCATION: (29)..(29)
<223> OTHER INFORMATION: Cys, wherein the cys is homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 27
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

```
<210> SEQ ID NO 28
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 28

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 29
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 29

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30
```

Tyr

```
<210> SEQ ID NO 30
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 30
```

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

```
<210> SEQ ID NO 31
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-Stear chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 31
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

```
<210> SEQ ID NO 32
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 32

Ile Ala Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Lys Cys Thr Arg Gln
            20                  25                  30

Arg Tyr

<210> SEQ ID NO 33
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Gln
<222> LOCATION: (32)..(32)
<223> OTHER INFORMATION: Gln with a N-Me chemical modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 33

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
```

-continued

```
                20                  25                  30
Arg Tyr

<210> SEQ ID NO 34
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 34

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
                20                  25                  30

Tyr

<210> SEQ ID NO 35
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 35

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
                20                  25                  30
```

Arg Tyr

```
<210> SEQ ID NO 36
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (32)..(32)
<223> OTHER INFORMATION: Arg with a N-Me and psi-(R35, Y36) chemical
      modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 36

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 37
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 37

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr
```

```
<210> SEQ ID NO 38
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a N-Me and a psi-(R35, Y36) chemical
      modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 38

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 39
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Arach chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 39

Ile Ser Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30
```

Arg Tyr

```
<210> SEQ ID NO 40
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-Pal chemical
      modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 40

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Leu Thr Arg Gln
            20                  25                  30

Arg Tyr

<210> SEQ ID NO 41
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 41

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Leu Thr Arg Gln
            20                  25                  30
```

Arg Tyr

```
<210> SEQ ID NO 42
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-COC16CO2H chemical
      modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 42

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Leu Thr Arg Gln
            20                  25                  30

Arg Tyr

<210> SEQ ID NO 43
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 43

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30
```

-continued

Arg Tyr

<210> SEQ ID NO 44
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a (OEG)2-gamma-Glu-COC16CO2H chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 44

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 45
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a COCH2CH2(OCH2CH2)24NH-gamma-Glu-Pal
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 45

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln

```
            20                  25                  30

Arg Tyr

<210> SEQ ID NO 46
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 46

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 47
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (5)..(5)
<223> OTHER INFORMATION: Lys with a (OEG)2-gamma-COC16CO2H chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 47

Ile Lys Pro Glu Lys Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
```

Arg Tyr

<210> SEQ ID NO 48
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (20)..(20)
<223> OTHER INFORMATION: Lys with a (OEG)2-gamma-COC16CO2H chemical
    modification
<220> FEATURE:
<221> NAME/KEY: Cys
<222> LOCATION: (29)..(29)
<223> OTHER INFORMATION: Cys, wherein the cys is a homocysteine with a
    cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 48

Ile Lys Pro Glu Ala Pro Gly Glu Asp Ala Ser Pro Glu Glu Leu Asn
1               5                   10                  15

Arg Tyr Tyr Lys Ser Leu Arg His Tyr Leu Asn Leu Cys Thr Arg Gln
            20                  25                  30

Arg Tyr

<210> SEQ ID NO 49
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-(Pal-16-OH) chemical
    modification
<220> FEATURE:
<221> NAME/KEY: Cys
<222> LOCATION: (29)..(29)
<223> OTHER INFORMATION: Cys, wherein the cys is a homocysteine with a
    cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 49

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 50
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (21)..(21)
<223> OTHER INFORMATION: Lys with a (OEG)2-gamma-COC16CO2H chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 50

Ile Lys Pro Glu Ala Pro Gly Glu Asp Ala Ser Pro Glu Glu Leu Asn
1               5                   10                  15

Arg Tyr Tyr Ala Lys Leu Arg His Tyr Leu Asn Leu Cys Thr Arg Gln
            20                  25                  30

Arg Tyr

<210> SEQ ID NO 51
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 51

Ile Ser Pro Glu Ala Pro Gly Glu Asp Ala Ser Pro Glu Glu Leu Asn
1               5                   10                  15

```
Arg Tyr Tyr Ala Ser Leu Arg His Tyr Leu Asn Lys Cys Thr Arg Gln
            20                  25                  30

Arg Tyr

<210> SEQ ID NO 52
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a COCH2CH2(OCH2CH2)12NH-gamma-Glu-Pal
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 52

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 53
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a (OEG)4-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 53

Ile Lys Pro Glu Ala Pro Gly Glu Lys Ala Ser Pro Glu Glu Leu Asn
1               5                   10                  15
```

Arg Tyr Tyr Ala Ser Leu Arg His Tyr Leu Asn Leu Cys Thr Arg Gln
            20                  25                  30

Arg Tyr

<210> SEQ ID NO 54
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 54

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 55
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (21)..(21)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 55

Ile Lys Pro Glu Ala Pro Gly Glu Asp Ala Ser Pro Glu Glu Leu Asn

```
                1               5                   10                  15
Arg Tyr Tyr Ala Lys Leu Arg His Tyr Leu Asn Leu Cys Thr Arg Gln
            20                  25                  30

Arg Tyr

<210> SEQ ID NO 56
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-COCH2Ph-(4-ClPh) chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 56

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 57
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)2PhO-(2,4-Cl2Ph)
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 57
```

-continued

```
Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 58
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-(4-F-Ph)
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 58

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 59
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (20)..(20)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 59
```

-continued

```
Ile Lys Pro Glu Ala Pro Gly Glu Asp Ala Ser Pro Glu Glu Leu Asn
1               5                   10                  15

Arg Tyr Tyr Lys Ser Leu Arg His Tyr Leu Asn Leu Cys Thr Arg Gln
            20                  25                  30

Arg Tyr

<210> SEQ ID NO 60
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (5)..(5)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 60

Ile Lys Pro Glu Lys Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 61
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-(4-F3C-Ph)
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification
```

```
<400> SEQUENCE: 61

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 62
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-CF3 chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 62

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 63
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)13-CF3 chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification
```

-continued

```
<400> SEQUENCE: 63

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 64
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-(Pal-16-OEt) chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 64

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 65
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)11(CD2)3CD3
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
```

-continued

<223> OTHER INFORMATION: Tyr with a psi-(R35, Y36) chemical modification

<400> SEQUENCE: 65

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 66
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-(2,4-(CF3)2-Ph)
    chemical modification
<220> FEATURE:
<221> NAME/KEY: Cys
<222> LOCATION: (29)..(29)
<223> OTHER INFORMATION: Cys, wherein the cys is a homocysteine with a
    cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 66

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 67
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-(3,5-(CF3)2-Ph)
    chemical modification
<220> FEATURE:
<221> NAME/KEY: Cys
<222> LOCATION: (29)..(29)
<223> OTHER INFORMATION: Cys, wherein the cys is a homocysteine with a
    cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr

```
<222> LOCATION: (34)..(34)
<223> OTHER INFORMATION: Tyr with a psi-(R35, Y36) chemical modification

<400> SEQUENCE: 67

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Lys Cys Thr Arg Gln
            20                  25                  30
Arg Tyr

<210> SEQ ID NO 68
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a (OEG)2-gamma-Glu-COC16CO2H chemical
      modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 68

Ile Lys Pro Glu Ala Pro Gly Glu Lys Ala Ser Pro Glu Glu Leu Asn
1               5                   10                  15
Arg Tyr Tyr Ala Ser Leu Arg His Tyr Leu Asn Cys Val Thr Arg Gln
            20                  25                  30
Arg Tyr

<210> SEQ ID NO 69
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (30)..(30)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 69

Gly Ile Ser Pro Glu Ala Pro Gly Glu Lys Ala Ser Pro Glu Glu Leu
```

```
                1               5                   10                  15
Asn Arg Tyr Tyr Ala Ser Leu Arg His Tyr Leu Asn Leu Glu Thr Arg
                20                  25                  30

Gln Arg Tyr
        35

<210> SEQ ID NO 70
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 70

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
                20                  25                  30

Gln Arg Tyr
        35

<210> SEQ ID NO 71
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 71

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
                20                  25                  30

Gln Arg Tyr
        35

<210> SEQ ID NO 72
<211> LENGTH: 35
<212> TYPE: PRT
<213> ORGANISM: Artificial Sequence
```

```
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a (OEG)2-gamma-Glu-COC16CO2H chemical
      modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 72

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 73
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG6-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 73

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 74
<211> LENGTH: 35
```

```
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 74

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 75
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 75

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 76
<211> LENGTH: 35
```

```
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Lys
<222> LOCATION: (29)..(29)
<223> OTHER INFORMATION: Lys with a mPEG16 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 76

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Lys Cys Thr Arg
            20                  25                  30

Gln Arg Tyr
        35

<210> SEQ ID NO 77
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Lys
<222> LOCATION: (19)..(19)
<223> OTHER INFORMATION: Lys with a mPEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 77

Ala Ile Lys Pro Glu Ala Pro Gly Glu Lys Ala Ser Pro Glu Glu Leu
```

```
                1               5                  10                 15
Asn Arg Lys Tyr Ala Ser Leu Arg His Tyr Leu Asn Leu Cys Thr Arg
              20                 25                 30

Gln Arg Tyr
        35

<210> SEQ ID NO 78
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Gln
<222> LOCATION: (33)..(33)
<223> OTHER INFORMATION: Gln with a N-Me chemical modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 78

Ala Ile Lys Pro Glu Ala Pro Gly Glu Lys Ala Ser Pro Glu Glu Leu
1               5                  10                 15

Asn Arg Tyr Tyr Ala Ser Leu Arg His Tyr Leu Asn Leu Cys Thr Arg
              20                 25                 30

Gln Arg Tyr
        35

<210> SEQ ID NO 79
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me and a psi-(R35, Y36) chemical
      modification
```

```
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 79

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 80
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 80

Ala Ile Arg Pro Glu Ala Pro Gly Glu Lys Ala Ser Pro Glu Glu Leu
1               5                   10                  15

Asn Arg Tyr Tyr Ala Ser Leu Arg His Tyr Leu Asn Trp Cys Thr Arg
            20                  25                  30

Gln Arg Tyr
        35

<210> SEQ ID NO 81
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
```

```
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 81

Ile Arg Pro Glu Ala Pro Gly Glu Lys Ala Ser Pro Glu Glu Leu Asn
1               5                   10                  15

Arg Tyr Tyr Ala Ser Leu Arg His Tyr Leu Asn Trp Cys Thr Arg Gln
            20                  25                  30

Arg Tyr

<210> SEQ ID NO 82
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (8)..(8)
<223> OTHER INFORMATION: Lys with a PEG12-AcBr chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 82

Lys Pro Glu Ala Pro Gly Glu Lys Ala Ser Pro Glu Glu Leu Asn Arg
1               5                   10                  15

Tyr Tyr Ala Ser Leu Arg His Tyr Leu Asn Leu Cys Thr Arg Gln Arg
            20                  25                  30

Tyr

<210> SEQ ID NO 83
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12-AcBr chemical modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
```

```
<221> NAME/KEY: Tyr
<222> LOCATION: (34)..(34)
<223> OTHER INFORMATION: Tyr with a psi-(R35, Y36) chemical modification

<400> SEQUENCE: 83

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Val Thr Arg
            20                  25                  30

Gln Arg Tyr
        35

<210> SEQ ID NO 84
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG-8-triazolyl-CH2CH2CO-PEG4-AcBr
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a (R35, Y36) chemical modification
<220> FEATURE:
<221> NAME/KEY: Tyr
<222> LOCATION: (34)..(34)
<223> OTHER INFORMATION: Tyr with a (R35, Y36) chemical modification

<400> SEQUENCE: 84

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Val Thr Arg
            20                  25                  30

Gln Arg Tyr
        35

<210> SEQ ID NO 85
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (22)..(22)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
```

```
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 85

Ala Ile Lys Pro Glu Ala Pro Gly Glu Asp Ala Ser Pro Glu Glu Leu
1               5                   10                  15

Asn Arg Tyr Tyr Ala Lys Leu Arg His Tyr Leu Asn Leu Cys Val Thr
            20                  25                  30

Arg Gln Arg Tyr
        35

<210> SEQ ID NO 86
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (21)..(21)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 86

Ala Ile Lys Pro Glu Ala Pro Gly Glu Asp Ala Ser Pro Glu Glu Leu
1               5                   10                  15

Asn Arg Tyr Tyr Lys Ser Leu Arg His Tyr Leu Asn Leu Cys Val Thr
            20                  25                  30

Arg Gln Arg Tyr
        35

<210> SEQ ID NO 87
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (6)..(6)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
```

```
                cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 87

Ala Ile Lys Pro Glu Lys Pro Gly Glu Asp Ala Ser Pro Glu Glu Leu
1               5                   10                  15

Asn Arg Tyr Tyr Ala Ser Leu Arg His Tyr Leu Asn Leu Cys Val Thr
            20                  25                  30

Arg Gln Arg Tyr
        35

<210> SEQ ID NO 88
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic chemical modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 88

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 89
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
```

```
<220> FEATURE:
<221> NAME/KEY: Arg
<222> LOCATION: (34)..(34)
<223> OTHER INFORMATION: Arg with a N-Me chemical modification

<400> SEQUENCE: 89

Gly Ile Lys Pro Glu Ala Pro Gly Glu Lys Ala Ser Pro Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 90
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 90

Ala Ile Lys Pro Glu Ala Pro Gly Glu Lys Ala Ser Pro Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 91
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 91
```

```
Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 92
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 92

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 93
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 93

Gly Ile Lys Pro Glu Ala Pro Gly Glu Lys Ala Ser Pro Glu Glu Leu
1               5                   10                  15
```

Asn Arg Tyr Tyr Ala Ser Leu Arg His Tyr Leu Asn Cys Val Thr Arg
            20                  25                  30

Gln Arg Tyr
        35

<210> SEQ ID NO 94
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 94

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 95
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 95

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 96
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG24-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 96

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 97
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 97

```
Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 98
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 98

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 99
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 99

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35
```

```
<210> SEQ ID NO 100
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 100

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 101
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 101

Ala Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35
```

```
<210> SEQ ID NO 102
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 102

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 103
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 103

Gly Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 104
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
```

```
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 104

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 105
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 105

Gly Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 106
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 106
```

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 107
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (29)..(29)
<223> OTHER INFORMATION: Cys with chemical modification described in the
      specification
<220> FEATURE:
<221> NAME/KEY: Arg
<222> LOCATION: (34)..(34)
<223> OTHER INFORMATION: Arg with a N-Me chemical modification

<400> SEQUENCE: 107

Ala Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 108
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me chemical modification

<400> SEQUENCE: 108

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 109
<211> LENGTH: 35
<212> TYPE: PRT

```
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with chemical modification described in the
      specification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 109

Ala Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 110
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 110

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 111
<211> LENGTH: 34
<212> TYPE: PRT
<213> ORGANISM: Homo sapiens

<400> SEQUENCE: 111

Ile Lys Pro Glu Ala Pro Gly Glu Asp Ala Ser Pro Glu Glu Leu Asn
1               5                   10                  15
```

```
Arg Tyr Tyr Ala Ser Leu Arg His Tyr Leu Asn Leu Val Thr Arg Gln
            20              25              30
Arg Tyr
```